US010418569B2

(12) United States Patent
Kwong et al.

(10) Patent No.: US 10,418,569 B2
(45) Date of Patent: Sep. 17, 2019

(54) ORGANIC ELECTROLUMINESCENT MATERIALS AND DEVICES

(71) Applicant: Universal Display Corporation, Ewing, NJ (US)

(72) Inventors: Raymond Kwong, Shatin (HK); Sze Kui Lam, Kowloon (HK); Siu Tung Lam, Apleichau (HK); Kit Yee Tsang, Shatin (HK); Chi Hang Lee, Chaiwan (HK); Geza Szigethy, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 392 days.

(21) Appl. No.: 14/982,109

(22) Filed: Dec. 29, 2015

(65) Prior Publication Data

US 2016/0218303 A1 Jul. 28, 2016

Related U.S. Application Data

(60) Provisional application No. 62/107,446, filed on Jan. 25, 2015.

(51) Int. Cl.
*H01L 51/00* (2006.01)
*C09K 11/02* (2006.01)
(Continued)

(52) U.S. Cl.
CPC ...... *H01L 51/0085* (2013.01); *C07F 15/0033* (2013.01); *C09K 11/025* (2013.01); (Continued)

(58) Field of Classification Search
CPC ............. H01L 51/0085; H01L 51/0072; H01L 51/0071; H01L 51/0074; H01L 51/0055; H01L 51/5016
See application file for complete search history.

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

EP 0650955 5/1995
EP 1725079 11/2006
(Continued)

OTHER PUBLICATIONS

Sajoto, S. et al., "Blue and Near-UV Phosphorescence from Iridium Complexes with Cyclometalated Pyrazolyl or N-Heterocyclic Carbene Ligands," Inorganic Chemistry (2005), 44(22), 7992-8003.
(Continued)

*Primary Examiner* — Bethany L Martin
(74) *Attorney, Agent, or Firm* — Duane Morris LLP

(57) ABSTRACT

A family of phosphorescent emitter compounds containing a carbene ligand $L_A$ selected from the group consisting of:

Formula I

, and (Continued)

100

-continued

Formula II

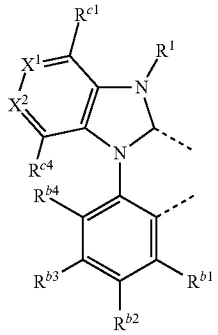

is disclosed. These compounds enhance the performance of OLEDs when incorporated therein.

20 Claims, 2 Drawing Sheets

(51) Int. Cl.
*C07F 15/00* (2006.01)
*H01L 51/50* (2006.01)

(52) U.S. Cl.
CPC ................. *C09K 2211/1007* (2013.01); *C09K 2211/1022* (2013.01); *C09K 2211/1029* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *C09K 2211/181* (2013.01); *C09K 2211/185* (2013.01); *C09K 2211/186* (2013.01); *C09K 2211/188* (2013.01); *H01L 51/0059* (2013.01); *H01L 51/0071* (2013.01); *H01L 51/0072* (2013.01); *H01L 51/0074* (2013.01); *H01L 51/5016* (2013.01)

(56) References Cited

U.S. PATENT DOCUMENTS

| | | | |
|---|---|---|---|
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 9,564,595 | B2 | 2/2017 | Kato et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260447 | A1* | 11/2005 | Brooks et al. ........ H01L 51/028 257/40 |
| 2005/0260449 | A1 | 11/2005 | Walters et al. |
| 2006/0008670 | A1 | 1/2006 | Lin et al. |
| 2006/0024522 | A1 | 2/2006 | Thompson |
| 2006/0202194 | A1 | 9/2006 | Jeong et al. |
| 2006/0240279 | A1 | 10/2006 | Adamovich |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Pakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2012/0319050 | A1 | 12/2012 | Metz et al. |
| 2014/0374728 | A1* | 12/2014 | Adamovich et al. ........................ H01L 51/0081 428/690 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2009-76509 | 4/2009 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005113704 | 12/2005 |
| WO | 2005123873 | 12/2005 |
| WO | 2006009024 | 1/2006 |
| WO | 2006056418 | 6/2006 |

(56) References Cited

FOREIGN PATENT DOCUMENTS

| | | | |
|---|---|---|---|
| WO | 2006072002 | 7/2006 | |
| WO | 2006082742 | 8/2006 | |
| WO | 2006098120 | 9/2006 | |
| WO | 2006100298 | 9/2006 | |
| WO | 2006103874 | 10/2006 | |
| WO | 2006114966 | 11/2006 | |
| WO | 2006132173 | 12/2006 | |
| WO | 2007002683 | 1/2007 | |
| WO | 2007004380 | 1/2007 | |
| WO | 2007063754 | 6/2007 | |
| WO | 2007063796 | 6/2007 | |
| WO | 2008056746 | 5/2008 | |
| WO | 2008101842 | 8/2008 | |
| WO | 2008132085 | 11/2008 | |
| WO | 2009000673 | 12/2008 | |
| WO | 2009003898 | 1/2009 | |
| WO | 2009008311 | 1/2009 | |
| WO | 2009018009 | 2/2009 | |
| WO | 2009021126 | 2/2009 | |
| WO | 2009050290 | 4/2009 | |
| WO | 2009062578 | 5/2009 | |
| WO | 2009063833 | 5/2009 | |
| WO | 2009066778 | 5/2009 | |
| WO | 2009066779 | 5/2009 | |
| WO | 2009086028 | 7/2009 | |
| WO | 2009100991 | 8/2009 | |
| WO | 2012172482 | 12/2012 | |
| WO | WO2013112557 | * 8/2013 | ........... H01L 51/028 |
| WO | 2015014944 | 2/2015 | |
| WO | 2015087739 | 6/2015 | |
| WO | 2015091716 | 6/2015 | |
| WO | 2015150203 | 10/2015 | |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., Apr. 30, 2007, 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato)beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater, 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

(56) References Cited

OTHER PUBLICATIONS

Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater, 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Office Action dated Jan. 16, 2019 for corresponding Chinese Application No. 201610049834.0.

* cited by examiner

ORGANIC ELECTROLUMINESCENT MATERIALS AND DEVICES

CROSS-REFERENCE TO RELATED APPLICATIONS

This application claims priority to U.S. Provisional Application Ser. No. 62/107,446, filed Jan. 25, 2015, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

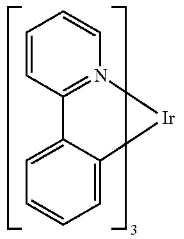

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an aspect of the present disclosure, a new compound is disclosed. The compound comprises a carbene ligand $L_A$ selected from the group consisting of:

Formula I

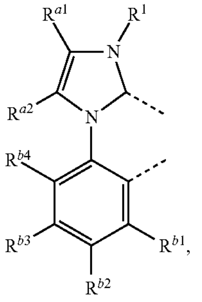

, and

Formula II

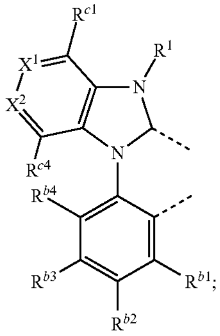

;

wherein $X^1$ is $CR^{c2}$ or N, $X^2$ is $CR^{c3}$ or N;

wherein $R^{a1}$, $R^{a2}$, $R^{b1}$, $R^{b2}$, $R^{b3}$, $R^{b4}$, $R^{c1}$, $R^{c2}$, $R^{c3}$, $R^{c4}$, $R^1$ and $R^2$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof;

wherein at least one of $R^1$, $R^{a1}$, $R^{a2}$, $R^{c1}$, $R^{c3}$, and $R^{c4}$ comprises an acceptor group selected from the group consisting of CN, F directly attached to an aromatic ring, $Si_mF_{2m+1}$, NCO, NCS, OCN, SCN, $OC_mF_{2m+1}$ and $SC_mF_{2m+1}$, where $m \geq 1$;

wherein any adjacent substituents of $R^{b1}$, $R^{b2}$, $R^{b3}$, and $R^{b4}$ are optionally joined or fused into a ring;

wherein the ligand $L_A$ is coordinated to a metal M; and wherein the ligand $L_A$ is optionally linked with other ligands to comprise a tridentate, tetradentate, pentadentate or hexadentate ligand.

According to another aspect of the present disclosure, an organic light emitting device (OLED) is disclosed. The OLED can include an anode, a cathode, and an organic layer, disposed between the anode and the cathode. The organic layer comprises a first compound comprising a carbene ligand $L_A$ selected from the group consisting of:

Formula I

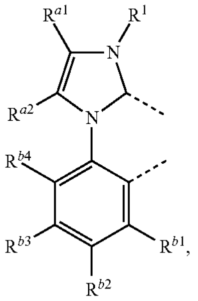

, and

Formula II

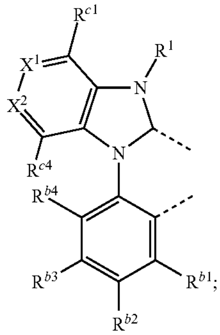

;

wherein $X^1$ is $CR^{c2}$ or N, $X^2$ is $CR^{c3}$ or N;

wherein $R^{a1}$, $R^{a2}$, $R^{b1}$, $R^{b2}$, $R^{b3}$, $R^{b4}$, $R^{c1}$, $R^{c2}$, $R^{c3}$, $R^{c4}$, $R^1$ and $R^2$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof;

wherein at least one of $R^1$, $R^{a1}$, $R^{a2}$, $R^{c1}$, $R^{c3}$, and $R^{c4}$ comprises an acceptor group selected from the group consisting of CN, F directly attached to an aromatic ring, $Si_mF_{2m+1}$, NCO, NCS, OCN, SCN, $OC_mF_{2m+1}$ and $SC_mF_{2m+1}$, where $m \geq 1$;

wherein any adjacent substituents of $R^{b1}$, $R^{b2}$, $R^{b3}$, and $R^{b4}$ are optionally joined or fused into a ring;

wherein the ligand $L_A$ is coordinated to a metal M; and wherein the ligand $L_A$ is optionally linked with other ligands to comprise a tridentate, tetradentate, pentadentate or hexadentate ligand.

According to yet another aspect of the present disclosure, a formulation comprising the first compound is disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
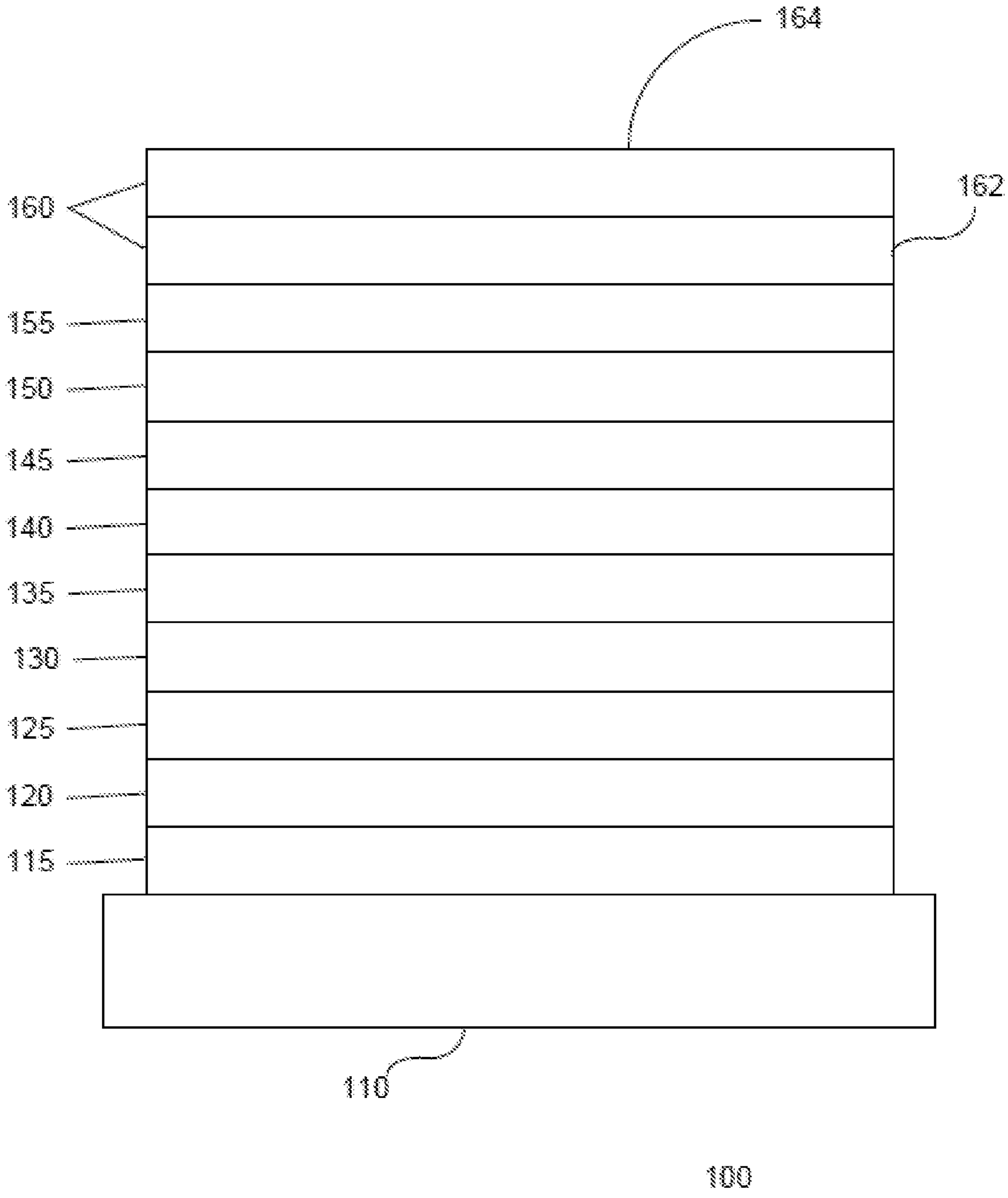
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
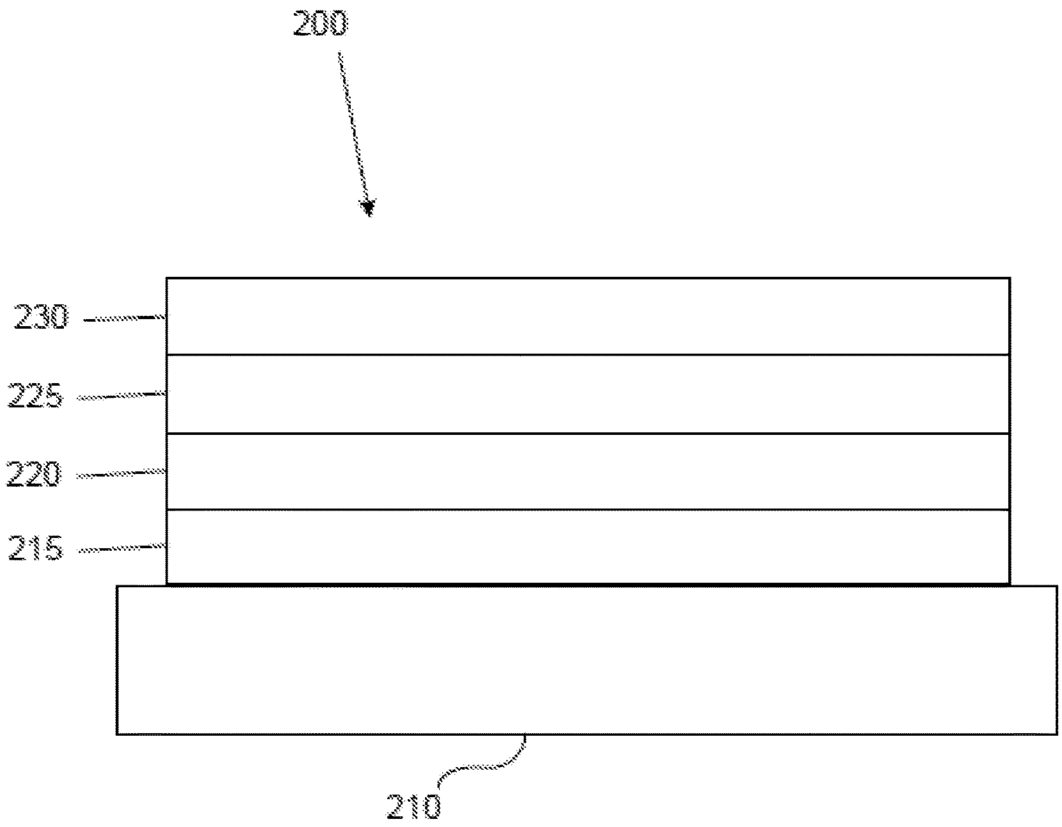
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

According to an aspect of the present disclosure, a new compound is disclosed. The compound comprises a carbene ligand $L_A$ selected from the group consisting of:

Formula I

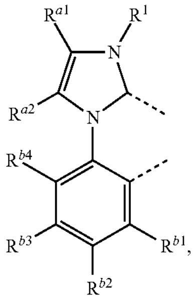

and

Formula II

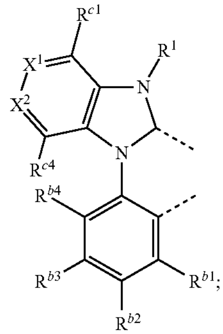

;

wherein $X^1$ is $CR^{c2}$ or N, $X^2$ is $CR^3$ or N;

wherein $R^{a1}$, $R^{a2}$, $R^{b1}$, $R^{b2}$, $R^{b3}$, $R^{b4}$, $R^{c1}$, $R^{c2}$, $R^{c3}$, $R^{c4}$, $R^1$ and $R^2$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof;

wherein at least one of $R^1$, $R^{a1}$, $R^{a2}$, $R^{c1}$, $R^{c3}$, and $R^{c4}$ comprises an acceptor group selected from the group consisting of CN, F directly attached to an aromatic ring, $Si_mF_{2m+1}$, NCO, NCS, OCN, SCN, $OC_mF_{2m+1}$ and $SC_mF_{2m+1}$, where $m \geq 1$;

wherein any adjacent substituents of $R^{b1}$, $R^{b2}$, $R^{b3}$, and $R^{b4}$ are optionally joined or fused into a ring;

wherein the ligand $L_A$ is coordinated to a metal M; and wherein the ligand $L_A$ is optionally linked with other ligands to comprise a tridentate, tetradentate, pentadentate or hexadentate ligand.

In some embodiments of the compound, M can be selected from the group consisting of Ir, Rh, Re, Ru, Os, Pt, Au, and Cu. In some embodiments, M is Ir or Pt.

The compound can be homoleptic or heteroleptic.

In some embodiments of the compound, $X^1$ is $CR^{c2}$, and $X^2$ is $CR^{c3}$.

In other embodiments of the compound, $X^1$ is $CR^{c2}$, and $X^2$ is N.

In other embodiments of the compound, $X^1$ is N, and $X^2$ is $CR^3$.

In other embodiments of the compound, $X^1$ is N, and $X^2$ is N.

In some embodiments of the compound, at least one of $R^1$, $R^{a1}$, $R^{a2}$, $R^{c1}$, $R^{c3}$, and $R^{c4}$ comprises a CN group.

In some embodiments of the compound, at least one of $R^{a1}$, $R^{a2}$, $R^{c1}$, $R^{c3}$, and $R^{c4}$ is CN.

In other embodiments of the compound, $R^1$ and $R^2$ are each independently selected from the group consisting of alkyl or cycloalkyl.

In other embodiments of the compound, $R^1$ and $R^2$ are each independently selected from the group consisting of aryl, substituted aryl, heteroaryl, and substituted heteroaryl.
In some other embodiments of the compound, the ligand $L_A$ is selected from the group consisting of:
LA1
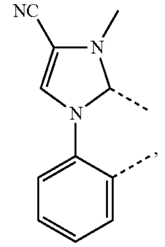
LA2
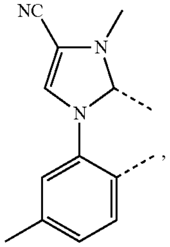
LA3
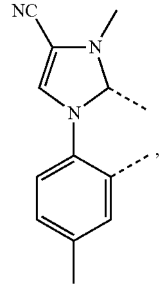
LA4
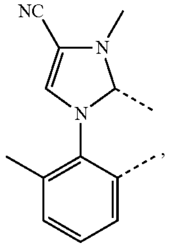
LA5
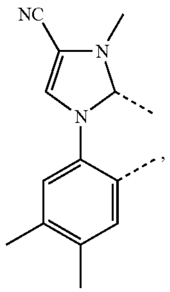
-continued
LA6
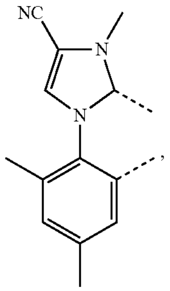
LA7
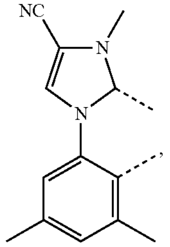
LA8
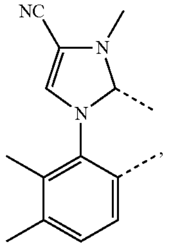
LA9
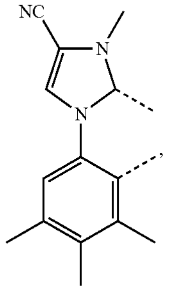
LA10
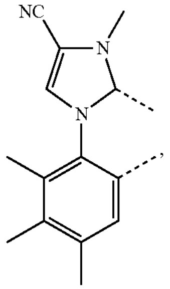

-continued
LA11
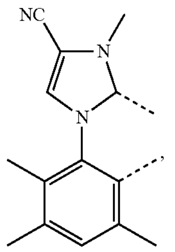
LA12
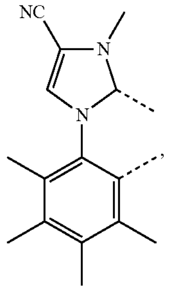
LA13
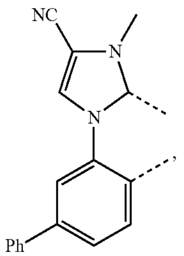
LA14
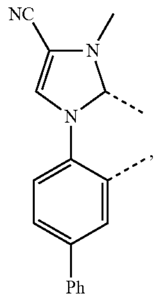
LA15
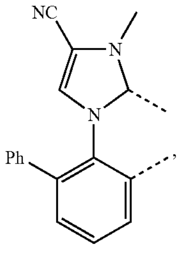
-continued
LA16
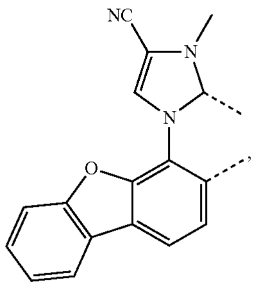
LA17
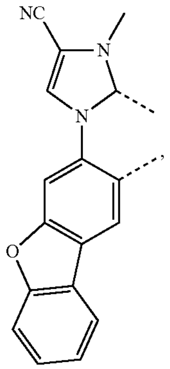
LA18
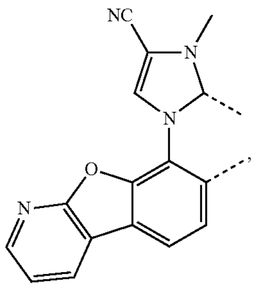
LA19
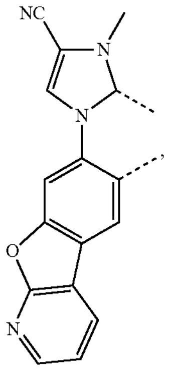
LA20
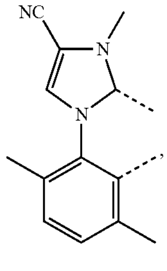

-continued
LA21
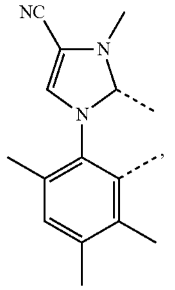
LA22
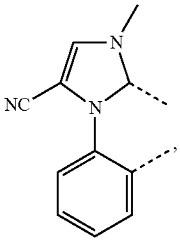
LA23
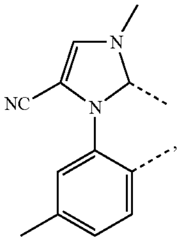
LA24
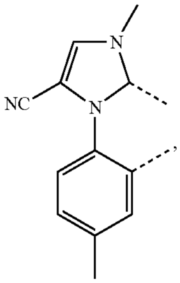
LA25
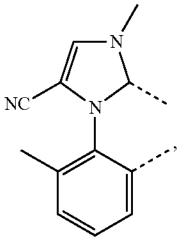
LA26
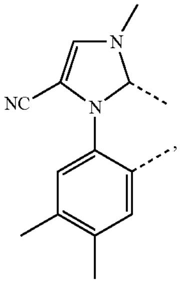
-continued
LA27
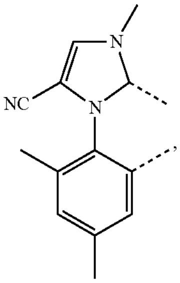
LA28
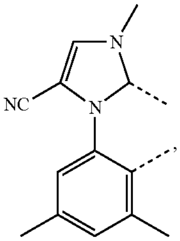
LA29
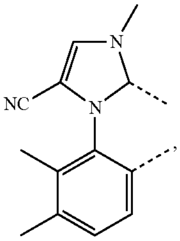
LA30
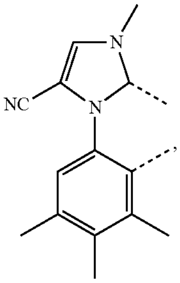
LA31
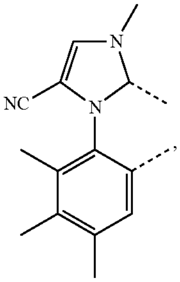
LA32
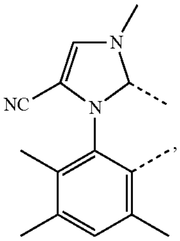

LA33
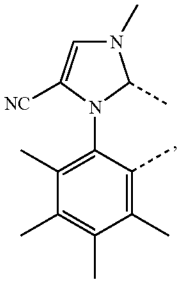
LA34
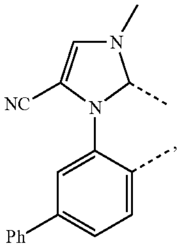
LA35
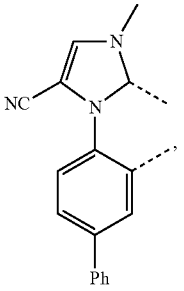
LA36
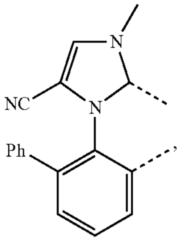
LA37
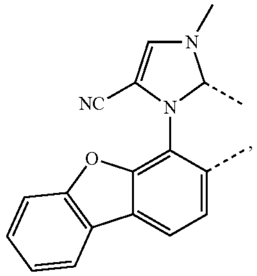
LA38
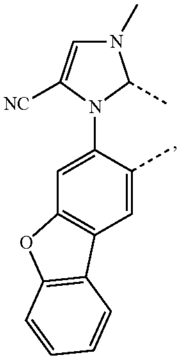
LA39
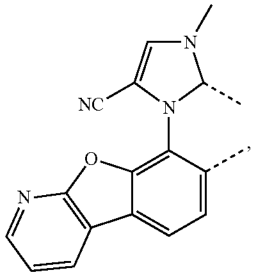
LA40
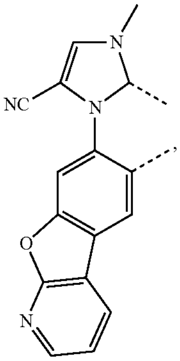
LA41
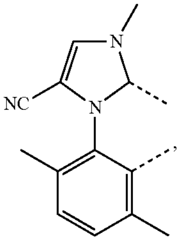
LA42
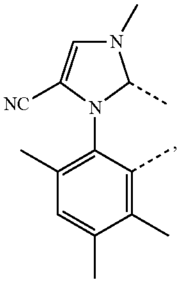

-continued
LA43
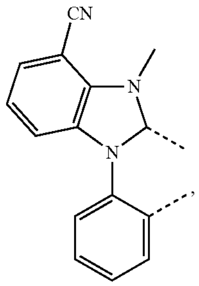
LA44
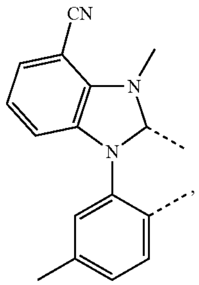
LA45
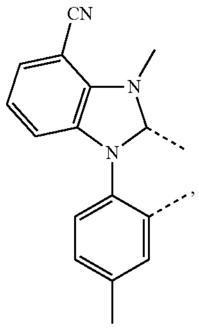
LA46
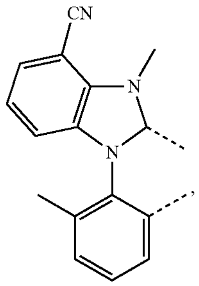
LA47
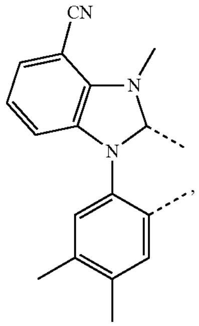
-continued
LA48
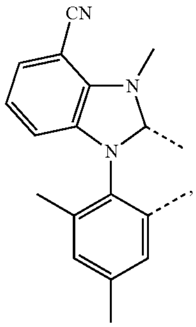
LA49
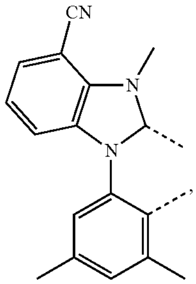
LA50
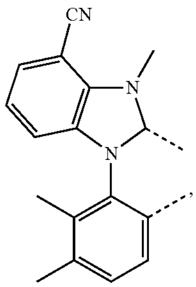
LA51
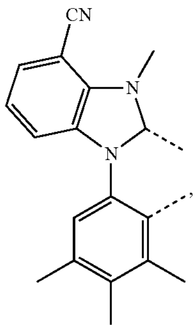
LA52
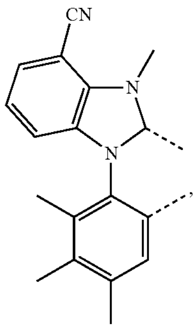

-continued
LA53
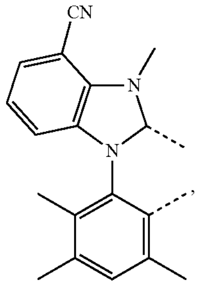
LA54
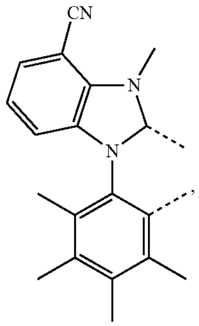
LA55
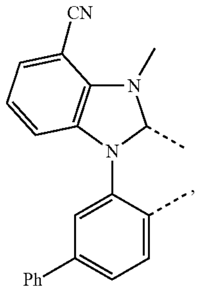
LA56
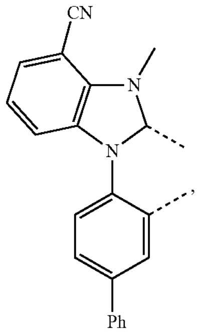
LA57
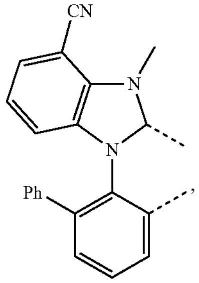
-continued
LA58
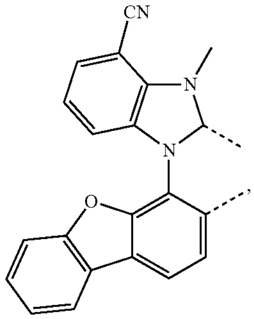
LA59
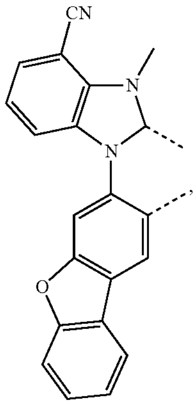
LA60
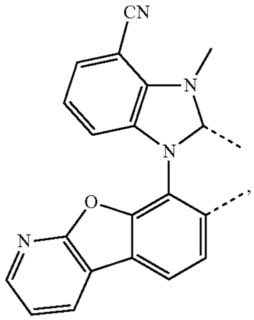
LA61
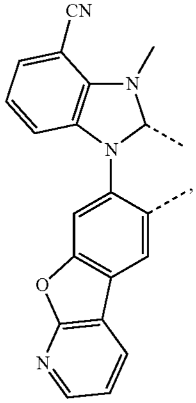

-continued
LA62
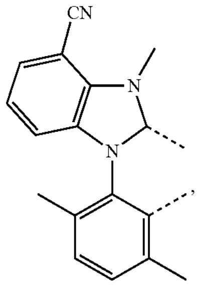
LA63
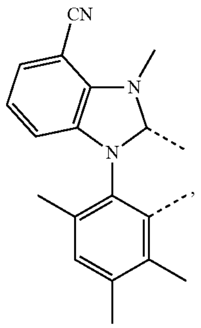
LA64
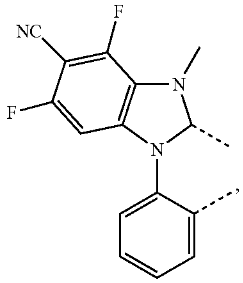
LA65
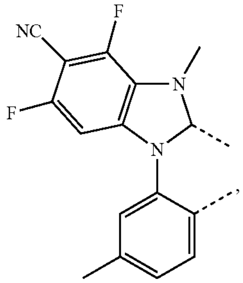
LA66
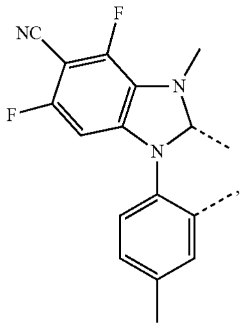
-continued
LA67
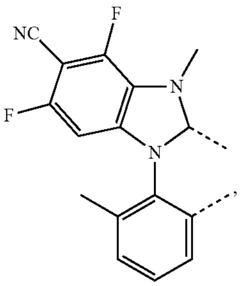
LA68
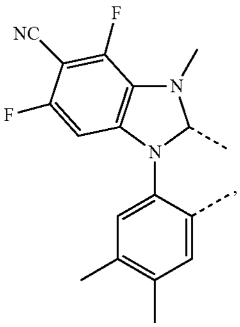
LA69
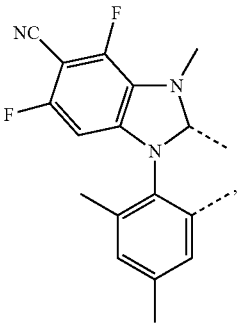
LA70
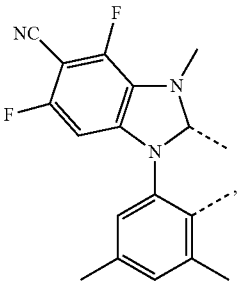
LA71
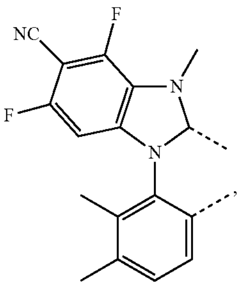

-continued
LA72
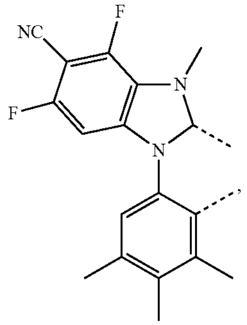
LA73
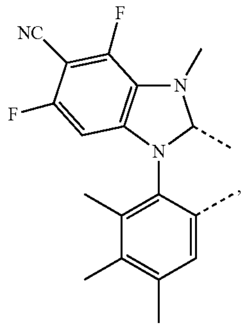
LA74
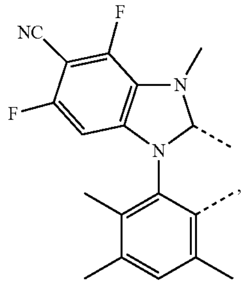
LA75
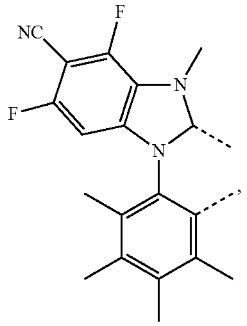
LA76
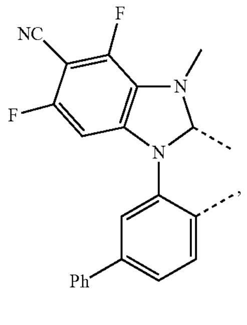
-continued
LA77
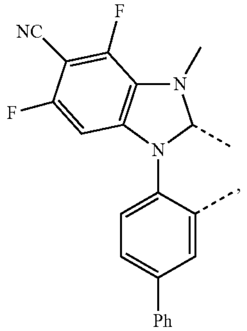
LA78
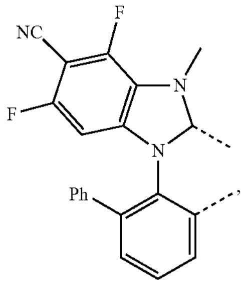
LA79
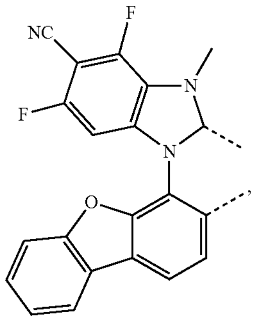
LA80
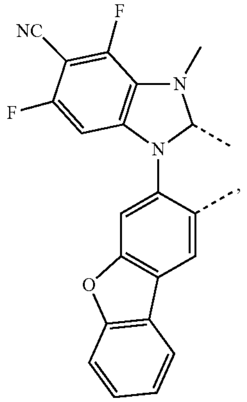

-continued
LA81
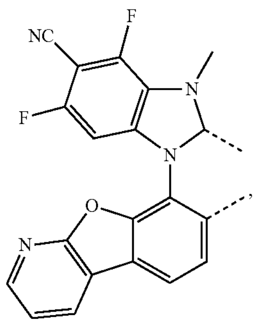
LA82
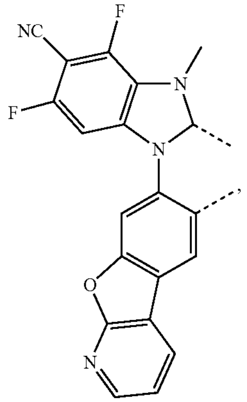
LA83
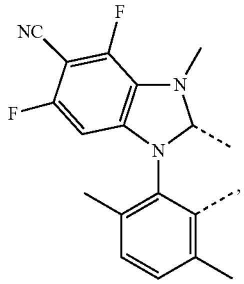
LA84
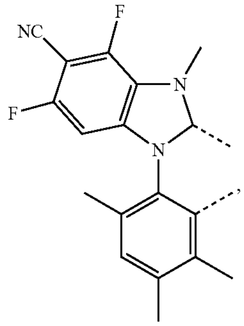
LA85
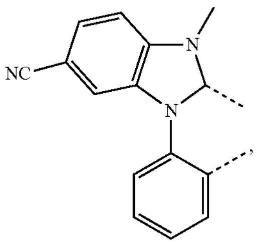
-continued
LA86
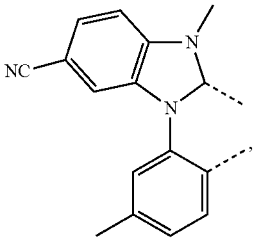
LA87
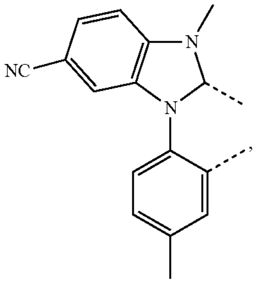
LA88
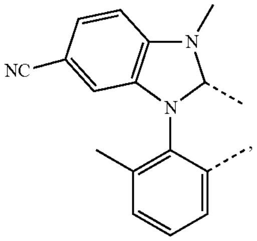
LA89
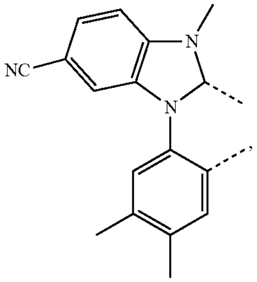
LA90
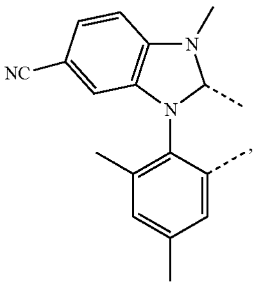
LA91
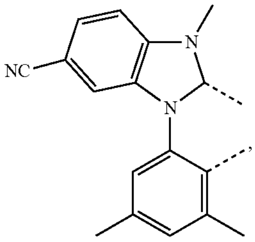

-continued
LA92
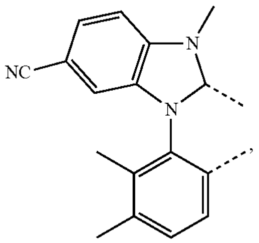
LA93
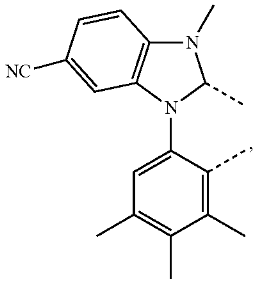
LA94
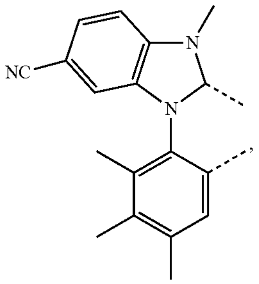
LA95
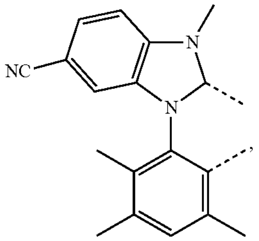
LA96
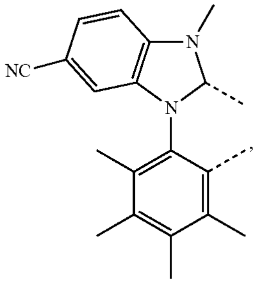
LA97
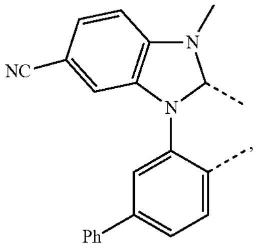
-continued
LA98
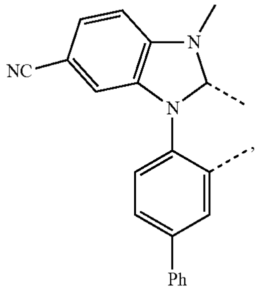
LA99
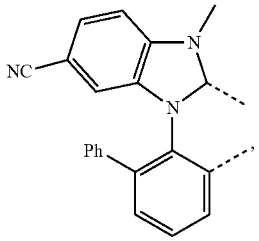
LA100
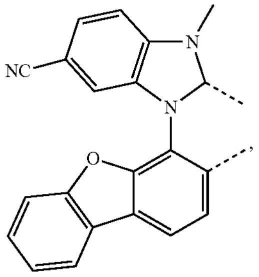
LA101
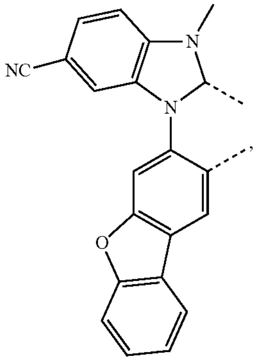
LA102
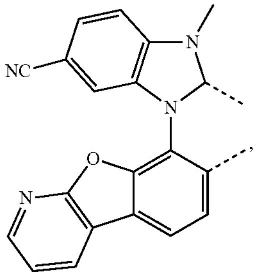

-continued
LA103
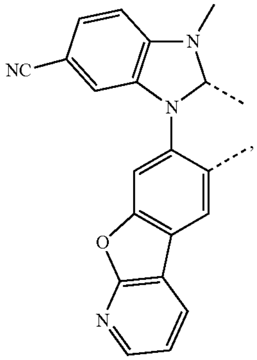
LA104
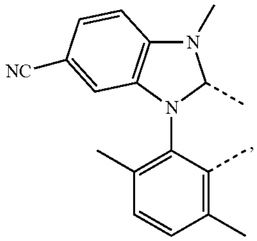
LA105
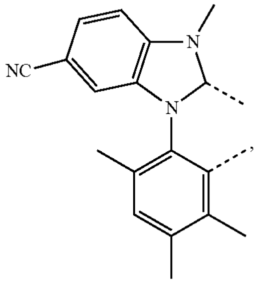
LA106
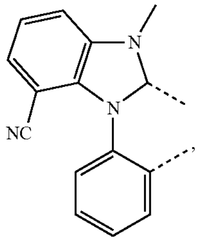
LA107
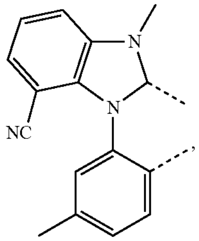
-continued
LA108
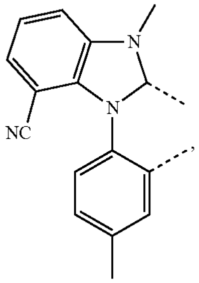
LA109
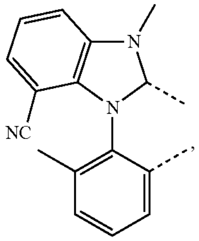
LA110
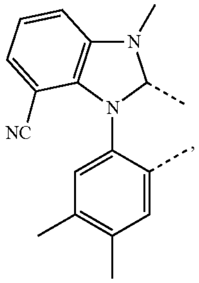
LA111
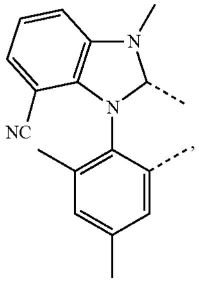
LA112
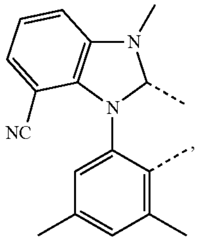
LA113
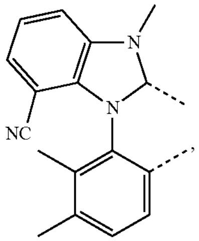

-continued
LA114
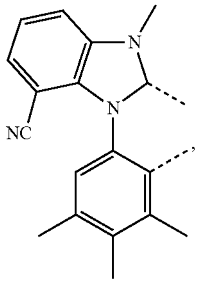
LA115
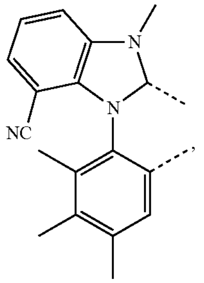
LA116
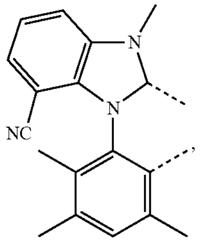
LA117
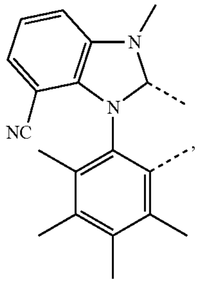
LA118
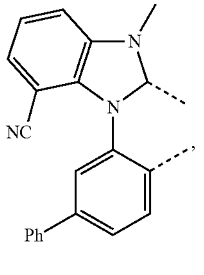
-continued
LA119
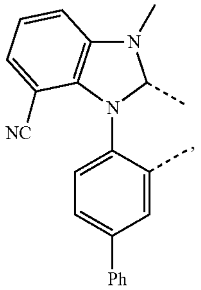
LA120
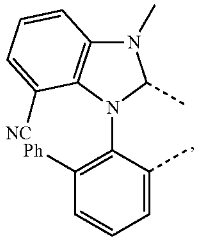
LA121
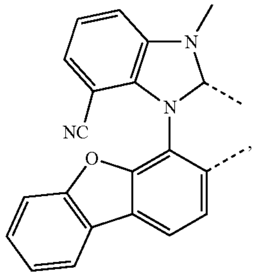
LA122
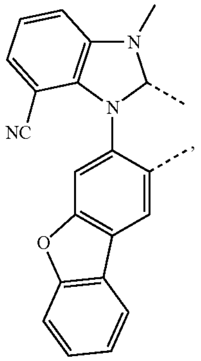
LA123
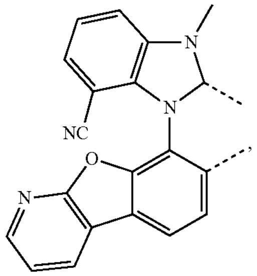

-continued
LA124
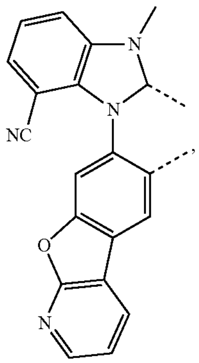
LA125
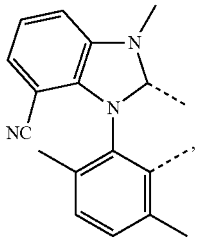
LA126
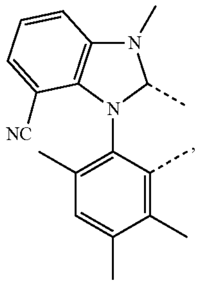
LA127
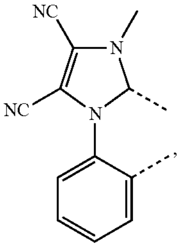
LA128
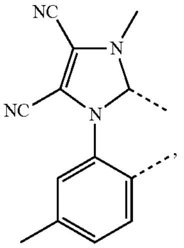
-continued
LA129
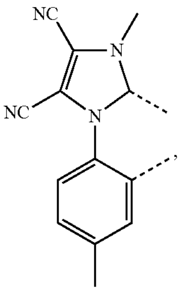
LA130
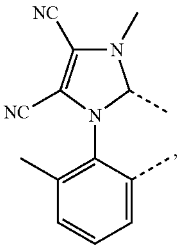
LA131
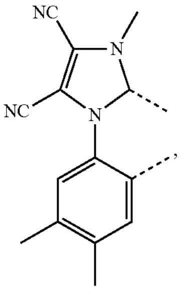
LA132
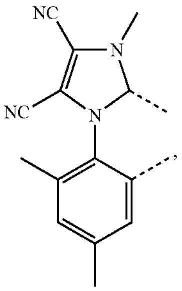
LA133
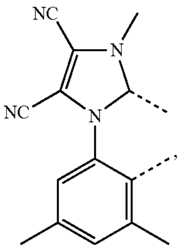
LA134
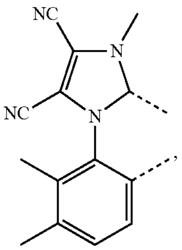

-continued
LA135
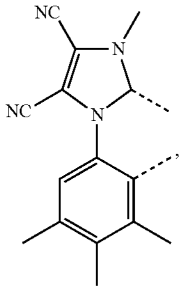
LA136
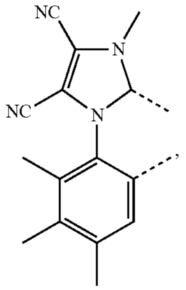
LA137
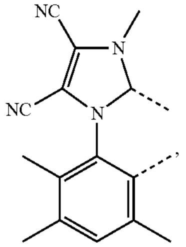
LA138
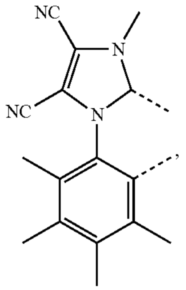
LA139
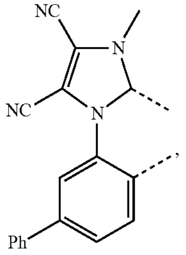
-continued
LA140
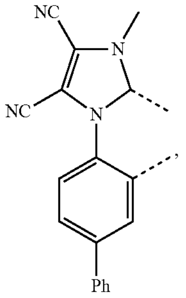
LA141
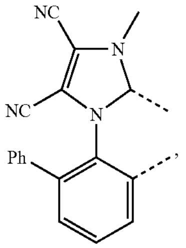
LA142
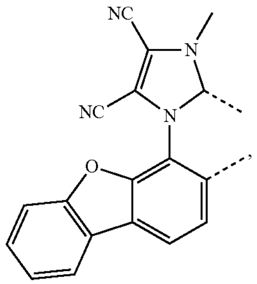
LA143
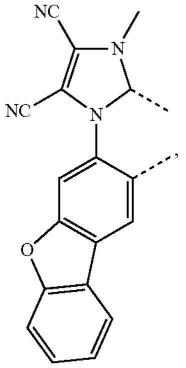
LA144
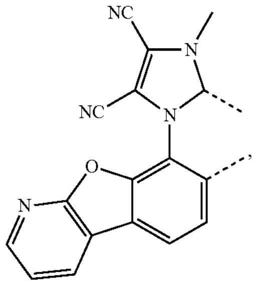

-continued
LA145
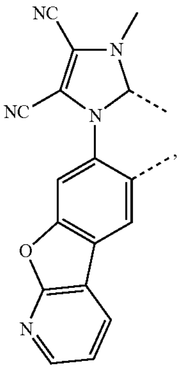
LA146
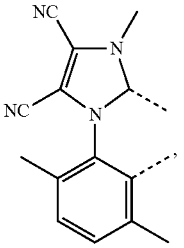
LA147
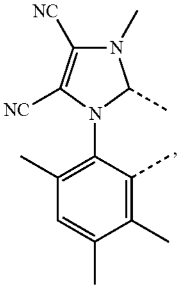
LA148
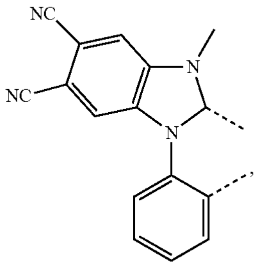
LA149
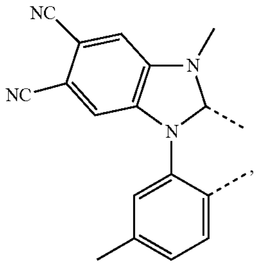
-continued
LA150
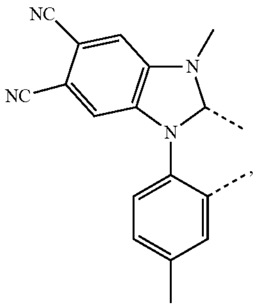
LA151
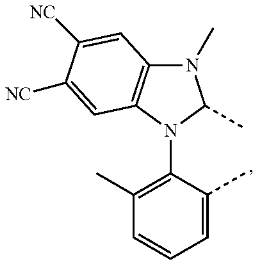
LA152
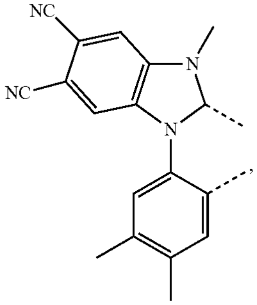
LA153
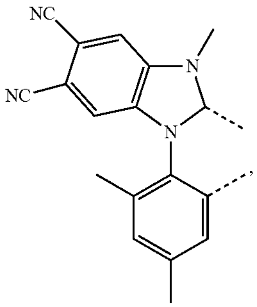
LA154
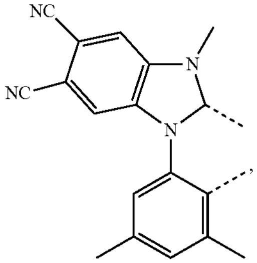

LA155
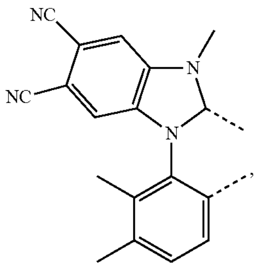
LA156
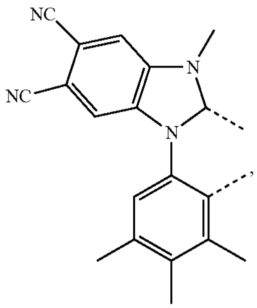
LA157
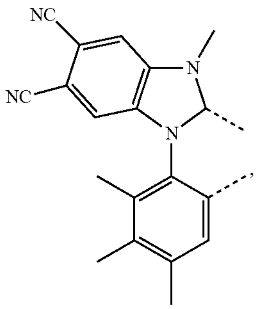
LA158
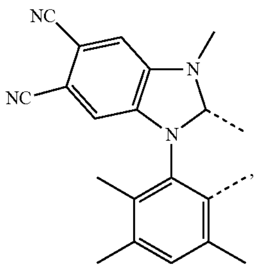
LA159
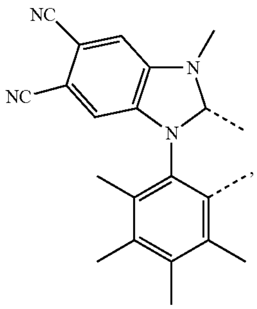
LA160
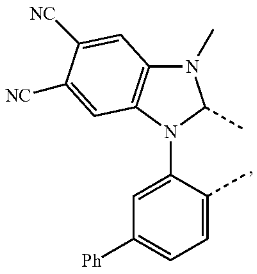
LA161
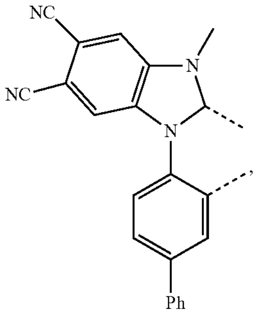
LA162
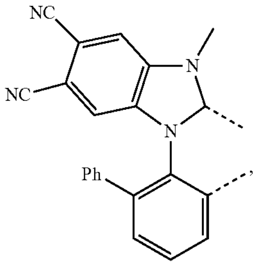
LA163
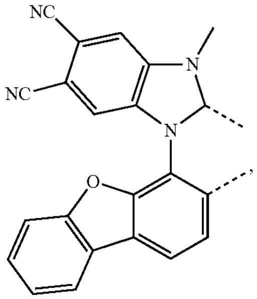
LA164
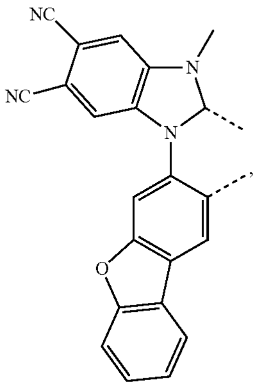

-continued
LA165
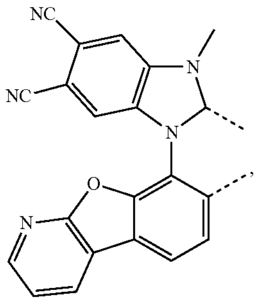
LA166
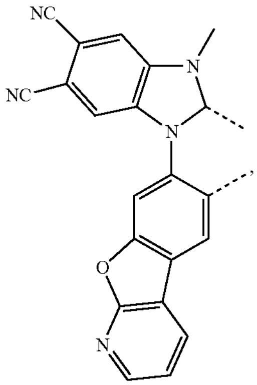
LA167
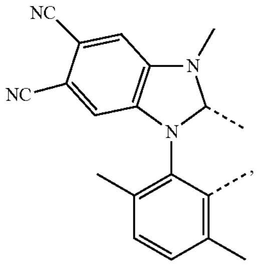
LA168
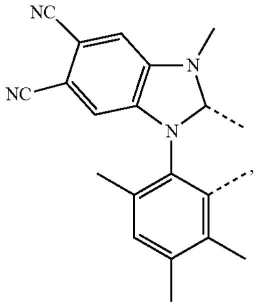
LA169
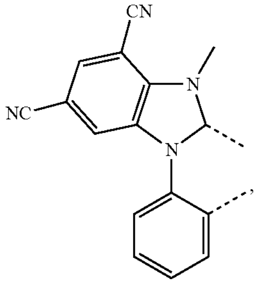
-continued
LA170
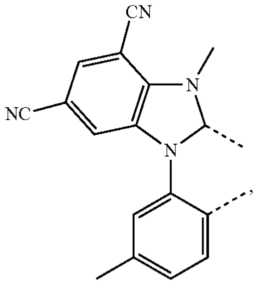
LA171
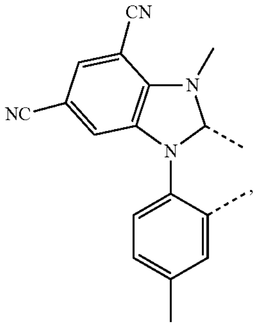
LA172
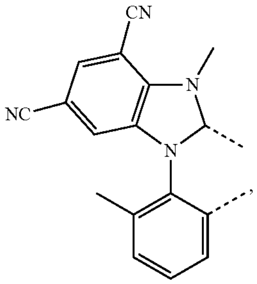
LA173
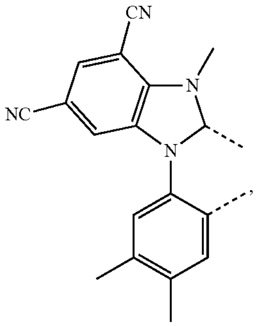
LA174
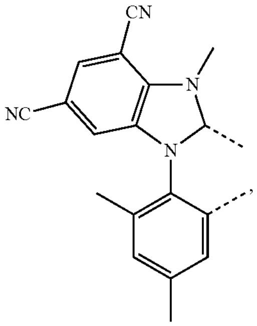

-continued
LA175
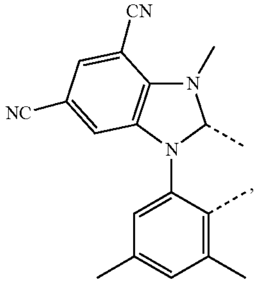
LA176
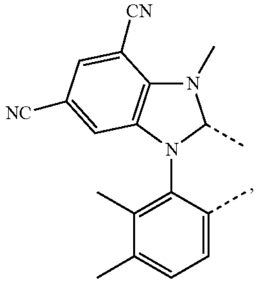
LA177
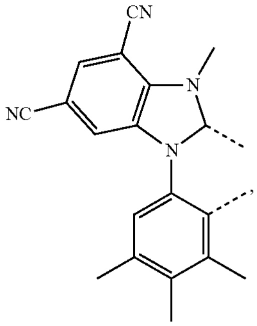
LA178
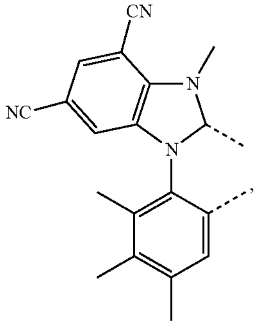
LA179
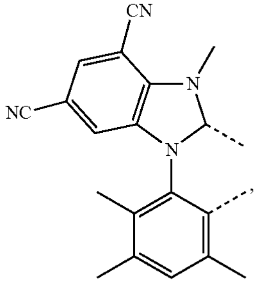
-continued
LA180
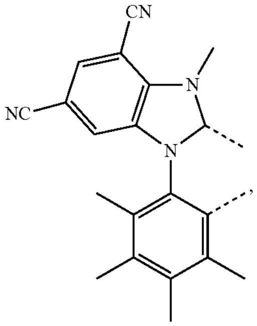
LA181
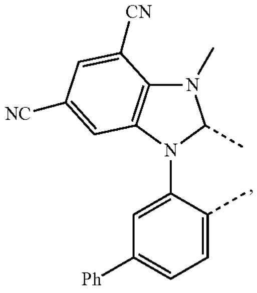
LA812
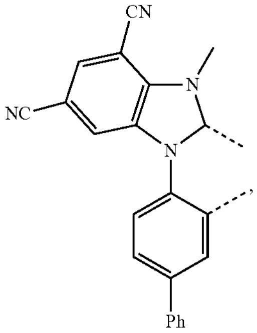
LA183
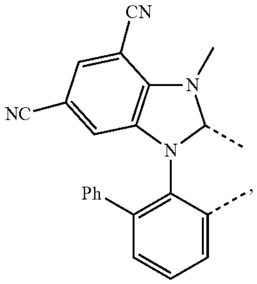
LA184
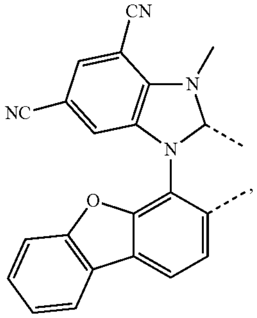

-continued
LA185
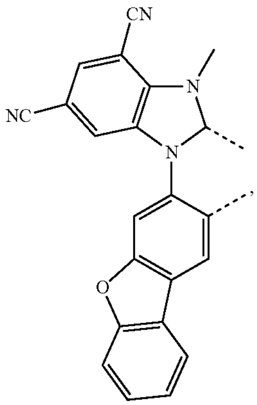
LA186
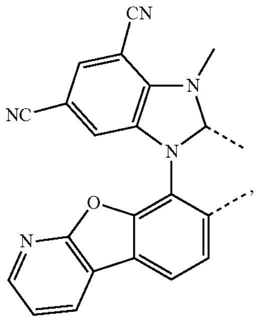
LA187
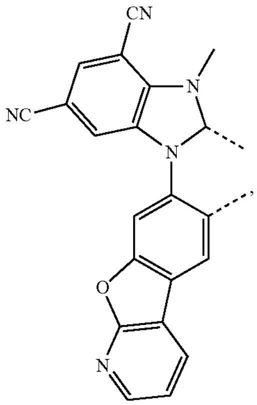
LA188
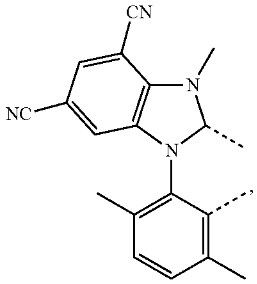
-continued
LA189
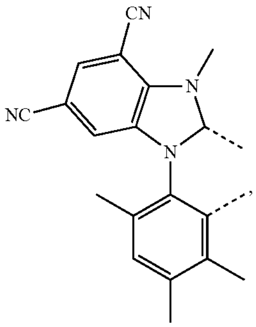
LA190
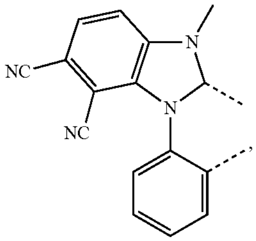
LA191
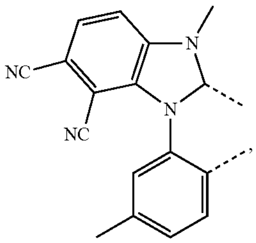
LA192
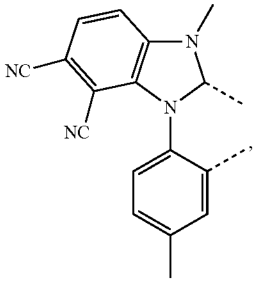
LA193
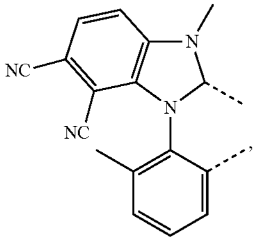

-continued
LA194
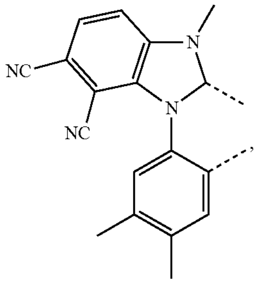
LA195
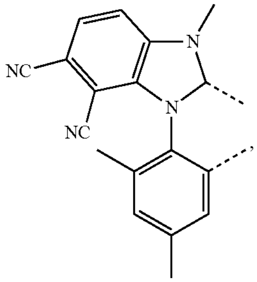
LA196
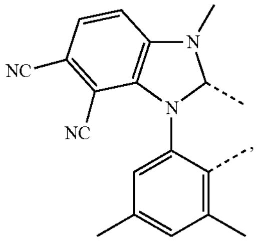
LA197
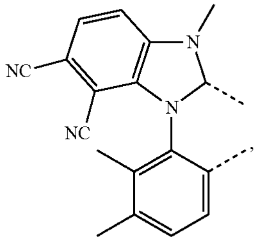
LA198
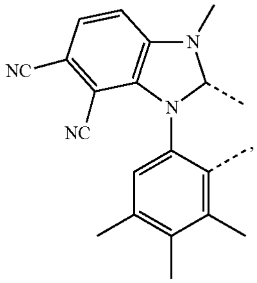
-continued
LA199
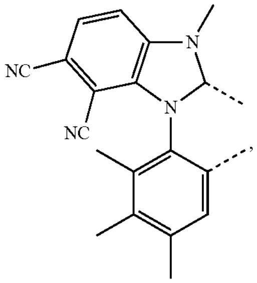
LA200
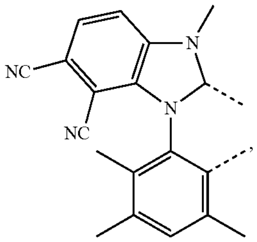
LA201
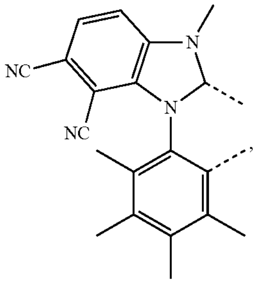
LA202
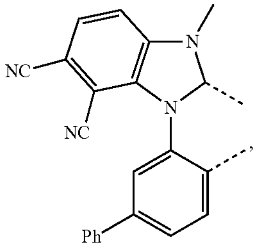
LA203
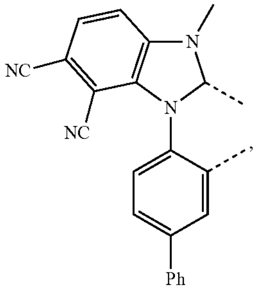
LA204
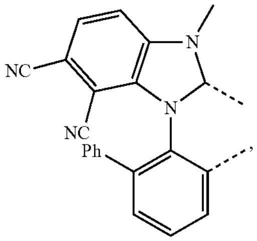

-continued
LA205
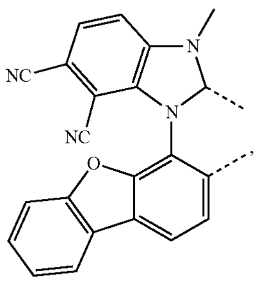
LA206
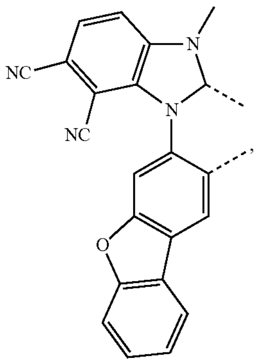
LA207
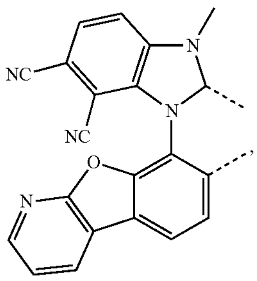
LA208
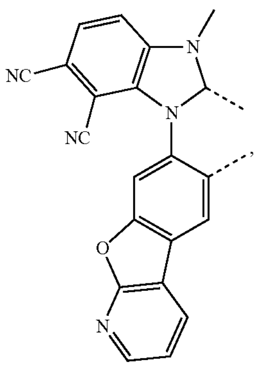
LA209
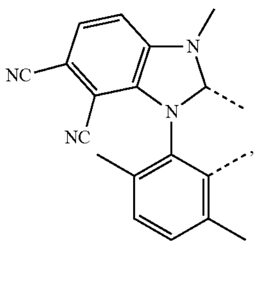
-continued
LA210
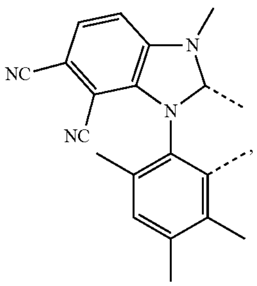
LA211
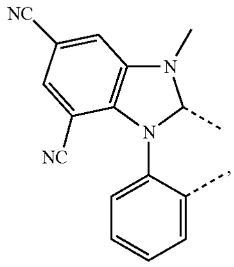
LA212
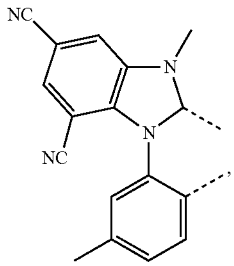
LA213
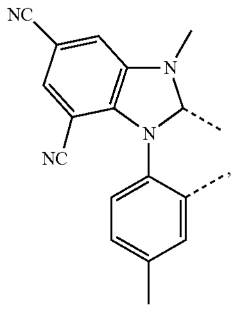
LA214
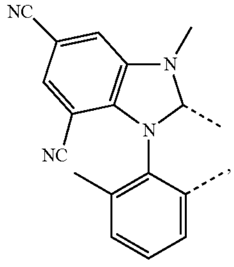

-continued
LA215
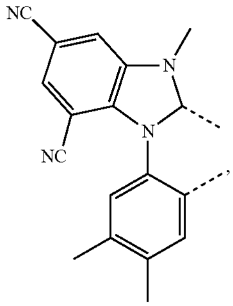
LA216
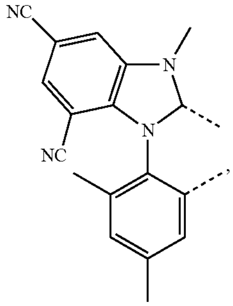
LA217
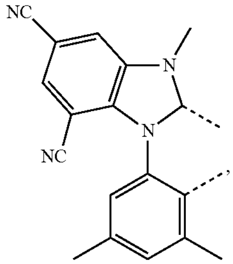
LA218
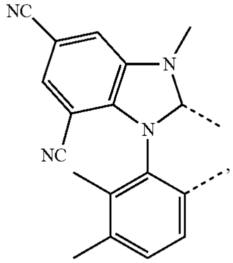
LA219
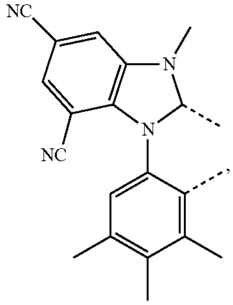
-continued
LA220
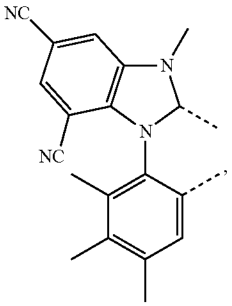
LA221
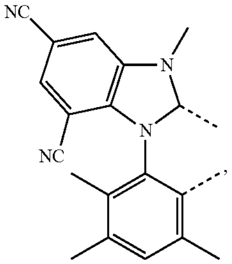
LA222
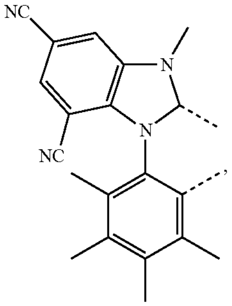
LA223
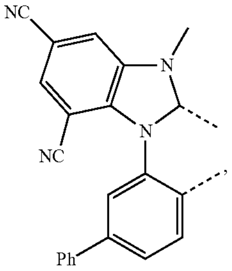
LA224
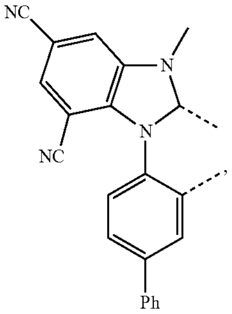

-continued
LA225
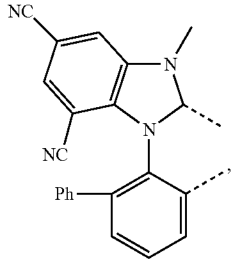
LA226
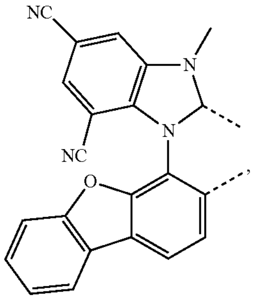
LA227
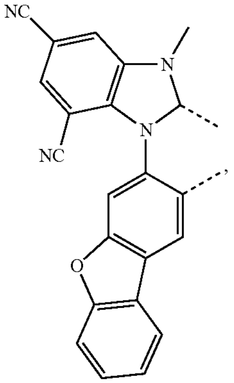
LA228
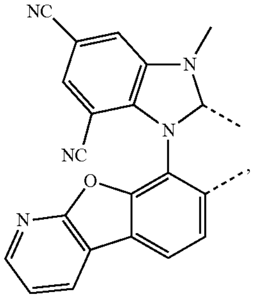
LA229
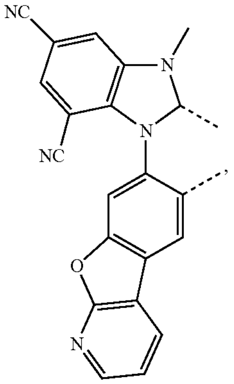
-continued
LA230
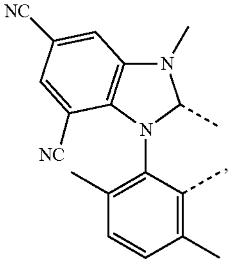
LA231
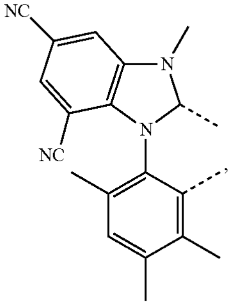
LA232
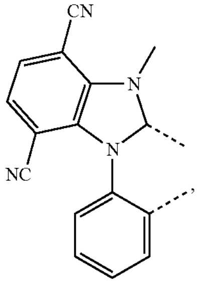
LA233
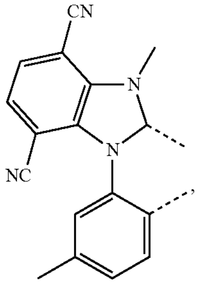
LA234
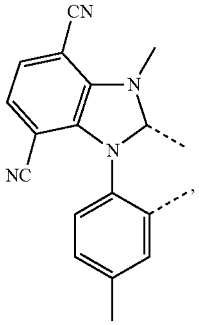

-continued
LA235
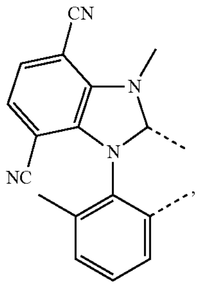
LA236
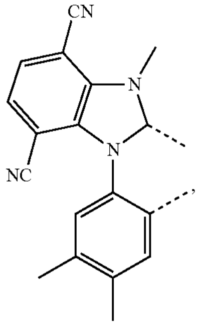
LA237
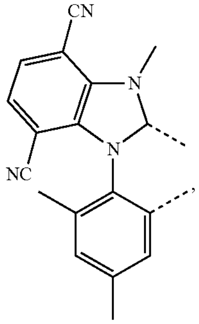
LA238
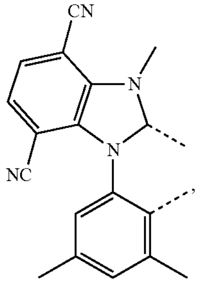
LA239
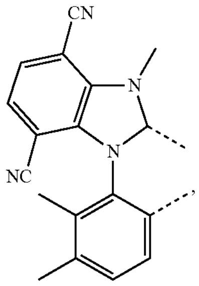
-continued
LA240
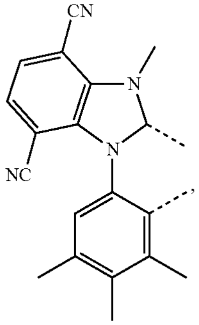
LA241
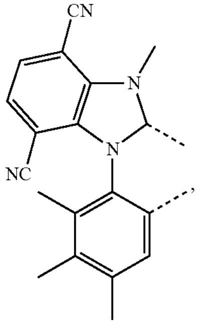
LA242
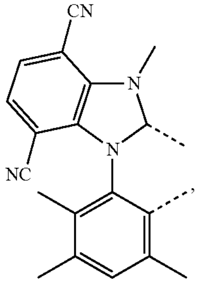
LA243
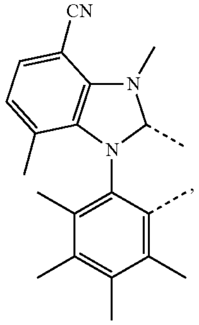
LA244
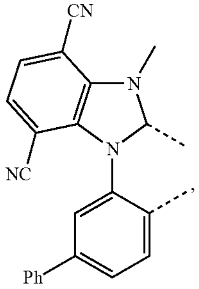

-continued
LA245
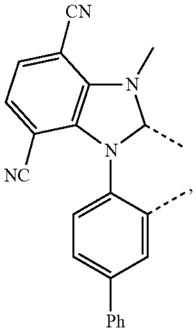
LA246
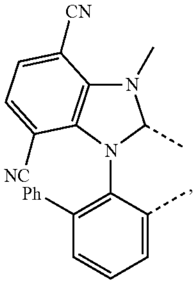
LA247
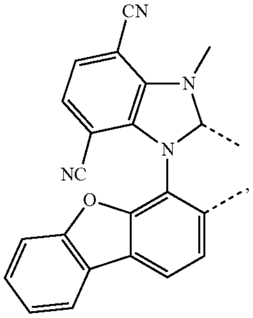
LA248
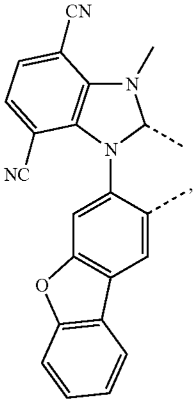
-continued
LA249
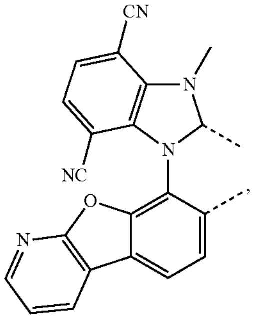
LA250
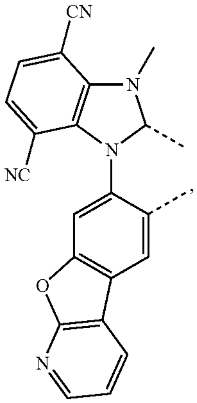
LA251
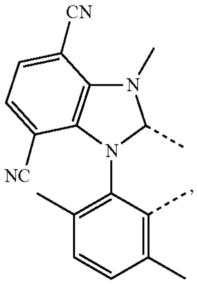
LA252
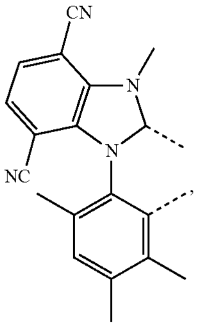
LA253
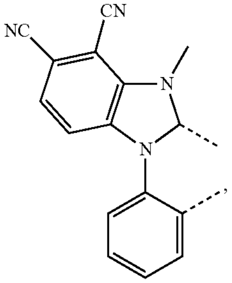

-continued
LA254
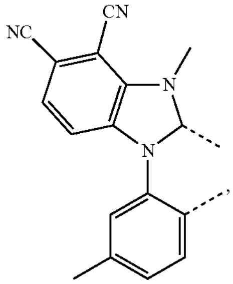
LA255
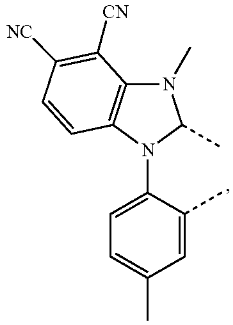
LA256
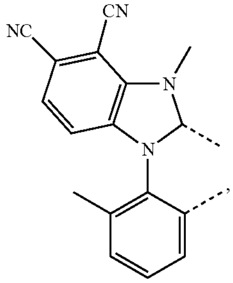
LA257
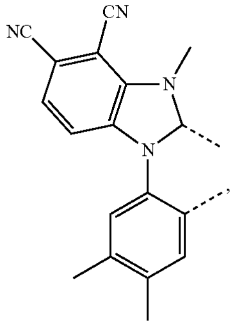
LA258
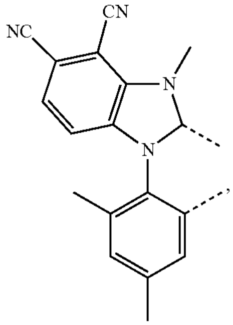
-continued
LA259
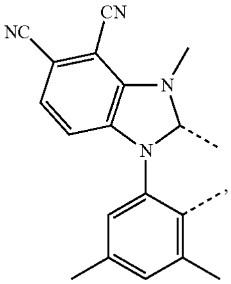
LA260
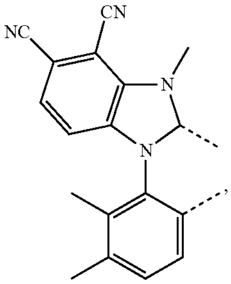
LA261
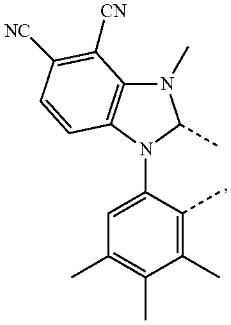
LA262
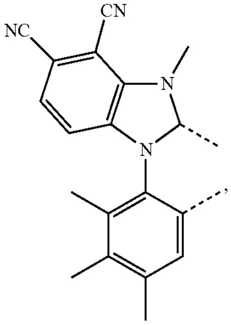
LA263
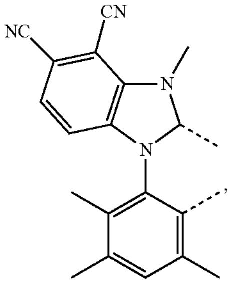

-continued
LA264
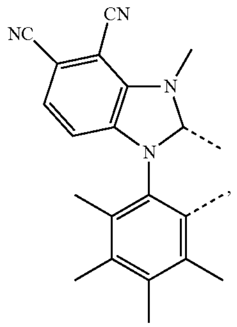
LA265
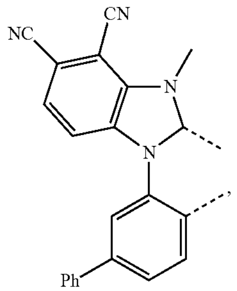
LA266
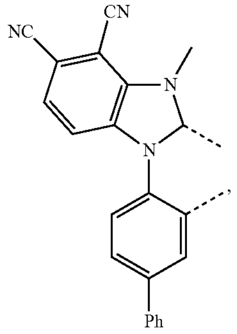
LA267
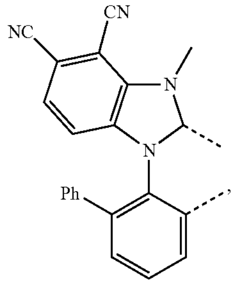
LA268
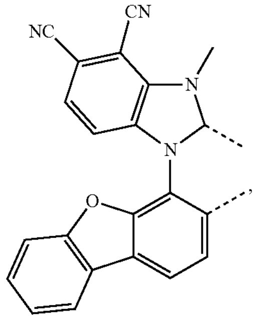
-continued
LA269
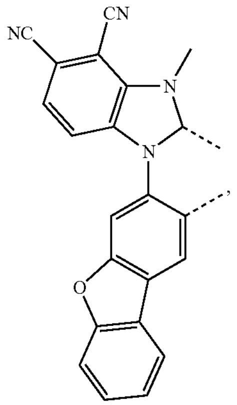
LA270
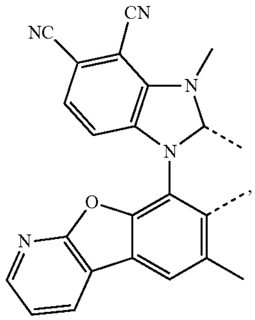
LA271
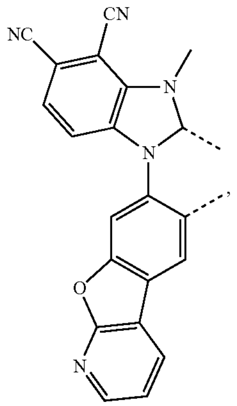
LA272
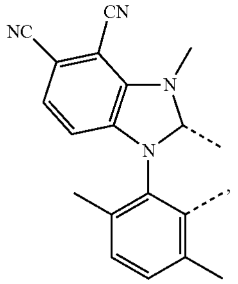
and

LA273

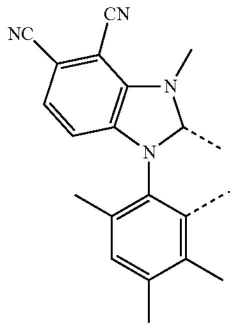

According to another aspect of the present disclosure, the compound has a formula of $M(L_A)_n(L_B)_{m-n}$; wherein M is Ir or Pt; $L_B$ is a bidentate ligand; and wherein when M is Ir, m is 3, and n is 1, 2, or 3; and when M is Pt, m is 2, and n is 1 or 2.

In some embodiments of the compound having the formula of $M(L_A)_n(L_B)_{m-n}$, the compound has a formula of $Ir(L_A)_3$.

In some embodiments of the compound having the formula of $M(L_A)_n(L_B)_{m-n}$, the compound has a formula of $Ir(L_A)(L_B)_2$; and wherein $L_B$ is different from $L_A$.

In some embodiments of the compound having the formula of $M(L_A)_n(L_B)_{m-n}$, the compound has a formula of $Ir(L_A)_2(L_B)$; and wherein $L_B$ is different from $L_A$.

In some embodiments of the compound having the formula of $M(L_A)_n(L_B)_{m-n}$, the compound has a formula of $Pt(L_A)(L_B)$; and wherein $L_A$ and $L_B$ can be same or different. $L_A$ and $L_B$ can be connected to form a tetradentate ligand. In some embodiments, $L_A$ and $L_B$ are connected at two places to form a marcrocyclic tetradentate ligand.

In some embodiments of the compound having the formula of $M(L_A)_n(L_B)_{m-n}$, $L_B$ is selected from the group consisting of:

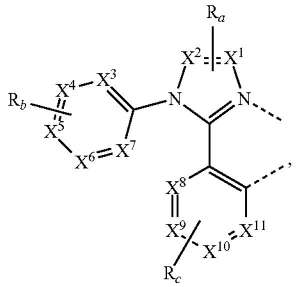

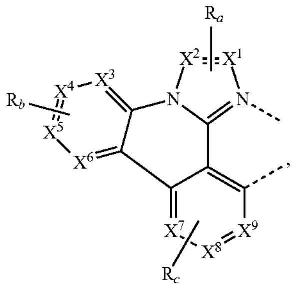

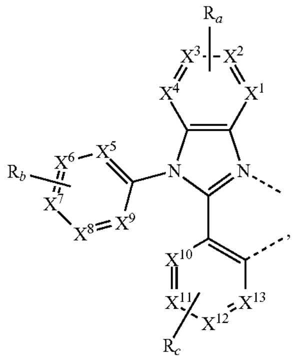

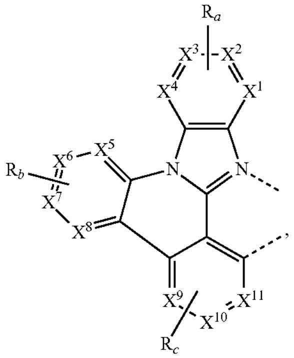

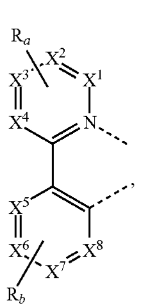

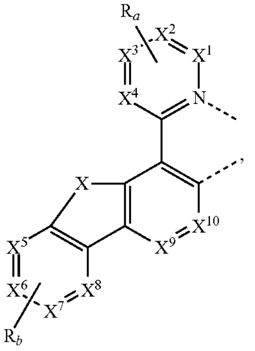

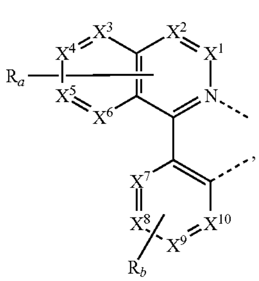

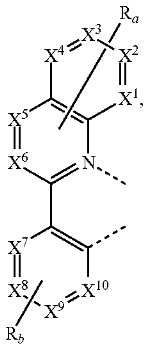

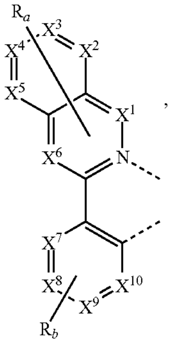

,

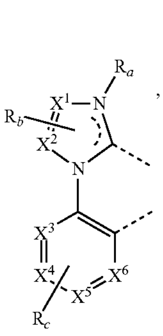

,

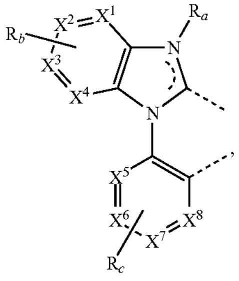

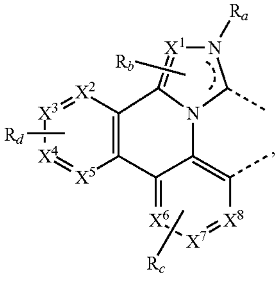

-continued

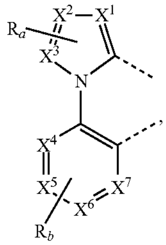

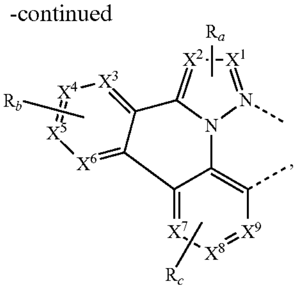

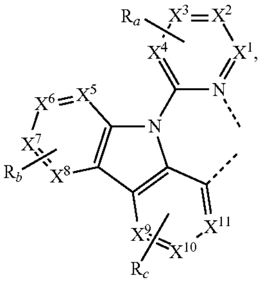

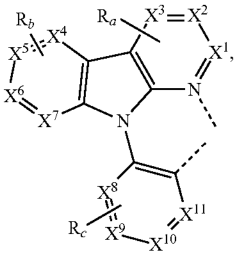

and

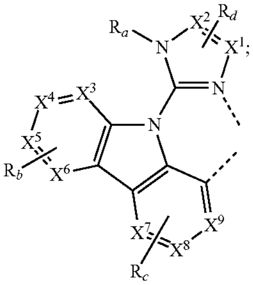

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R", wherein R' and R" are optionally fused or joined to form a ring;

wherein each $R_a$, $R_b$, $R_d$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutents of $R_a$, $R_b$, $R_c$, and $R_d$ are optionally fused or joined to form a ring or form a multidentate ligand.

In some embodiments of the compound having the formula of $M(L_A)_n(L_B)_{m-n}$, $L_B$ is selected from the group consisting of:

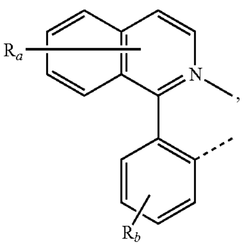

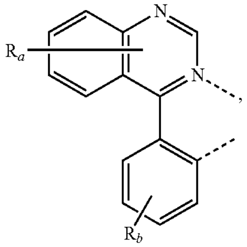

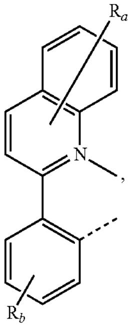

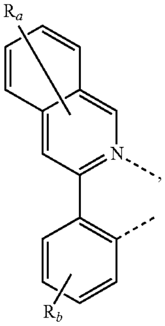

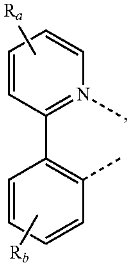

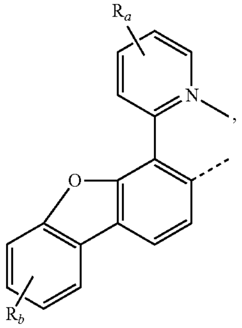

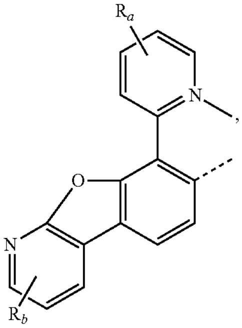

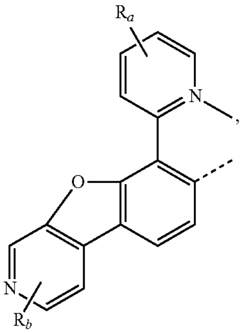

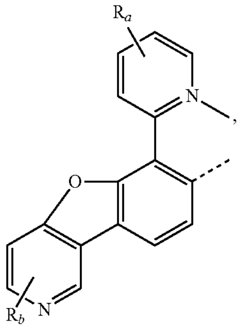

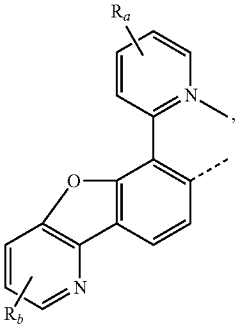

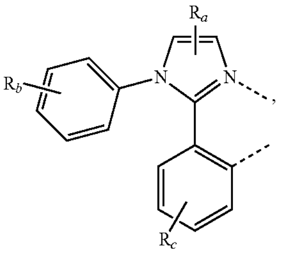

-continued
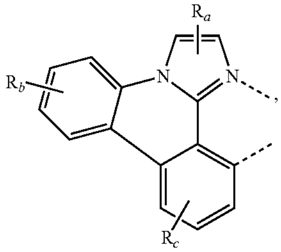
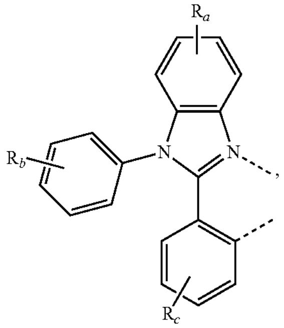
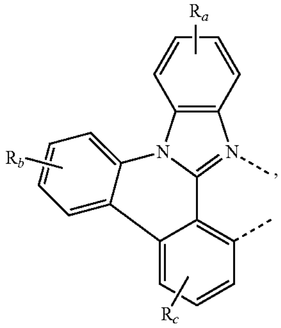
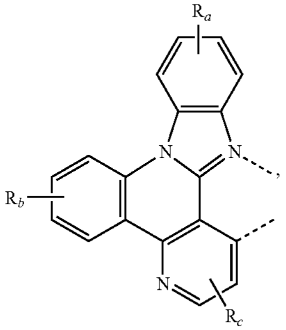
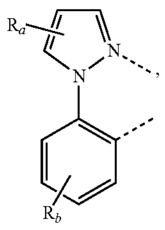
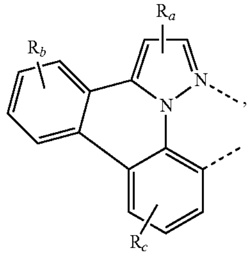
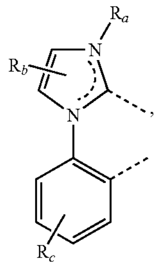
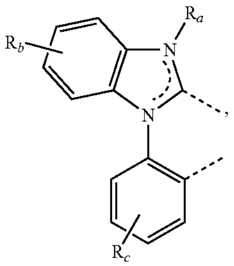
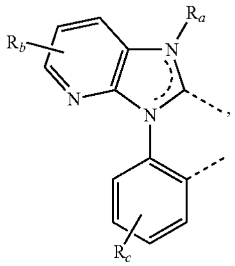
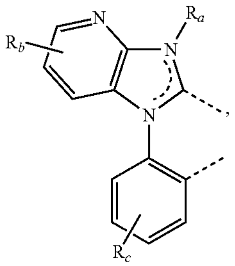
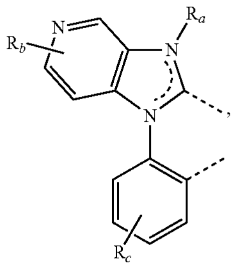
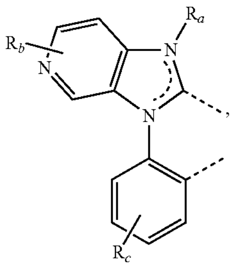
-continued
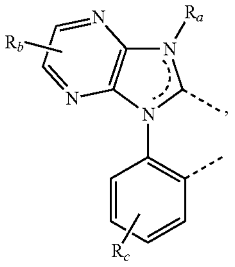
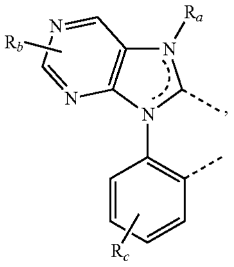
and
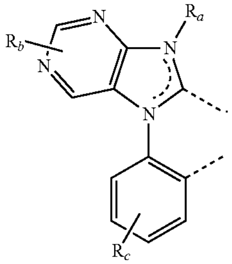
In some embodiments of the compound having the formula of $M(L_A)_n(L_B)_{m-n}$, $L_B$ is selected from the group consisting of:
LB1
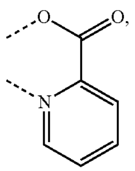
LB2
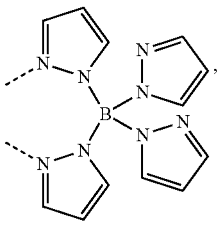
LB3
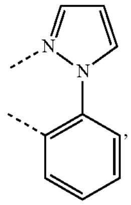
LB4
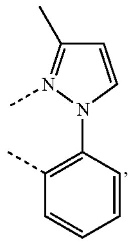

-continued
LB5
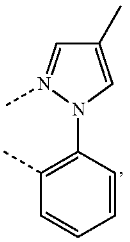
LB6
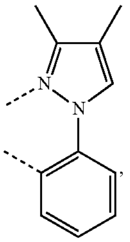
LB7
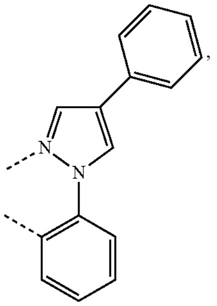
LB8
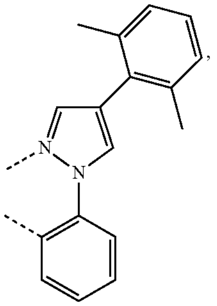
LB9
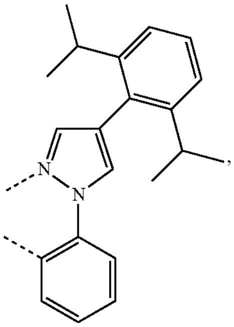
-continued
LB10
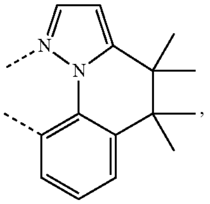
LB11
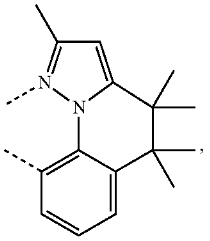
LB12
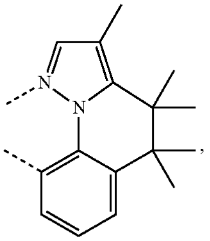
LB13
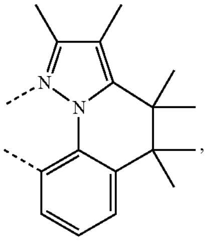
LB14
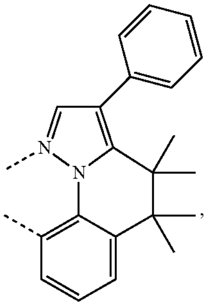
LB15
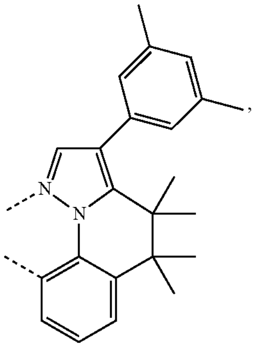

-continued
LB16
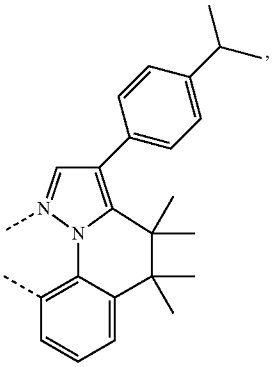
,
LB17
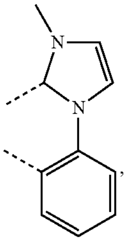
,
LB18
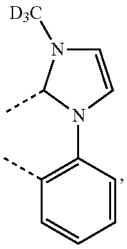
,
LB19
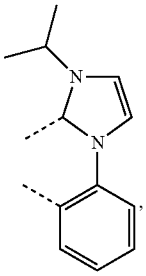
,
LB20
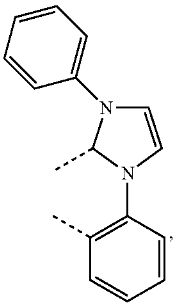
,
-continued
LB21
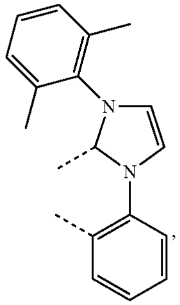
,
LB22
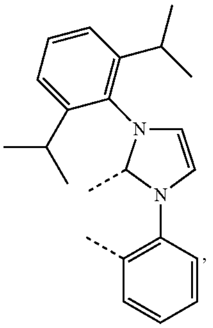
,
LB23
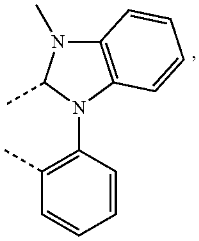
,
LB24
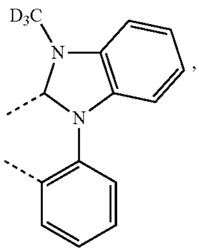
,
LB25
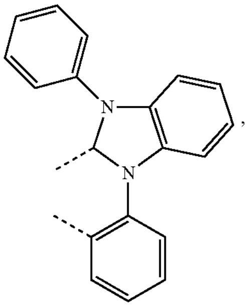
, -continued
LB26
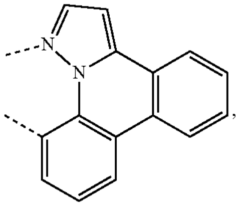,
LB27
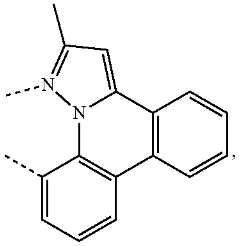,
LB28
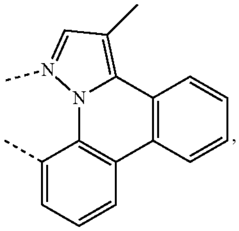,
LB29
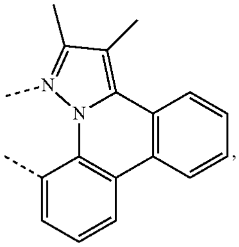,
LB30
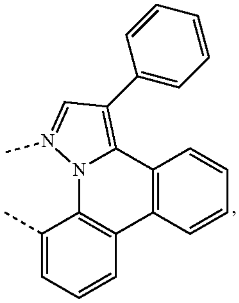,
LB31
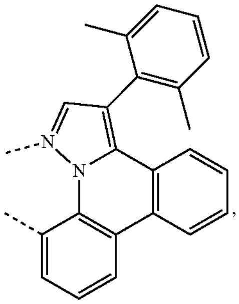,
-continued
LB32
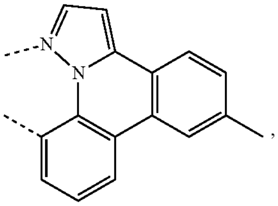,
LB33
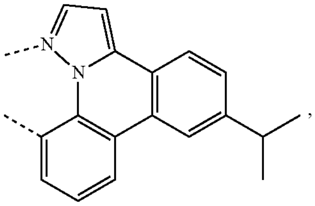,
LB34
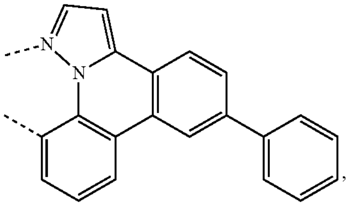,
LB35
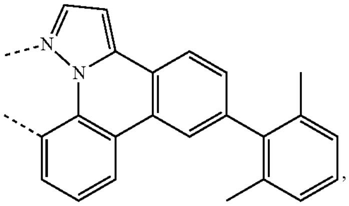,
LB36
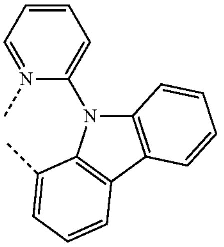,
LB37
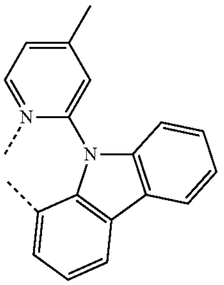, LB38
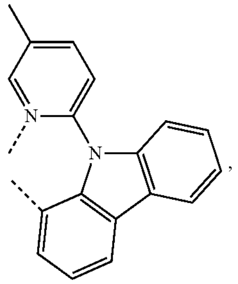
LB39
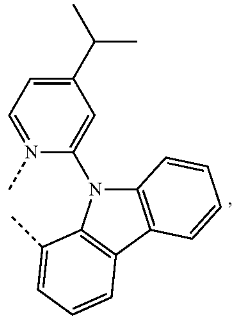
LB40
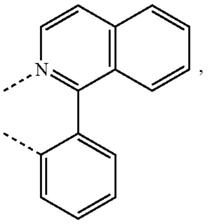
LB41
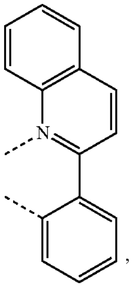
LB42
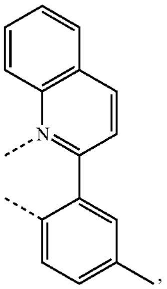
LB43
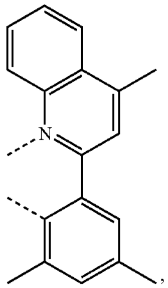
LB44
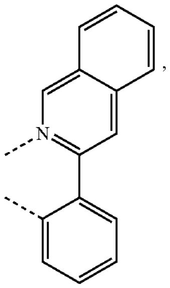
LB45
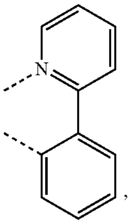
LB46
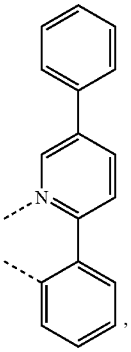
LB47
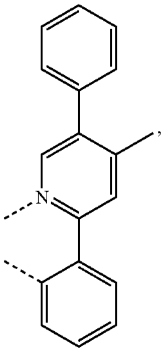

-continued

LB48

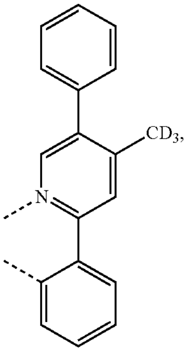

LB49

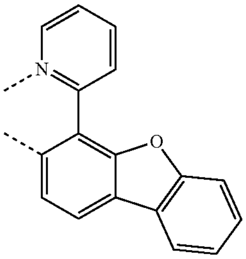,

LB50

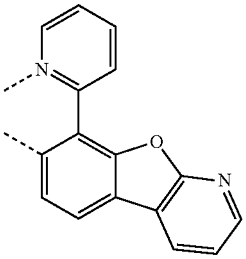,

LB51

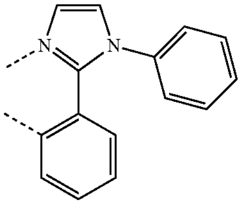,

LB52

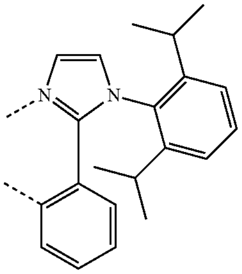,

-continued

LB53

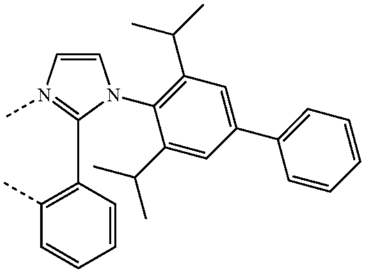,

LB54

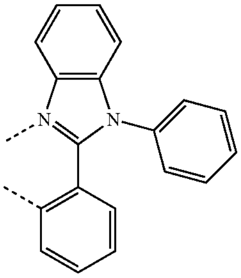

and

LB55

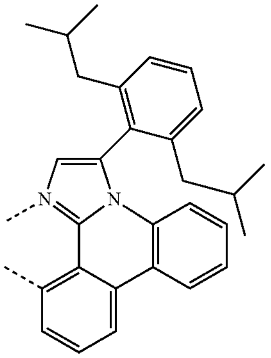.

In the embodiments of the compound where the ligand $L_A$ is selected from the group consisting of $L_{A1}$ through $L_{A273}$, the compound is Compound Ax having the formula $Ir(L_{Ai})_3$; and wherein x=i; i is an integer from 1 to 273.

In other embodiments of the compound where the ligand $L_A$ is selected from the group consisting of $L_{A1}$ through $L_{A273}$, the compound is the Compound By having the formula $Ir(L_{Ai})(L_{Bj})_2$ or Compound Cz having the formula $Ir(L_{Ai})_2(L_{Bj})$;

wherein y=55i+j−55; i is an integer from 1 to 273, and j is an integer from 1 to 55;

wherein z=55i+j−55; i is an integer from 1 to 273, and j is an integer from 1 to 55; and wherein $L_{B1}$ to $L_{B55}$ have the structures as defined above.

According to another aspect of the present disclosure, an organic light emitting device (OLED) is disclosed. The OLED can include an anode, a cathode, and an organic layer, disposed between the anode and the cathode. The organic layer comprises a first compound comprising a carbene ligand $L_A$ selected from the group consisting of:

Formula I

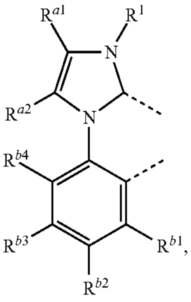

, and

Formula II

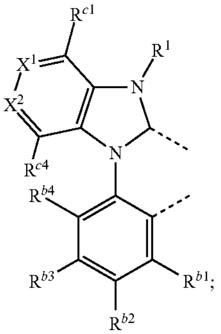

;

wherein $X^1$ is $CR^{c2}$ or N, $X^2$ is $CR^{c3}$ or N;

wherein $R^{a1}$, $R^{a2}$, $R^{b1}$, $R^{b2}$, $R^{b3}$, $R^{b4}$, $R^{c1}$, $R^{c2}$, $R^{c3}$, $R^{c4}$, $R^1$ and $R^2$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof;

wherein at least one of $R^1$, $R^{a1}$, $R^{a2}$, $R^{c1}$, $R^{c3}$, and $R^{c4}$ comprises an acceptor group selected from the group consisting of CN, F directly attached to an aromatic ring, $Si_mF_{2m+1}$, NCO, NCS, OCN, SCN, $OC_mF_{2m+1}$ and $SC_mF_{2m+1}$, where $m \geq 1$;

wherein any adjacent substituents of $R^{b1}$, $R^{b2}$, $R^{b3}$, and $R^{b4}$ are optionally joined or fused into a ring;

wherein the ligand $L_A$ is coordinated to a metal M; and wherein the ligand $L_A$ is optionally linked with other ligands to comprise a tridentate, tetradentate, pentadentate or hexadentate ligand.

In some embodiments of the OLED, the first compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

The first organic light emitting device can be incorporated into a device selected from the group consisting of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH{=}CH{-}C_nH_{2n+1}$, $C{\equiv}C{-}C_nH_{2n+1}$, $Ar_1$, $Ar_1{-}Ar_2$, and $C_nH_{2n}{-}Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound comprising at least one chemical group selected from the group consisting of triphenylene, tetraphenylene, carbazole, dibenzothiphene, dibenzofuran, dibenzoselenophene, azatriphenylene, azacarbazole, aza-dibenzothiophene, aza-dibenzofuran, and aza-dibenzoselenophene. The host can include a metal complex. The host can be a specific compound selected from the group consisting of:

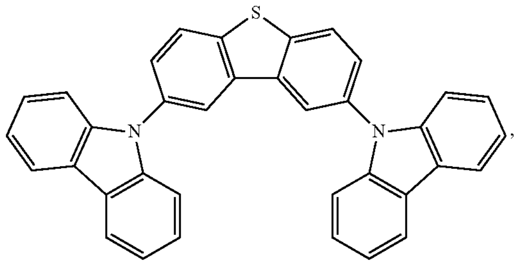

,

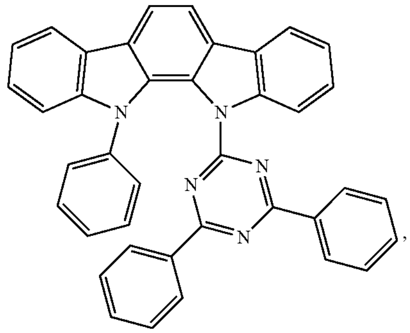

,

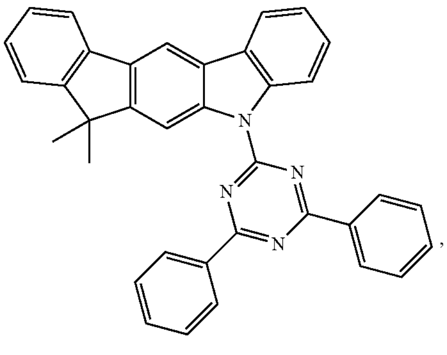

,

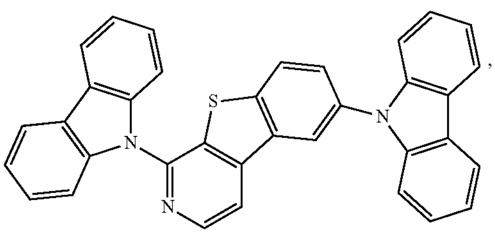

,

-continued
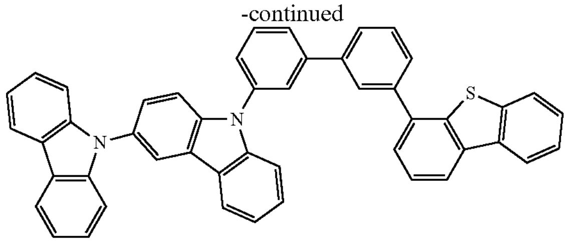
,
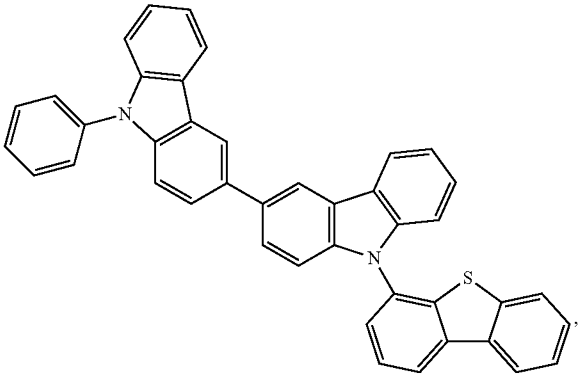
,
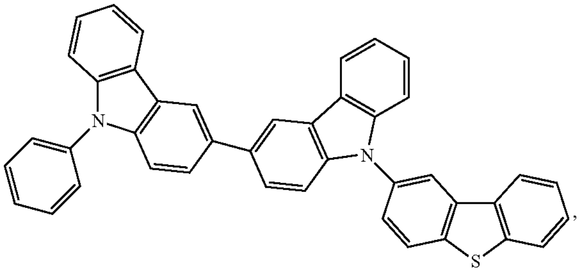
,
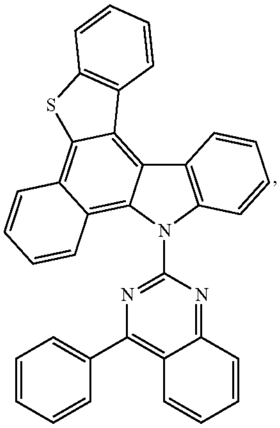
,
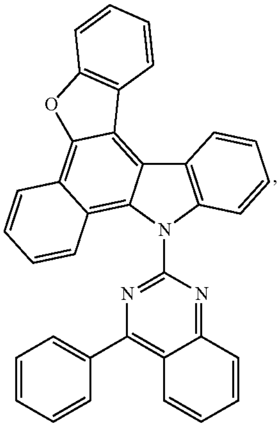
,
-continued
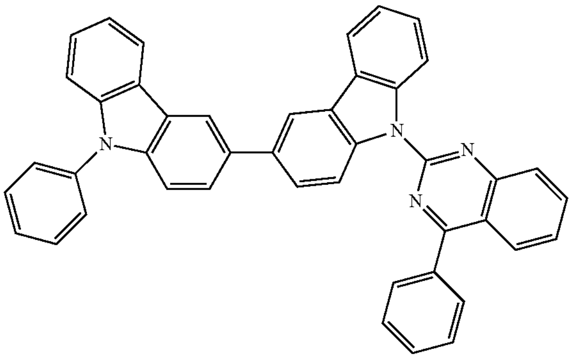
,
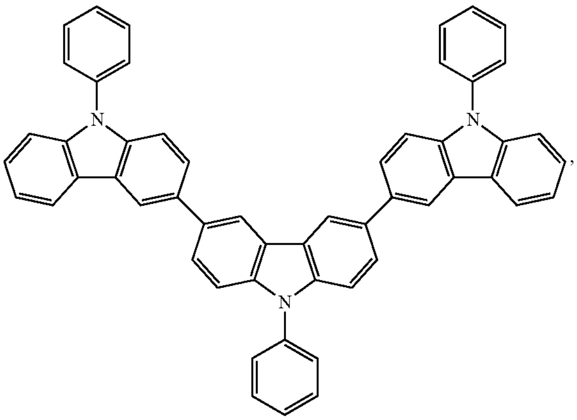
,
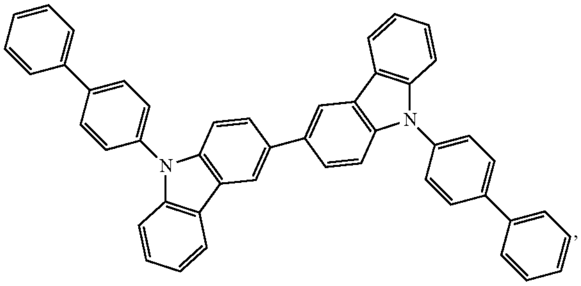
,
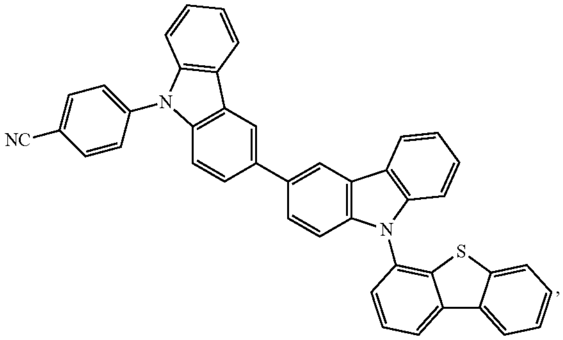
, -continued
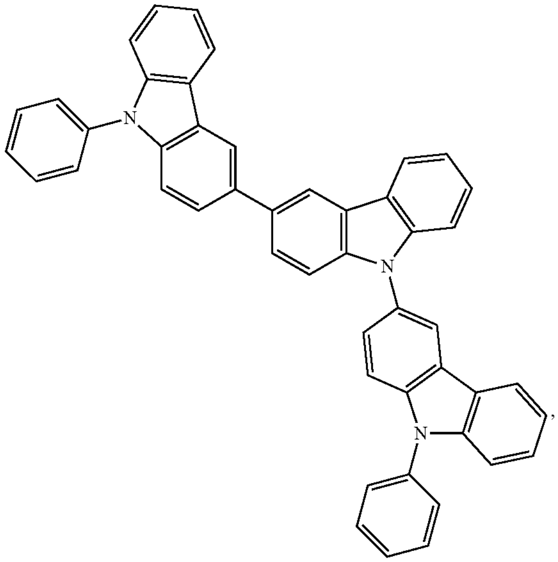
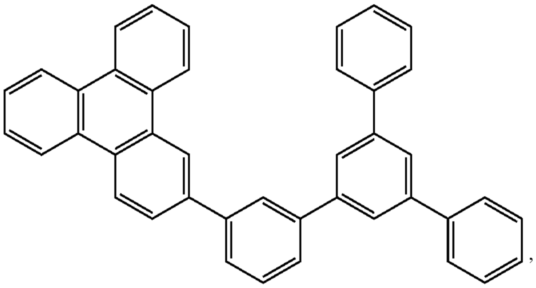
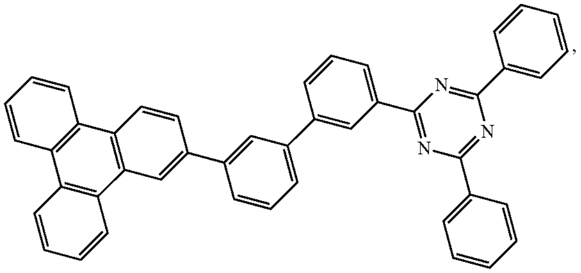
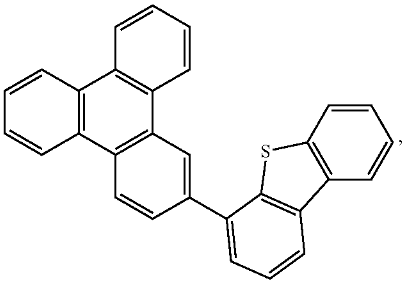
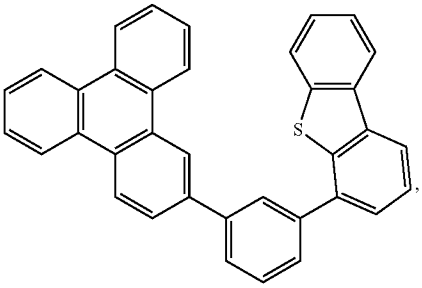
-continued
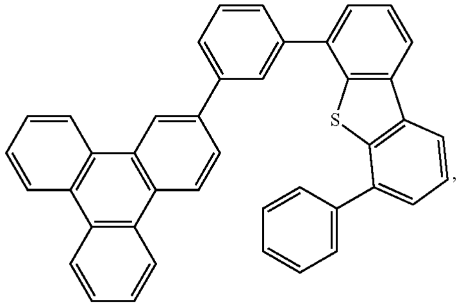
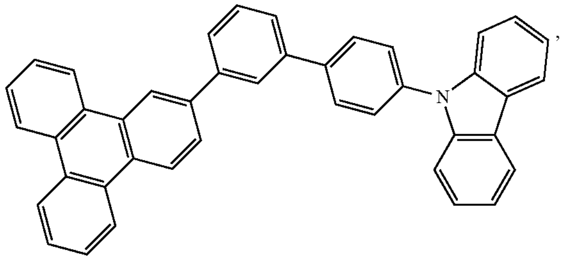
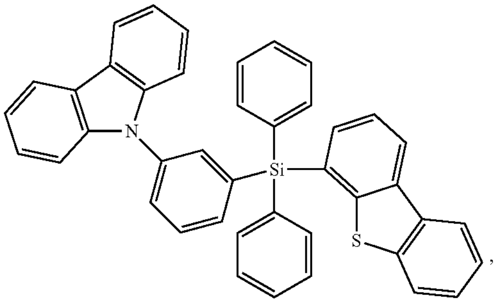
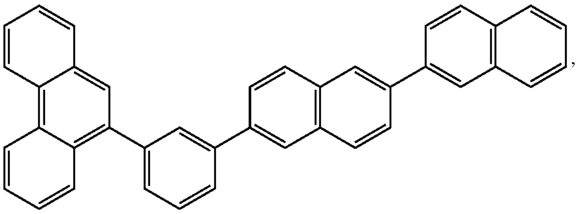
and combinations thereof.
In yet another aspect of the present disclosure, a formulation comprising the compound comprising a carbene ligand $L_A$ selected from the group consisting of:
Formula I
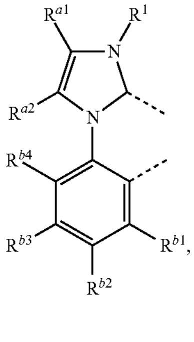
and -continued Formula II

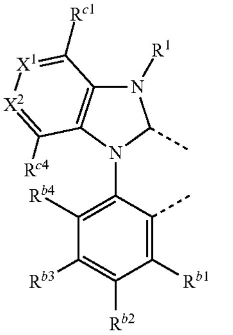

is disclosed;

wherein $X^1$ is $CR^{c2}$ or N, $X^2$ is $CR^{c3}$ or N;

wherein $R^{a1}$, $R^{a2}$, $R^{b1}$, $R^{b2}$, $R^{b3}$, $R^{b4}$, $R^{c1}$, $R^{c2}$, $R^{c3}$, $R^{c4}$, $R^1$ and $R^2$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof;

wherein at least one of $R^1$, $R^{a1}$, $R^{a2}$, $R^{c1}$, $R^{c3}$, and $R^{c4}$ comprises an acceptor group selected from the group consisting of CN, F directly attached to an aromatic ring, $Si_mF_{2m+1}$, NCO, NCS, OCN, SCN, $OC_mF_{2m+1}$ and $SC_mF_{2m+1}$, where $m \geq 1$;

wherein any adjacent substituents of $R^{b1}$, $R^{b2}$, $R^{b3}$, and $R^{b4}$ are optionally joined or fused into a ring;

wherein the ligand $L_A$ is coordinated to a metal M; and wherein the ligand $L_A$ is optionally linked with other ligands to comprise a tridentate, tetradentate, pentadentate or hexadentate ligand.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

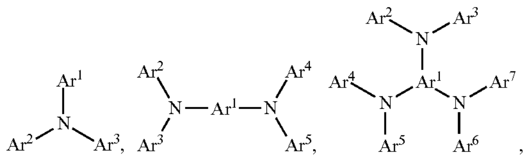

,

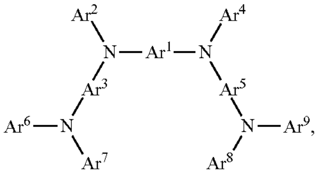

, and

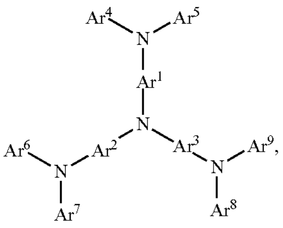

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

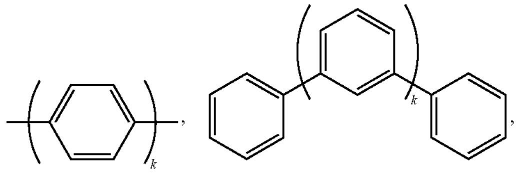

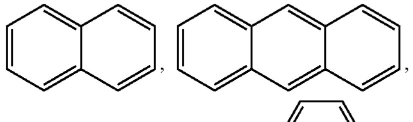

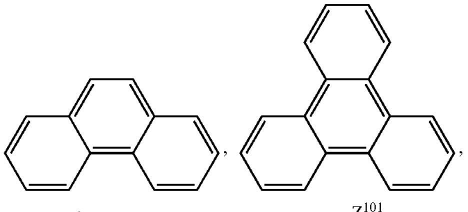

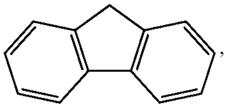

, and

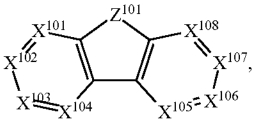

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

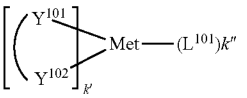

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

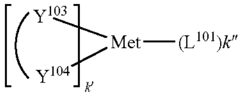

wherein Met is a metal; ($Y^{103}$-$Y^{104}$) is a bidentate ligand. $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

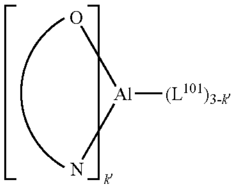

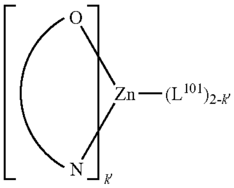

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

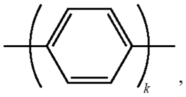
,
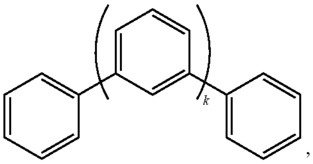
,
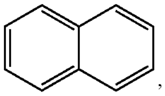
,
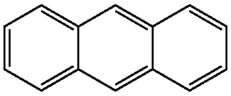
,
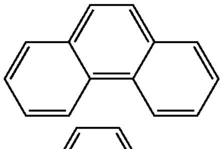
,
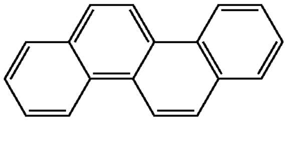
,
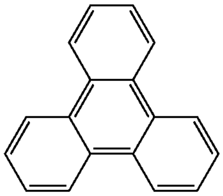
,
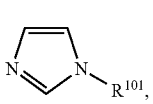
,
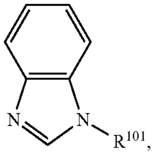
,
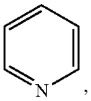
,
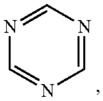
,
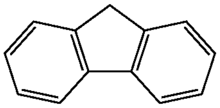
,
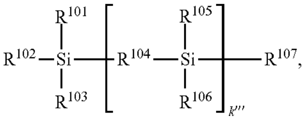
,
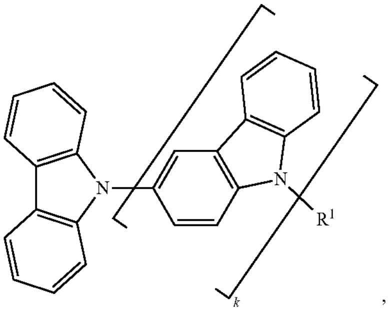
,
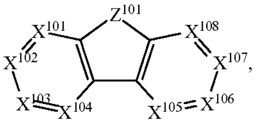
,
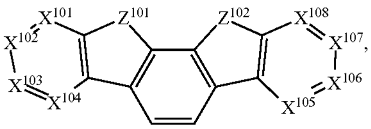
,
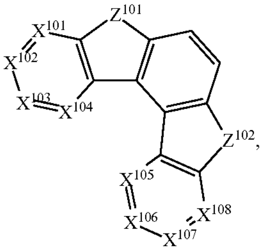
, -continued

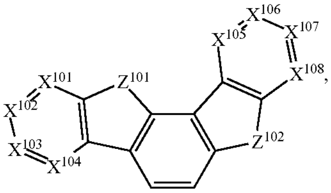
,
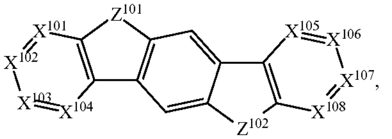
, and
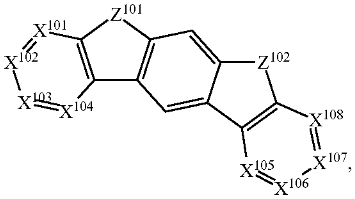
, wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

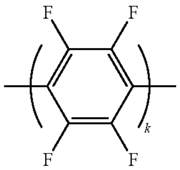
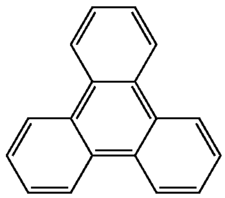
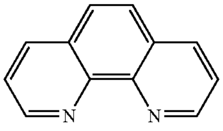
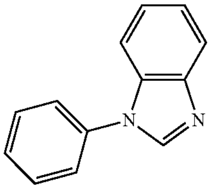

-continued

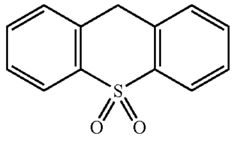
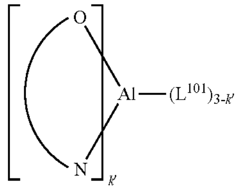

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

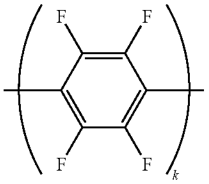
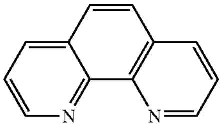

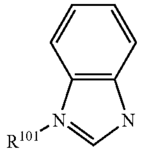
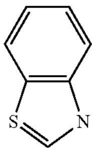
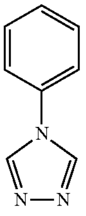
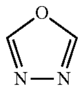
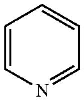

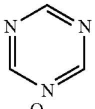
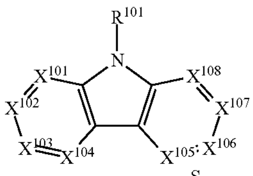

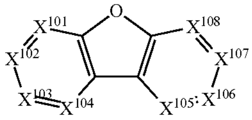
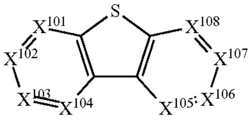

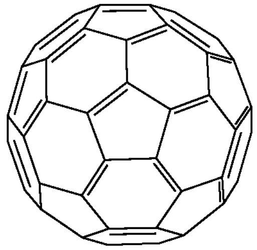
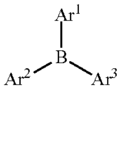

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

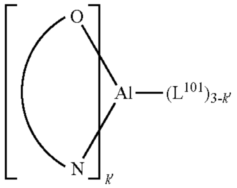
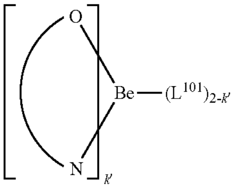

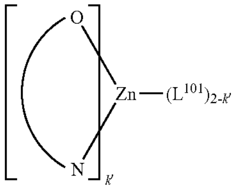
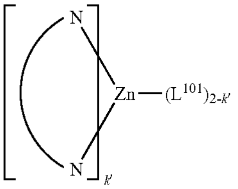

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A
| MATERIAL | EXAMPLES OF MATERIAL | PUBLICATIONS |
|---|---|---|
| | Hole injection materials | |
| Phthalocyanine and porphyrin compounds | 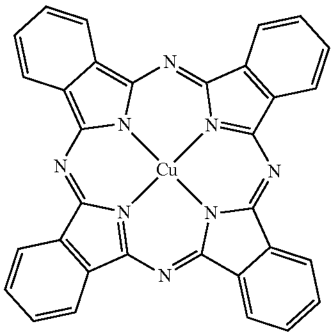 | Appl. Phys. Lett. 69, 2160 (1996) |
| Starburst triarylamines | 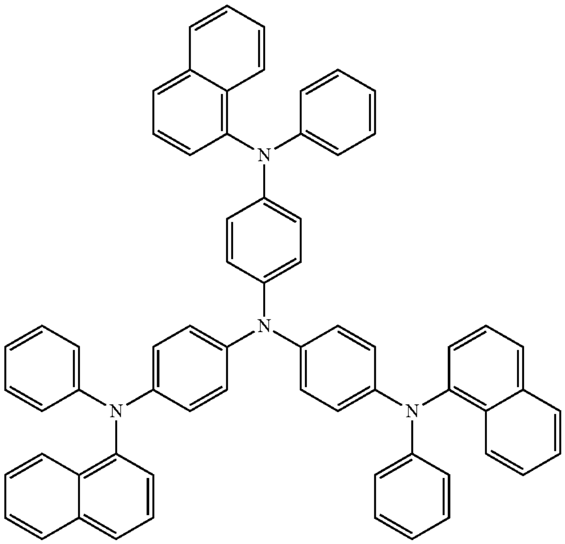 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydro-carbon polymer | $-[CH_xF_y]_n-$ | Appl. Phys. Lett. 78, 673 (2001) |
| Conducting polymers (e.g., PEDOT:PSS, polyaniline, polythiophene) | 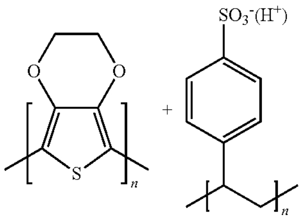 | Synth. Met. 87, 171 (1997) WO2007002683 |
| Phosphonic acid and silane SAMs | 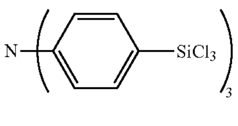 | US20030162053 |

TABLE A-continued
| MATERIAL | EXAMPLES OF MATERIAL | PUBLICATIONS |
|---|---|---|
| Triarylamine or polythiophene polymers with conductivity dopants | 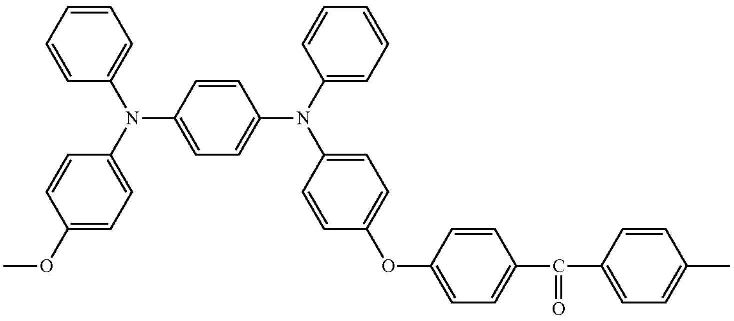 and 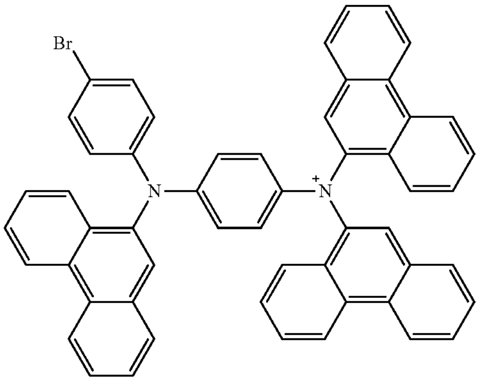 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 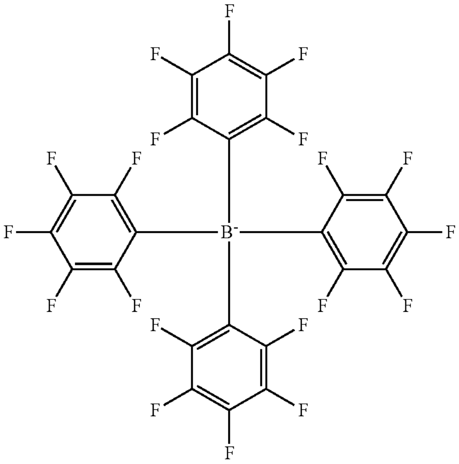 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 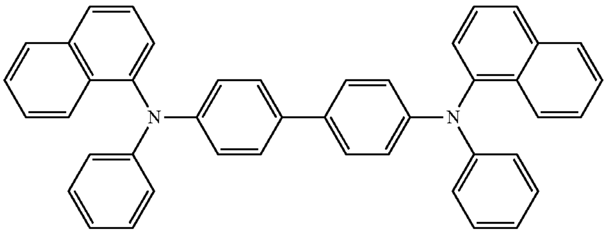 + $MoO_x$ | US20050123751 SID Symposium Digest, 37, 923 (2006) WO2009018009 |

TABLE A-continued
| MATERIAL | EXAMPLES OF MATERIAL | PUBLICATIONS |
|---|---|---|
| n-type semiconducting organic complexes | 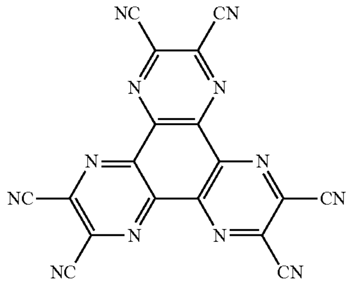 [SMILES: N#Cc1nc2c3nc(C#N)c(C#N)nc3c3nc(C#N)c(C#N)nc3c2nc1C#N] | US20020158242 |
| Metal organometallic complexes | 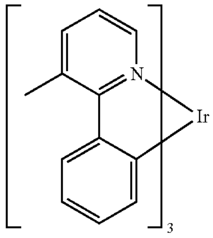 | US20060240279 |
| Cross-linkable compounds | 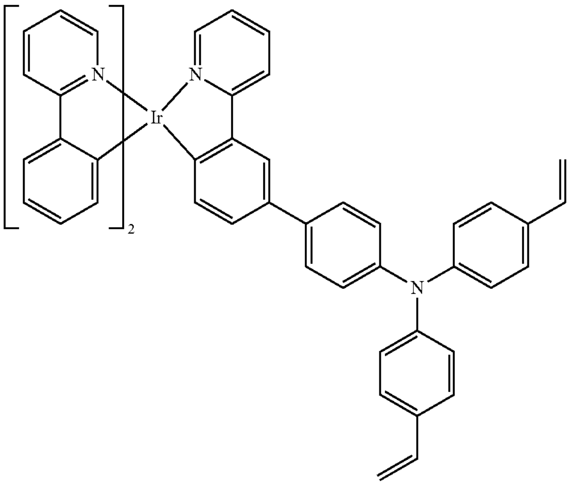 | US20080220265 |
| Polythiophene based polymers and copolymers | 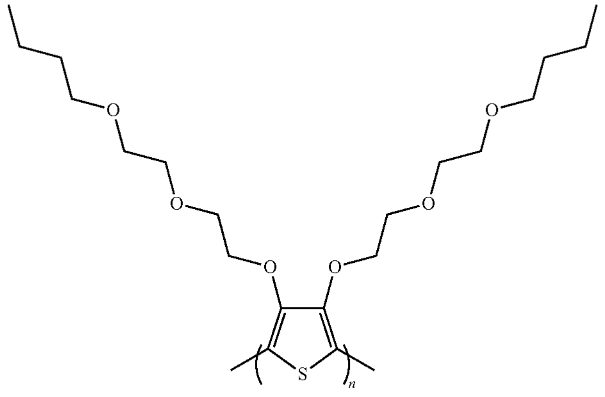 | WO 2011075644 EP2350216 |
| | Hole transporting materials | |

TABLE A-continued
| MATERIAL | EXAMPLES OF MATERIAL | PUBLICATIONS |
|---|---|---|
| Triarylamines (e.g., TPD, α-NPD) | 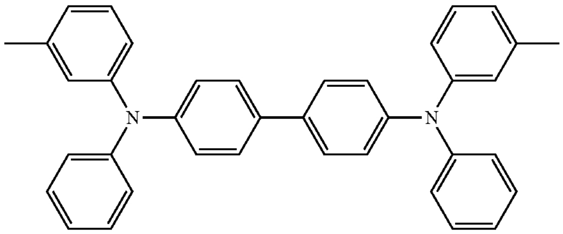 | Appl. Phys. Lett. 51, 913 (1987) |
| | 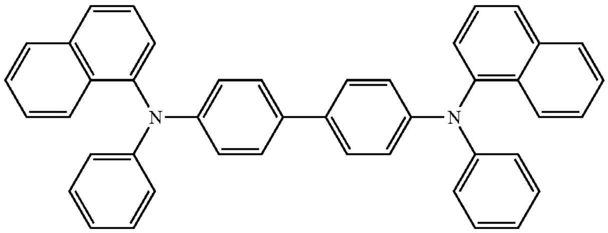 [SMILES: c1ccc(N(c2ccc(-c3ccc(N(c4ccccc4)c4cccc5ccccc45)cc3)cc2)c2cccc3ccccc23)cc1] | U.S. Pat No. 5,061,569 |
| | 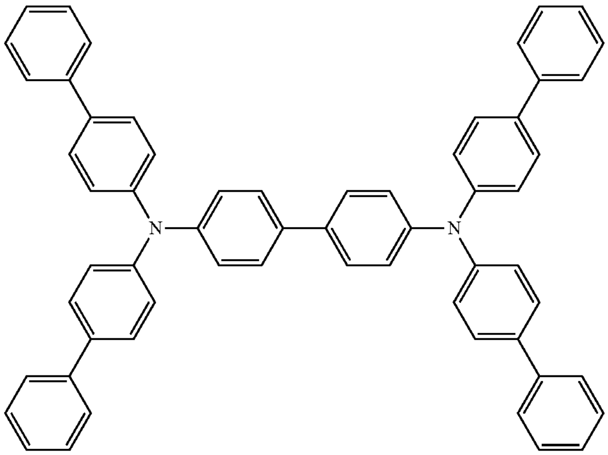 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 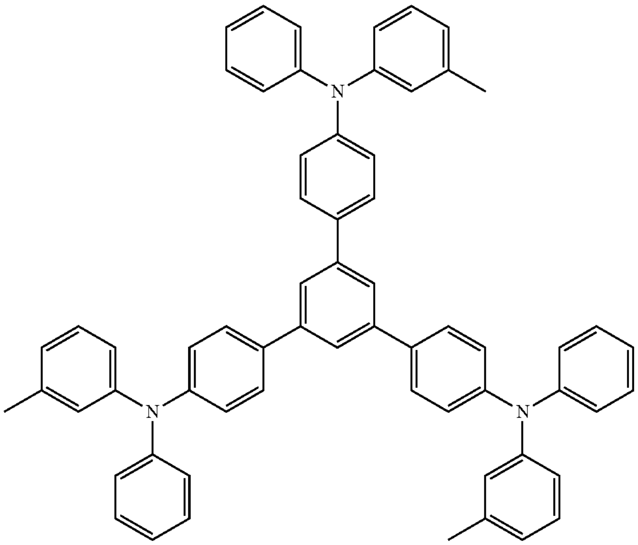 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE A-continued
| MATERIAL | EXAMPLES OF MATERIAL | PUBLICATIONS |
|---|---|---|
| | 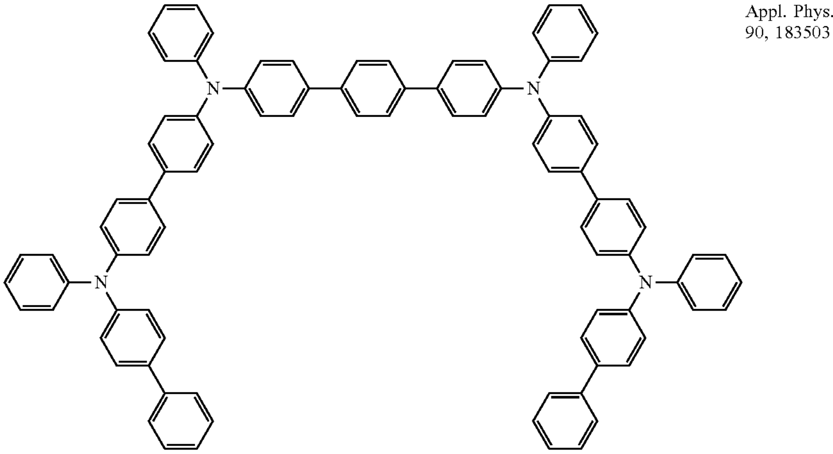 | Appl. Phys. Lett. 90, 183503 (2007) |
| | 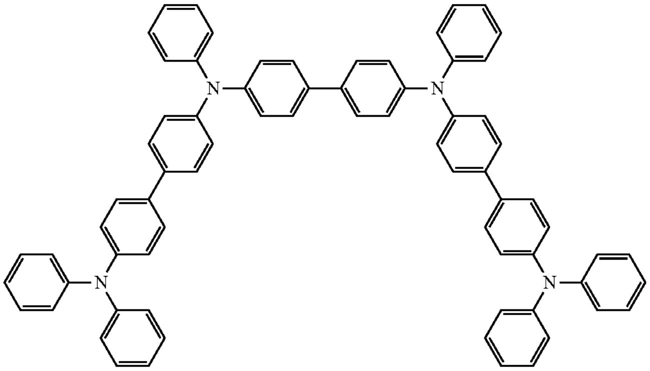 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys, Lett. 90, 183503 (2007) |
| Triarylamine on spirofluorene core | 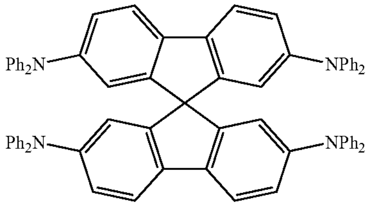 | Synth. Met. 91, 209 (1997) |
| Arylamine carbazole compounds | 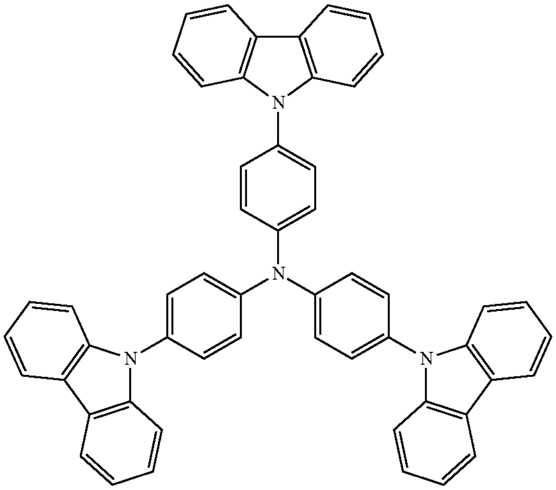 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv, Mater. 6, 677 (1994), US20080124572 |

TABLE A-continued
| MATERIAL | EXAMPLES OF MATERIAL | PUBLICATIONS |
| --- | --- | --- |
| Triarylamine with (di)benzo-thiophene/(di)benzofuran | 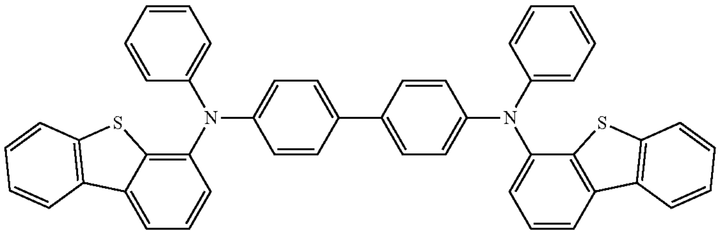 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 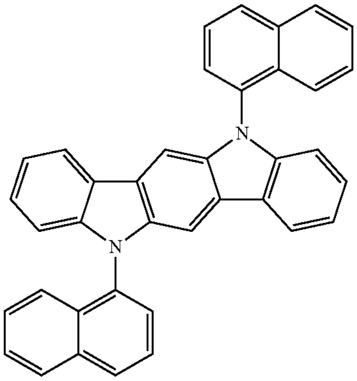 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 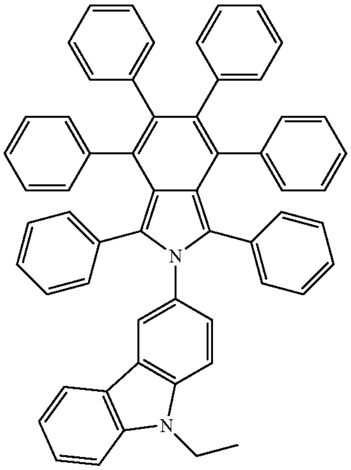 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 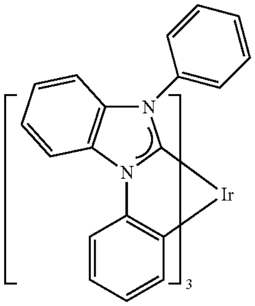 | US20080018221 |
Phosphorescent OLED host materials TABLE A-continued
| MATERIAL | EXAMPLES OF MATERIAL | PUBLICATIONS |
|---|---|---|
| Red hosts | | |
| Arylcarbazoles | 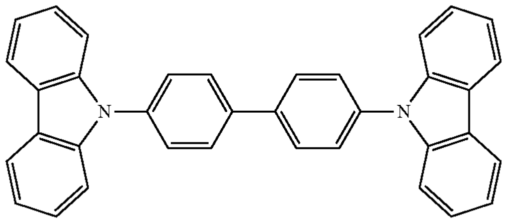 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq3, BAlq) | 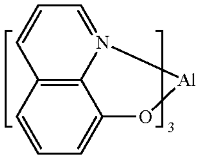 | Nature 395, 151 (1998) |
| | 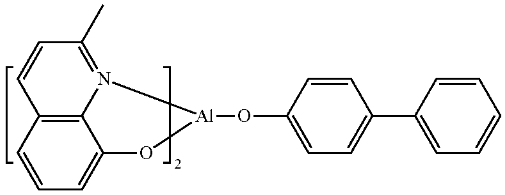 | US20060202194 |
| | 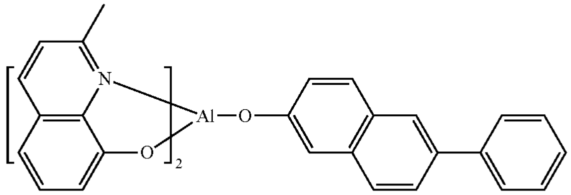 | WO2005014551 |
| | 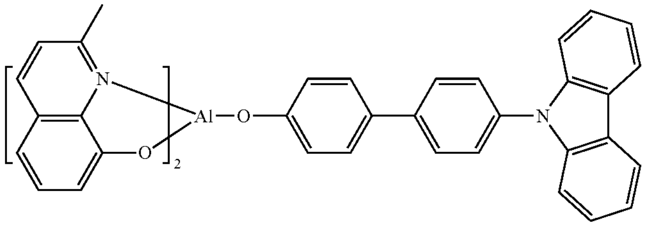 | WO2006072002 |
| Metal phenoxy-benzothiazole compounds | 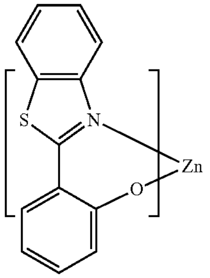 | Appl. Phys. Lett. 90, 123509 (2007) |
| Conjugated oligomers and polymers (e.g., polyfluorene) | 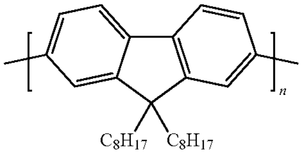 | Org. Electron. 1, 15 (2000) |

TABLE A-continued
| MATERIAL | EXAMPLES OF MATERIAL | PUBLICATIONS |
|---|---|---|
| Aromatic fused rings | 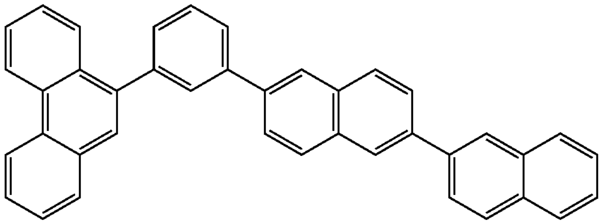 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 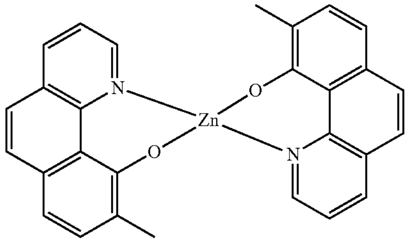 | WO2010056066 |
| Chrysene based compounds | 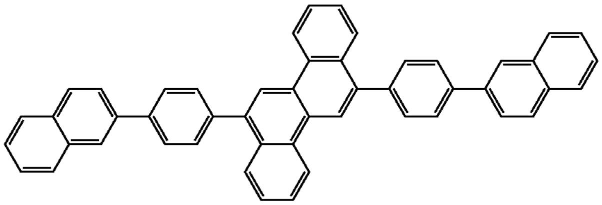 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
| | Green hosts | |
| Arylcarbazoles | 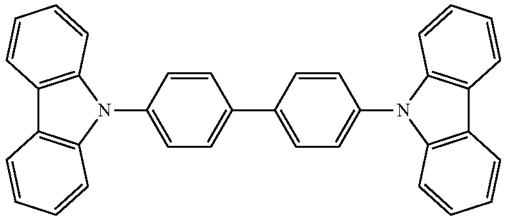 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 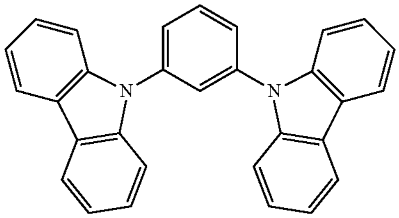 [SMILES: c1cc(-n2c3ccccc3c3ccccc32)cc(-n2c3ccccc3c3ccccc32)c1] | US20030175553 |
| | 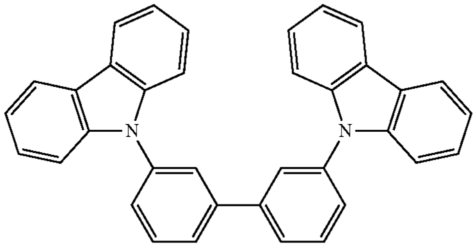 [SMILES: c1cc(-c2cccc(-n3c4ccccc4c4ccccc43)c2)cc(-n2c3ccccc3c3ccccc32)c1] | WO2001039234 |

TABLE A-continued
| MATERIAL | EXAMPLES OF MATERIAL | PUBLICATIONS |
|---|---|---|
| Aryltriphenylene compounds | 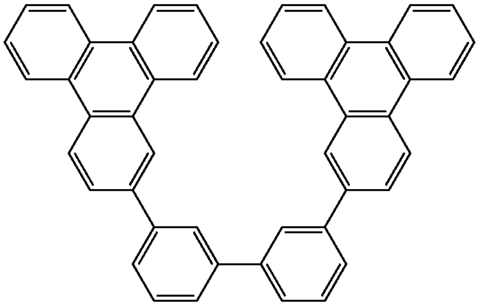 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 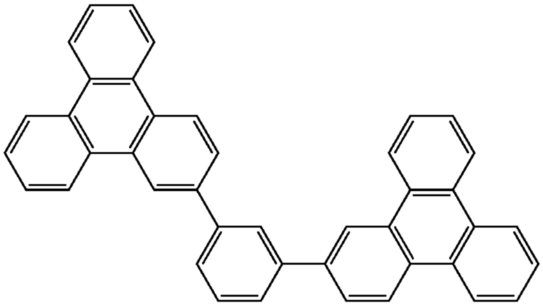 [SMILES: c1cc(-c2ccc3c4ccccc4c4ccccc4c3c2)cc(-c2ccc3c4ccccc4c4ccccc4c3c2)c1] | US20060280965 |
| | 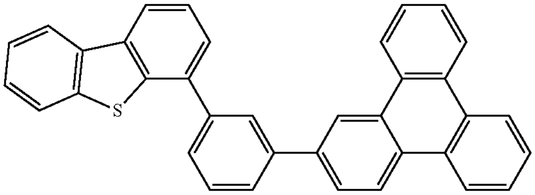 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 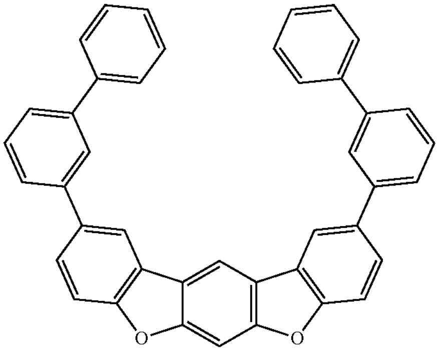 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 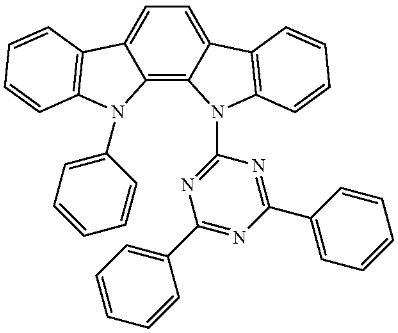 [SMILES: c1ccc(-c2nc(-c3ccccc3)nc(-n3c4ccccc4c4ccc5c6ccccc6n(-c6ccccc6)c5c43)n2)cc1] | WO2008056746 |

TABLE A-continued
| MATERIAL | EXAMPLES OF MATERIAL | PUBLICATIONS |
|---|---|---|
| | 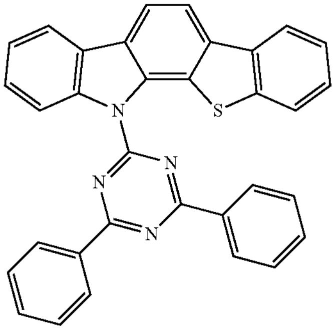 [SMILES: c1ccc(-c2nc(-c3ccccc3)nc(-n3c4ccccc4c4ccc5c6ccccc6sc5c43)n2)cc1] | WO2010107244 |
| Aza-carbazole/ DBT/DBF | 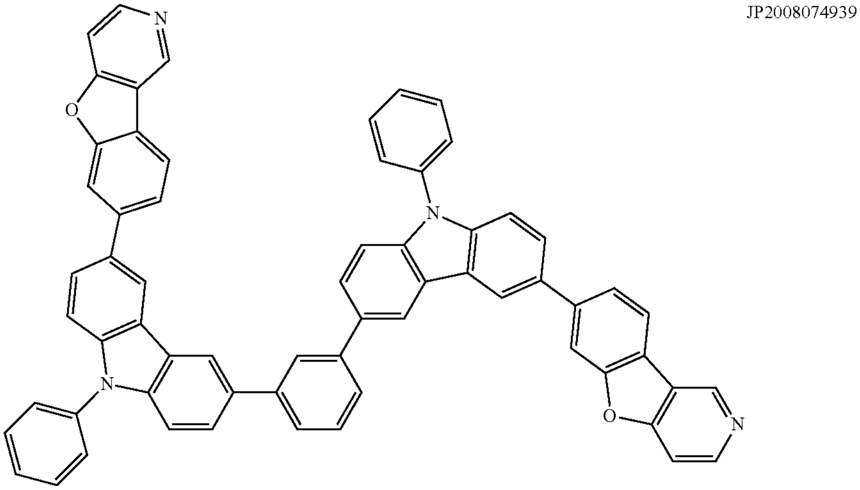 | JP2008074939 |
| | 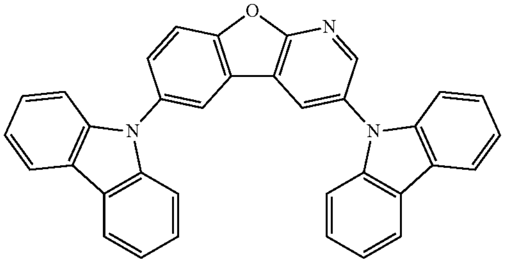 [SMILES: c1ccc2c(c1)c1ccccc1n2-c1ccc2oc3ncc(-n4c5ccccc5c5ccccc54)cc3c2c1] | US20100187984 |
| Polymers (e.g, PVK) | 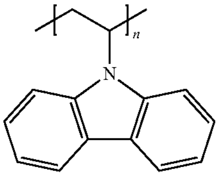 | Appl. Phys, Lett. 77, 2280 (2000) |
| Spirofluorene compounds | 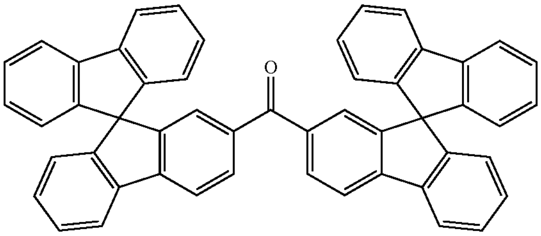 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE A-continued
| MATERIAL | EXAMPLES OF MATERIAL | PUBLICATIONS |
|---|---|---|
| Metal phenoxy-benzooxazole compounds | 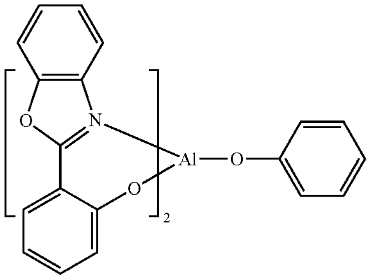 | WO2005089025 |
| | 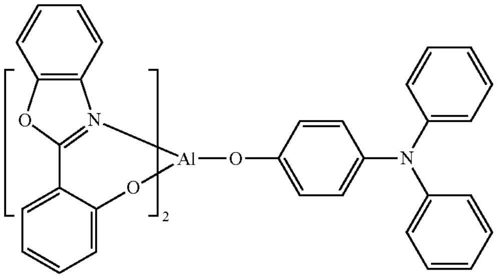 | WO2006132173 |
| | 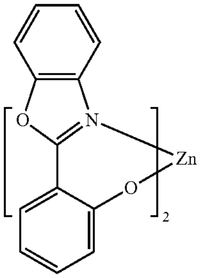 | JP200511610 |
| Spirofluorene-carbazole compounds | 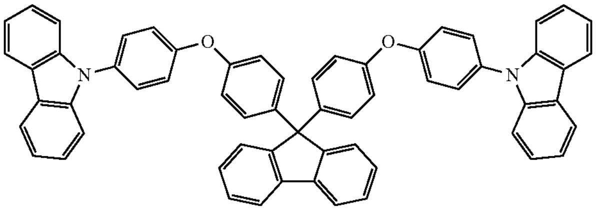 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 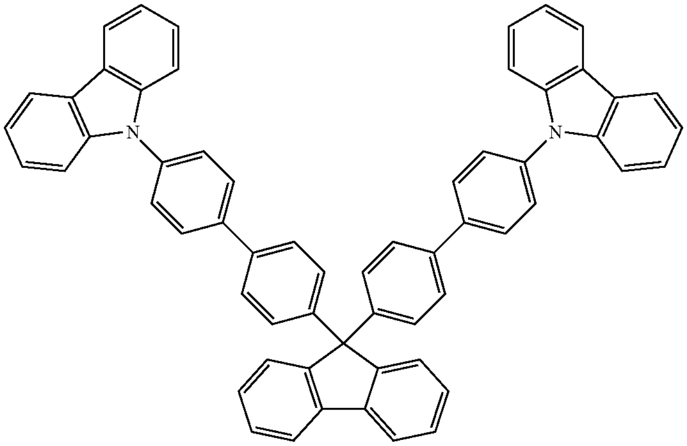 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |

TABLE A-continued
| MATERIAL | EXAMPLES OF MATERIAL | PUBLICATIONS |
|---|---|---|
| Indolocarbazoles | 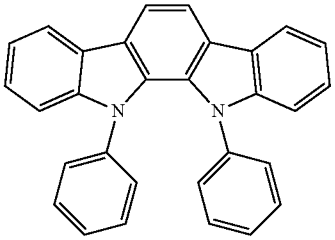 [SMILES: c1ccc(-n2c3ccccc3c3ccc4c5ccccc5n(-c5ccccc5)c4c32)cc1] | WO2007063796 |
| | 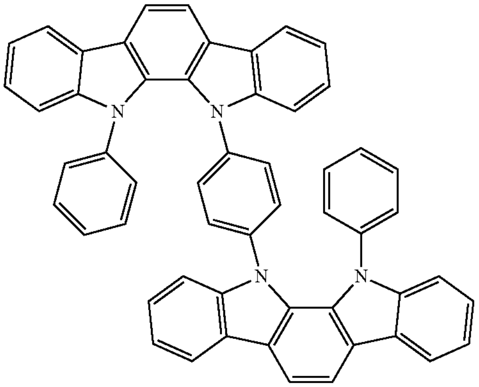 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 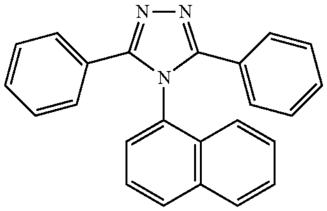 [SMILES: c1ccc(-c2nnc(-c3ccccc3)n2-c2cccc3ccccc23)cc1] | J. Appl. Phys. 90, 5048 (2001) |
| | 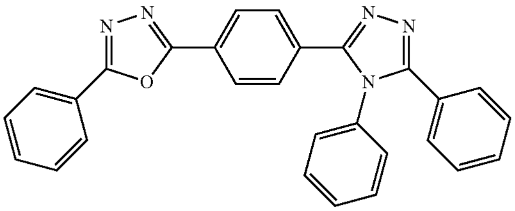 [SMILES: c1ccc(-c2nnc(-c3ccc(-c4nnc(-c5ccccc5)n4-c4ccccc4)cc3)o2)cc1] | WO2004107822 |
| Tetraphenylene complexes | 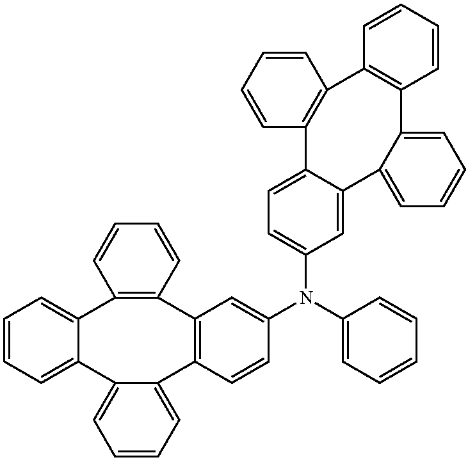 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |

TABLE A-continued
| MATERIAL | EXAMPLES OF MATERIAL | PUBLICATIONS |
|---|---|---|
| Metal phenoxypyridine compounds | 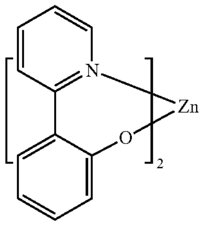 | WO2005030900 |
| | 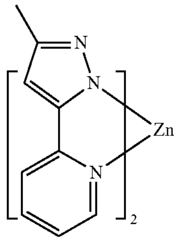 | US20040137268, US20040137267 |
| | Blue hosts | |
| Arylcarbazoles | 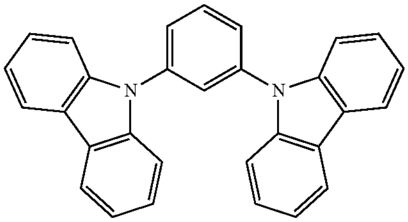 [SMILES: c1cc(-n2c3ccccc3c3ccccc32)cc(-n2c3ccccc3c3ccccc32)c1] | Appl. Phys. Lett, 82, 2422 (2003) |
| | 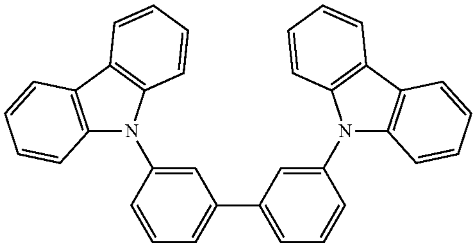 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran-carbazole compounds | 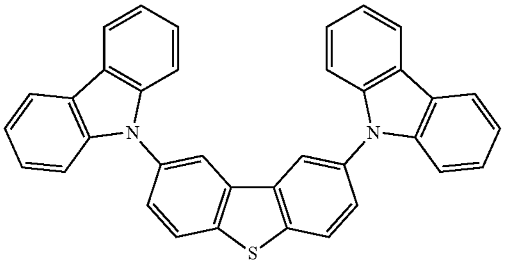 [SMILES: c1ccc2c(c1)c1ccccc1n2-c1ccc2sc3ccc(-n4c5ccccc5c5ccccc54)cc3c2c1] | WO2006114966, US20090167162 |
| | 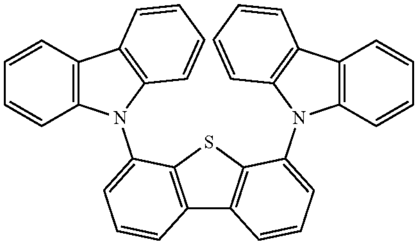 [SMILES: c1cc(-n2c3ccccc3c3ccccc32)c2sc3c(-n4c5ccccc5c5ccccc54)cccc3c2c1] | US20090167162 |

TABLE A-continued
| MATERIAL | EXAMPLES OF MATERIAL | PUBLICATIONS |
|---|---|---|
| | 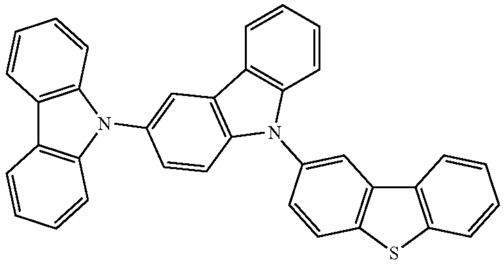 [SMILES: c1ccc2c(c1)sc1ccc(-n3c4ccccc4c4cc(-n5c6ccccc6c6ccccc65)ccc43)cc12] | WO2009086028 |
| | 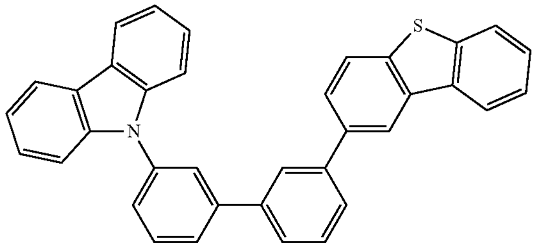 [SMILES: c1cc(-c2cccc(-n3c4ccccc4c4ccccc43)c2)cc(-c2ccc3sc4ccccc4c3c2)c1] | US20090030202, US20090017330 |
| | 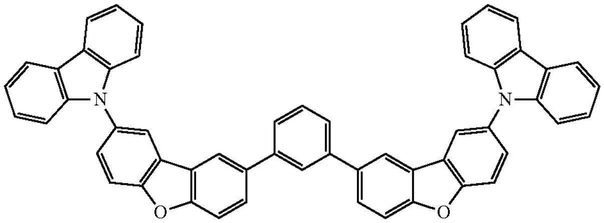 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 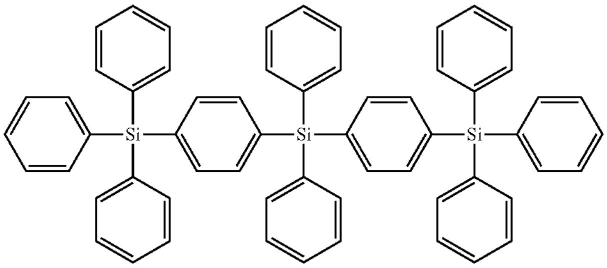 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 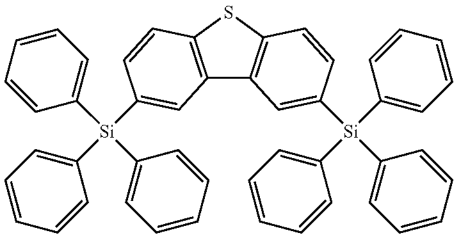 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 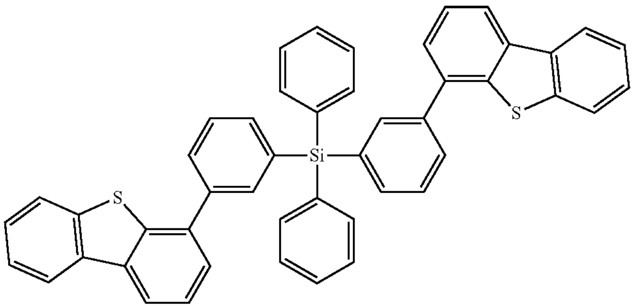 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |

TABLE A-continued
| MATERIAL | EXAMPLES OF MATERIAL | PUBLICATIONS |
|---|---|---|
| Aryl benzoyl ester | 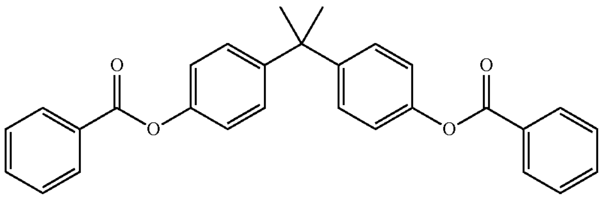 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 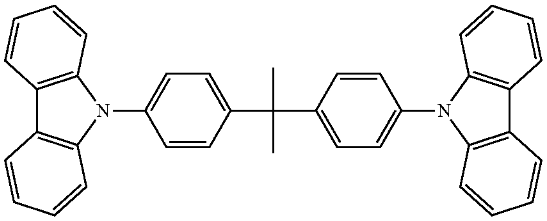 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 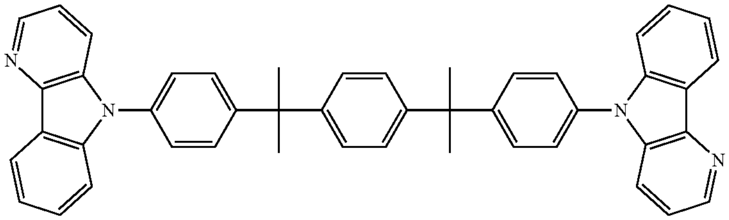 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 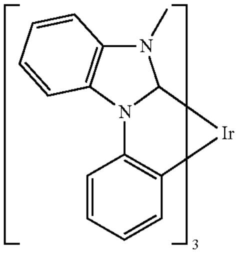 | U.S. Pat No. 7,154,114 |
| Phosphorescent dopants | | |
| Red dopants | | |
| Heavy metal porphyrins (e.g., PtOEP) | 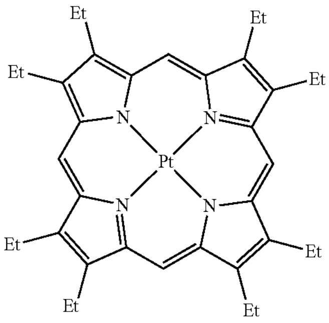 | Nature 395, 151 (1998) |

TABLE A-continued
| MATERIAL | EXAMPLES OF MATERIAL | PUBLICATIONS |
| --- | --- | --- |
| Iridium(III) organometallic complexes | 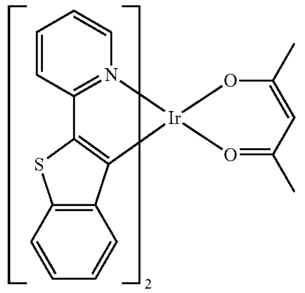 | Appl. Phys. Lett. 78, 1622 (2001) |
| | 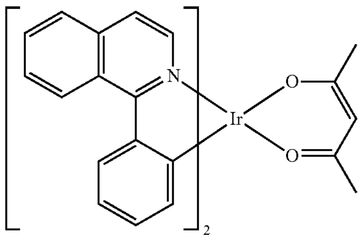 | US20030072964 |
| | 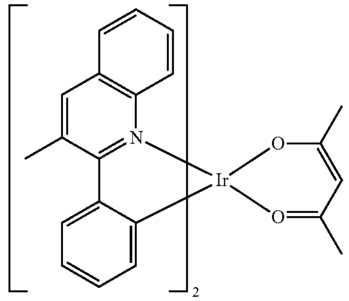 | US20030072964 |
| | 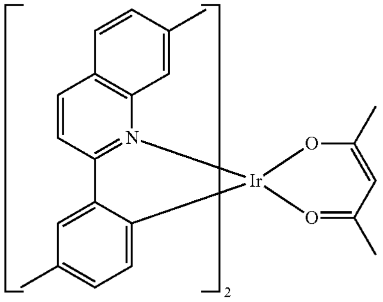 | US20060202194 |
| | 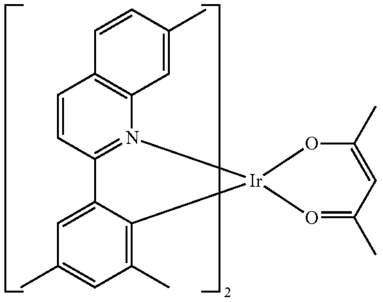 | US20060202194 |

TABLE A-continued
| MATERIAL | EXAMPLES OF MATERIAL | PUBLICATIONS |
|---|---|---|
| | 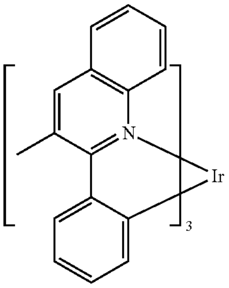 | US20070087321 |
| | 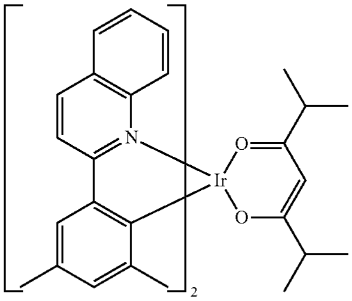 | US20080261076<br>US20100090591 |
| | 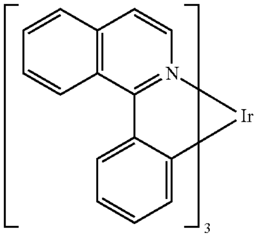 | US20070087321 |
| | 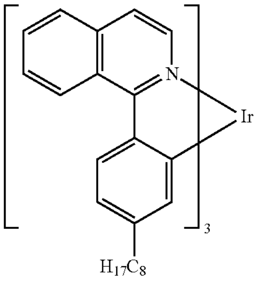 | Adv. Mater. 19, 739 (2007) |
| | 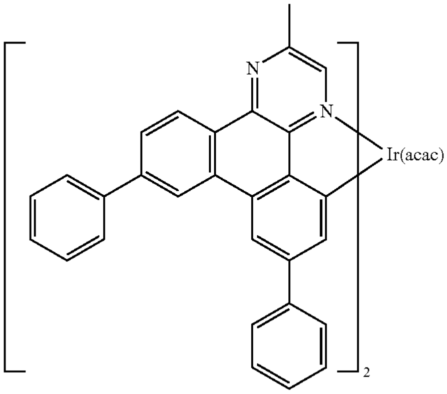 | WO2009100991 |

TABLE A-continued
| MATERIAL | EXAMPLES OF MATERIAL | PUBLICATIONS |
| --- | --- | --- |
| | 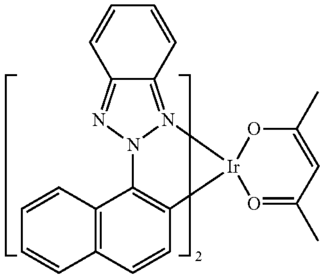 | WO2008101842 |
| | 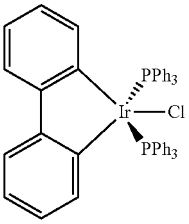 | U.S. Pat No. 7,232,618 |
| Platinum(II) organometallic complexes | 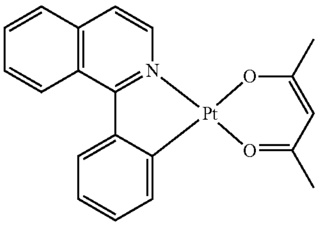 | WO2003040257 |
| | 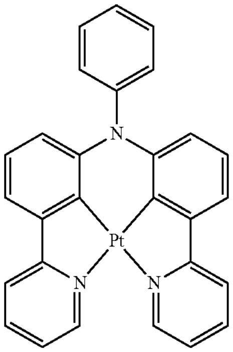 | US20070103060 |
| Osmium(III) complexes | 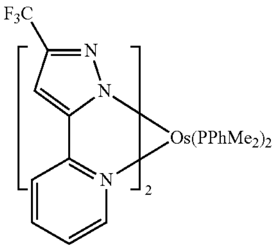 | Chem. Mater. 17, 3532 (2005) |

TABLE A-continued
| MATERIAL | EXAMPLES OF MATERIAL | PUBLICATIONS |
|---|---|---|
| Ruthenium(II) complexes | 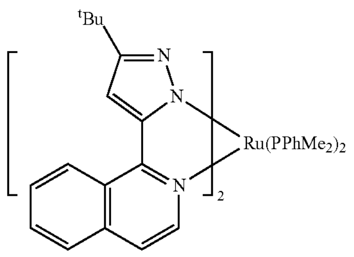 | Adv. Mater. 17, 1059 (2005) |
| Rhenium (I), (II), and (III) complexes | 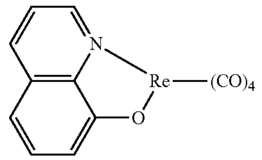 | US20050244673 |
| | Green dopants | |
| Iridium(III) organometallic complexes | 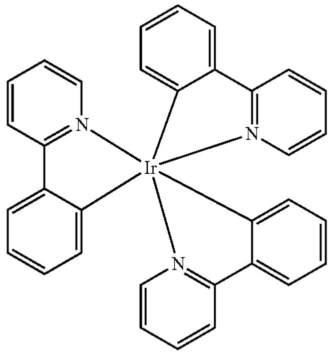 and its derivatives | Inorg. Chem. 40, 1704 (2001) |
| | 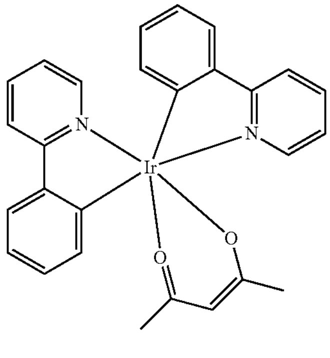 | US20020034656 |

TABLE A-continued
| MATERIAL | EXAMPLES OF MATERIAL | PUBLICATIONS |
|---|---|---|
| | 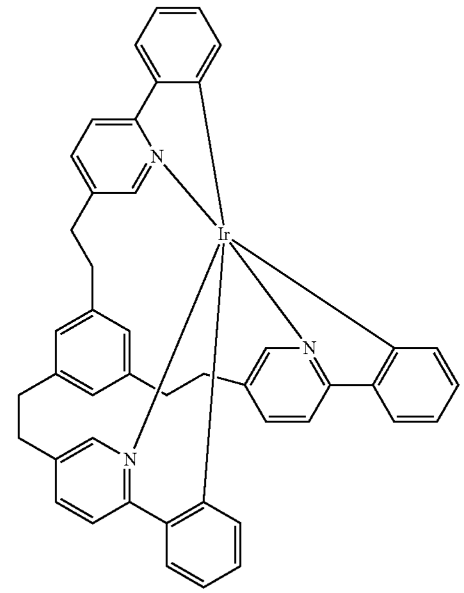 | U.S. Pat No. 7,332,232 |
| | 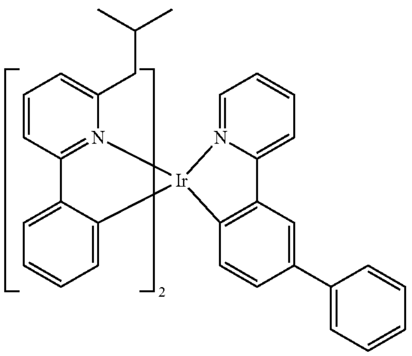 | US20090108737 |
| | 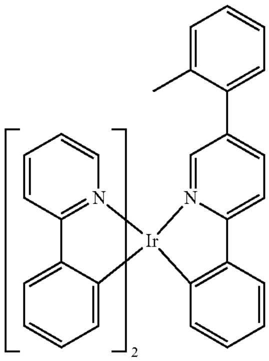 | WO2010028151 |

TABLE A-continued
| MATERIAL | EXAMPLES OF MATERIAL | PUBLICATIONS |
|---|---|---|
| | 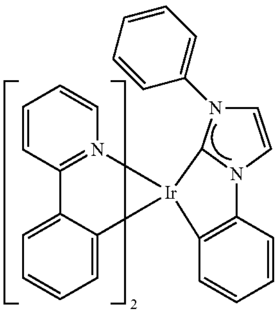 | EP1841834B |
| | 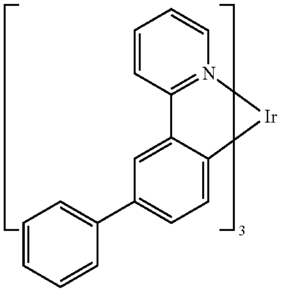 | US20060127696 |
| | 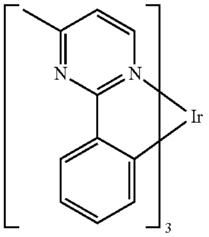 | US20090039776 |
| | 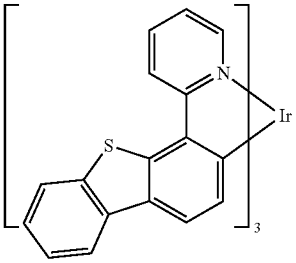 | U.S. Pat No. 6,921,915 |
| | 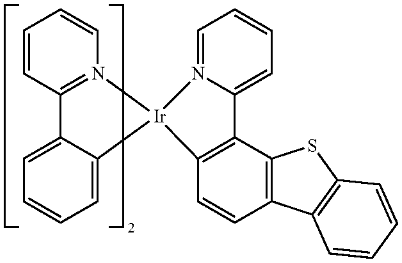 | US20100244004 |

TABLE A-continued
| MATERIAL | EXAMPLES OF MATERIAL | PUBLICATIONS |
|---|---|---|
| | 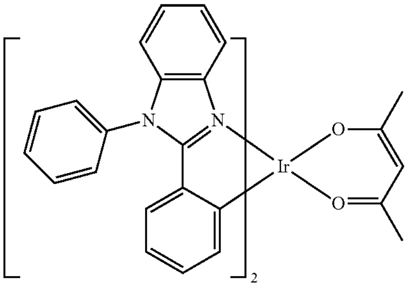 | U.S. Pat No. 6,687,266 |
| | 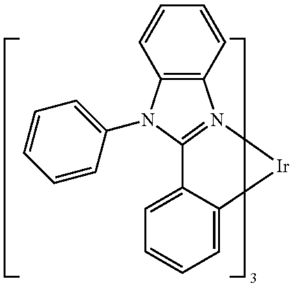 | Chem. Mater. 16, 2480 (2004) |
| | 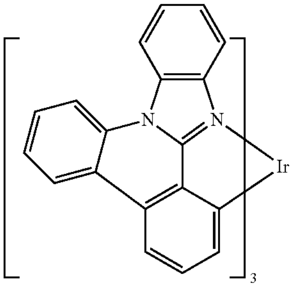 | US20070190359 |
| | 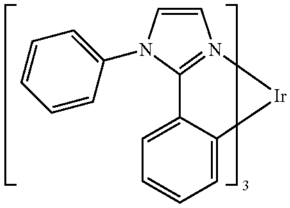 | US 20060008670 JP2007123392 |
| | 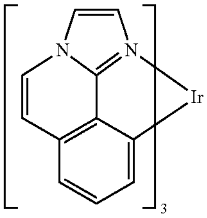 | WO2010086089, WO2011044988 |
| | 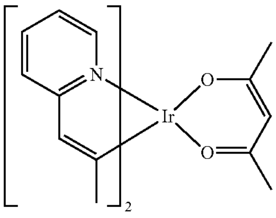 | Adv. Mater. 16, 2003 (2004) |

TABLE A-continued
| MATERIAL | EXAMPLES OF MATERIAL | PUBLICATIONS |
|---|---|---|
| | 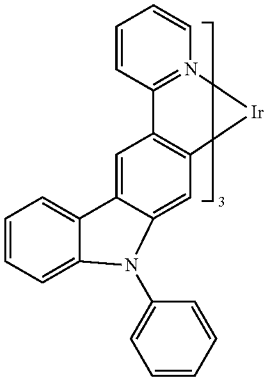 | Angew. Chem. Int. Ed. 2006, 45, 7800 |
| | 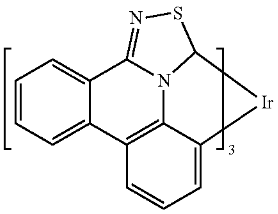 | WO2009050290 |
| | 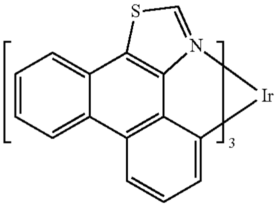 | US20090165846 |
| | 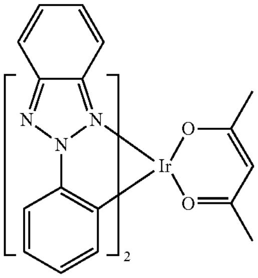 | US20080015355 |
| | 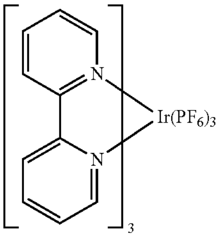 | US20010015432 |
| | 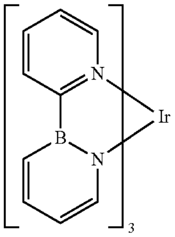 | US20100295032 |

TABLE A-continued
| MATERIAL | EXAMPLES OF MATERIAL | PUBLICATIONS |
|---|---|---|
| Monomer for polymeric metal organometallic compounds | 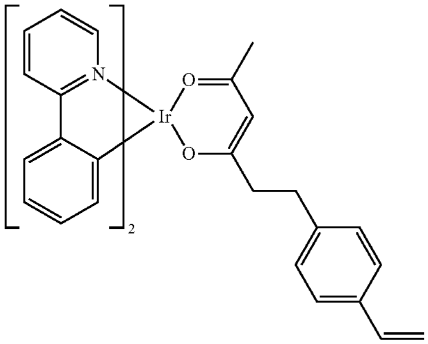 | U.S. Pat No. 7,250,226, U.S. Pat No. 7,396,598 |
| Pt (II) organometallic complexes, including polydentate ligands | 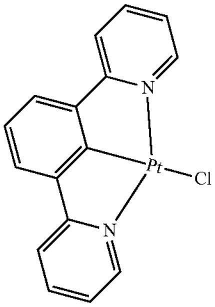 | Appl. Phys. Lett. 86, 153505 (2005) |
| | 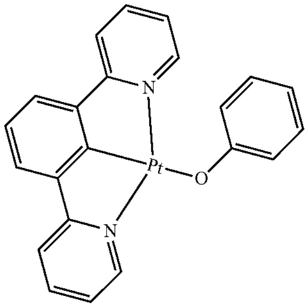 | Appl. Phys. Lett. 86, 153505 (2005) |
| | 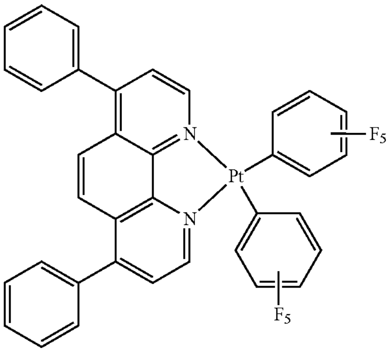 | Chem. Lett. 34, 592 (2005) |
| | 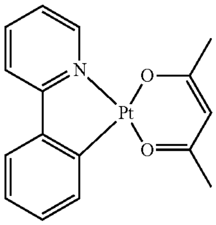 | WO2002015645 |

TABLE A-continued
| MATERIAL | EXAMPLES OF MATERIAL | PUBLICATIONS |
|---|---|---|
| | 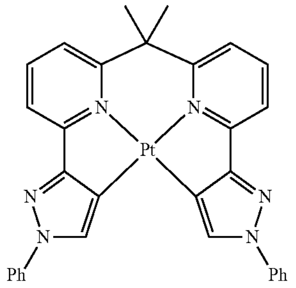 | US20060263635 |
| | 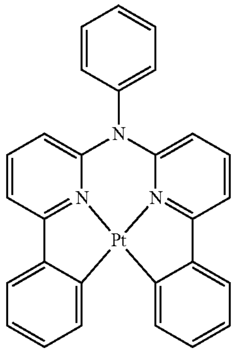 | US20060182992<br>US20070103060 |
| Cu complexes | 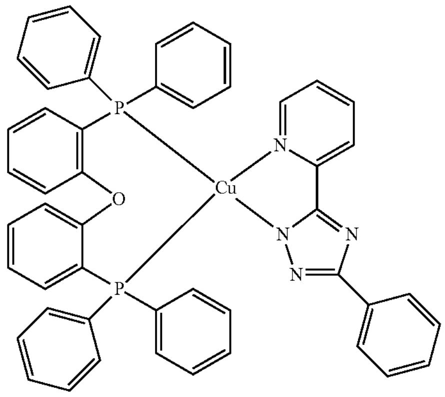 | WO2009000673 |
| | 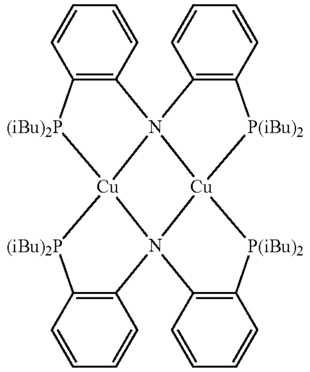 | US2007011126 |

TABLE A-continued
| MATERIAL | EXAMPLES OF MATERIAL | PUBLICATIONS |
|---|---|---|
| Gold complexes | 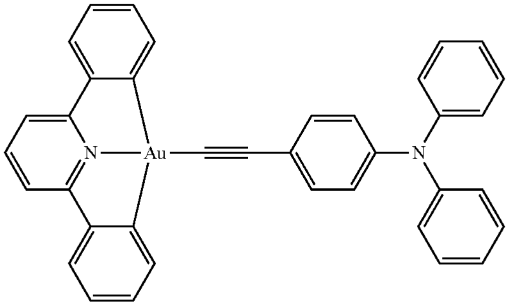 | Chem. Commun. 2906 (2005) |
| Rhenium(III) complexes | 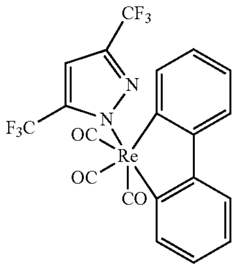 | Inorg. Chem. 42, 1248 (2003) |
| Osmium(II) complexes | 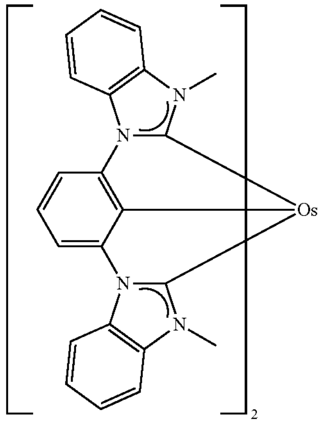 | U.S. Pat No. 7,279,704 |
| Deuterated organometallic complexes | 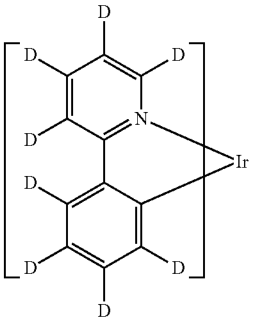 | US20030138657 |

TABLE A-continued
| MATERIAL | EXAMPLES OF MATERIAL | PUBLICATIONS |
|---|---|---|
| Organometallic complexes with two or more metal centers | 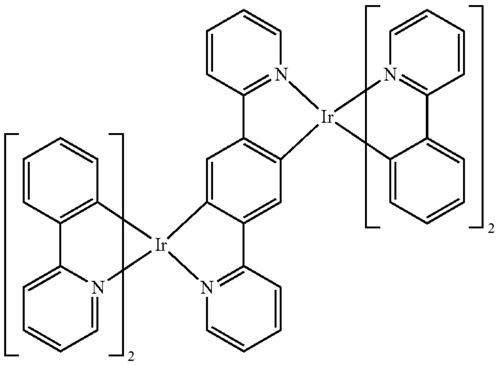 | US20030152802 |
| | 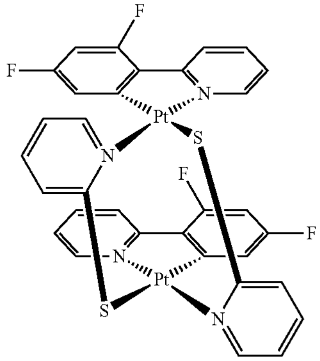 | U.S. Pat No. 7,090,928 |
| | Blue dopants | |
| Iridium(III) organometallic complexes | 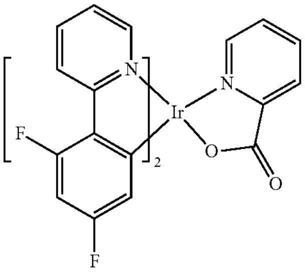 | WO2002002714 |
| | 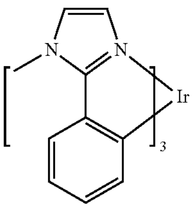 | WO2006009024 |
| | 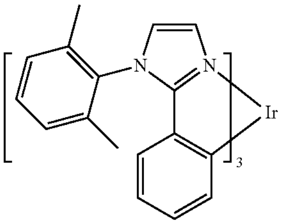 | US20060251923 US20110057559 US20110204333 |

TABLE A-continued
| MATERIAL | EXAMPLES OF MATERIAL | PUBLICATIONS |
|---|---|---|
| | 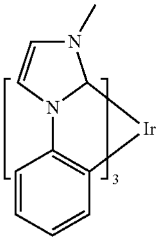 | US7393599, WO2006056418, US20050260441, WO2005019373 |
| | 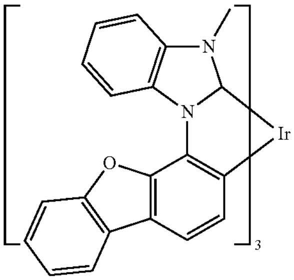 | U.S. Pat No. 7,534,505 |
| | 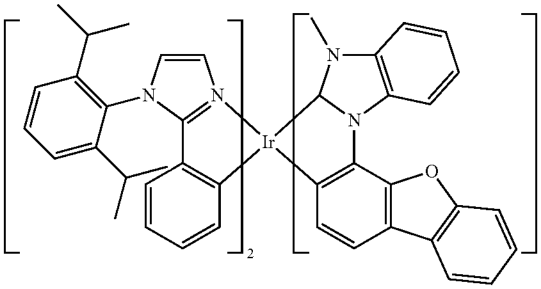 | WO2011051404 |
| | 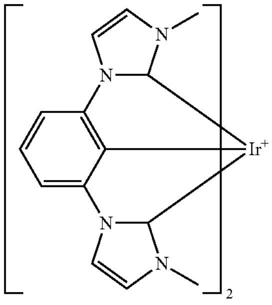 | U.S. Pat No. 7,445,855 |
| | 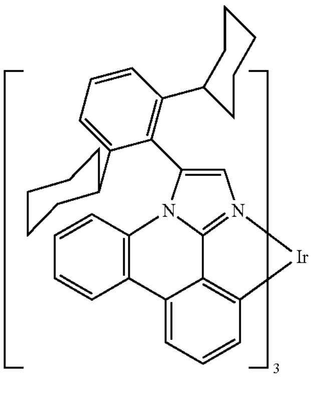 | US20070190359, US20080297033 US20100148663 |

TABLE A-continued
| MATERIAL | EXAMPLES OF MATERIAL | PUBLICATIONS |
|---|---|---|
| | 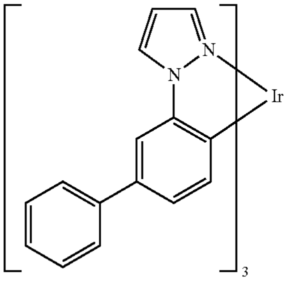 | U.S. Pat No. 7,338,722 |
| | 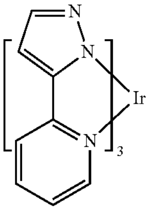 | US20020134984 |
| | 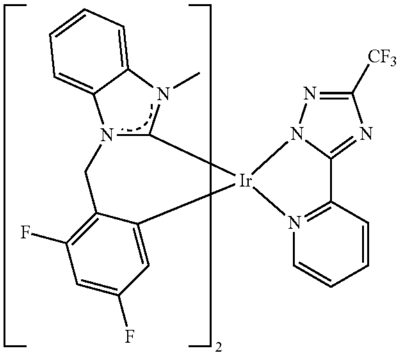 | Angew. Chem. Int. Ed. 47, 4542 (2008) |
| | 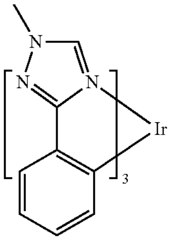 | Chem. Mater. 18, 5119 (2006) |
| | 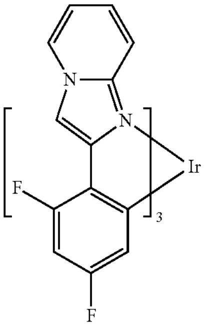 | Inorg. Chem. 46, 4308 (2007) |

TABLE A-continued
| MATERIAL | EXAMPLES OF MATERIAL | PUBLICATIONS |
|---|---|---|
| | 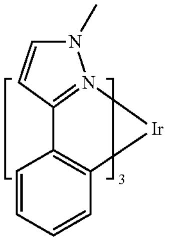 | WO2005123873 |
| | 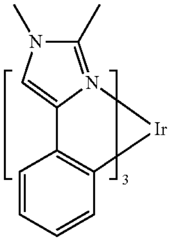 | WO2005123873 |
| | 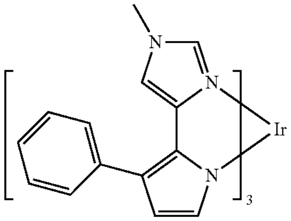 | WO2007004380 |
| | 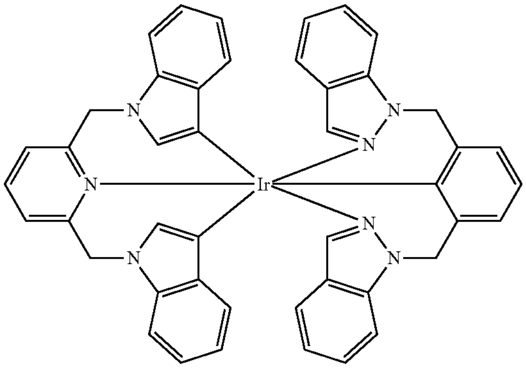 | WO2006082742 |
| Osmium(II) complexes | 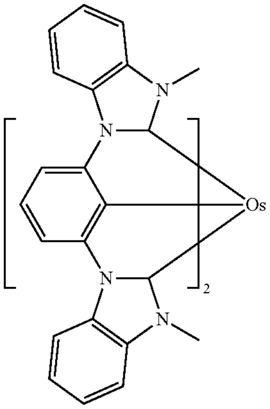 | U.S. Pat No. 7,279,704 |

TABLE A-continued

| MATERIAL | EXAMPLES OF MATERIAL | PUBLICATIONS |
|---|---|---|
| | 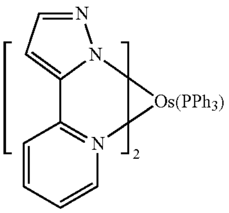 | Organometallics 23, 3745 (2004) |
| Gold complexes | 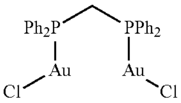 | Appl. Phys. Lett. 74, 1361 (1999) |
| Platinum(II) complexes | 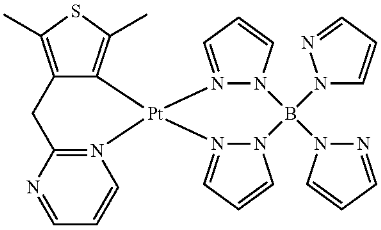 | WO2006098120, WO2006103874 |
| Pt tetradentate complexes with at least one metal-carbene bond | 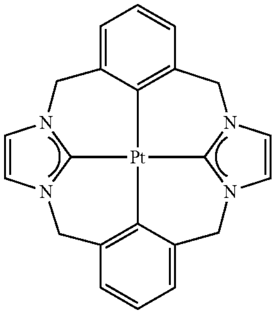 | U.S. Pat No. 7,655,323 |
| Exciton/hole blocking layer materials | | |
| Bathocuproine compounds (e.g., BCP, BPhen) | 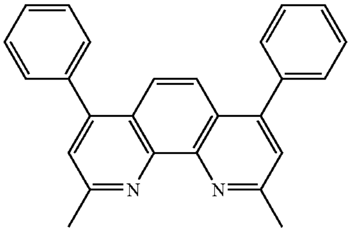 [SMILES: Cc1cc(-c2ccccc2)c2ccc3c(-c4ccccc4)cc(C)nc3c2n1] | Appl. Phys. Lett. 75, 4 (1999) |
| | 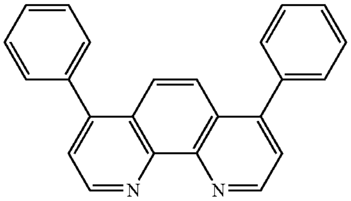 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 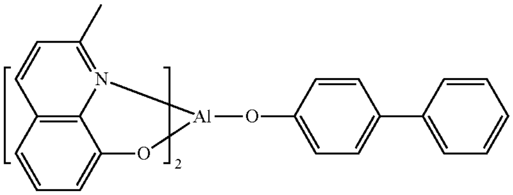 | Appl. Phys. Lett. 81, 162 (2002) |

TABLE A-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 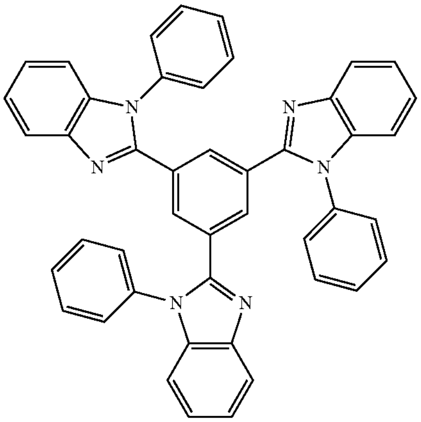 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 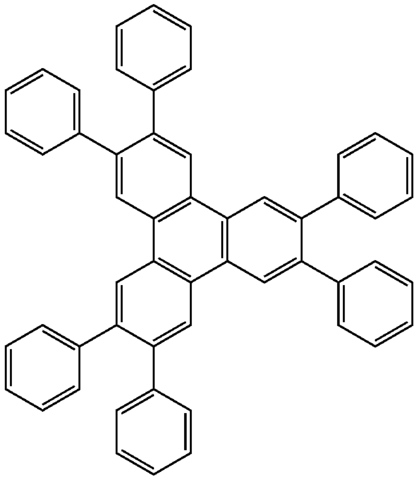 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 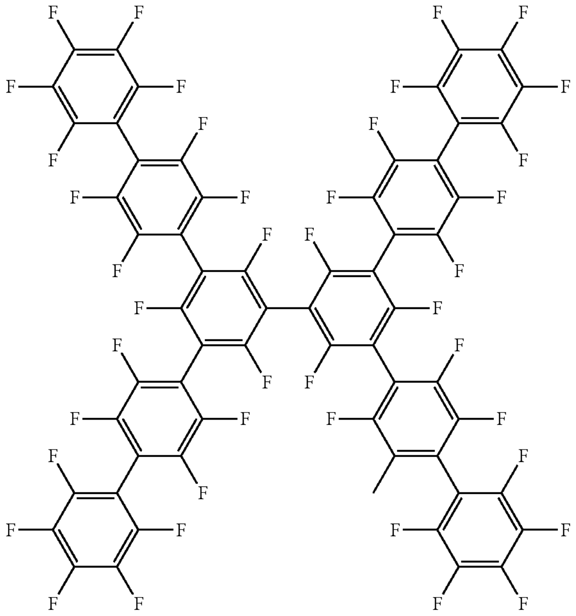 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE A-continued
| MATERIAL | EXAMPLES OF MATERIAL | PUBLICATIONS |
|---|---|---|
| Phenothiazine-S-oxide | 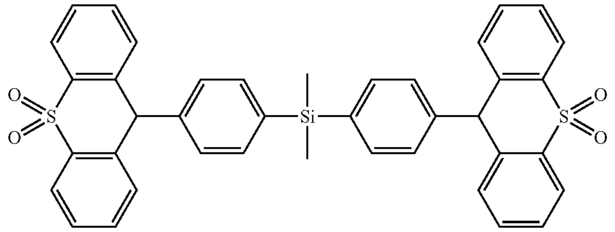 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzo-heterocycles | 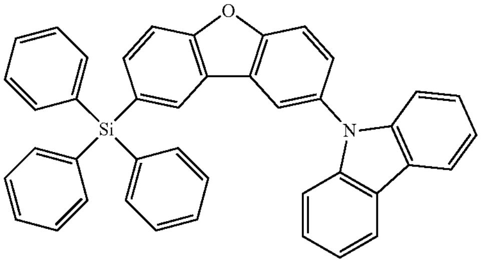 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 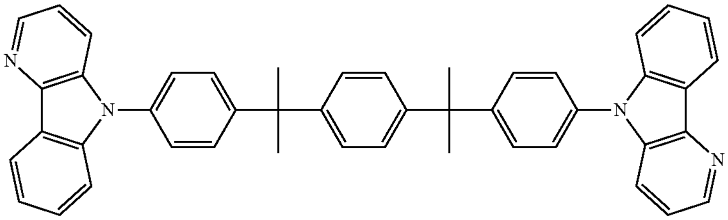 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| | Electron transporting materials | |
| Anthracene-benzoimidazole compounds | 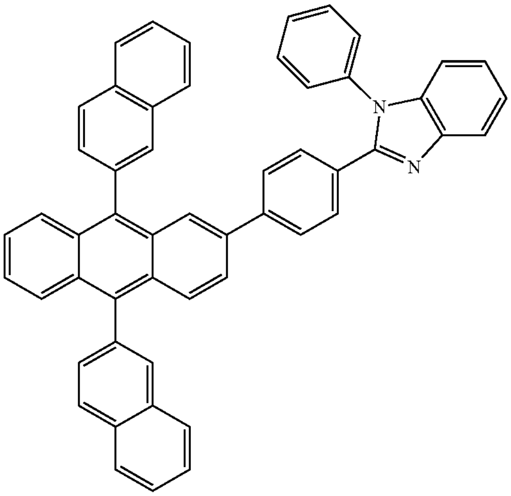 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 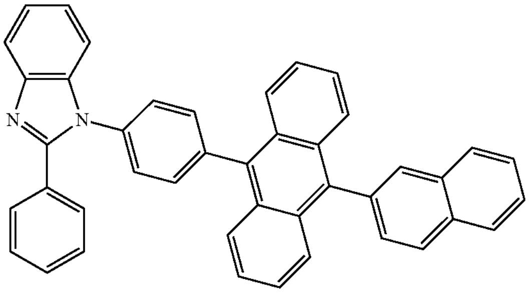 [SMILES: c1ccc(-c2nc3ccccc3n2-c2ccc(-c3c4ccccc4c(-c4ccc5ccccc5c4)c4ccccc34)cc2)cc1] | US20090179554 |

TABLE A-continued
| MATERIAL | EXAMPLES OF MATERIAL | PUBLICATIONS |
| --- | --- | --- |
| Aza triphenylene derivatives | 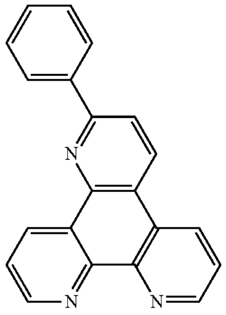 [SMILES: c1ccc(-c2ccc3c4cccnc4c4ncccc4c3n2)cc1] | US20090115316 |
| Anthracene-benzothiazole compounds | 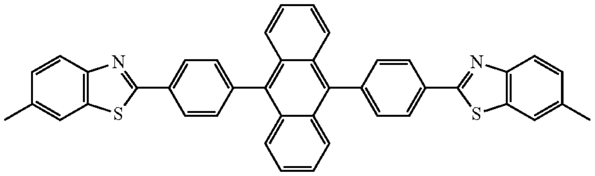 | Appl. Phys. Lett. 89, 063504 (2006) |
| Metal 8-hydroxyquinolates (e.g., Alq3, Zrq4) | 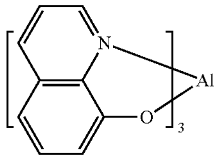 | Appl. Phys. Lett. 51, 913 (1987) U.S. Pat No. 7,230,107 |
| Metal hydroxy-benzoquinolates | 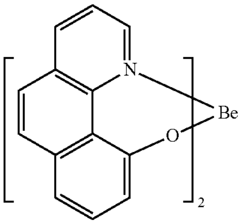 | Chem. Lett. 5, 905 (1993) |
| Bathocuproine compounds such as BCP, BPhen, etc | 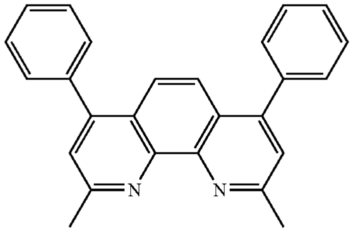 [SMILES: Cc1cc(-c2ccccc2)c2ccc3c(-c4ccccc4)cc(C)nc3c2n1] | Appl. Phys. Lett. 91, 263503 (2007) |
| | 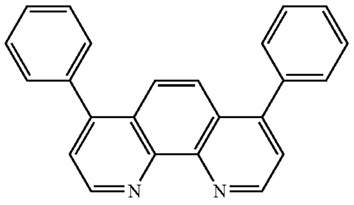 [SMILES: c1ccc(-c2ccnc3c2ccc2c(-c4ccccc4)ccnc23)cc1] | Appl. Phys. Lett. 79, 449 (2001) |

TABLE A-continued
| MATERIAL | EXAMPLES OF MATERIAL | PUBLICATIONS |
| --- | --- | --- |
| 5-member ring electron deficient heterocycles (e.g., triazole, oxadiazole, imidazole, benzoimidazole) | 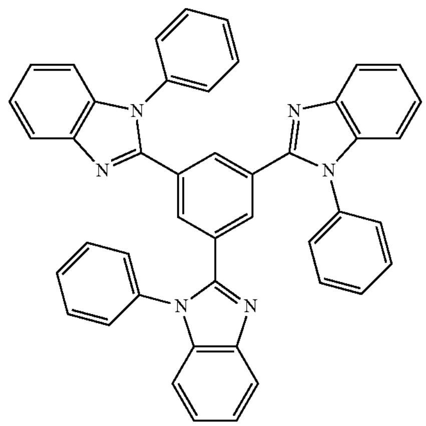 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 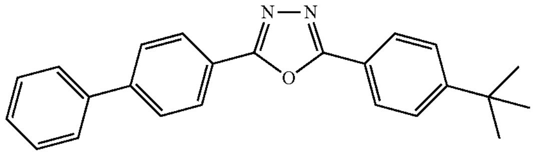 [SMILES: CC(C)(C)c1ccc(-c2nnc(-c3ccc(-c4ccccc4)cc3)o2)cc1] | Appl. Phys. Lett. 55, 1489 (1989) |
| | 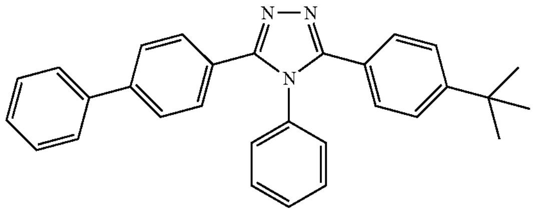 [SMILES: CC(C)(C)c1ccc(-c2nnc(-c3ccc(-c4ccccc4)cc3)n2-c2ccccc2)cc1] | Jpn, J. Apply. Phys. 32, L917 (1993) |
| Silole compounds | 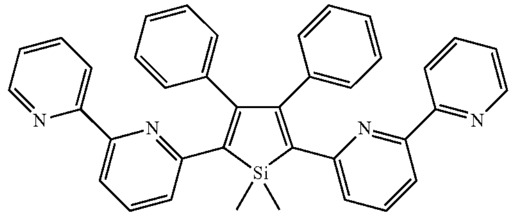 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 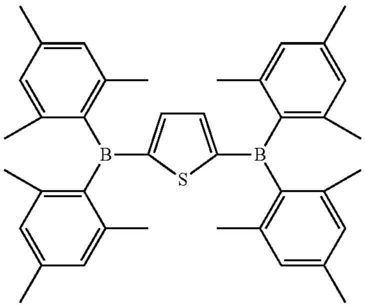 | J. Am. Chem. Soc. 120, 9714 (1998) |
| Fluorinated aromatic compounds | 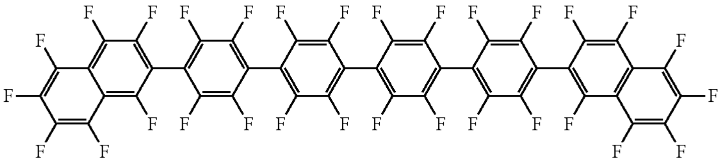 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE A-continued

| MATERIAL | EXAMPLES OF MATERIAL | PUBLICATIONS |
|---|---|---|
| Fullerene (e.g., $C_{60}$) | 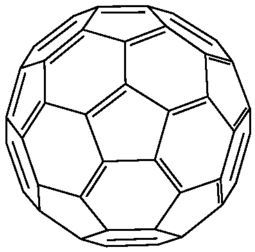 [SMILES: C1=CC2C3C4=c5c6c7c8c(ccc9c%10ccc%11c%12ccc%13c1c3c1c5c3c6c(c89)c%10c%11c3c%12c%131)C1C=CC2C4C71] | US20090101870 |
| Triazine complexes | 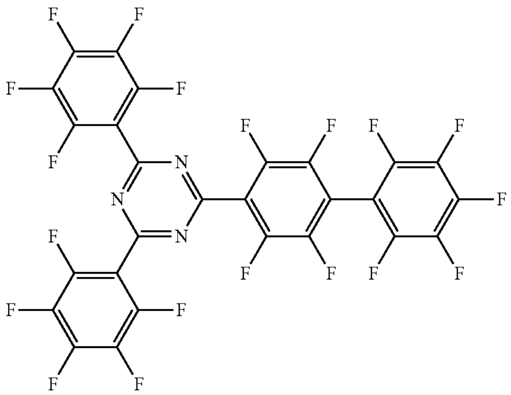 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 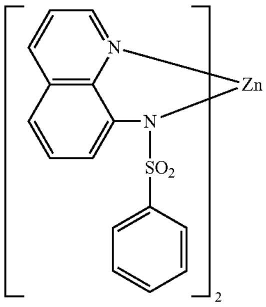 | U.S. Pat No. 6,528,187 |

Materials Synthesis

Synthesis of 1-phenyl-1H-imidazole-4-carbaldehyde

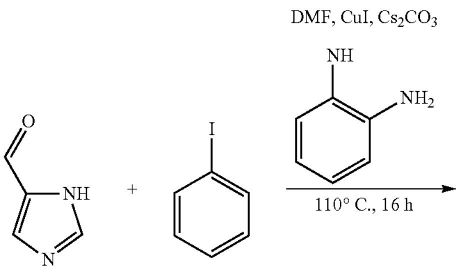

-continued

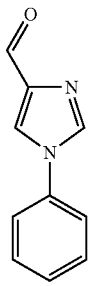

To a stirred solution of 1H-imidazole-5-carbaldehyde (10 g, 104 mmol) in DMF (135 mL), iodobenzene (31.8 g, 156 mmol), cyclohexane-1,2-diamine (2.377 g, 20.8 mmol), cesium carbonate (67.8 g, 208 mmol), and copper(I) iodide (0.991 g, 5.2 mmol) were added. The reaction mixture was stirred at 110° C. for about 16 hours. It was precipitated in water and filtered. The residue was column chromatographed with THF:hexane (1:4). 1-Phenyl-1H-imidazole-4-carbaldehyde (3.5 g, 20.3 mmol, 19.5% yield) was isolated as white solid.

Synthesis of 1-phenyl-1H-imidazole-4-carbonitrile

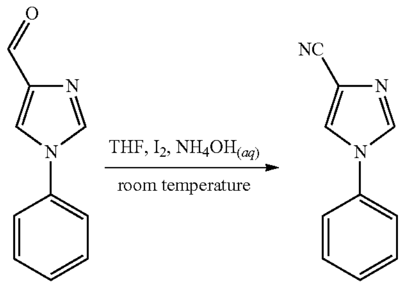 [SMILES: O=Cc1cn(-c2ccccc2)cn1 ; N#Cc1cn(-c2ccccc2)cn1]

To a stirred solution of 1-phenyl-1H-imidazole-4-carbaldehyde (3.5 g, 20.3 mmol) in THF (60 mL), ammonium hydroxide (22 mL, 224 mmol) was added. Iodine (15.48 g, 61.0 mmol) was added in portions at room temperature. The reaction was monitored with HPLC for the completion of the reaction. Diethyl ether and saturated sodium thiosulphate were added. The organic layer was separated, dried and column chromatographed with THF:hexane (1:4) yielded 1-phenyl-1H-imidazole-4-carbonitrile (3.1 g, 18.3 mmol, 90% yield).

Synthesis of 4-cyano-3-methyl-1-phenyl-1H-imidazol-3-ium trifluoromethanesulfonate (LA1)

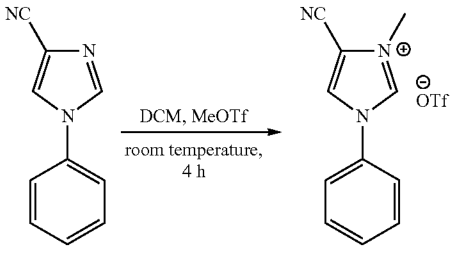

To a stirred solution of 1-phenyl-1H-imidazole-4-carbonitrile (1.6 g, 9.5 mmol) in DCM (25 mL), methyl trifluoromethanesulfonate (1.7 g, 10.4 mmol) was added and stirred at room temperature for 4 hours. The precipitate was filtered and washed with DCM yielded 4-cyano-3-methyl-1-phenyl-1H-imidazol-3-ium trifluoromethanesulfonate (3.0 g, 9.0 mmol, 95% yield).

Synthesis of 1-(m-tolyl)-1H-imidazole-4-carbaldehyde and 1-(m-tolyl)-1H-imidazole-5-carbaldehyde

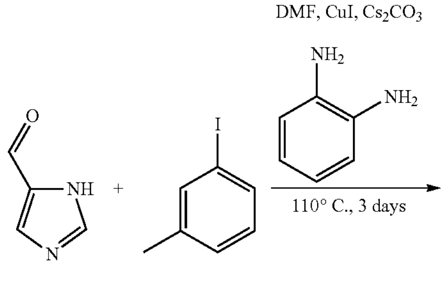

-continued

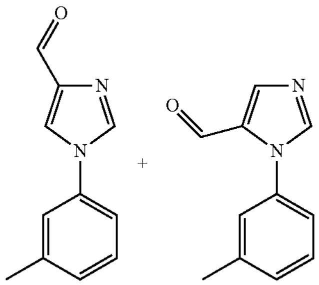

1H-imidazole-5-carbaldehyde (10.0 g, 104 mmol), 1-iodo-3-methylbenzene (34.0 g, 156 mmol), cyclohexane-1,2-diamine (2.4 g, 20.8 mmol), cesium carbonate (67.8 g, 208 mmol), and copper(I) iodide (0.991 g, 5.2 mmol) were stirred in DMF (135 mL) at 110° C. for 3 days. The reaction mixture was precipitated in water and filtered. The residue was column chromatographed with THF:hexane (1:4) yielded a mixture of 1-(m-tolyl)-1H-imidazole-4-carbaldehyde and 1-(m-tolyl)-1H-imidazole-5-carbaldehyde (19.0 g) were used for next step without further purification.

Synthesis of 1-(m-tolyl)-1H-imidazole-5-carbonitrile and 1-(m-tolyl)-1H-imidazole-4-carbonitrile

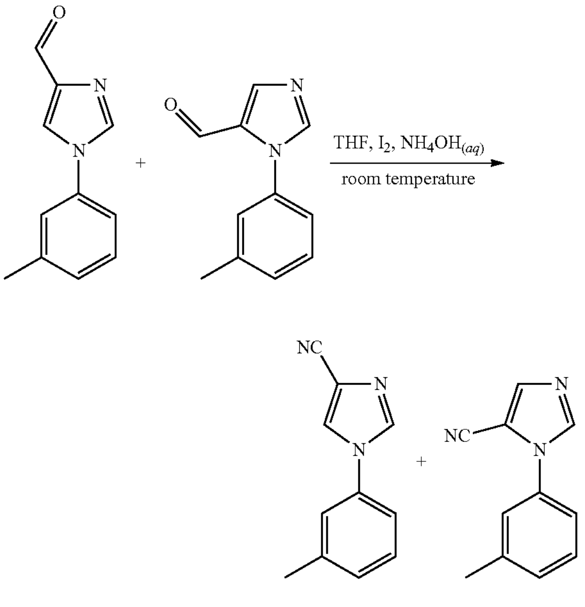

To a stirred solution of mixture of 1-(m-tolyl)-1H-imidazole-4-carbaldehyde and 1-(m-tolyl)-1H-imidazole-5-carbaldehyde (15 g, 80.6 mmol) in THF (100 mL), ammonium hydroxide (47 mL, 403 mmol) was added. Iodine (30.7 g, 121 mmol) was added in portions at room temperature. The reaction was monitored with HPLC for the completion of the reaction. Ether and saturated sodium thiosulphate were added. The organic layer was separated, dried and column chromatographed with EA:hexane (1:3) yielded 1-(m-tolyl)-1H-imidazole-5-carbonitrile (4.0 g, 21.8 mmol, 27% yield) and 1-(m-tolyl)-1H-imidazole-4-carbonitrile (4.9 g, 26.7 mmol, 33% yield).

Synthesis of 4-cyano-3-methyl-1-(m-tolyl)-1H-imidazol-3-ium trifluoromethanesulfonate (LA2)

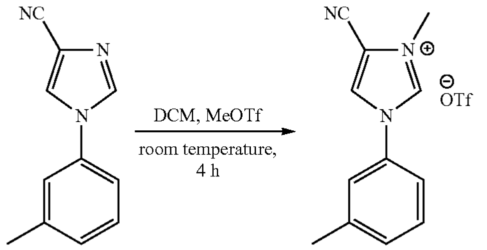

To a stirred solution of 1-(m-tolyl)-1H-imidazole-4-carbonitrile (2.0 g, 10.9 mmol) in DCM (30 mL), methyl trifluoromethanesulfonate (2.0 g, 12.0 mmol) was added and stirred at room temperature for 4 hours. The precipitate was filtered and washed with diethyl ether yielded 4-cyano-3-methyl-1-(m-tolyl)-1H-imidazol-3-ium trifluoromethanesulfonate (3.4 g, 9.8 mmol, 90% yield).

Synthesis of 5-cyano-3-methyl-1-(m-tolyl)-1H-imidazol-3-ium trifluoromethanesulfonate (LA23)

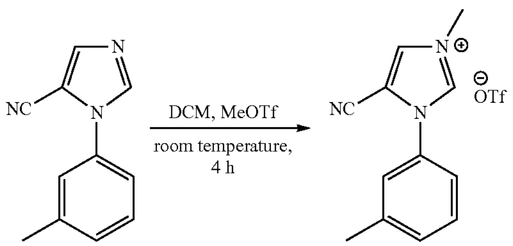

To a stirred solution of 1-(m-tolyl)-1H-imidazole-5-carbonitrile (2 g, 10.9 mmol) in DCM (30 mL), methyl trifluoromethanesulfonate (1.8 g, 10.9 mmol) was added and stirred at room temperature for 4 hours. The precipitate was filtered and washed with diethyl ether yielded 5-cyano-3-methyl-1-(m-tolyl)-1H-imidazol-3-ium trifluoromethanesulfonate (3.2 g, 9.2 mmol, 84% yield).

Synthesis of 1-(3,5-dimethylphenyl)-1H-imidazole-4-carbaldehyde and 1-(3,5-dimethylphenyl)-1H-imidazole-5-carbaldehyde

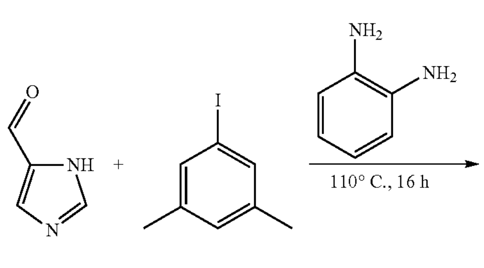

-continued

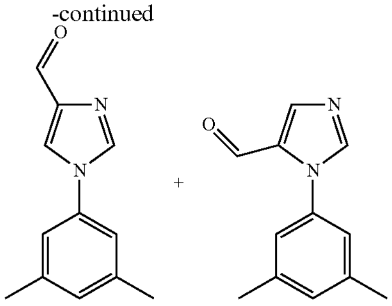

To a stirred solution of 1H-imidazole-5-carbaldehyde (10 g 104 mmol) in DMF (135 mL), 1-iodo-3,5-dimethylbenzene (18 mL, 125 mmol), cyclohexane-1,2-diamine (2.5 mL, 20.8 mmol), cesium carbonate (67.8 g, 208 mmol), copper(I) iodide (0.991 g, 5.2 mmol) were added. The solution mixture was stirred at 110° C. for about 16 hours. The reaction was precipitated in water and filtered. The residue was column chromatographed with THF:hexane (1:4). The crude (a mixture of 1-(3,5-dimethylphenyl)-1H-imidazole-4-carbaldehyde and 1-(3,5-dimethylphenyl)-1H-imidazole-5-carbaldehyde, 18 g) was used for next step without further purification.

Synthesis of 1-(3,5-dimethylphenyl)-1H-imidazole-5-carbonitrile and 1-(3,5-dimethylphenyl)-1H-imidazole-4-carbonitrile

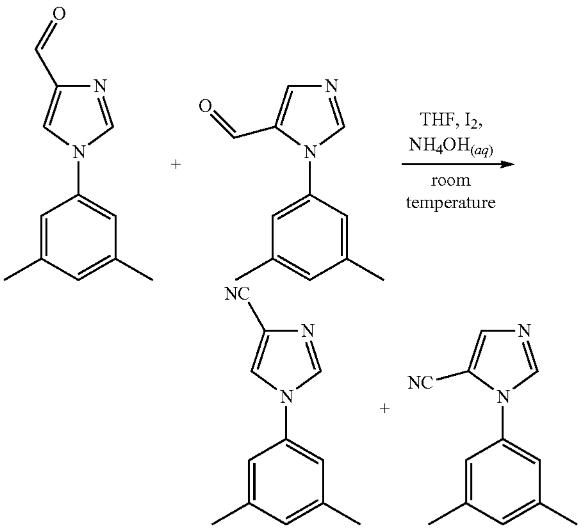

To a stirred solution of a mixture of 15.0 g of 1-(3,5-dimethylphenyl)-1H-imidazole-4-carbaldehyde and 1-(3,5-dimethylphenyl)-1H-imidazole-5-carbaldehyde in THF (88 mL), ammonium hydroxide (44 mL, 375 mmol) was added. Iodine (28.5 g, 112 mmol) was added in portions at room temperature. The reaction was monitored with HPLC for the completion of the reaction. Ether and saturated sodium thiosulphate were added. The organic layer was separated, dried and column chromatographed with THF:hexane (1:4) yielded 1-(3,5-dimethylphenyl)-1H-imidazole-5-carbonitrile (0.4 g, 2.0 mmol, 2.7% yield) and 1-(3,5-dimethylphenyl)-1H-imidazole-4-carbonitrile (2.0 g, 10.1 mmol, 14% yield).

Synthesis of 4-cyano-1-(3,5-dimethylphenyl)-3-methyl-1H-imidazol-3-ium trifluoromethanesulfonate (LA7)

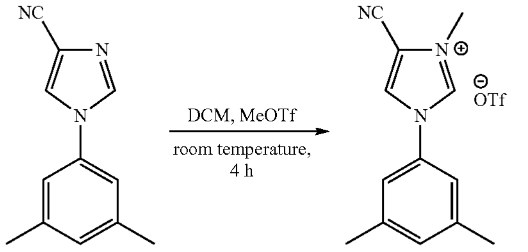

To a stirred solution of 1-(3,5-dimethylphenyl)-1H-imidazole-4-carbonitrile (1.6 g, 8.1 mmol) in DCM (25 mL), methyl trifluoromethanesulfonate (1.3 g, 8.1 mmol) was added and stirred at room temperature for 4 hours. The precipitate was filtered and washed with DCM yielded 4-cyano-1-(3,5-dimethylphenyl)-3-methyl-1H-imidazol-3-ium trifluoromethanesulfonate (2.4 g, 6.6 mmol, 82% yield).

Synthesis of 5-cyano-1-(3,5-dimethylphenyl)-3-methyl-1H-imidazol-3-ium trifluoromethanesulfonate (LA28)

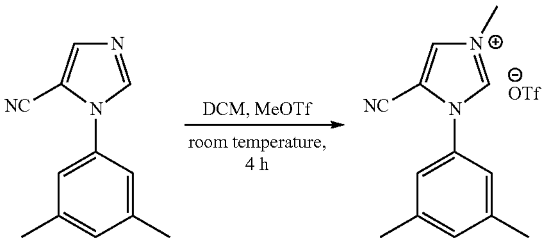

To a stirred solution of 1-(3,5-dimethylphenyl)-1H-imidazole-5-carbonitrile (0.4 g, 2.0 mmol) in DCM (3 mL), methyl trifluoromethanesulfonate (0.3 g, 2.0 mmol) was added and stirred at room temperature for 4 hours. The precipitate was filtered and washed with DCM yielded 5-cyano-1-(3,5-dimethylphenyl)-3-methyl-1H-imidazol-3-ium trifluoromethanesulfonate (0.5 g, 1.5 mmol, 72.3% yield).

Synthesis of 2-nitro-3-(phenylamino)benzonitrile

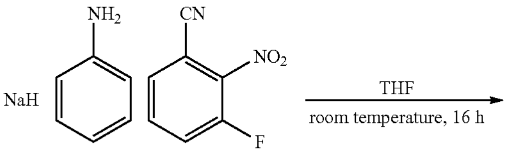

-continued

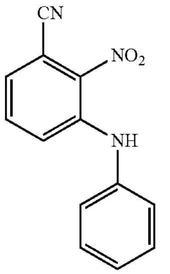

Aniline (2.75 mL, 30.1 mmol) was added into THF (60 mL). Sodium hydride (0.867 g, 36.1 mmol) was added and stirred for 1 hour. 3-Fluoro-2-nitrobenzonitrile (5 g, 30.1 mmol) was added and stirred for about 16 hours at room temperature. Water (2 mL) was added to quench the unreacted sodium hydride. The solvent was then evaporated and the residue was then purified by column chromatography using THF:hexane (1:4, v/v) as the eluent. 6.0 g (83% yield) of a red solid was obtained.

Synthesis of 2-amino-3-(phenylamino)benzonitrile

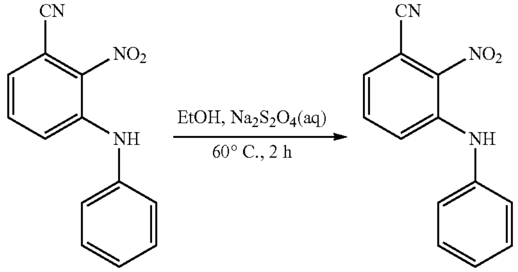 [SMILES: N#Cc1cccc(Nc2ccccc2)c1[N+](=O)[O-] ; N#Cc1cccc(Nc2ccccc2)c1[N+](=O)[O-]]

2-Nitro-3-(phenylamino)benzonitrile (6 g, 25 mmol) was dissolved in ethanol (200 mL). Sodium dithionite (26 g, 150 mmol) was dissolved in water (200 mL) and added to the ethanol solution. The reaction mixture was heated at 60° C. for 2 hours. The reaction was cooled down to room temperature and filtered off the insoluble inorganic salt. The filtrate was then evaporated and the residue was then purified by column chromatography using THF:hexane (1:4, v/v) as the eluent. 3.0 g (57% yield) of a pale yellow oil was obtained.

Synthesis of 1-phenyl-1H-benzo[d]imidazole-4-carbonitrile

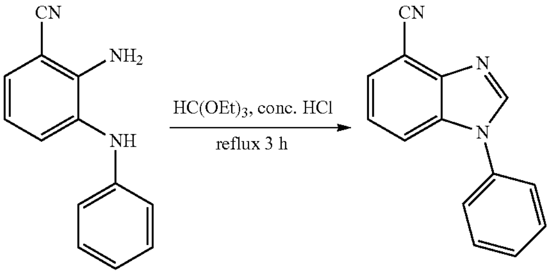 [SMILES: N#Cc1cccc(Nc2ccccc2)c1N ; N#Cc1cccc2c1ncn2-c1ccccc1]

2-Amino-3-(phenylamino)benzonitrile (3 g, 14.3 mmol) was dissolved in triethyl orthoformate (40 mL, 239 mmol). 12.4 M hydrochloric acid (2 mL) was added and heated at 140° C. for 3 hours. The solvent was then evaporated and the residue was then purified by boiling by heptane:toluene (9:1). 2.5 g (83% yield) of an off-white solid was obtained.

Synthesis of 4-cyano-3-methyl-1-phenyl-1H-benzo[d]imidazol-3-ium iodide (LA43)

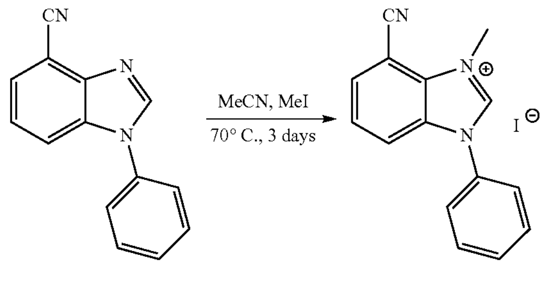 [SMILES: N#Cc1cccc2c1ncn2-c1ccccc1 ; C[n+]1cn(-c2ccccc2)c2cccc(C#N)c21 ; [I-]]

1-Phenyl-1H-benzo[d]imidazole-4-carbonitrile (2.5 g, 11.4 mmol) was dissolved in MeCN. Iodomethane (40 mL, 2M in tert-butyl methyl ether) was added and heated at 70° C. for 3 days. The solid formed was filtered and washed by diethyl ether. The off white solid was further purified by boiling by 1,2-dimethoxyethane:MeCN (19:1). 2.6 g (65% yield) of a white solid was obtained.

Synthesis of $Ir(LA43)_3$

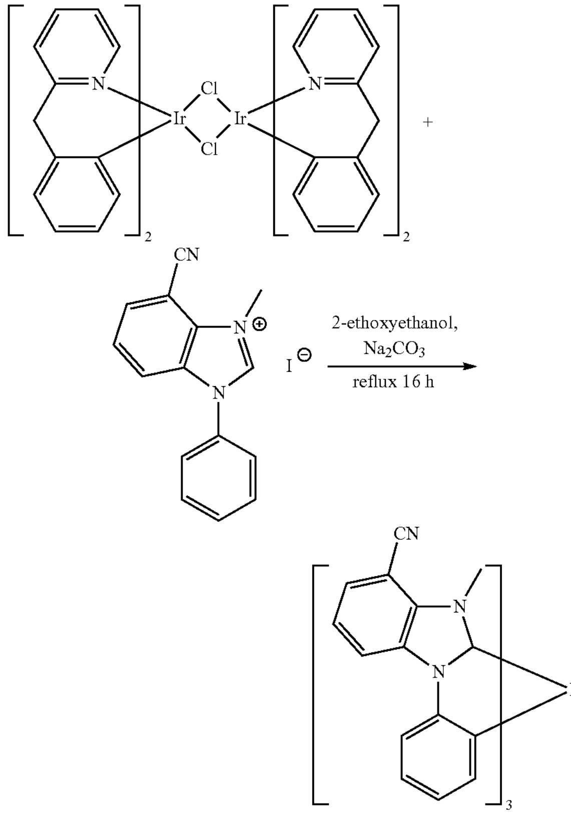

A mixture of LA43 (1.02 g, 2.83 mmol), sodium carbonate (0.100 g, 0.940 mmol) and 2-benzylpyridine iridium (IIII) chloro dimer (0.530 g, 0.470 mmol) in 2-ethoxyethanol (10 mL) was degassed using vacuum/backfill cycles and heated at reflux under nitrogen for 16 hours. The mixture was cooled to room temperature, diluted with water and extracted three times with DCM. The organic extracts were washed with brine, dried with $MgSO_4$, and coated on celite. Purification by column chromatography yielded 71 mg (9% yield) of mer-$Ir(LA43)_3$ and 230 mg (28% yield) of fac-Ir$(LA43)_3$, both as pale yellow solids.

Synthesis of 2-nitro-3-(tolylamino)benzonitrile

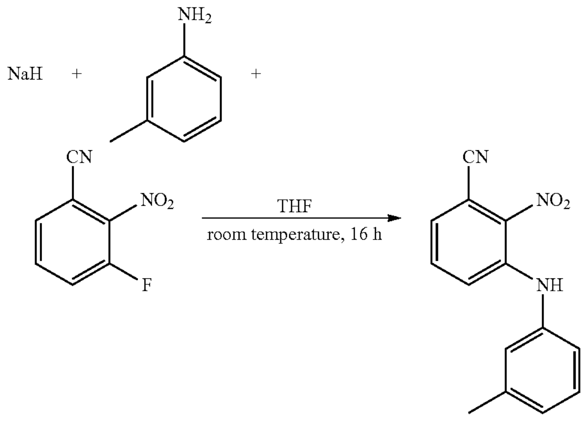

m-Toluidine (3.87 mL, 36.1 mmol) was added into THF (60 mL). Sodium hydride (1.1 g, 45.2 mmol) was added and stirred for 1 hour. 3-Fluoro-2-nitrobenzonitrile (5.0 g, 30.1 mmol) was added and stirred for 16 hours at room temperature. Water (2 mL) was added to quench the unreacted sodium hydride. The solvent was then evaporated and the residue was then purified by column chromatography using THF:hexane (1:4, v/v) as the eluent. 6.0 g (79% yield) of a red solid was obtained.

Synthesis of 2-amino-3-(tolylamino)benzonitrile

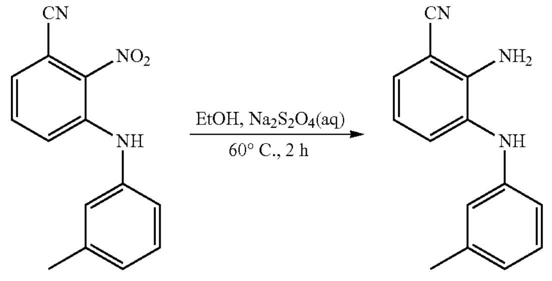 [SMILES: Cc1cccc(Nc2cccc(C#N)c2[N+](=O)[O-])c1 ; "EtOH, Na2S2O4(aq)" ; Cc1cccc(Nc2cccc(C#N)c2N)c1]

2-Nitro-3-(tolylamino)benzonitrile (6 g, 23.7 mmol) was dissolved in ethanol (200 mL). Sodium dithionite (26 g, 150 mmol) was dissolved in water (200 mL) and added to the ethanol solution. The reaction mixture was heated at 60° C. for 2 hours. The reaction was cooled down to room temperature and filtered off the insoluble inorganic salt. The filtrate was then evaporated and the residue was then purified by column chromatography using THF:hexane (1:4, v/v) as the eluent. 3.0 g (47% yield) of a pale yellow oil was obtained.

Synthesis of 1-(m-toly)-1H-benzo[d]imidazole-4-carbonitrile

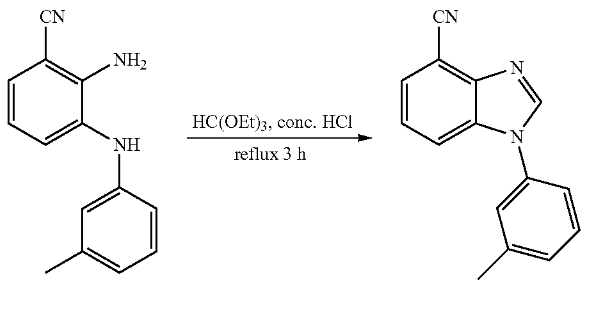 [SMILES: Cc1cccc(Nc2cccc(C#N)c2N)c1 ; "HC(OEt)3, conc. HCl" ; Cc1cccc(-n2cnc3c(C#N)cccc32)c1]

2-Amino-3-(tolylamino)benzonitrile (3.0 g, 13.4 mmol) was dissolved in triethyl orthoformate (40 mL, 239 mmol), 12.4 M hydrochloric acid (2 mL) was added and heated at 140° C. for 3 hours. The solvent was then evaporated and the residue was then purified by boiling by heptane:toluene (9:1). 2.5 g of (80% yield) an off-white solid was obtained.

Synthesis of 4-cyano-3-methyl-1-(m-toly)-1H-benzo[d]imidazol-3-ium iodide (LA44)

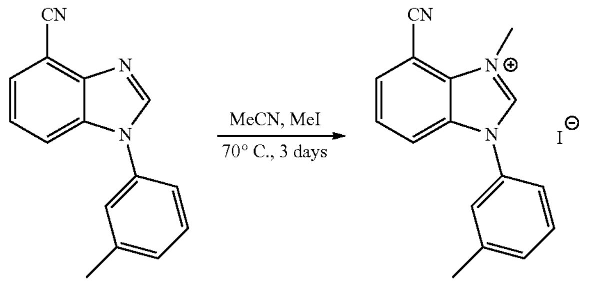

1-(m-Toly)-1H-benzo[d]imidazole-4-carbonitrile (2.5 g, 10.7 mmol) was dissolved in MeCN. Iodomethane (40 mL, 2M in tert-butyl methyl ether) was added and heated at 70° C. for 3 days. The solid formed was filtered and washed by diethyl ether. The off white solid was further purified by boiling by 1,2-dimethoxyethane:MeCN (19:1), 2.6 g (67% yield) of a white solid was obtained.

Synthesis of $Ir(LA44)_3$

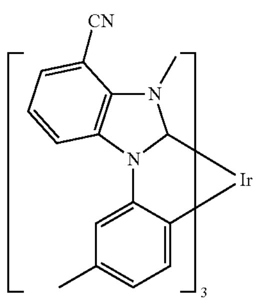

Synthesis of $Ir(LA44)_3$ was prepared from LA44 according to the general iridium complexation procedure as described for $Ir(LA43)_3$ to afford 24% yield of fac-$Ir(LA44)_3$ and 3% yield of mer-$Ir(LA44)_3$ as pale yellow solids.

Synthesis of 2-nitro-2-(tolylamino)benzonitrile

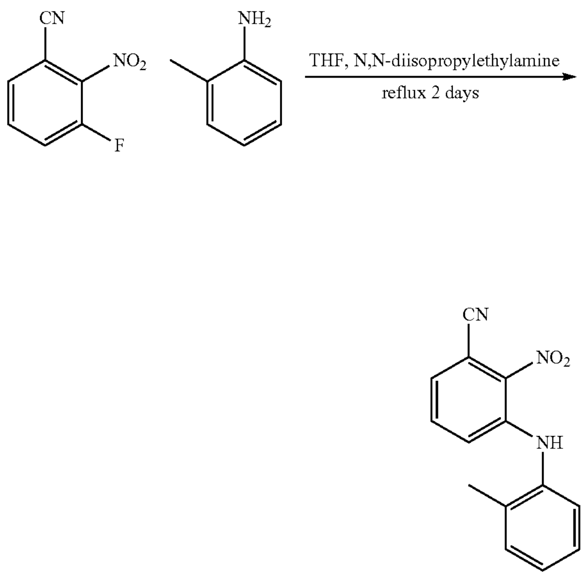

o-Toluidine (2.75 g, 29 mmol) and 3-fluoro-2-nitrobenzonitrile (4.5 g, 27.1 mmol) was added into THF (20 mL) and N,N-diisopropylethylamine (20 mL) and heated at 85° C. for 2 days. The solvent was then evaporated and the residue was then purified by column chromatography using THF:hexane (1:4, v/v) as the eluent. 4.5 g (67% yield) of a red solid was obtained.

Synthesis of 2-amino-2-(tolylamino)benzonitrile

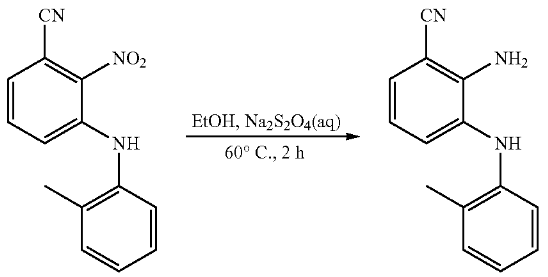 [SMILES: Cc1ccccc1Nc1cccc(C#N)c1[N+](=O)[O-] ; "EtOH, Na2S2O4(aq)" ; Cc1ccccc1Nc1cccc(C#N)c1N]

2-Nitro-2-(tolylamino)benzonitrile (4.5 g, 18.1 mmol) was dissolved in ethanol (200 mL), sodium dithionite (18.8 g, 108 mmol) was dissolved in water (200 mL) and added to the ethanol solution. The reaction mixture was heated at 60° C. for 2 hours. The reaction was cooled down to room temperature and filtered off the insoluble inorganic salt. The filtrate was then evaporated and the residue was then purified by column chromatography using THF:hexane (1:4, v/v) as the eluent. 2.0 g (49% yield) of a pale yellow oil was obtained.

Synthesis of 1-(o-toly)-1H-benzo[d]imidazole-4-carbonitrile

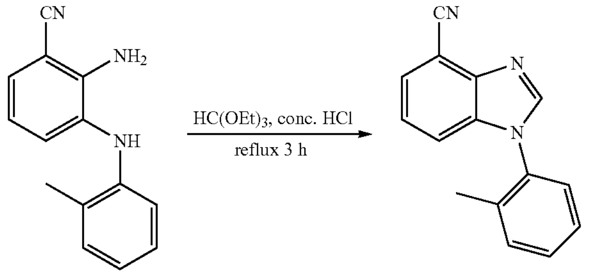 [SMILES: Cc1ccccc1Nc1cccc(C#N)c1N ; "HC(OEt)3, conc. HCl" ; Cc1ccccc1-n1cnc2c(C#N)cccc21]

2-Amino-2-(tolylamino)benzonitrile (2 g, 9 mmol) was dissolved in triethyl orthoformate (20 mL, 120 mmol), 12.4 M hydrochloric acid (2 mL) was added and heated at 140° C. for 3 hours. The solvent was then evaporated and the residue was then purified by boiling by heptane:toluene (9:1). 1.7 g (80% yield) of an offwhite solid was obtained.

Synthesis of 4-cyano-3-methyl-1-(o-toly)-1H-benzo[d]imidazol-3-ium iodide (LA46)

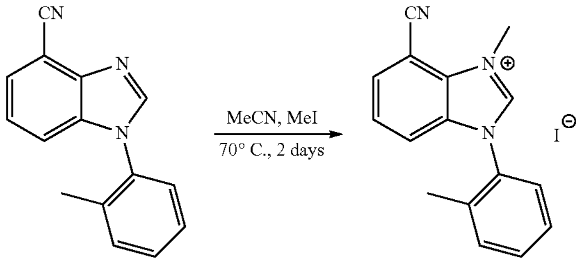

1-(o-toly)-1H-benzo[d]imidazole-4-carbonitrile (1.7 g, 7.2 mmol) was dissolved in MeCN. Iodomethane (40 ml, 2M in tert-butyl methyl ether) was added and heated at 70° C. for 2 days. The solid formed was filtered and washed by diethyl ether. The off white solid was further purified by boiling by 1,2-dimethoxyethane:MeCN (19:1). 1.8 g (67% yield) of a white solid was obtained.

Synthesis of 3-((3,4-dimethylphenyl)amino)-2-nitrobenzonitrile

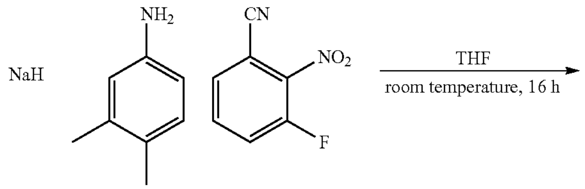

-continued

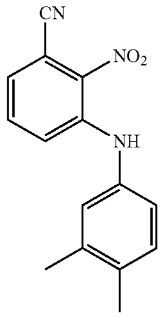

3,4-Dimethylaniline (4.4 g, 36.1 mmol) was added into THF (60 mL). Sodium hydride (1.1 g, 45.2 mmol) was added and stirred for 1 hour. 3-Fluoro-2-nitrobenzonitrile (5 g, 30.1 mmol) was added and stirred for about 16 hours at room temperature. Water (2 mL) was added to quench the unreacted sodium hydride. The solvent was then evaporated and the residue was then purified by column chromatography using THF:hexane (1:4, v/v) as the eluent. 6.5 g (81% yield) of a red solid was obtained.

Synthesis of 2-amino-3-((3,4-dimethylphenyl)amino)benzonitrile

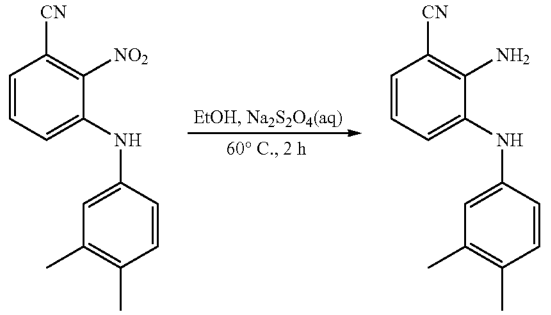 [SMILES: Cc1ccc(Nc2cccc(C#N)c2[N+](=O)[O-])cc1C ; "EtOH, Na2S2O4(aq)" ; Cc1ccc(Nc2cccc(C#N)c2N)cc1C]

2-Nitro-3-(3,4-dimethylphenyl)benzonitrile (6.5 g, 24.3 mmol) was dissolved in ethanol (200 mL). Sodium dithionite (26 g, 150 mmol) was dissolved in water (200 mL) and added to the ethanol solution. The reaction mixture was heated at 60° C. for 2 hours. The reaction was cooled down to room temperature and filtered off the insoluble inorganic salt. The filtrate was then evaporated and the residue was then purified by column chromatography using THF:hexane (1:4, v/v) as the eluent. 3.0 g (52% yield) of a pale yellow oil was obtained.

Synthesis of 1-(3,4-dimethylphenyl)-1H-benzo[d]imidazole-4-carbonitrile

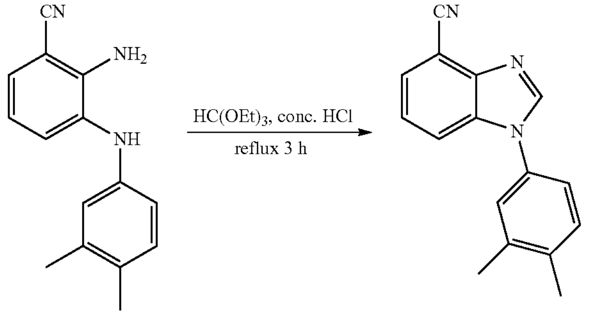 [SMILES: Cc1ccc(Nc2cccc(C#N)c2N)cc1C ; "HC(OEt)3, conc. HCl" ; Cc1ccc(-n2cnc3c(C#N)cccc32)cc1C]

2-Amino-3-(3,4-dimethylphenyl)benzonitrile (3.0 g, 12.6 mmol) was dissolved in triethyl orthoformate (40 mL, 239 mmol). 12.4 M hydrochloric acid (2 mL) was added and heated at 140° C. for 3 hours. The solvent was then evaporated and the residue was then purified by boiling by heptane:toluene (9:1). 2.5 g (79% yield) of an off-white solid was obtained.

Synthesis of 4-cyano-3-methyl-1-(3,4-dimethylphenyl)-1H-benzo[d]imidazol-3-ium iodide (LA47)

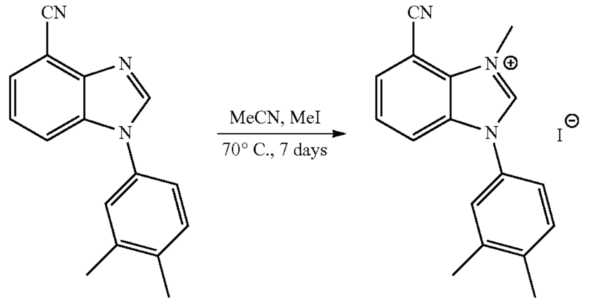

1-(3,4-Dimethylphenyl)-1H-benzo[d]imidazole-4-carbonitrile (2.5 g, 10.1 mmol) was dissolved in MeCN. Iodomethane (40 mL, 2M in tert-butyl methyl ether) was added and heated at 70° C. for 7 days. The solid formed was filtered and washed by diethyl ether. The off white solid was further purified by boiling by 1,2-dimethoxyethane:MeCN (19:1). 2.6 g (69% yield) of a white solid was obtained.

Synthesis of $Ir(LA47)_3$

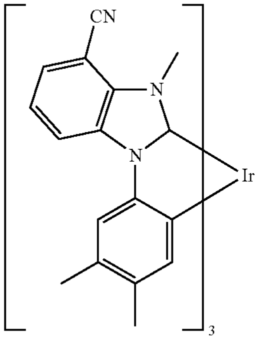

Synthesis of $Ir(LA47)_3$ was prepared from LA47 according to the general iridium complexation procedure as described for $Ir(LA43)_3$ to afford 0.5% yield of fac-Ir $(LA47)_3$ as a pale yellow solid.

Synthesis of 3-((3,5-dimethylphenyl)amino)-2-nitrobenzonitrile

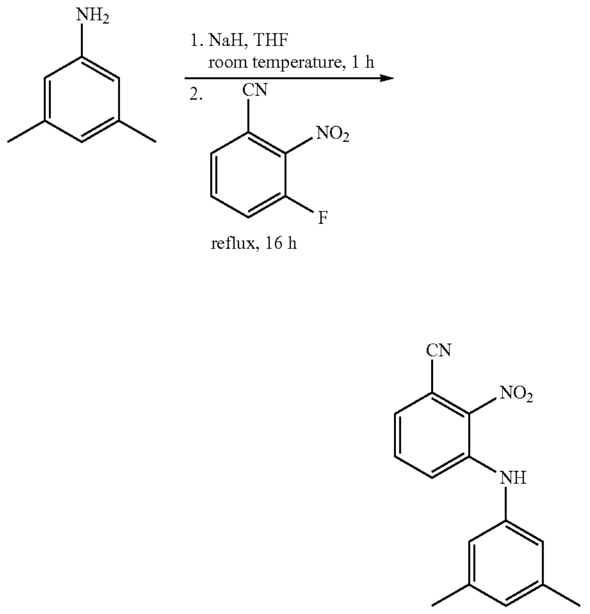

To 3,5-dimethylaniline (3.9 g, 32.2 mmol) in THF (90 mL) was added sodium hydride (95% in mineral oil, 1.23 g, 48.9 mmol) and stirred for 1 hour. 3-Fluoro-2-nitrobenzonitrile (4.3 g, 25.9 mmol) was added and the reaction mixture was heated to reflux for about 16 hours. Reaction mixture cooled to room temperature, then water was added and filtered through silica gel, washed with 5% THF in hexane and concentrated in vacuo. The crude mixture was purified by flash column chromatography with 10% THF in hexane to give orange powder which was recrystallised with 10% 1,2-dimethoxyethane in hexane to give 3-((3,5-dimethylphenyl)amino)-2-nitrobenzonitrile (3.8 g, 55% yield) as an orange powder.

Synthesis of 2-amino-3-((3,5-dimethylphenyl)amino)benzonitrile

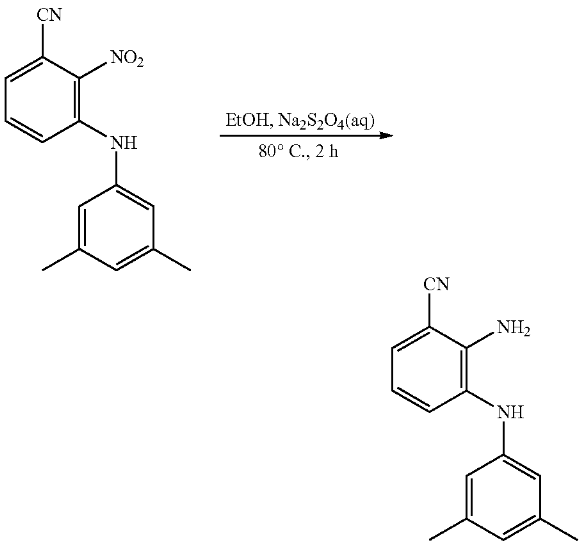

A mixture of 3-((3,5-dimethylphenyl)amino)-2-nitrobenzonitrile (3.8 g, 14.31 mmol) in EtOH (150 mL) and $Na_2S_2O_4$ (14.9 g, 85 mmol) in water (110 mL) was heated to 80° C. for 2 hours. Reaction mixture was filtered, the filtrate was concentrated and filtered through a Celite/$MgSO_4$ pad and concentrated in vacuo. The crude mixture was purified by flash column chromatography with 10% THF in hexane to give 2-amino-3-((3,5-dimethylphenyl)amino)benzonitrile (2.8 g, 82% yield) as off-white powder.

Synthesis of 1-(3,5-dimethylphenyl)-1H-benzo[d]imidazole-4-carbonitrile

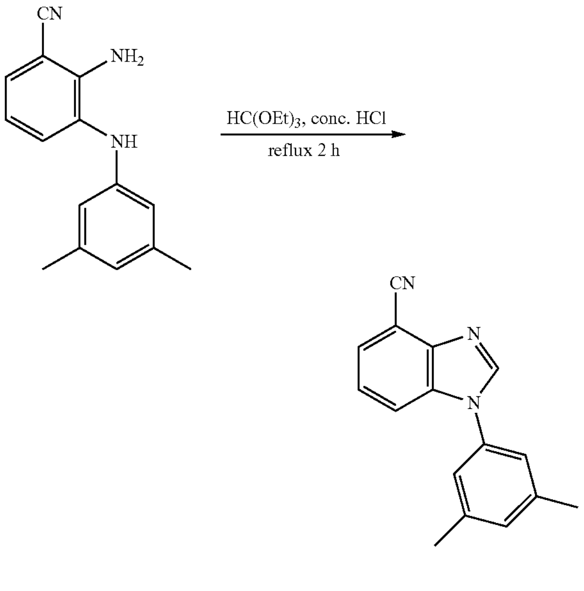

A mixture of 2-amino-3-((3,5-dimethylphenyl)amino)benzonitrile (2.8 g, 11.81 mmol) in triethyl orthoformate (30 mL) was added concentrated HCl (2.0 mL, 24.0 mmol) and heated to reflux for 2 hours. Reaction mixture cooled to room temperature and concentrated in vacuo. The crude mixture was purified by flash column chromatography with 10-20% THF in hexane to give 1-(3,5-dimethylphenyl)-1H-benzo[d]imidazole-4-carbonitrile (2.5 g, 87% yield) as white powder.

Synthesis of 4-cyano-1-(3,5-dimethylphenyl)-3-methyl-1H-benzo[d]imidazol-3-ium trifluoromethanesulfonate (LA49)

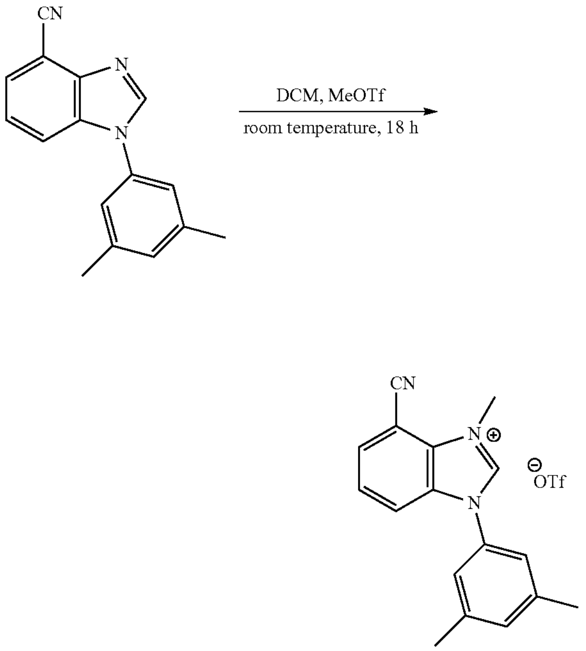

A mixture of 1-(3,5-dimethylphenyl)-1H-benzo[d]imidazole-4-carbonitrile (2.5 g, 10.23 mmol) and methyl trifluoromethanesulfonate (1.8 mL, 16.3 mmol) in DCM (50 mL) was stirred for 18 hours. Solid formed was filtered (4.0 g) and the white powder was recrystallised with 10% 1,2-dimethoxyethane in hexane to give 4-cyano-1-(3,5-dimethylphenyl)-3-methyl-1H-benzo[d]imidazol-3-ium trifluoromethanesulfonate (3.6 g, 86% yield) as white powder.

Synthesis of $Ir(LA49)_3$

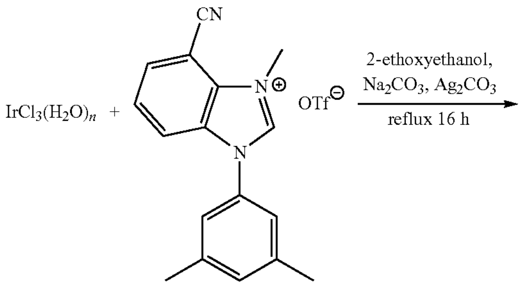

-continued

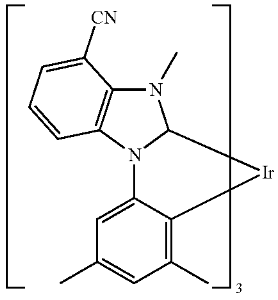

A mixture of LA49 (0.82 g, 2.0 mmol), sodium carbonate (0.21 g, 2.0 mmol), silver carbonate (0.55 g, 2.0 mmol), and iridium (III) chloride hydrate (0.22 g, 0.6 mmol) in 2-ethoxyethanol (15. mL) was degassed using vacuum/backfill cycles and heated at reflux for 16 hours. This reaction was combined with another reaction run at 50%-scale and then diluted with water and extracted three times with DCM. The combined organic layers were dried, coated on celite, and purified by column chromatography to yield 29 mg (3%) of mer-Ir(LA49)$_3$ as a pale yellow solid.

Synthesis of 2-nitro-3-((3,4,5-trimethylphenyl)amino)benzonitrile

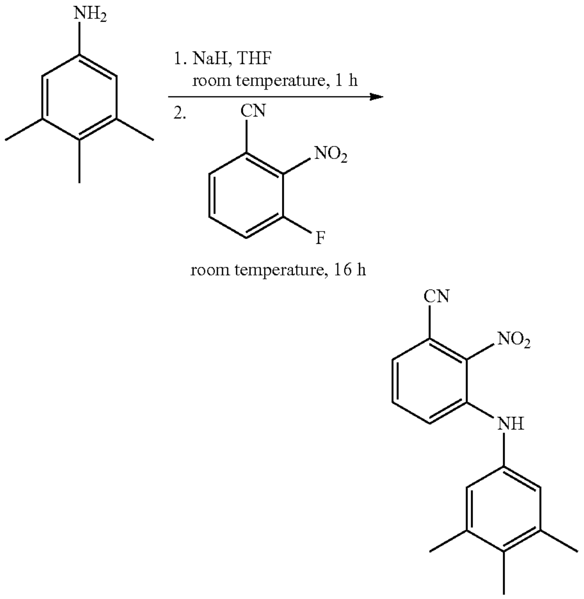

3,4,5-Trimethylaniline (4.9 g, 36.1 mmol) was added into THF (60 mL). Sodium hydride (1.1 g, 45.2 mmol) was added and stirred for 1 hour. 3-Fluoro-2-nitrobenzonitrile (5.0 g, 30.1 mmol) was added and stirred for about 16 hours at room temperature. Water (2 mL) was added to quench the unreacted sodium hydride. The reaction mixture was concentrated in vacuo and the residue was purified by flash column chromatography using THF:hexane (1:4, v/v) as the eluent to give 2-nitro-3-((3,4,5-trimethylphenyl)amino)benzonitrile (7.0 g, 82% yield) as red solid.

Synthesis of 2-amino-3-((3,4,5-trimethylphenyl)amino)benzonitrile

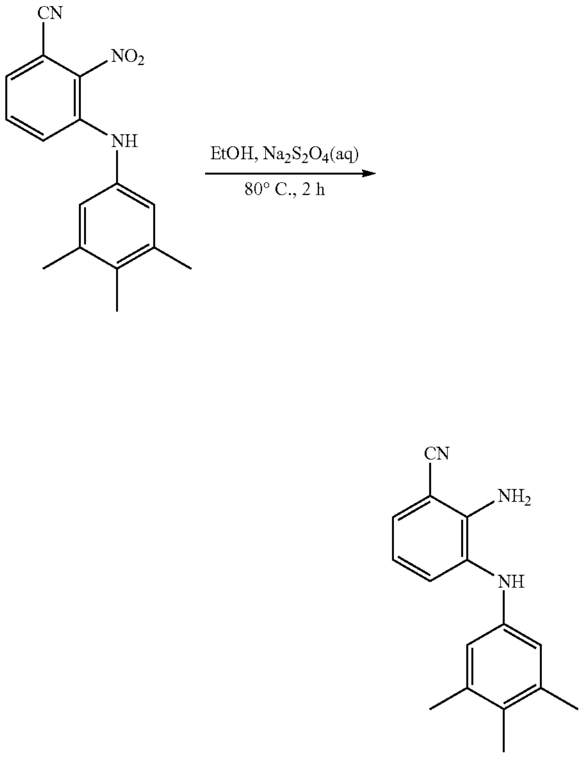

A mixture of 2-nitro-3-((3,4,5-trimethylphenyl)amino)benzonitrile (6.56 g, 23.4 mmol) in EtOH (275 mL), THF (25 mL) and $Na_2S_2O_4$ (20.3 g, 117 mmol) in water (200 mL) was heated to 80° C. for 2 hours. Reaction mixture was filtered. The filtrate was concentrated and filtered through a Celite/$MgSO_4$ pad and concentrated in vacuo. The crude mixture was purified by flash column chromatography with 5-15% THF in hexane to give white powder (3.1 g) which was recrystallised with 10% 1,2-dimethoxyethane in heptane to give 2-amino-3-((3,4,5-trimethylphenyl)amino)benzonitrile (2.6 g, 44% yield) as white powder.

Synthesis of 1-(3,4,5-trimethylphenyl)-1H-benzo[d]imidazole-4-carbonitrile

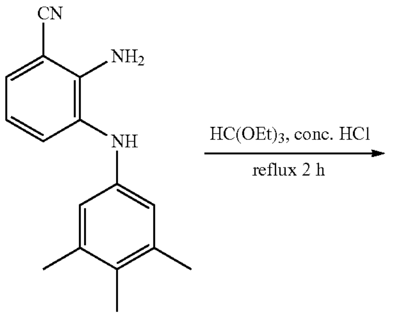

-continued

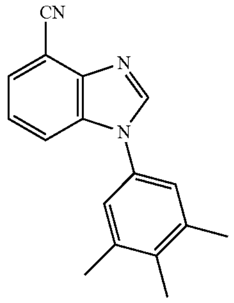

A mixture of 2-amino-3-((3,4,5-trimethylphenyl)amino) benzonitrile (2.6 g, 10.3 mmol) in triethyl orthoformate (30 mL) was added concentrated HCl (1.8 mL, 21.6 mmol) and heated to reflux for 2 hours. Reaction mixture cooled to room temperature and concentrated in vacuo. The crude mixture was purified by flash column chromatography with 5-10% THF in hexane to give 1-(3,4-dimethylphenyl)-1H-benzo[d]imidazole-6-carbonitrile (2.6 g, 96% yield) as white powder.

Synthesis of 4-cyano-3-methyl-1-(3,4,5-trimethylphenyl)-1H-benzo[d]imidazol-3-ium trifluoromethanesulfonate (LA51)

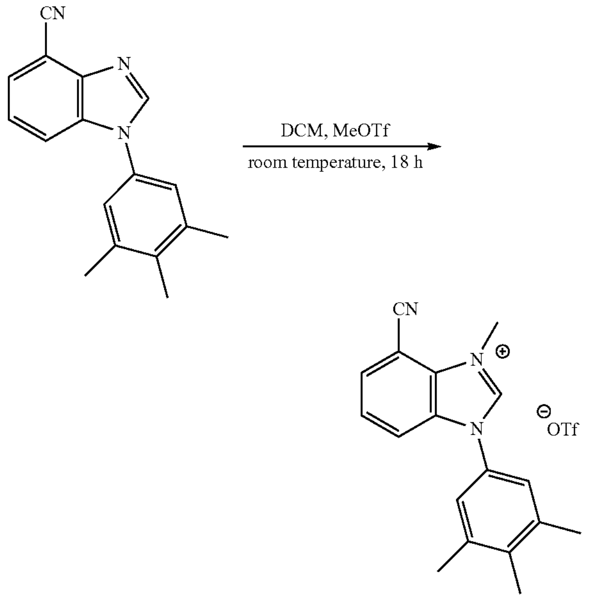

A mixture of 1-(3,4-dimethylphenyl)-1H-benzo[d]imidazole-6-carbonitrile (2.6 g, 10.0 mmol) and methyl trifluoromethanesulfonate (1.8 mL, 15.91 mmol) in DCM (100 mL) was stirred for 18 h. Reaction mixture was concentrated to 40-50 mL and added diethyl ether (30 mL). The solid formed was filtered and the white powder was recrystallised with 10% 1,2-dimethoxyethane in MeCN to give 4-cyano-3-methyl-1-(3,4,5-trimethylphenyl)-1H-benzo[d]imidazol-3-ium trifluoromethanesulfonate (2.3 g, 51% yield) as white powder.

Synthesis of 3-([1,1'-biphenyl]-3-ylamino)-2-nitrobenzonitrile

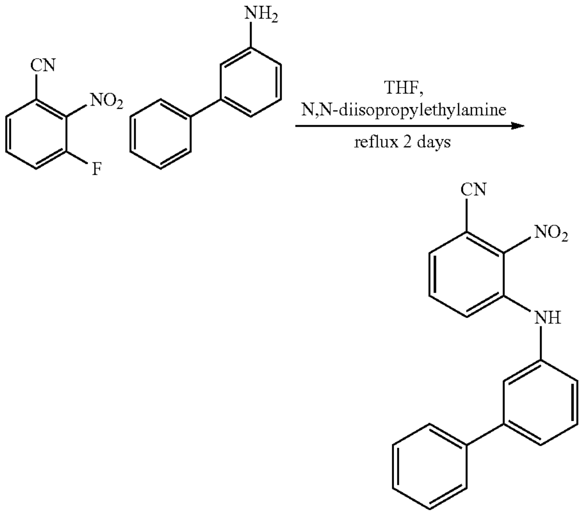

Biphenylamine (4.6 g, 27 mmol) and 3-fluoro-2-nitrobenzonitrile (5.0 g, 30.1 mmol) was added into THF (20 mL) and N,N-diisopropylethylamine (20 mL) and heated at 85° C. for 2 days. The solvent was then evaporated and the residue was then purified by column chromatography using THF:hexane (1:4, v/v) as the eluent. 7.0 g (82% yield) of a red solid was obtained.

Synthesis of 3-([1,1'-biphenyl]-3-ylamino)-2-aminobenzonitrile

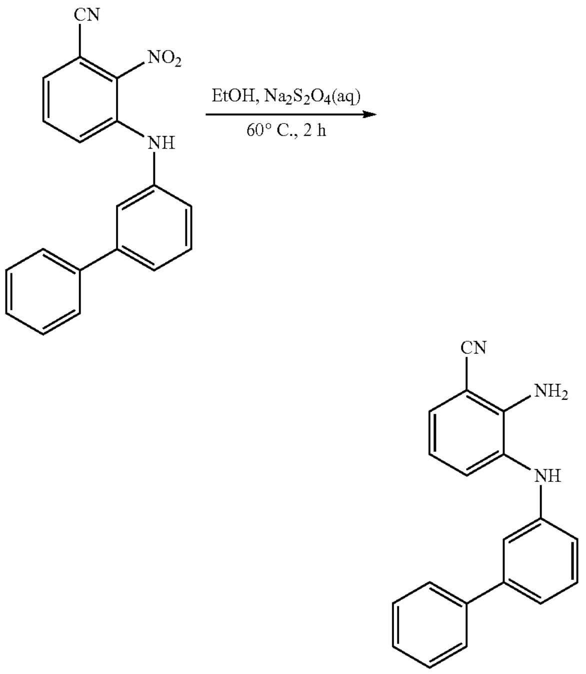

3-([1,1'-Biphenyl]-3-ylamino)-2-nitrobenzonitrile (7.0 g, 22 mmol) was dissolved in ethanol (200 mL). Sodium dithionite (26 g, 150 mmol) was dissolved in water (200 mL) and added to the ethanol solution. The reaction mixture was heated at 60° C. for 2 hours. The reaction was cooled down to room temperature and filtered off the insoluble inorganic salt. The filtrate was then evaporated and the residue was then purified by column chromatography using THF:hexane (1:4, v/v) as the eluent. 3.5 g (56% yield) of a pale yellow oil was obtained.

Synthesis of 1-([1,1'-biphenyl]-3-yl)-1H-benzo[d]imidazole-4-carbonitrile

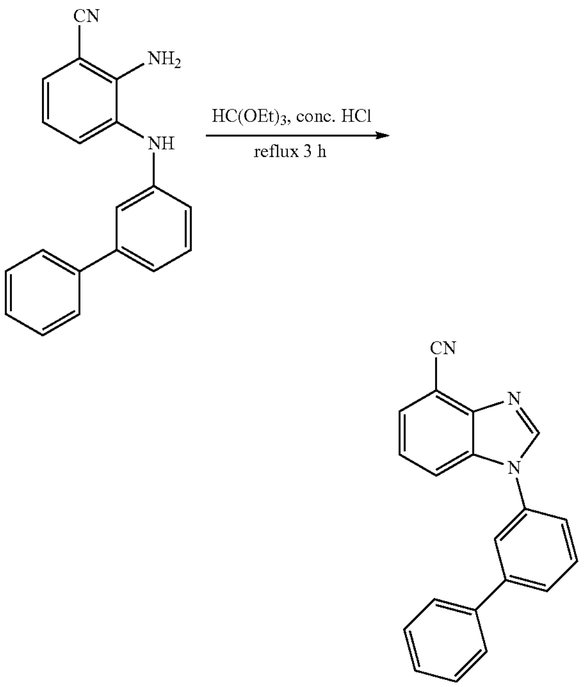

3-([1,1'-Biphenyl]-3-ylamino)-2-aminobenzonitrile (3.5 g, 12.2 mmol) was dissolved in triethyl orthoformate (40 mL, 239 mmol), 12.4 M hydrochloric acid (2 mL) was added and heated at 140° C. for 3 hours. The solvent was then evaporated and the residue was then purified by boiling by heptane:toluene (9:1). 3.0 g (82% yield) of an off-white solid was obtained.

Synthesis of 1-([1,1'-biphenyl]-3-yl)-4-cyano-3-methyl-1H-benzo[d]imidazol-3-ium iodide (LA55)

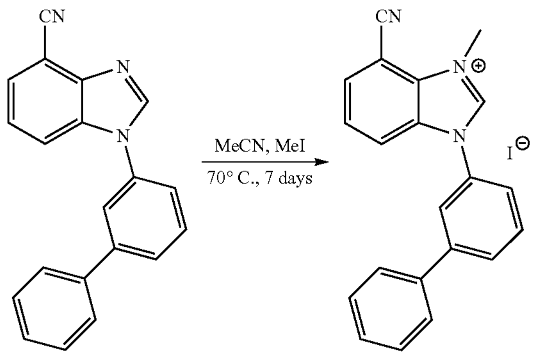 [SMILES: N#Cc1cccc2c1ncn2-c1cccc(-c2ccccc2)c1 ; C[n+]1cn(-c2cccc(-c3ccccc3)c2)c2cccc(C#N)c21 ; [I-]]

1-([1,1'-Biphenyl]-3-yl)-1H-benzo[d]imidazole-4-carbonitrile (3.0 g, 10.1 mmol) was dissolved in MeCN. Iodomethane (40 mL, 2M in tert-butyl methyl ether) was added and heated at 70° C. for 7 days. The solid formed was filtered and washed by diethyl ether. The off white solid was further purified by boiling by 1,2-dimethoxyethane:MeCN (19:1). 2.2 g of a white solid was obtained.

Synthesis of 2-nitro-3-(dibenzo[b,d]furan-3-ylamino)benzonitrile

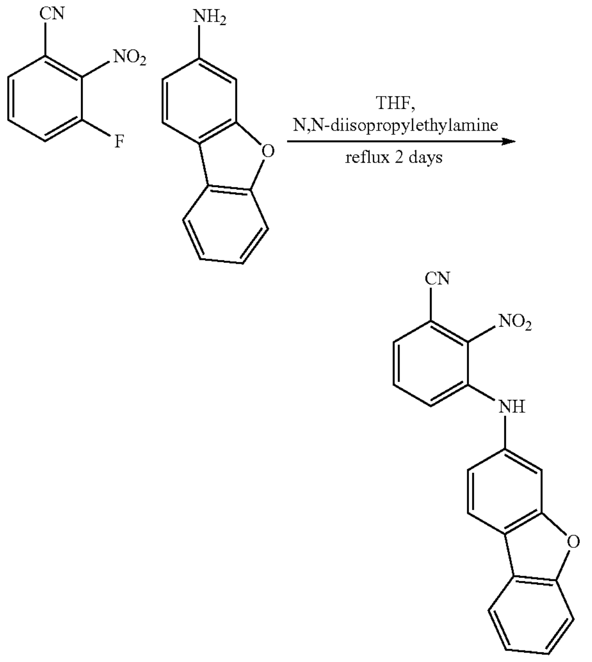

3-Dibenzofuranamine (4.2 g, 23 mmol) and 3-fluoro-2-nitrobenzonitrile (5.0 g, 30.1 mmol) were added into THF (20 mL) and N,N-diisopropylethylamine (20 mL) and heated at 85° C. for 2 days. The solvent was then evaporated and the residue was then purified by column chromatography using THF:hexane (1:4, v/v) as the eluent. 6.0 g (79% yield) of a red solid was obtained.

Synthesis of 2-amino-3-(dibenzo[b,d]furan-3-ylamino)benzonitrile

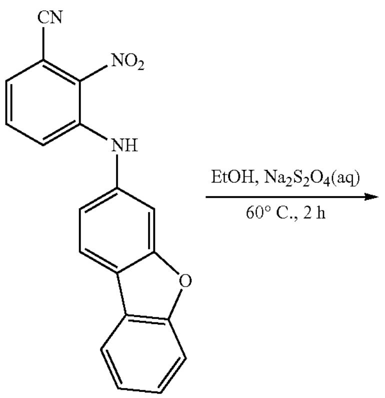

-continued

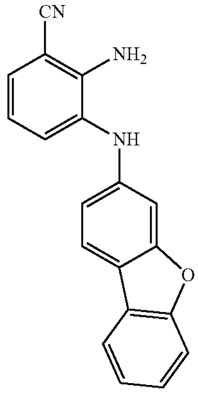

2-Nitro-3-(dibenzo[b,d]furan-3-ylamino)benzonitrile (6.0 g, 18.2 mmol) was dissolved in ethanol (200 mL). Sodium dithionite (26 g, 150 mmol) was dissolved in water (200 mL) and added to the ethanol solution. The reaction mixture was heated at 60° C. for 2 hours. The reaction was cooled down to room temperature and filtered off the insoluble inorganic salt. The filtrate was then evaporated and the residue was then purified by column chromatography using THF:hexane (1:4, v/v) as the eluent. 3.0 g (55% yield) of a pale yellow oil was obtained.

Synthesis of 1-(dibenzo[b,d]furan-3-yl)-1H-benzo[d]imidazole-4-carbonitrile

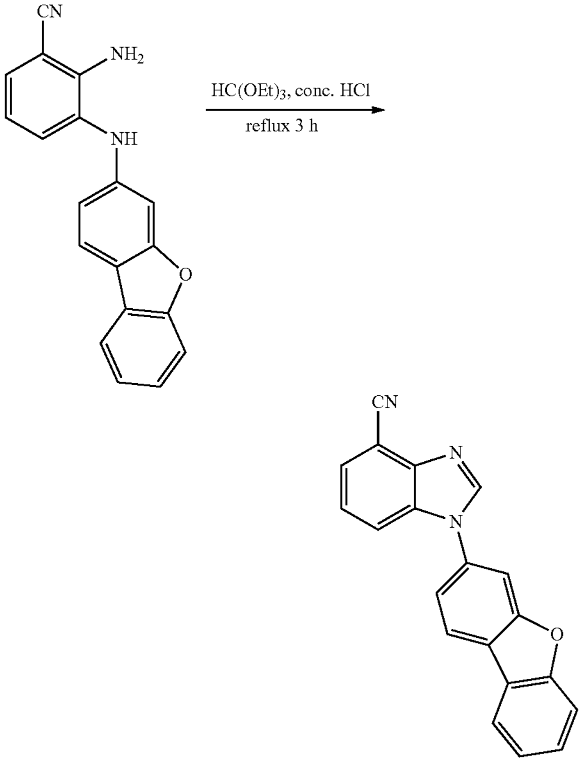

2-Amino-3-(dibenzo[b,d]furan-3-ylamino)benzonitrile (3.0 g, 10 mmol) was dissolved in triethyl orthoformate (40 mL, 239 mmol). 12.4 M hydrochloric acid (2 mL) was added and heated at 140° C. for 3 h. The solvent was then evaporated and the residue was then purified by boiling by heptane:toluene (9:1). 2.5 g (81% yield) of an off-white solid was obtained.

Synthesis of 4-cyano-3-methyl-1-dibenzo[b,d]furan-3-yl-1H-benzo[d]imidazol-3-ium iodide (LA59)

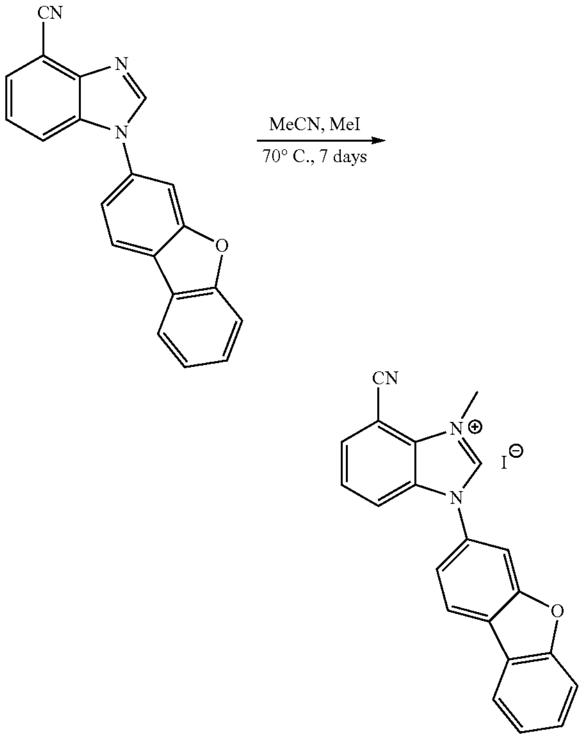

1-(Dibenzo[b,d]furan-3-ylamino)-1H-benzo[d]imidazole-4-carbonitrile (2.5 g, 8.1 mmol) was dissolved in MeCN. Iodomethane (40 mL, 2M in tert-butyl methyl ether) was added and heated at 70° C. for 7 days. The solid formed was filtered and washed by diethyl ether. The off white solid was further purified by boiling by 1,2-dimethoxyethane: MeCN (19:1). 2.6 g (70% yield) of a white solid was obtained.

Synthesis of $Ir(LA59)_3$

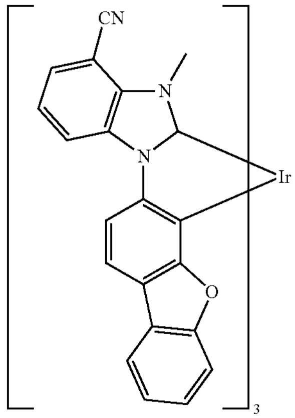

Synthesis of Ir(LA59)$_3$ was prepared from LA59 according to the general iridium complexation procedure as described for Ir(LA43)$_3$ to afford 17% yield of mer-Ir (LA59)$_3$ as a pale yellow solid.

Synthesis of (1-phenyl-1H-benzo[d]imidazol-6-yl) methanol

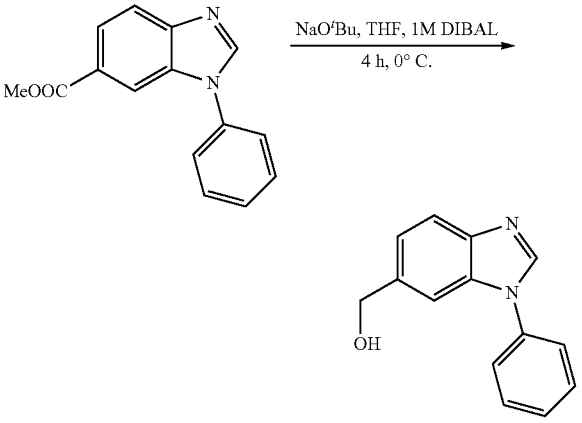

Sodium tert-butoxide (2.5 g, 26.4 mmol) and THF (50 mL) were mixed at 0° C. 1M DIBAL (24 mL, 24.0 mmol) was added at 0° C. The mixture was stirred for 1 h at 0° C. Methyl 1-phenyl-1H-benzo[d]imidazole-6-carboxylate (3.0 g. 12.0 mmol) in THF (50 mL) was added at 0° C. The resultant mixture was stirred for 4 hours at 0° C. The reaction mixture was quenched by the addition of water and extracted with DCM. The extracts were dried over $MgSO_4$ and a silica pad and the solvent was removed in vacuo. The residue was purified by flash chromatography using 5% MeOH in DCM to afford (1-phenyl-1H-benzo[d]imidazol-6-yl)methanol (2.4 g, 88% yield) as a brown oil.

Synthesis of 1-phenyl-1H-benzo[d]imidazole-6-carbaldehyde

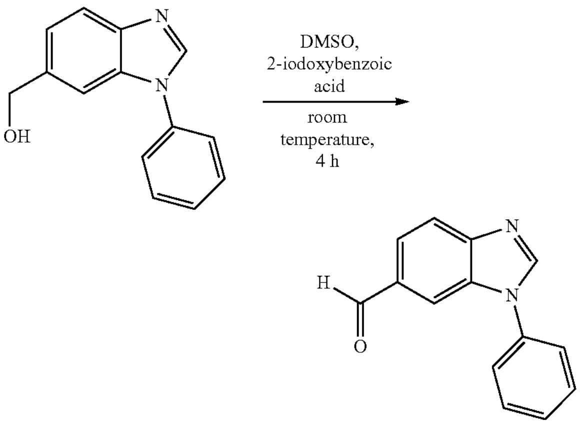

45% 2-Iodoxybenzoic acid (9.0 g, 14.4 mmol) and DMSO (20 mL) were mixed and stirred for 20 min at room temperature. (1-phenyl-1H-benzo[d]imidazol-6-yl)methanol (2.4 g, 10.6 mmol) was added and stirred for 4 hours at room temperature. The mixture was quenched by MeOH. The reaction mixture was filtered through a silica pad and washed with 10% MeOH in DCM. The solvent was removed in vacuo. The residue was purified by flash chromatography using 2% MeOH in DCM. The product was purified by re-crystallization in 40% DCE in heptane to afford 1-phenyl-1H-benzo[d]imidazole-6-carbaldehyde (2.0 g, 85% yield) as a white solid.

Synthesis of 1-phenyl-1H-benzo[d]imidazole-6-carbonitrile

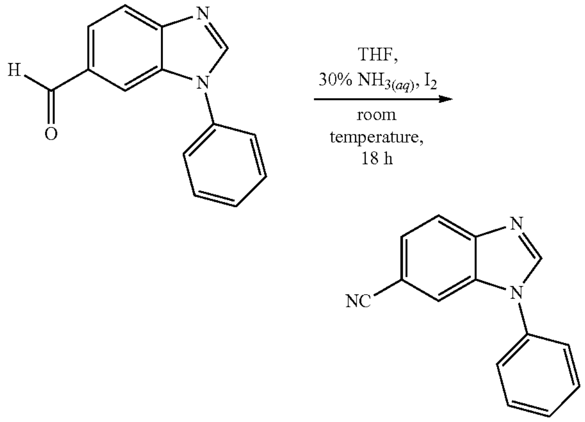

1-Phenyl-1H-benzo[d]imidazole-6-carbaldehyde (2.0 g, 9.0 mmol), THF (75 mL), 30% $NH_{3(aq)}$ (11.7 mL, 90.0 mmol) and iodine (6.9 g, 27.0 mmol) were mixed at and stirred for 18 hours at room temperature. The reaction mixture was quenched by the addition of saturated $Na_2S_2O_3$ and extracted with DCM. The extracts were dried over $MgSO_4$ and a silica pad and washed with 2% MeOH in DCM. The solvent was removed in vacuo. The residue was purified by flash chromatography using 2% MeOH in DCM. The product was purified by re-crystallization in 30% 1,4-dioxane in heptane to afford 1-phenyl-1H-benzo[d]imidazole-6-carbonitrile (1.5 g, 76% yield) as a white solid.

Synthesis of 6-cyano-3-methyl-1-phenyl-1H-benzo [d]imidazol-3-ium iodide (LA85)

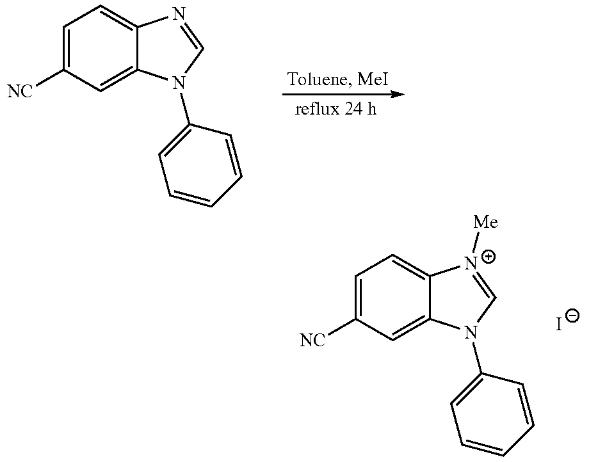

1-Phenyl-1H-benzo[d]imidazole-6-carbonitrile (1.5 g, 6.8 mmol), toluene (10 mL) and iodomethane (10 mL) were mixed. The resultant mixture was refluxed for 24 hours. After cooling, the precipitate was filtered and further purified by re-crystallization in 10% MeCN in 1,2-dimethoxyethane to afford 6-cyano-3-methyl-1-phenyl-1H-benzo[d]imidazol-3-ium iodide (1.9 g, 77% yield) as a white solid.

Synthesis of $Ir(LA85)_3$

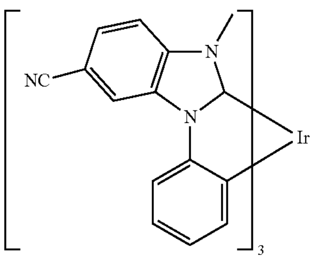

Synthesis of $Ir(LA85)_3$ was prepared from LA85 according to the general iridium complexation procedure as described for $Ir(LA43)_3$ to afford 17% yield of fac-Ir$(LA85)_3$ and 9% yield of mer-$Ir(LA85)_3$ as pale yellow solids.

Synthesis of 4-nitro-3-(m-tolylamino)benzonitrile

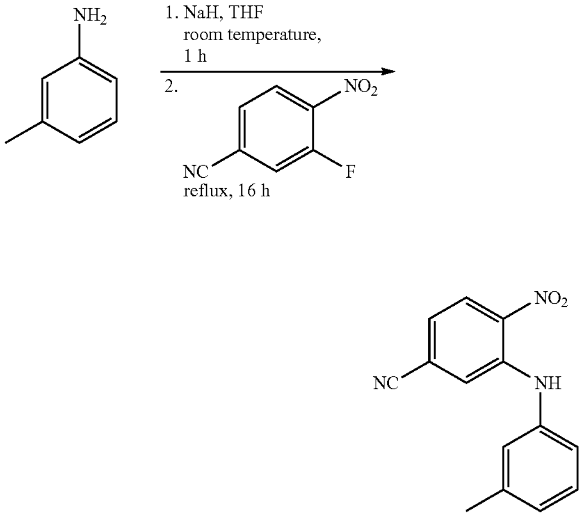

To m-toluidine (4.5 g, 42.0 mmol) in THF (100 mL) was added sodium hydride (95% in mineral oil, 1.6 g, 62.9 mmol) and stirred for 1 hour. 3-Fluoro-4-nitrobenzonitrile (5.8 g, 35.0 mmol) was added and the reaction mixture was heated to reflux overnight. The reaction mixture cooled to room temperature, water was added and filtered through silica gel, washed with 5% THF in hexane and concentrated in vacuo. The crude mixture was purified by flash column chromatography with 5-10% THF in hexane to give 4-nitro-3-(m-tolylamino)benzonitrile (5.5 g, 61% yield) as an orange powder.

Synthesis of 4-amino-3-(m-tolylamino)benzonitrile

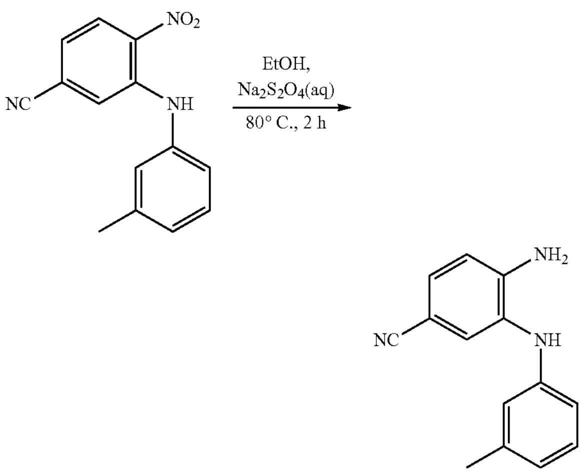

A mixture of 4-nitro-3-(m-tolylamino)benzonitrile (5.2 g, 20.7 mmol) in EtOH (200 mL) and $Na_2S_2O_4$ (14.4 g, 83.0 mmol) in water (100 mL) was heated to 80° C. for 2 hours. Reaction mixture was filtered, the filtrate was concentrated and filtered through a Celite/$MgSO_4$ pad and concentrated in vacuo. The crude mixture was purified by flash column chromatography with 5-15% THF in hexane to give 4-amino-3-(m-tolylamino)benzonitrile (4.3 g, 93% yield) as yellow oil.

Synthesis of 1-(m-tolyl)-1H-benzo[d]imidazole-6-carbonitrile

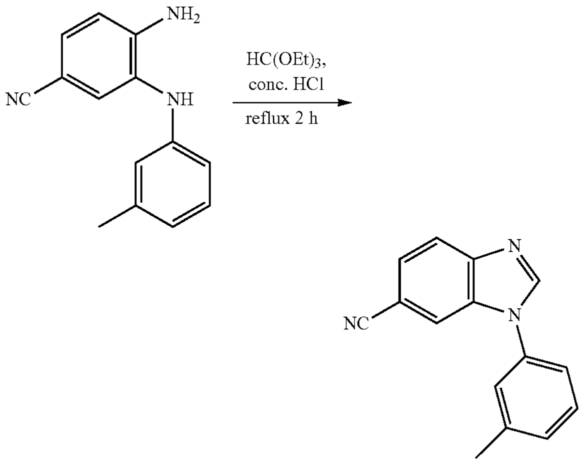

A mixture of 4-amino-3-(m-tolylamino)benzonitrile (4.6 g, 20.6 mmol) in triethyl orthoformate (75 mL) was added concentrated HCl (1.25 mL, 41.1 mmol) and heated to reflux for 2 hours. Reaction mixture was cooled to room temperature and concentrated in vacuo. The crude mixture was purified by flash column chromatography with 5-10% THF in hexane to give 1-(m-tolyl)-1H-benzo[d]imidazole-6-carbonitrile (4.3 g, 900/% yield) as white powder.

Synthesis of 6-cyano-3-methyl-1-(m-tolyl)-1H-benzo[d]imidazol-3-ium iodide (LA86)

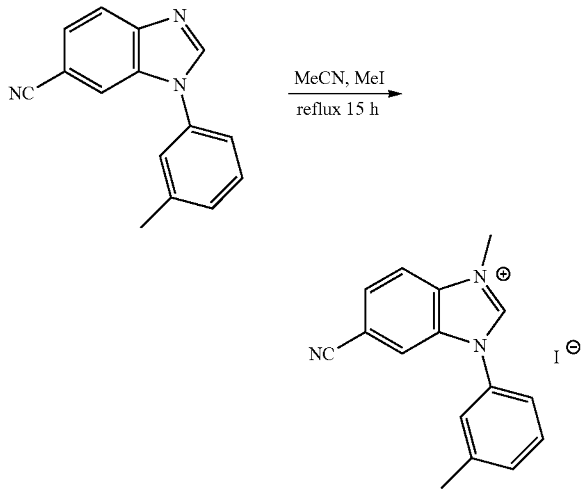

To 1-(m-tolyl)-1H-benzo[d]imidazole-6-carbonitrile (3.6 g, 15.5 mmol) in MeCN (35 mL) was added iodomethane (2.0 M in tert-butylmethylether, 38.8 mL, 78 mmol) and heated to reflux for 15 hours. The white solid was filtered and recrystallised with 10% 1,2-dimethoxyethane in MeCN to give 6-cyano-3-methyl-1-(m-tolyl)-1H-benzo[d]imidazol-3-ium iodide (4.7 g, 81% yield) as white powder.

Synthesis of $Ir(LA86)_3$

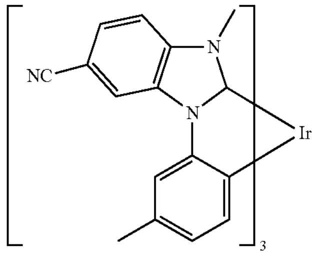

Synthesis of $Ir(LA86)_3$ was prepared from LA86 according to the general iridium complexation procedure as described for $Ir(LA43)_3$ to afford 3% yield of fac-$Ir(LA86)_3$ and 4% yield of mer-$Ir(LA86)_3$ as pale yellow solids.

Synthesis of 3-((3,4-dimethylphenyl)amino)-4-nitrobenzonitrile

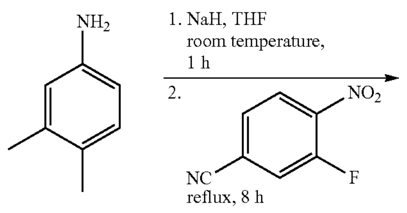

-continued

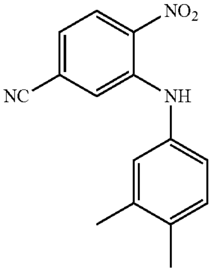

To 3,4-dimethylaniline (4.4 g, 35.9 mmol) in THF (100 mL) was added sodium hydride (95% in mineral oil, 1.34 g, 55.8 mmol) and stirred for 1 hour. 3-Fluoro-4-nitrobenzonitrile (5.0 g, 30.1 mmol) was added and the reaction mixture was heated to reflux for 8 hours. Reaction mixture was cooled to room temperature, water was added and filtered through silica gel, washed with 5% THF in hexane and concentrated in vacuo. The crude mixture was purified by flash column chromatography with 5-10% THF in hexane to give 3-((3,4-dimethylphenyl)amino)-4-nitrobenzonitrile (3.4 g, 36% yield) as an orange powder.

Synthesis of 4-amino-3-((3,4-dimethylphenyl)amino)benzonitrile

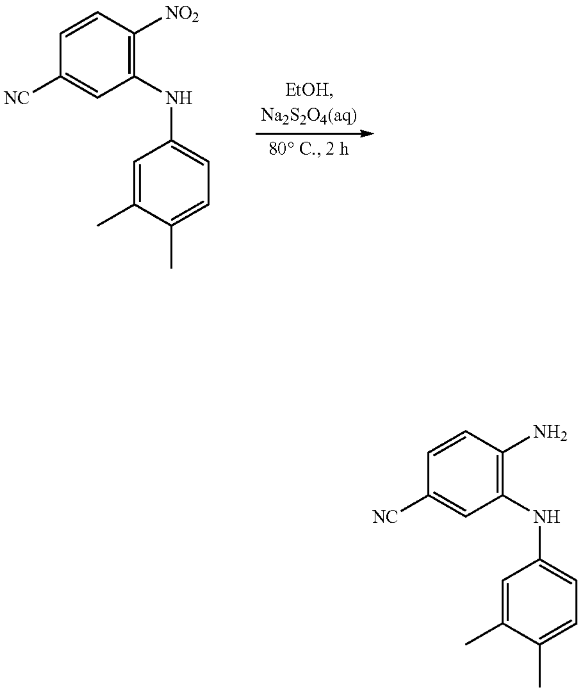

A mixture of 3-((3,4-dimethylphenyl)amino)-4-nitrobenzonitrile (2.89 g, 10.7 mmol) in EtOH (100 mL) and $Na_2S_2O_4$ (7.5 g, 43.1 mmol) in water (75 mL) was heated to 80° C. for 2 hours. Reaction mixture was filtered, the filtrate was concentrated and filtered through a Celite/$MgSO_4$ pad and concentrated in vacuo. The crude mixture was purified by flash column chromatography with 5-15% THF in hexane to give 4-amino-3-((3,4-dimethylphenyl)amino)benzonitrile (2.3 g, 91% yield) as yellow oil.

Synthesis of 1-(3,4-dimethylphenyl)-1H-benzo[d]imidazole-6-carbonitrile

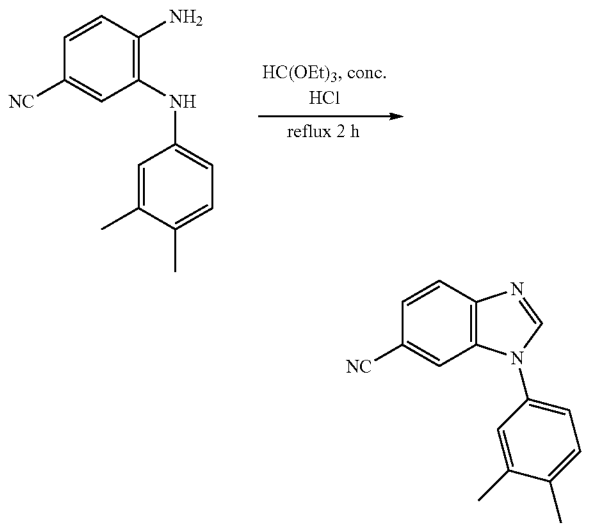

A mixture of 4-amino-3-((3,4-dimethylphenyl)amino)benzonitrile (2.3 g, 9.5 mmol) in triethyl orthoformate (35 mL) was added concentrated HCl (0.6 mL, 19.0 mmol) and heated to reflux for 2 hours. Reaction mixture was cooled to room temperature and concentrated in vacuo. The crude mixture was purified by flash column chromatography with 5-10% THF in hexane to give 1-(3,4-dimethylphenyl)-1H-benzo[d]imidazole-6-carbonitrile (2.3 g, 99% yield) as white powder.

Synthesis of 6-cyano-1-(3,4-dimethylphenyl)-3-methyl-1H-benzo[d]imidazol-3-ium iodide (LA89)

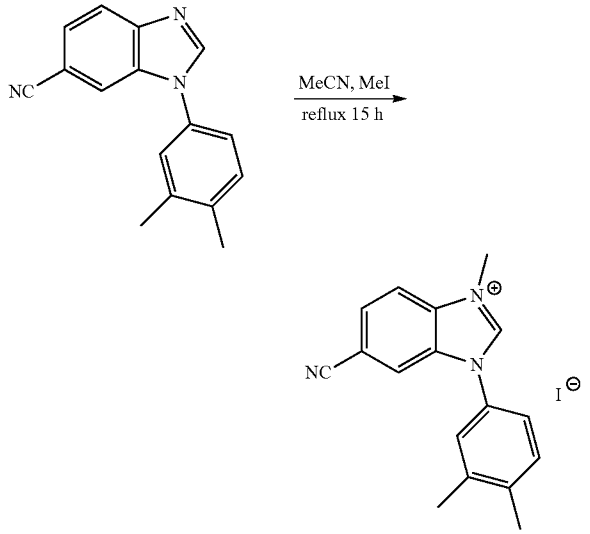

To 1-(3,4-dimethylphenyl)-1H-benzo[d]imidazole-6-carbonitrile (2.0 g, 8.2 mmol) in MeCN (10 mL) was added iodomethane (2.0 M in tert-butylmethylether, 21 mL, 42 mmol) and heated to reflux for 15 hours. The white solid was filtered and recrystallised with 10% 1,2-dimethoxyethane in MeCN to give 6-cyano-1-(3,4-dimethylphenyl)-3-methyl-1H-benzo[d]imidazol-3-ium iodide (2.5 g, 78% yield) as white powder.

Synthesis of $Ir(LA89)_3$

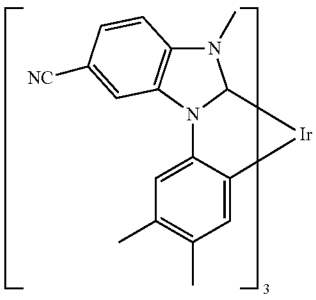

Synthesis of $Ir(LA89)_3$ was prepared from LA89 according to the general iridium complexation procedure as described for $Ir(LA43)_3$ to afford 3% yield of fac-$Ir(LA89)_3$ and 7% yield of mer-$Ir(LA89)_3$ as pale yellow solids.

Synthesis of 3-nitro-2-(phenylamino)benzonitrile

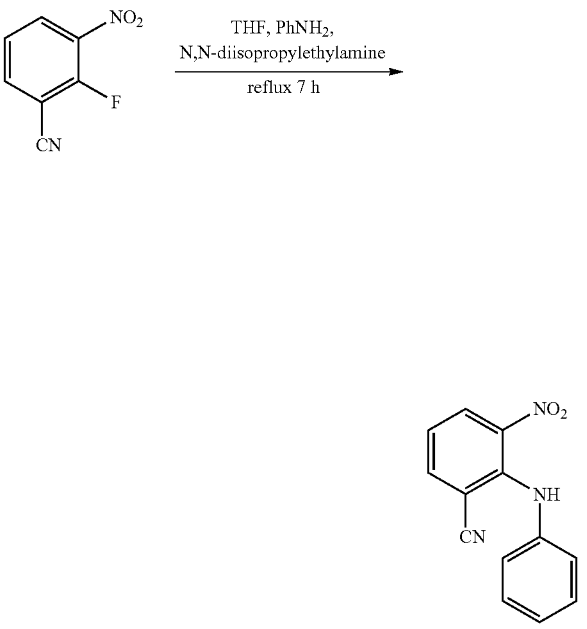

2-Fluoro-3-nitrobenzonitrile (3.8 g, 23.0 mmol), THF (70 mL), aniline (2.7 mL, 30.0 mmol) and N,N-diisopropylethylamine (17.4 mL, 100.0 mmol) were mixed at room temperature. The resultant mixture was refluxed for 7 hours. The reaction mixture was filtered through a silica pad and $MgSO_4$ and washed with 80% THF in hexane. The solvent was removed in vacuo. The product was purified by recrystallization in 5% THF in hexane to afford 3-nitro-2-(phenylamino)benzonitrile (5.2 g, 77% yield) as an orange solid.

Synthesis of 3-amino-2-(phenylamino)benzonitrile

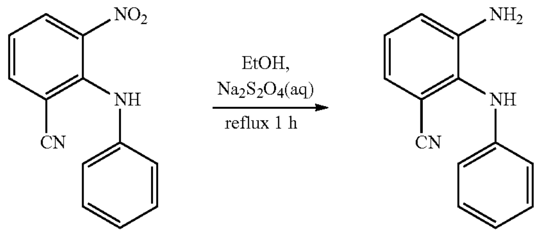 [SMILES: N#Cc1cccc([N+](=O)[O-])c1Nc1ccccc1 ; N#Cc1cccc(N)c1Nc1ccccc1]

3-Nitro-2-(phenylamino)benzonitrile (4.8 g, 20.0 mmol), EtOH (150 mL) and $Na_2S_2O_4$ (13.9 g, 80.0 mmol in 150 mL $H_2O$) were mixed at room temperature. The resultant mixture was refluxed for 1 hours. The solvent was removed in vacuo. The reaction mixture was filtered through a silica pad and $MgSO_4$ and washed with THF. The solvent was removed in vacuo. The product was purified by re-crystallization in 20% THF in heptane to afford 3-amino-2-(phenylamino) benzonitrile (2.4 g, 57% yield) as a white solid.

Synthesis of 1-phenyl-1H-benzo[d]imidazole-7-carbonitrile

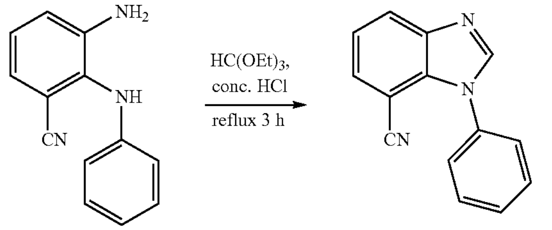 [SMILES: N#Cc1cccc(N)c1Nc1ccccc1 ; N#Cc1cccc2ncn(-c3ccccc3)c12]

3-Amino-2-(phenylamino)benzonitrile (0.9 g, 4.5 mmol), triethyl orthoformate (50 mL) and 12.4 M hydrochloric acid (0.7 mL, 9.0 mmol) were mixed. The resultant mixture was refluxed for 3 hours. After cooling, the solvent was removed in vacuo. The residue was purified by flash chromatography using 2% MeOH in DCM to afford 1-phenyl-1H-benzo[d] imidazole-7-carbonitrile (0.9 g, 89% yield) as a white solid.

Synthesis of 7-cyano-3-methyl-1-phenyl-1H-benzo [d]imidazol-3-ium trifluoromethanesulfonate (LA106)

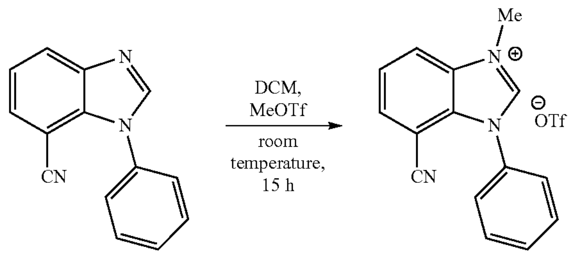 [SMILES: N#Cc1cccc2ncn(-c3ccccc3)c12 ; C[n+]1cn(-c2ccccc2)c2c(C#N)cccc21]

1-Phenyl-1H-benzo[d]imidazole-7-carbonitrile (098 g, 4.0 mmol), DCM (20 mL) and methyl trifluoromethanesulfonate (0.8 mL, 7.0 mmol) were mixed and stirred for 15 hours at room temperature. The resultant mixture was diluted by $Et_2O$. The precipitate was filtered and dried to afford 7-cyano-3-methyl-1-phenyl-1H-benzo[d]imidazol-3-ium trifluoromethanesulfonate (1.4 g, 91% yield) as a white solid.

Synthesis of $Ir(LA106)_3$

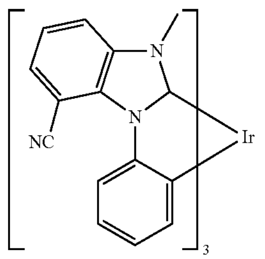

Synthesis of $Ir(LA106)_3$ was prepared from LA106 according to the general iridium complexation procedure as described for $Ir(LA43)_3$ to afford 14% yield of fac-Ir $(LA106)_3$ and 6% yield of mer-$Ir(LA106)_3$ as pale yellow solids.

Synthesis of 3-nitro-2-(m-tolylamino)benzonitrile

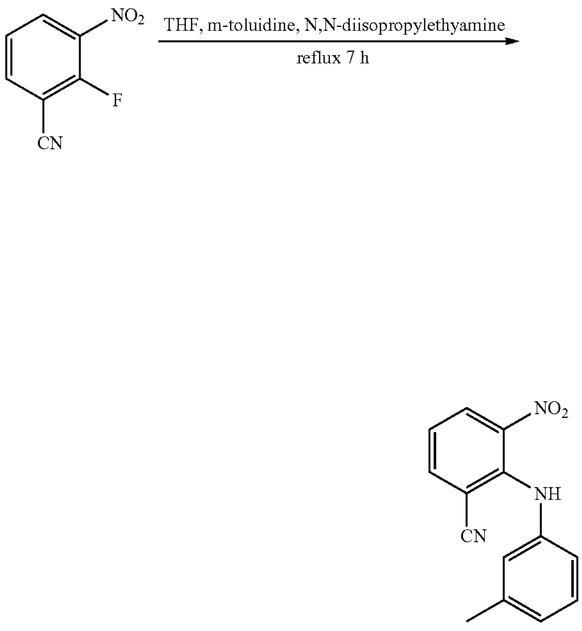

2-Fluoro-3-nitrobenzonitrile (4.2 g, 25.0 mmol), THF (50 mL), m-toluidine (4.0 mL, 37.5 mmol) and N,N-diisopropylethylamine (13.0 mL, 75.0 mmol) were mixed at room temperature. The resultant mixture was refluxed for 7 hour. The reaction mixture was filtered through a silica pad and $MgSO_4$ and washed with THF. The solvent was removed in vacuo. The product was purified by re-crystallization in 10% THF in hexane to afford 3-nitro-2-(m-tolylamino)benzonitrile (6.0 g, 94% yield) as an orange solid.

Synthesis of 1-(m-tolyl)-1H-benzo[d]imidazole-7-carbonitrile

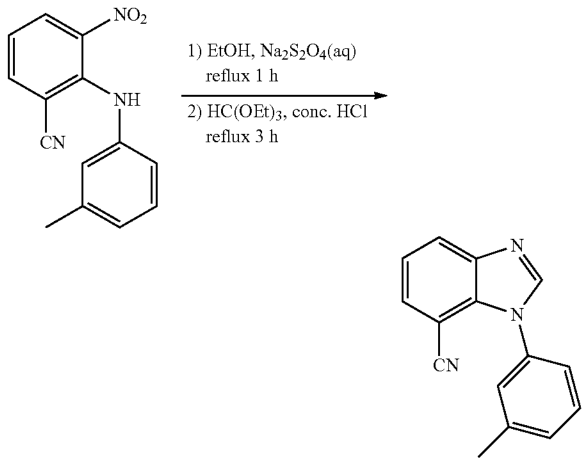

3-Nitro-2-(m-tolylamino)benzonitrile (5.9 g, 23.5 mmol), EtOH (150 mL) and $Na_2S_2O_4$ (16.4 g, 94.0 mmol in 150 mL $H_2O$) were mixed at room temperature. The resultant mixture was refluxed for 1 hour. The solvent was removed in vacuo. The reaction mixture was filtered through a silica pad and $MgSO_4$ and washed with THF. The solvent was removed in vacuo. Then, the solid was dissolved in triethyl orthoformate (50 mL). 12.4 M hydrochloric acid (3.8 mL, 47.0 mmol) was added. The resultant mixture was refluxed for 3 hours. The resultant mixture was diluted by 20% $Et_2O$ in hexane. The precipitate was filtered to afford 1-(m-tolyl)-1H-benzo[d]imidazole-5,6-dicarbonitrile (4.6 g, 83% yield over 2 steps) as a white solid.

Synthesis of 7-cyano-3-methyl-1-(m-tolyl)-1H-benzo[d]imidazol-3-ium trifluoromethanesulfonate (LA107)

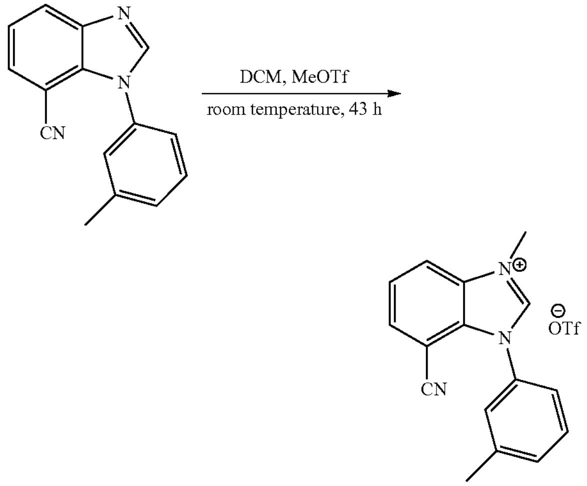

1-(m-Tolyl)-1H-benzo[d]imidazole-5,6-dicarbonitrile (4.6 g, 20.0 mmol), DCM (300 mL) and methyl trifluoromethanesulfonate (2.5 mL, 22.8 mmol) were mixed and stirred for 43 hours at room temperature. The resultant mixture was diluted by $Et_2O$ and filtered. The product was further purified by re-crystallization in 60% 1,2-dimethoxyethane in heptane and then 10% MeCN in ether to afford 7-cyano-3-methyl-1-(m-tolyl)-1H-benzo[d]imidazol-3-ium trifluoromethanesulfonate (6.6 g, 84% yield) as a pale yellow solid.

Synthesis of 2-((3,5-dimethylphenyl)amino)-3-nitrobenzonitrile

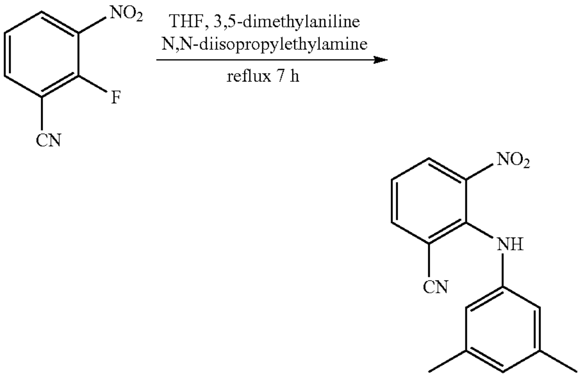

2-Fluoro-3-nitrobenzonitrile (4.2 g, 25.0 mmol), THF (50 mL), 3,5-dimethylaniline (4.0 mL, 32.0 mmol) and N,N-diisopropylethylamine (17.3 mL, 100.0 mmol) were mixed at room temperature. The resultant mixture was refluxed for 9 hours. The reaction mixture was filtered through a silica pad and $MgSO_4$ and washed with THF. The solvent was removed in vacuo. The product was purified by re-crystallization in 10% THF in hexane to afford 2-((3,5-dimethylphenyl)amino)-3-nitrobenzonitrile (6.4 g, 96% yield) as an orange solid.

Synthesis of 1-(3,5-dimethylphenyl)-1H-benzo[d]imidazole-7-carbonitrile

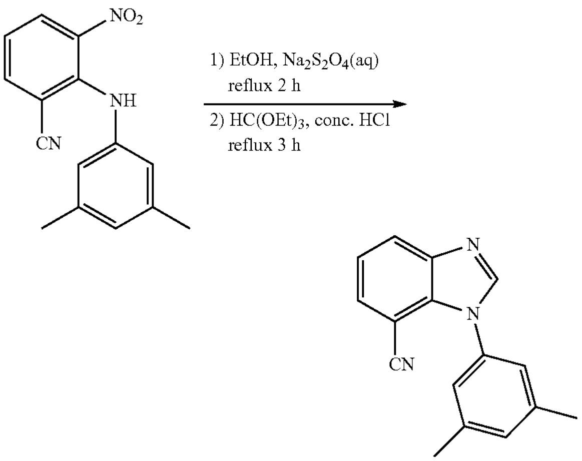

2-((3,5-Dimethylphenyl)amino)-3-nitrobenzonitrile (6.4 g, 24.0 mmol), EtOH (150 mL) and $Na_2S_2O_4$(16.7 g, 96.0 mmol in 150 mL $H_2O$) were mixed at room temperature. The resultant mixture was refluxed for 2 hours. The solvent was removed in vacuo. The reaction mixture was filtered through a silica pad and $MgSO_4$ and washed with THF. The solvent was removed in vacuo. Then, the solid was dissolved in orthoformate (80 mL). 12.4 M hydrochloric acid (3.9 mL, 48.0 mmol) was added. The resultant mixture was refluxed for 3 hours. The solvent was removed in vacuo. The residue was purified by flash chromatography using 65% THF in hexane. The product was purified by re-crystallization in 10% THF in hexane to afford 1-(3,5-dimethylphenyl)-1H-benzo[d]imidazole-7-carbonitrile (4.2 g, 71% yield over 2 steps) as a white solid.

Synthesis of 7-cyano-1-(3,5-dimethylphenyl)-3-methyl-1H-benzo[d]imidazol-3-ium trifluoromethanesulfonate (LA112)

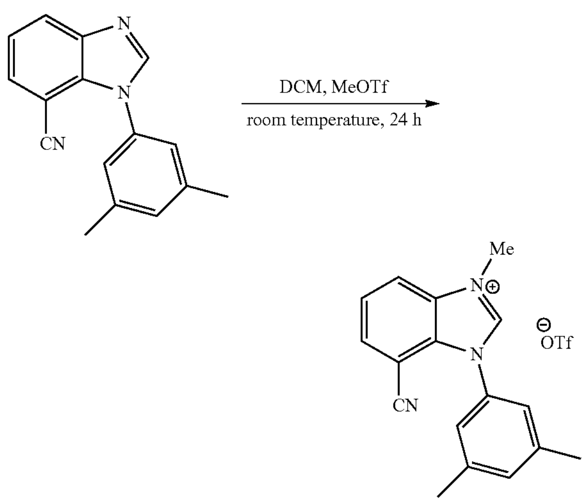

1-(3,5-Dimethylphenyl)-1H-benzo[d]imidazole-7-carbonitrile (4.2 g, 17.0 mmol), DCM (50 mL) and methyl trifluoromethanesulfonate (2.0 mL, 18.3 mmol) were mixed and stirred for 24 hours at room temperature. The resultant mixture was diluted by $Et_2O$ and filtered. The product was further purified by re-crystallization in 30% 1,2-dimethoxyethane in heptane and then 6% MeCN in ether to afford 7-cyano-1-(3,5-dimethylphenyl)-3-methyl-1H-benzo[d]imidazol-3-ium trifluoromethanesulfonate (6.6 g, 94% yield) as a white solid.

Synthesis of 4-nitro-5-(phenylamino)phthalonitrile

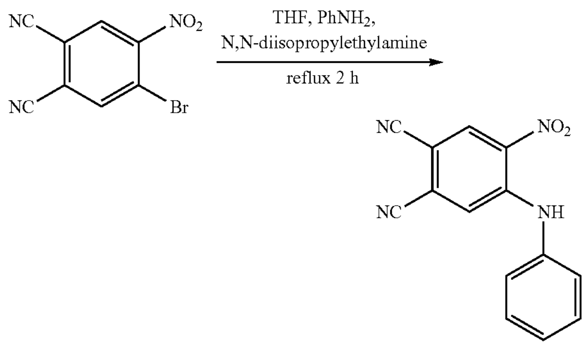

4-Bromo-5-nitrophthalonitrile (5.0 g, 20.0 mmol), THF (70 mL), aniline (2.7 mL, 30.0 mmol) and N,N-diisopropylethylamine (17.4 mL, 100.0 mmol) were mixed at room temperature. The resultant mixture was refluxed for 2 hours. The reaction mixture was filtered through a silica pad and $MgSO_4$ and washed with THF. The solvent was removed in vacuo. The product was purified by re-crystallization in 5% THF in hexane to afford 4-nitro-5-(phenylamino)phthalonitrile (5.2 g, 98% yield) as an orange solid.

Synthesis of 4-amino-5-(phenylamino)phthalonitrile

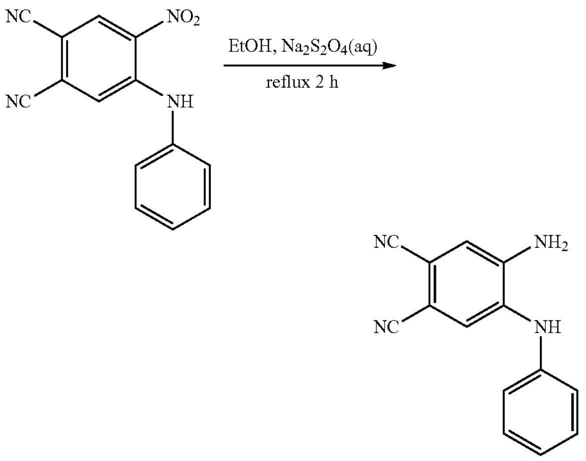

4-Nitro-5-(phenylamino)phthalonitrile (4.5 g, 17.0 mmol), EtOH (150 mL) and $Na_2S_2O_4$ (11.8 g, 68.0 mmol in 150 mL $H_2O$) were mixed at room temperature. The resultant mixture was refluxed for 1 hour. The solvent was removed in vacuo. The reaction mixture was filtered through a silica pad and $MgSO_4$ and washed with THF. The solvent was removed in vacuo. The product was purified by re-crystallization in 20% THF in hexane to afford 4-amino-5-(phenylamino)phthalonitrile (3.3 g, 83% yield) as a white solid.

Synthesis of 1-phenyl-1H-benzo[d]imidazole-5,6-dicarbonitrile

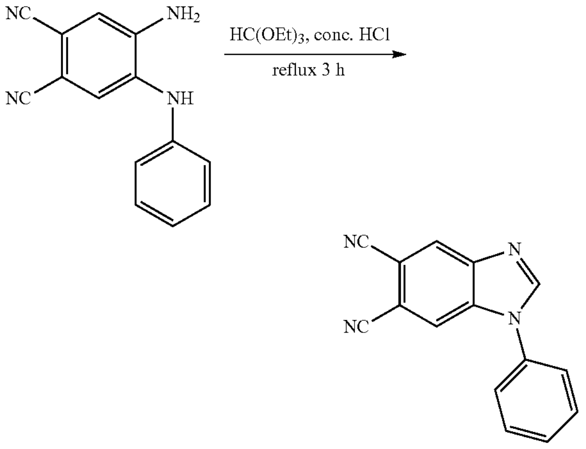

4-Amino-5-(phenylamino)phthalonitrile (3.3 g, 14.0 mmol), triethyl orthoformate (80 mL) and 12.4 M hydrochloric acid (2.3 mL, 28.0 mmol) were mixed. The resultant mixture was refluxed for 3 hours. The resultant mixture was diluted by 50% $Et_2O$ in hexane. The precipitate was filtered and dried to afford 1-phenyl-1H-benzo[d]imidazole-5,6-dicarbonitrile (2.6 g, 77% yield) as a white solid.

Synthesis of 5,6-dicyano-3-methyl-1-phenyl-1H-benzo[d]imidazol-3-ium trifluoromethanesulfonate (LA148)

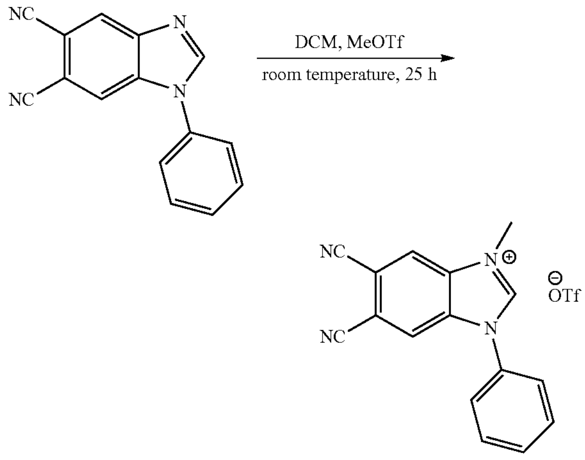

1-Phenyl-1H-benzo[d]imidazole-5,6-dicarbonitrile (3.9 g, 16.0 mmol), DCM (150 mL) and methyl trifluoromethanesulfonate (3.4 mL, 31.0 mmol) were mixed and stirred for 25 h at room temperature. The resultant mixture was diluted by $Et_2O$. The precipitate was filtered and further purified by re-crystallization in 20% MeCN in 1,2-dimethoxyethane to afford 5,6-dicyano-3-methyl-1-phenyl-1H-benzo[d]imidazol-3-ium trifluoromethanesulfonate (4.9 g, 75% yield) as a white solid.

Synthesis of 4-nitro-5-(m-tolylamino)phthalonitrile

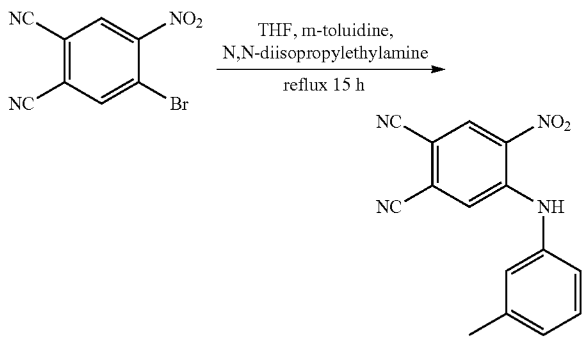

4-Bromo-5-nitrophthalonitrile (5.0 g, 20.0 mmol), THF (50 mL), m-toluidine (3.2 mL, 30.0 mmol) and N,N-diisopropylethylamine (15.0 mL, 86.0 mmol) were mixed at room temperature. The resultant mixture was refluxed for 15 hours. The reaction mixture was filtered through a silica pad and $MgSO_4$ and washed with THF. The solvent was removed in vacuo. The product was purified by re-crystallization in 10% THF in hexane to afford 4-nitro-5-(m-tolylamino) phthalonitrile (5.5 g, 99% yield) as an orange solid.

Synthesis of 1-(m-tolyl)-1H-benzo[d]imidazole-5,6-dicarbonitrile

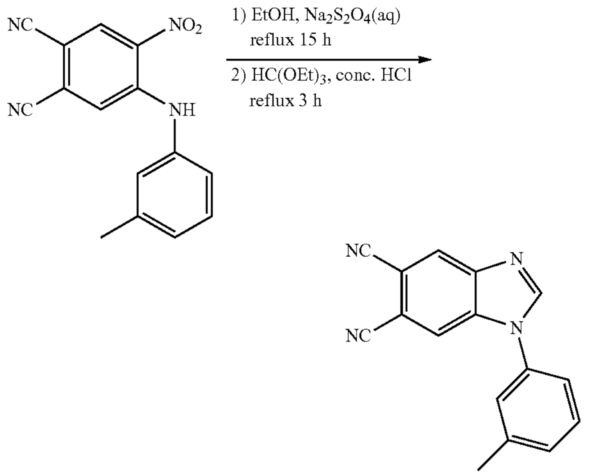

4-Nitro-5-(m-tolylamino)phthalonitrile (5.5 g, 20.0 mmol), EtOH (150 mL) and $Na_2S_2O_4$ (13.9 g, 80.0 mmol in 150 mL $H_2O$) were mixed at room temperature. The resultant mixture was refluxed for 2 hours. The solvent was removed in vacuo. The reaction mixture was filtered through a silica pad and $MgSO_4$ and washed with THF. The solvent was removed in vacuo. Then, the solid was dissolved in triethyl orthoformate (90 mL). 12.4 M hydrochloric acid (3.2 mL, 40.0 mmol) was added. The resultant mixture was refluxed for 3 hours. The resultant mixture was diluted by 20% $Et_2O$ in hexane. The precipitate was filtered and dried to afford 1-(m-tolyl)-1H-benzo[d]imidazole-5,6-dicarbonitrile (3.3 g, 65% yield over 2 steps) as a white solid.

Synthesis of 5,6-dicyano-3-methyl-1-(m-tolyl)-1H-benzo[d]imidazol-3-ium trifluoromethanesulfonate (LA149)

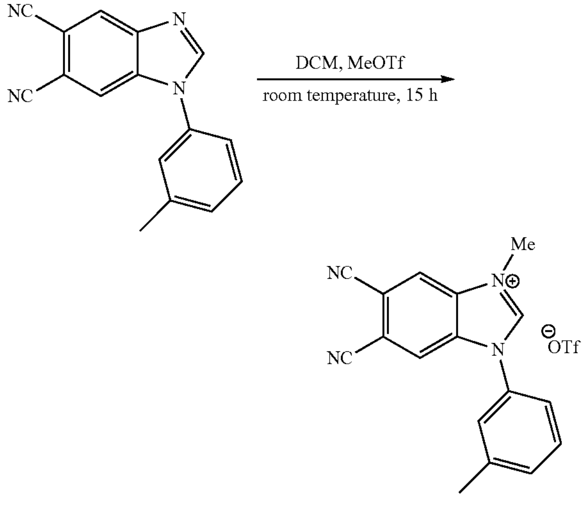

1-(m-Tolyl)-1H-benzo[d]imidazole-5,6-dicarbonitrile (3.4 g, 13.0 mmol), DCM (300 mL) and methyl trifluoromethanesulfonate (2.0 mL, 18.2 mmol) were mixed and stirred for 15 hours at room temperature. The resultant mixture was diluted by $Et_2O$. The precipitate was filtered and further purified by re-crystallization in 25% MeCN in 1,2-dimethoxyethane to afford 5,6-dicyano-3-methyl-1-(m-tolyl)-1H-benzo[d]imidazol-3-ium trifluoromethanesulfonate (4.6 g, 83% yield) as a white solid.

Synthesis of 1-phenyl-1H-benzo[d]imidazole-5-carbonitrile

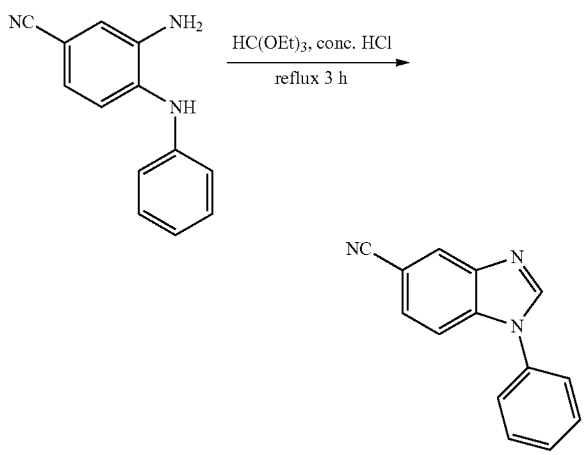

3-Amino-4-(phenylamino)benzonitrile (6.0 g, 20.0 mmol), triethyl orthoformate (50 mL) and 12.4 M hydrochloric acid (3.2 mL, 40.0 mmol) were mixed. The resultant mixture was refluxed for 3 hours. After cooling, the solvent was removed in vacuo. The residue was purified by flash chromatography using 5% MeOH in DCM. The product was further purified by re-crystallization in 60% $Et_2O$ in hexane to afford 1-phenyl-1H-benzo[d]imidazole-5-carbonitrile (3.8 g, 88% yield) as a white solid.

Synthesis of 5-cyano-3-methyl-1-phenyl-1H-benzo[d]imidazol-3-ium iodide

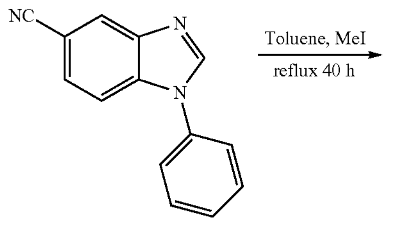

-continued

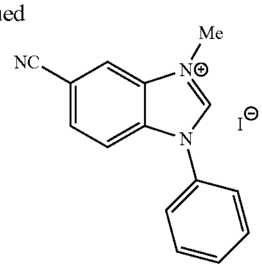

1-Phenyl-1H-benzo[d]imidazole-5-carbonitrile (3.7 g, 17.0 mmol), toluene (50 mL) and iodomethane (25 mL) were mixed. The resultant mixture was refluxed for 40 hours. After cooling, the precipitate was filtered and further purified by re-crystallization in 10% MeCN in 1,2-dimethoxyethane to afford 5-cyano-3-methyl-1-phenyl-1H-benzo[d]imidazol-3-ium iodide (5.8 g, 95% yield) as a white solid.

fac-

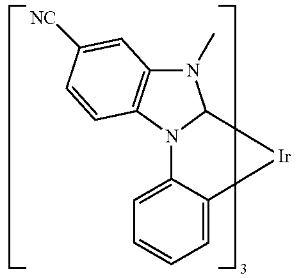

Synthesis of Comparative Compound 1

Synthesis of Comparative Compound 1 was prepared according to the general iridium complexation procedure as described for $Ir(LA43)_3$ to afford 21% yield of Comparative Compound 1 as a white solid.

The photophysical and electrochemical properties (oxidation potential, $E_{ox}$ and reduction potential, $E_{red}$, determined by solution cyclic voltammetry using $Fc/Fc^+$ as the reference) of various examples of the inventive compounds and comparative compounds are summarized in Table 1 below. For $E_{ox}$ and $E_{red}$, (R) means the wave is reversible and (IR) means the wave is irreversible.

TABLE 1

| | Emission $\lambda_{max}$ (nm) | PLQY (%) | FWHM (nm) | excited state lifetime (μs) | $E_{ox}$ (V) | $E_{red}$ (V) |
|---|---|---|---|---|---|---|
| fac-$Ir(LA43)_3$ | 437 | 94 | 60 | 2.52 | 0.64 (IR) | −2.44 (R) |
| mer-$Ir(LA43)_3$ | 464 | 93 | 74 | 1.43 | 0.44 (IR) | −2.45 (R) |
| fac-$Ir(LA44)_3$ | 454 | 92 | 61 | 1.86 | 0.54 (R) | −2.45 (R) |
| mer-$Ir(LA44)_3$ | 481 | 96 | 82 | 1.49 | 0.32 (IR) | −2.47 (R) |
| fac-$Ir(LA47)_3$ | 465 | 91 | 68 | 1.92 | 0.49 (R) | −2.46 (R) |
| mer-$Ir(LA49)_3$ | 492 | 86 | 92 | 1.60 | 0.35 (R) | −2.40 (R) |
| mer-$Ir(LA59)_3$ | 443 | 92 | 65 | 22 | 0.59 (IR) | −2.42 (R) |

TABLE 1-continued

| | Emission $\lambda_{max}$ (nm) | PLQY (%) | FWHM (nm) | excited state lifetime (μs) | $E_{ox}$ (V) | $E_{red}$ (V) |
|---|---|---|---|---|---|---|
| fac-Ir(LA85)$_3$ | 425 | 84 | 54 | 1.92 | 0.64 (R) | −2.64 (R) |
| mer-Ir(LA85)$_3$ | 440 | 86 | 67 | 1.27 | 0.43 (IR) | −2.62 (R) |
| fac-Ir(LA86)$_3$ | 434 | 73 | 61 | 1.42 | 0.55 (R) | −2.41 (R) |
| mer-Ir(LA86)$_3$ | 455 | 81 | 73 | 1.45 | 0.34 (IR) | −2.46 (R) |
| fac-Ir(LA89)$_3$ | 448 | 59 | 63 | 1.50 | 0.49 (IR) | −2.65 (R) |
| mer-Ir(LA89)$_3$ | 459 | 66 | 75 | 1.40 | 0.28 (IR) | −2.65 (R) |
| fac-Ir(LA106)$_3$ | 452 | 55 | 72 | 3.19 | 0.65 (IR) | −2.38 (R) |
| mer-Ir(LA106)$_3$ | 477 | 86 | 90 | 1.59 | 0.40 (IR) | −2.45 (R) |
| Comparative Compound 1 | 410 | 51 | 47 | 23 | 0.64 (R) | −2.59 (IR) |
| Comparative Compound 2 | 378 | 48 | 54 | 3.18 | 0.50 (R) | Not detected |

The structure of the comparative compounds are as follows:

Comparative Compound 1

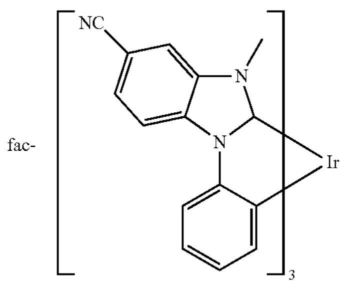

Comparative Compound 2

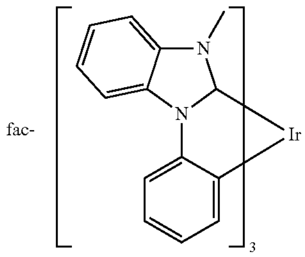

The data shows that having an electron withdrawing group such as CN at certain positions of the carbene can dramatically improve the photophysical and electromchemically properties of the compounds. For example, fac-Ir (LA44)$_3$ has a CN group at the $R^{c1}$ position. The Emission $\lambda_{max}$ is 454 nm, PLQY is 92%, excited state lifetime is 1.86 μs, $E_{ox}$, is 0.54 V (R) and $E_{red}$ is −2.45V (R). On the other hand, for Comparative Compound 1 having a CN group at the $R^{c2}$ position Emission $\lambda_{max}$ is 410 nm, PLQY is 51%, excited state lifetime is 27 μs, $E_{ox}$ is 0.64 V (R) and $E_{red}$ is −2.59 V (IR). For the unsubstituted compound Comparative Compound 2, the Emission $\lambda_{max}$ is 378 nm, PLQY is 48%, excited state lifetime is 3.18 μs, $E_{ox}$ is 0.50 V (R) and $E_{red}$ is undetected. The dramatic difference in the emission, PLQY and excited state lifetime demonstrate that the position of the electron withdrawing group is important in obtaining high-efficiency blue phosphorescent emitters. The data has shown that for the benzimidazole carbene system (Formular II), the electron withdrawing groups at $R^{c1}$, $R^{c3}$ and $R^{c4}$ positions exhibited unexpected substantial difference compared to having an electron withdrawing group at $R^{c2}$ position. Namely, having electron withdrawing groups at $R^{c1}$, $R^{c3}$ and $R^{c4}$ positions result in more favorable effect on the photophysical and electrochemical properties compared to the $R^{c2}$ position.

Device Examples

All device examples were fabricated by high vacuum (<$10^{-7}$ Torr) thermal evaporation. The anode electrode was ~800 Å of indium tin oxide (ITO). The cathode consisted of 5 Å of LiF followed by 1,000 Å of Al. All devices were encapsulated with a glass lid sealed with an epoxy resin in a nitrogen glove box (<1 ppm of $H_2O$ and $O_2$) and a moisture getter was incorporated inside the package. Some of the compounds used in fabricating the device examples are shown below.

Compound A

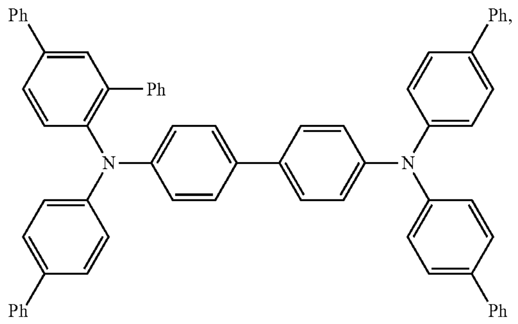

-continued

Compound B

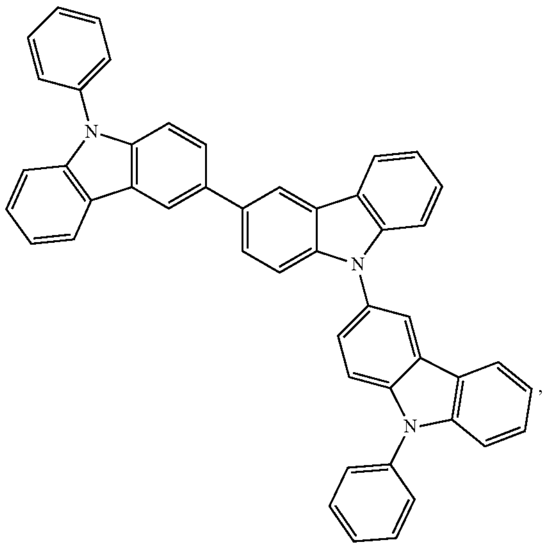

Compound C

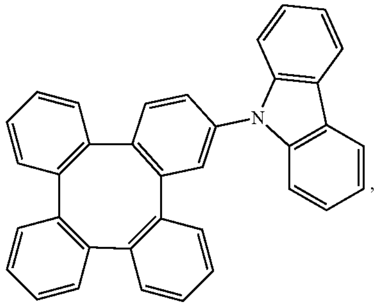

Compond D

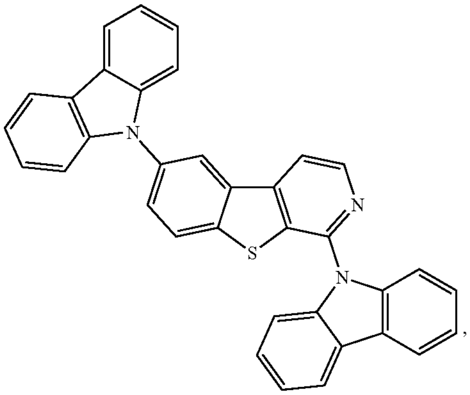

-continued

Compound E

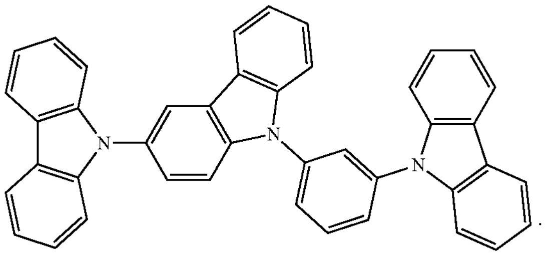

Compound F

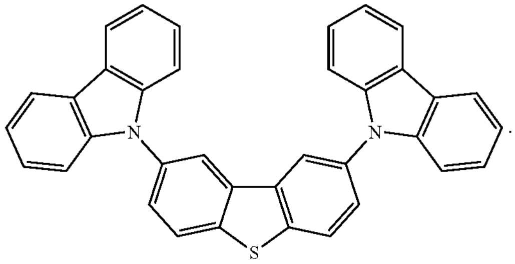

The organic stack of Device Example 1-6 consists of 100 Å of LG101 (from LG Chem, Korea) as the hole injection layer (HIL), 250 Å of Compound A as the hole transporting layer (HTL), 50 Å of Compound B or Compound E as the electron blocking layer (EBL) when EBL was used, 300 Å of host doped with 10% of Compound fac-Ir(LA44)$_3$ as the emissive layer (EML), 50 Å of Compound D or F as the hole blocking layer (HBL), and 300 Å of Liq (Li(8 hydroxyquinolate) doped with 35% of LG201 (from LG Chem, Korea) as the electron transporting layer (ETL). The data is summarized in Table 2.

TABLE 2

| Device Ex. | EBL [Å] | EML [Å] | HBL [Å] | x | y | λ max [nm] | FWHM [nm] | V [V] | LE [cd/A] | EQE [%] |
|---|---|---|---|---|---|---|---|---|---|---|
| 1 | Cpd E 50 | Cpd E:fac-Ir(LA44)$_3$ (90:10) 300 | Cpd D 50 | 0.149 | 0.209 | 470 | 62 | 6.2 | 7.4 | 4.9 |
| 2 | Cpd E 50 | Cpd E:Cpd D:fac-Ir(LA44)$_3$ (50:40:10) 300 | Cpd D 50 | 0.149 | 0.225 | 470 | 64 | 4.9 | 10.3 | 6.6 |
| 3 | none | Cpd C:fac-Ir(LA44)$_3$ (90:10) 300 | Cpd D 50 | 0.145 | 0.165 | 462 | 61 | 6.3 | 7.6 | 6.0 |

TABLE 2-continued

| Device Ex. | EBL [Å] | EML [Å] | HBL [Å] | x | y | λ max [nm] | FWHM [nm] | V [V] | LE [cd/A] | EQE [%] |
|---|---|---|---|---|---|---|---|---|---|---|
| 4 | Cpd B 50 | Cpd C:fac-Ir(LA44)$_3$ (90:10) 300 | Cpd D 50 | 0.145 | 0.172 | 464 | 62 | 5.8 | 8.3 | 6.4 |
| 5 | none | Cpd C:fac-Ir(LA44)$_3$ (90:10) 300 | Cpd F 50 | 0.148 | 0.166 | 460 | 60 | 7.0 | 5.8 | 4.6 |
| 6 | Cpd B 50 | Cpd C:fac-Ir(LA44)$_3$ (90:10) 300 | Cpd F 50 | 0.149 | 0.174 | 462 | 61 | 6.5 | 6.2 | 4.6 |

As shown in Table 2, blue emitting phosphorescent OLED can be achieved with CIE of <0.15, <0.17 with external quantum efficiency of >4%. Guassian emission profiles are also obtained instead of vibronic emission profiles commonly observed in blue phosphorescent OLED, suggesting increased MLCT and π backbonding character between the metal center and the imidazole carbene. These features indicate a strong bond between the metal center and the imidazole carbene cyclometallating carbon. Additionally, UV photoisomerization under nitrogen, typically an effective way of converting mer to fac isomers in Ir cyclometallated complexes, did not cause isomerization of mer-Ir (LA49)$_3$. This result suggests that the metal-carbon bond is indeed strong.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound comprising a carbene ligand $L_A$ selected from the group consisting of:

Formula I

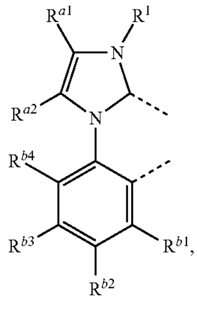

and

-continued

Formula II

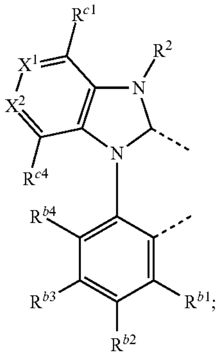

wherein $X^1$ is $CR^{c2}$ or N, $X^2$ is $CR^{c3}$ or N;

wherein $R^{a1}$, $R^{a2}$, $R^{b1}$, $R^{b2}$, $R^{b3}$, $R^{b4}$, $R^{c1}$, $R^{c2}$, $R^{c3}$, $R^{c4}$, $R^1$ an $R^2$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof;

wherein at least one of $R^1$, $R^{a1}$, $R^{a2}$, $R^{c1}$, $R^{c3}$, and $R^{c4}$ comprises an acceptor group selected from the group consisting of CN, F directly attached to an aromatic ring, $Si_mF_{2m+1}$, NCO, NCS, OCN, SCN, $OC_mF_{2m+1}$, and $SC_mF_{2m+1}$, where m≥1, but $R^{a1}$ cannot be CN;

wherein any adjacent substituents of $R^{b1}$, $R^{b2}$, $R^{b3}$, and $R^{b4}$ are optionally joined or fused into a ring;

wherein the ligand $L_A$ is coordinated to a metal M; and wherein the ligand $L_A$ is optionally linked with other ligands to comprise a tridentate, tetradentate, pentadentate or hexadentate ligand;

wherein at least one of the following is true:

(i) $R^1$ and $R^2$ are each independently selected from the group consisting of halide, haloalkyl, cycloalkyl, heteroalkyl, alkoxy, thioalkoxy, aryloxy, thioaryloxy, amino, silyl, halosilyl, cycloalkenyl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof;

(ii) at least one of $R^1$, $R^{a1}$, $R^{a2}$, $R^{c1}$, $R^{c3}$, and $R^{c4}$ comprises an acceptor group selected from the group consisting of $Si_mF_{2m+1}$, NCO, NCS, OCN, SCN, $OC_mF_{2m+1}$, and $SC_mF_{2m+1}$, where m≥1;

(iii) the ligand $L_A$ is a ligand of Formula II and at least one of $R^{c1}$, $R^{c3}$, and $R^{c4}$ is CN.
2. The compound of claim 1, wherein M is selected from the group consisting of Ir, Rh, Re, Ru, Os, Pt, Au, and Cu.
3. The compound of claim 1, wherein the ligand $L_A$ is selected from the group consisting of:
LA1
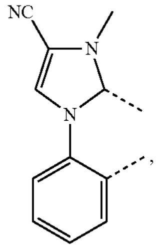
LA2
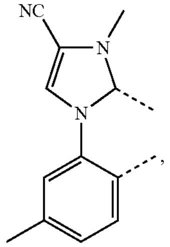
LA3
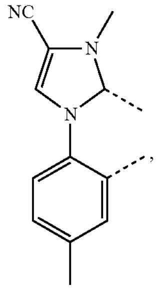
LA4
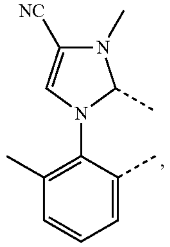
LA5
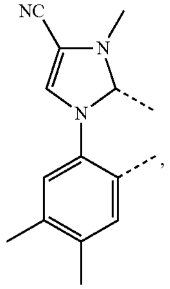
-continued
LA6
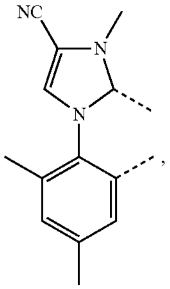
LA7
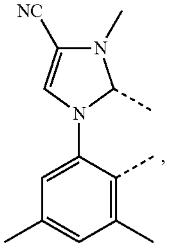
LA8
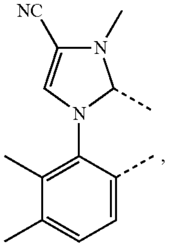
LA9
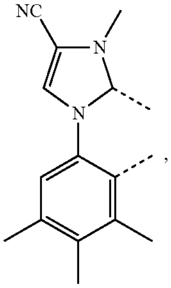
LA10
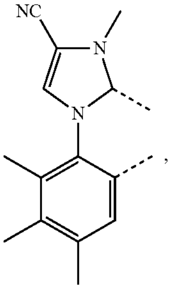
LA11
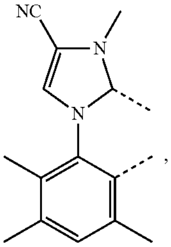

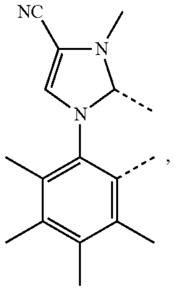
LA12
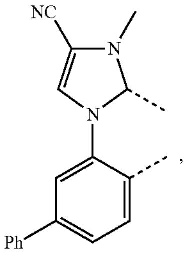
LA13
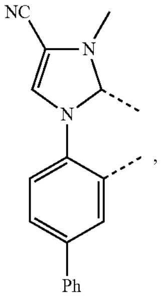
LA14
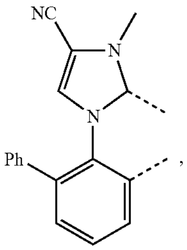
LA15
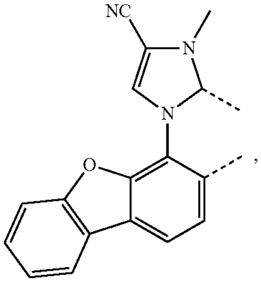
LA16
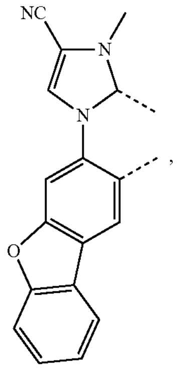
LA17
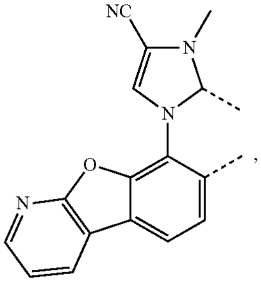
LA18
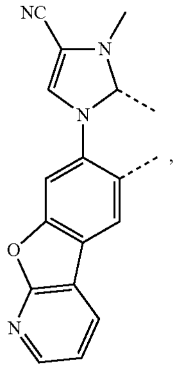
LA19
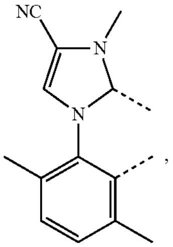
LA20
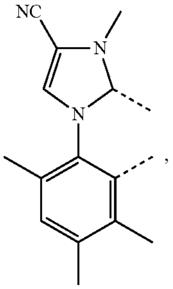
LA21

-continued
LA22
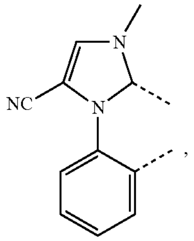
LA23
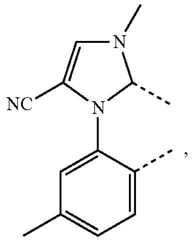
LA24
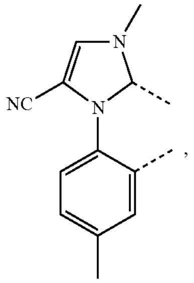
LA25
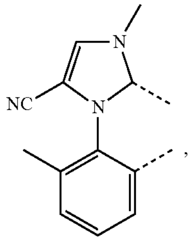
LA26
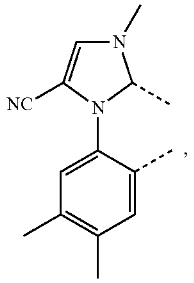
LA27
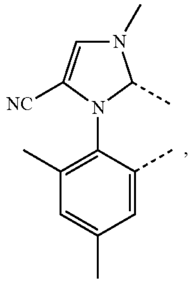
-continued
LA28
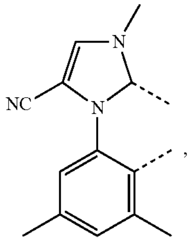
LA29
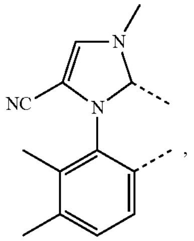
LA30
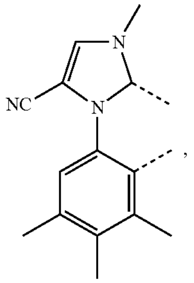
LA31
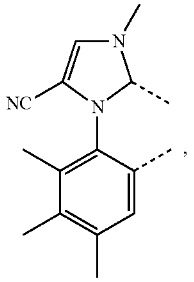
LA32
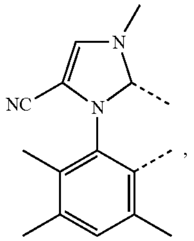
LA33
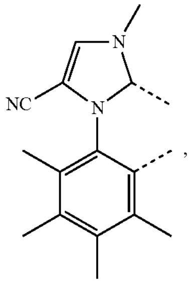

LA34
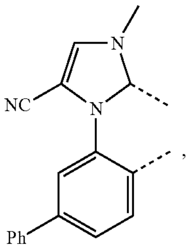
LA35
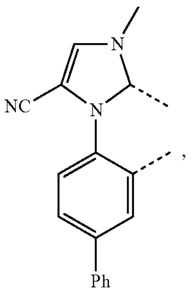
LA36
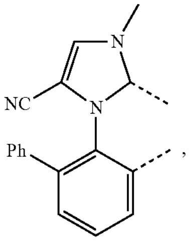
LA37
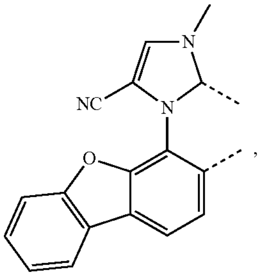
LA38
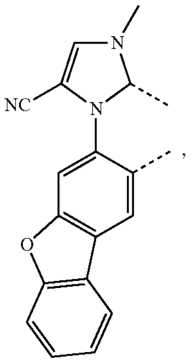
LA39
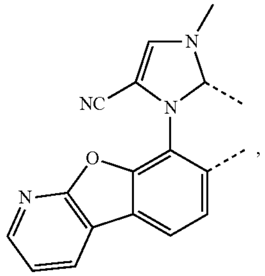
LA40
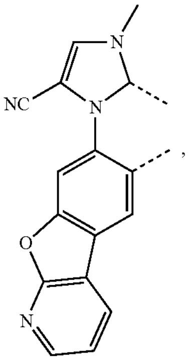
LA41
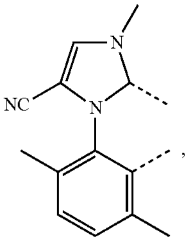
LA42
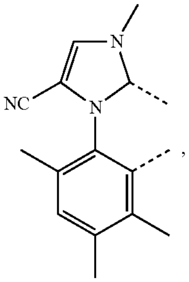
LA43
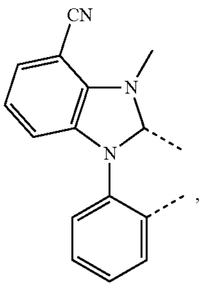

-continued
LA44
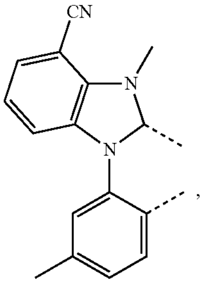
LA45
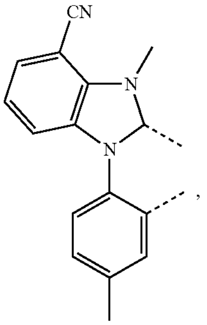
LA46
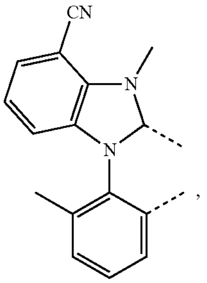
LA47
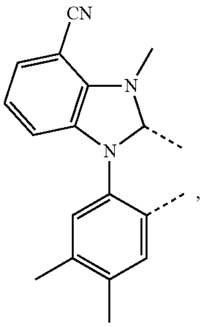
LA48
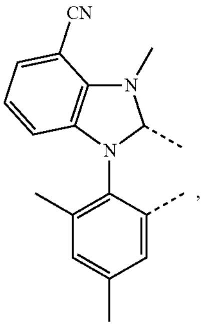
-continued
LA49
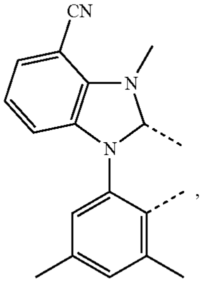
LA50
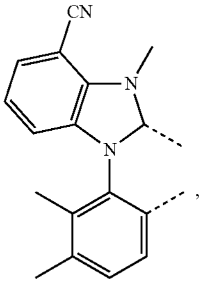
LA51
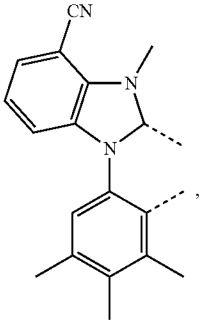
LA52
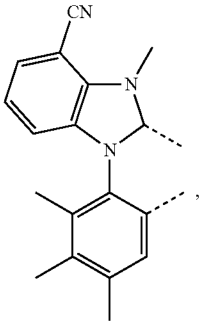
LA53
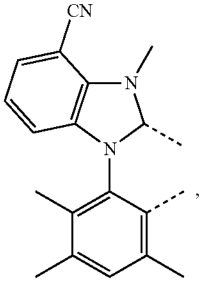

-continued
LA54
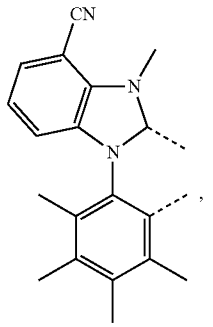
LA55
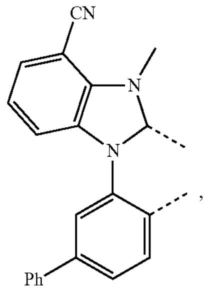
LA56
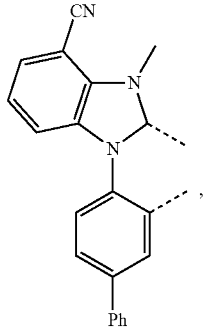
LA57
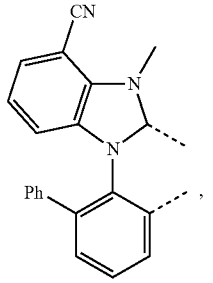
LA58
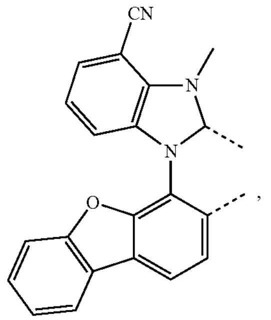
-continued
LA59
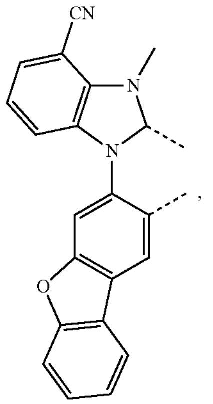
LA60
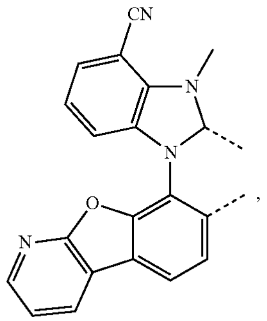
LA61
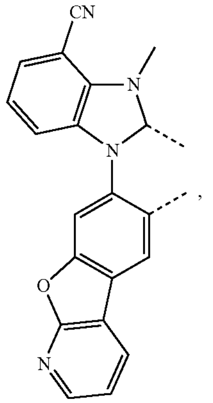
LA62
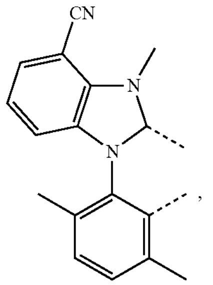

-continued
LA63
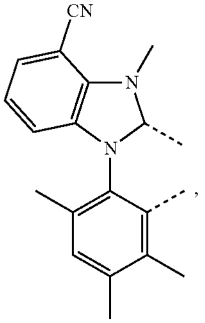
LA64
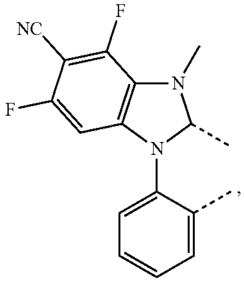
LA65
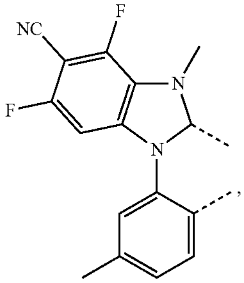
LA66
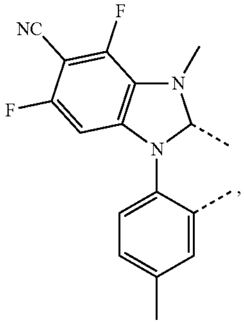
LA67
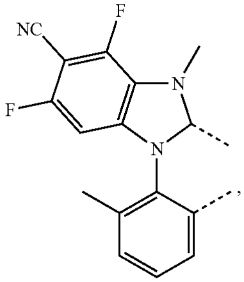
-continued
LA68
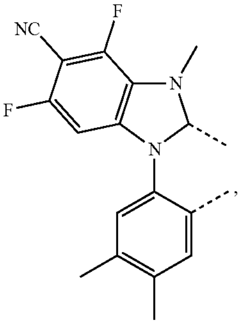
LA69
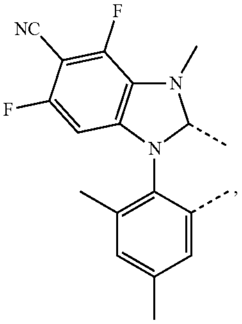
LA70
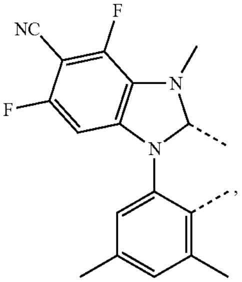
LA71
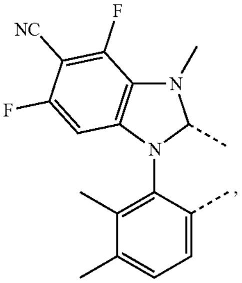
LA72
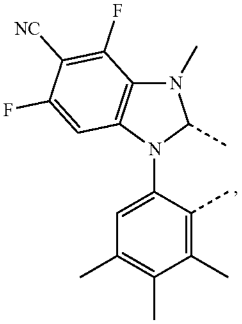

-continued
LA73
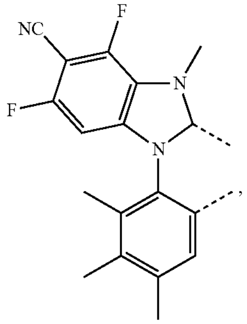
LA74
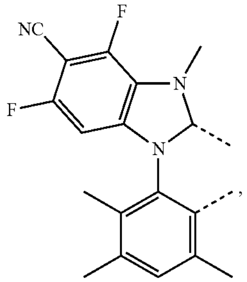
LA75
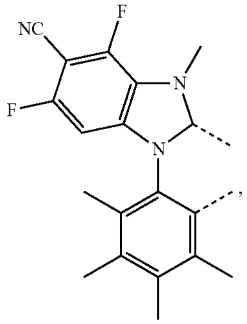
LA76
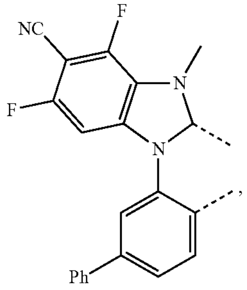
LA77
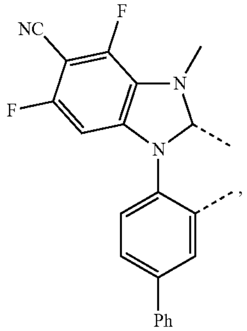
-continued
LA78
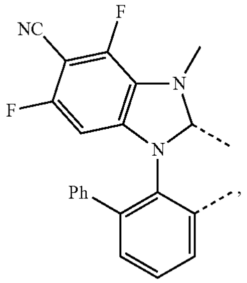
LA79
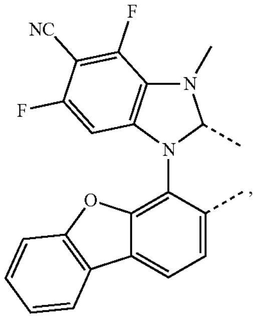
LA80
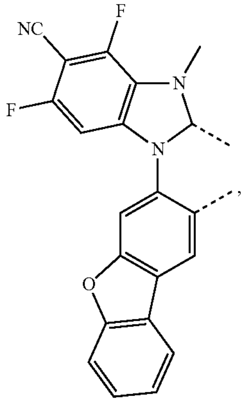
LA81
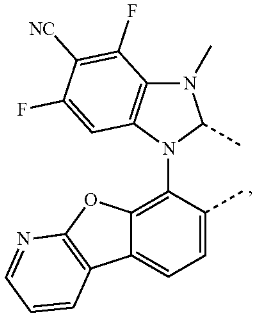

-continued
LA82
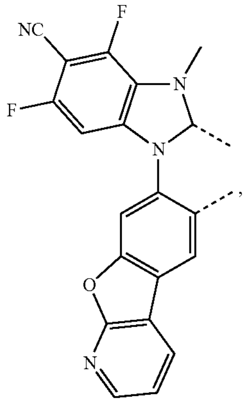
LA83
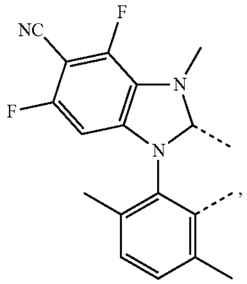
LA84
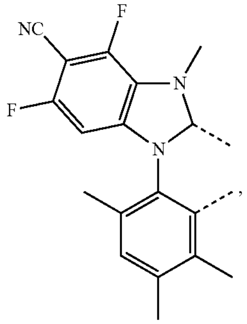
LA85
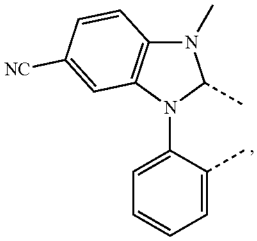
LA86
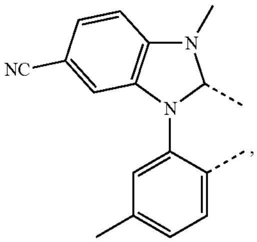
-continued
LA87
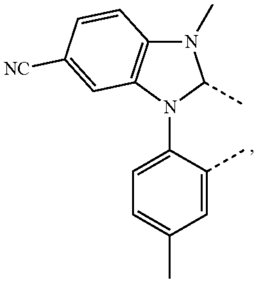
LA88
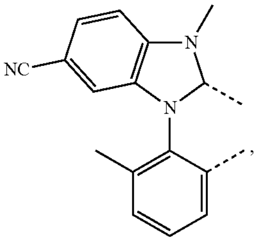
LA89
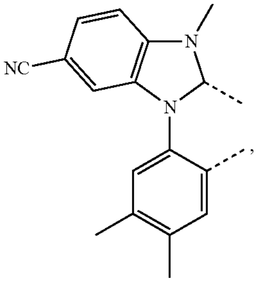
LA90
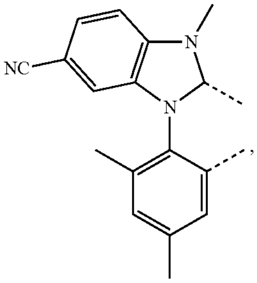
LA91
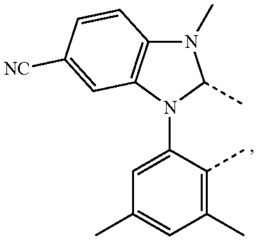
LA92
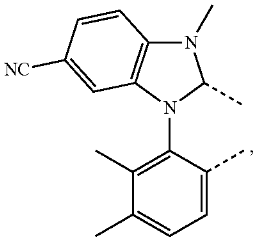

-continued
LA93
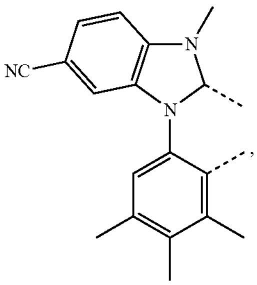
LA94
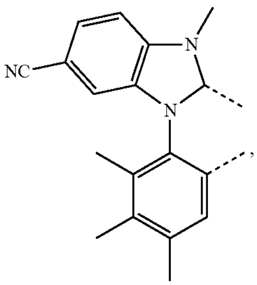
LA95
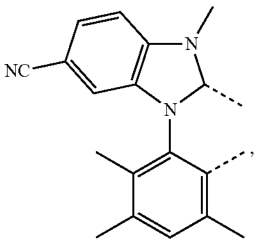
LA96
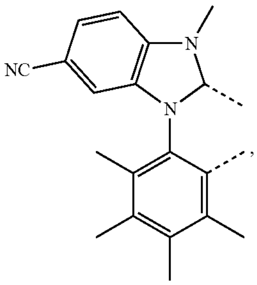
LA97
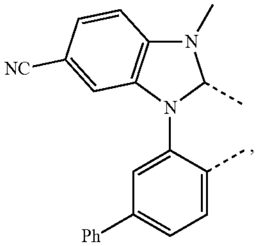
-continued
LA98
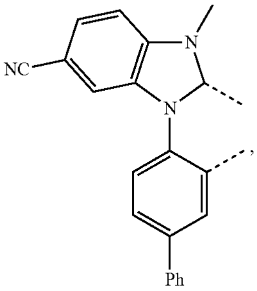
LA99
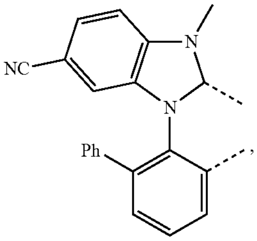
LA100
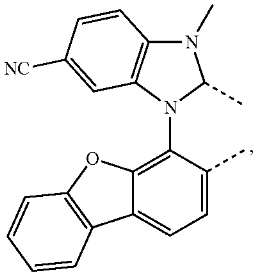
LA101
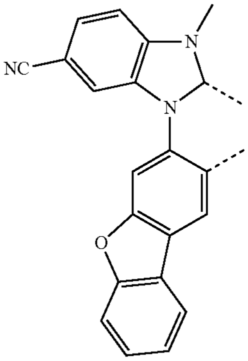
LA102
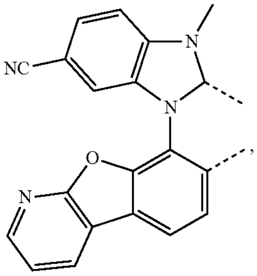

-continued
LA103
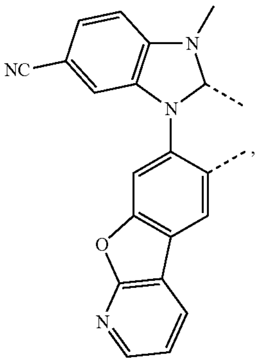
LA104
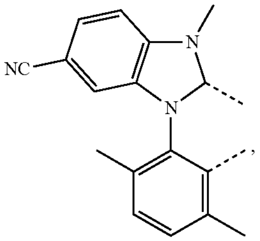
LA105
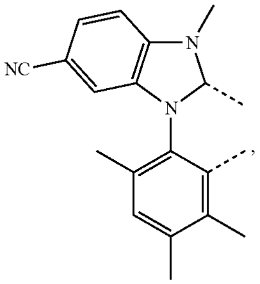
LA106
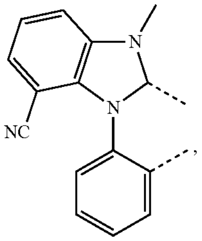
LA107
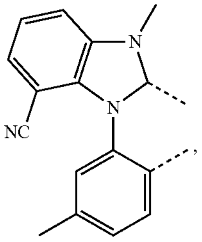
-continued
LA108
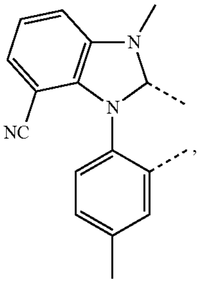
LA109
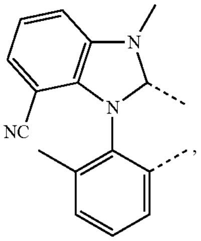
LA110
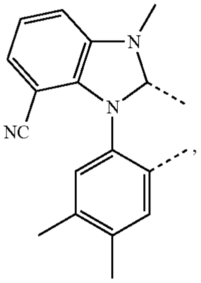
LA111
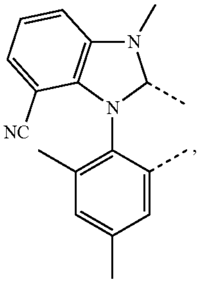
LA112
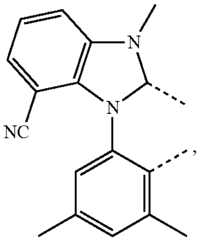
LA113
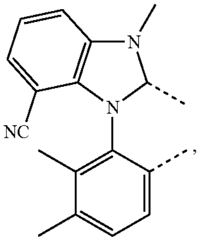

-continued
LA114
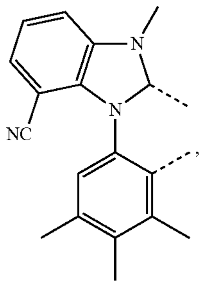
LA115
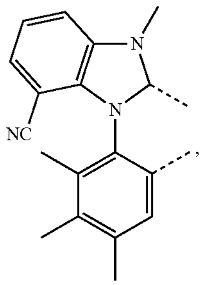
LA116
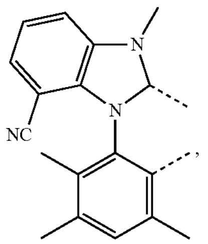
LA117
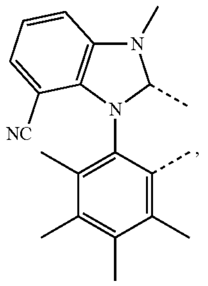
LA118
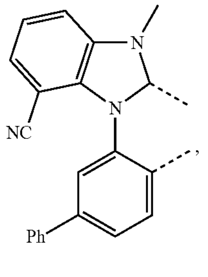
-continued
LA119
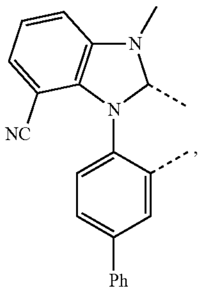
LA120
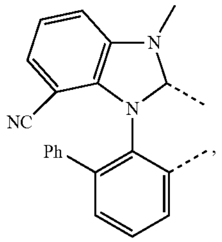
LA121
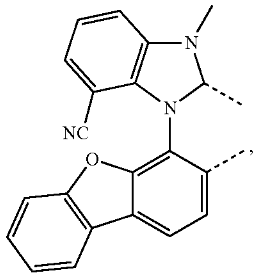
LA122
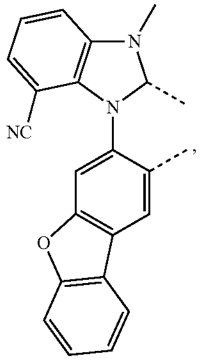
LA123
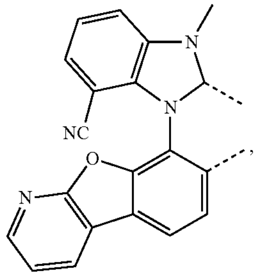

-continued
LA124
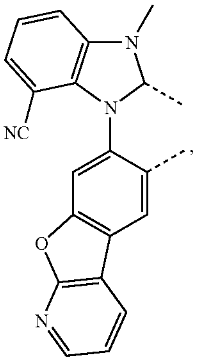
LA125
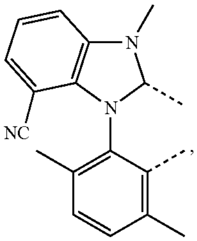
LA126
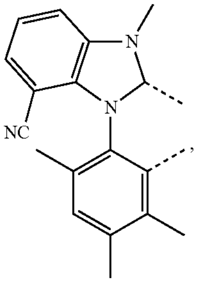
LA127
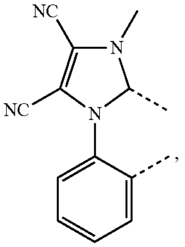
LA128
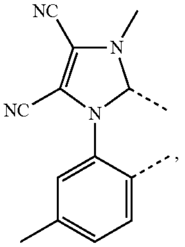
-continued
LA129
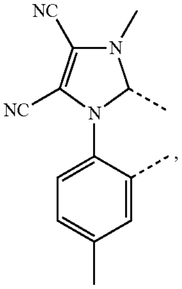
LA130
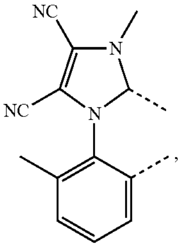
LA131
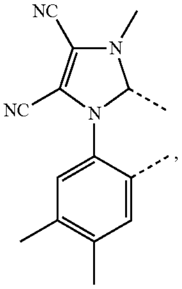
LA132
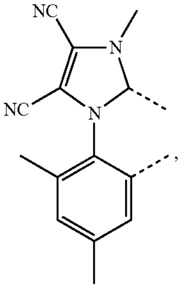
LA133
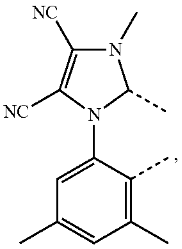
LA134
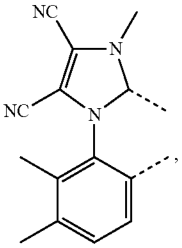

-continued
LA135
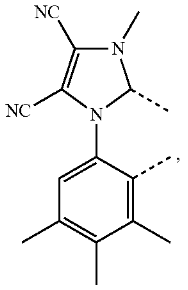
LA136
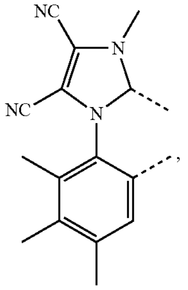
LA137
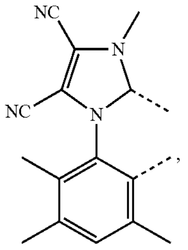
LA138
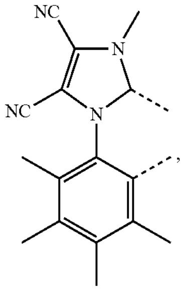
LA139
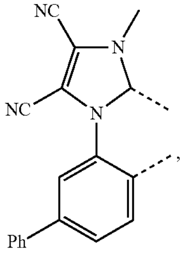
-continued
LA140
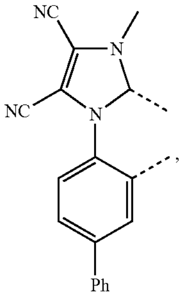
LA141
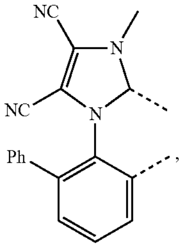
LA142
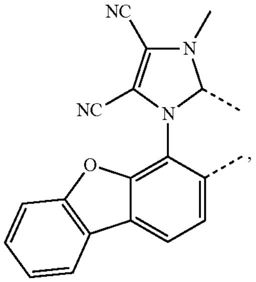
LA143
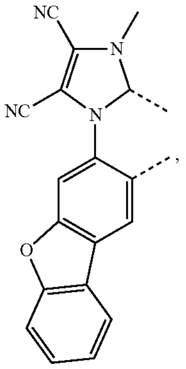
LA144
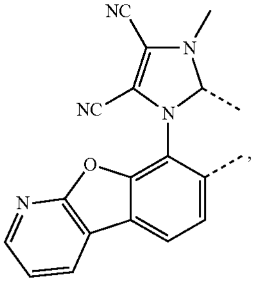

-continued
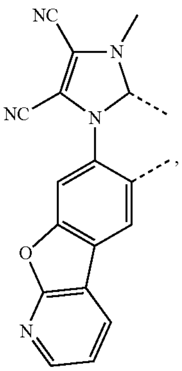
LA145
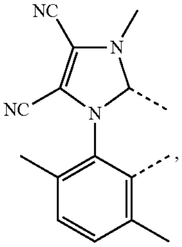
LA146
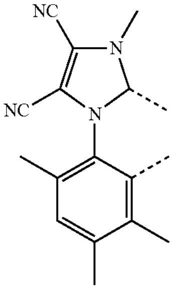
LA147
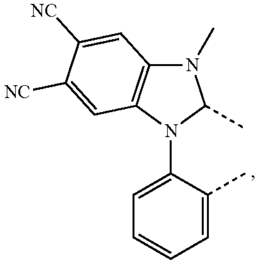
LA148
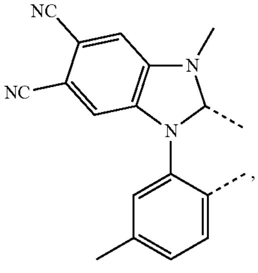
LA149
-continued
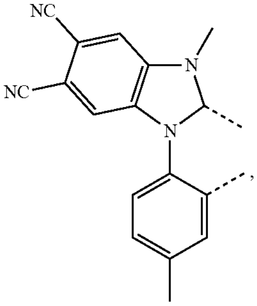
LA150
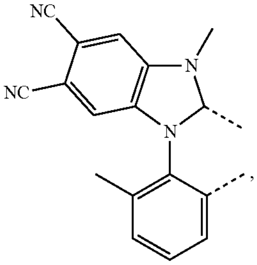
LA151
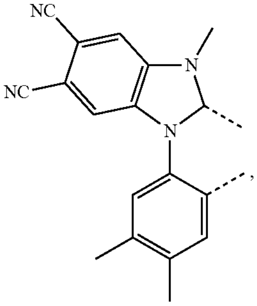
LA152
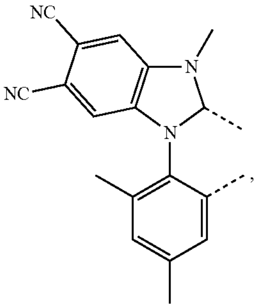
LA153
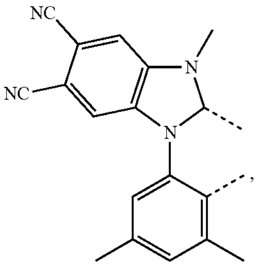
LA154

-continued
LA155
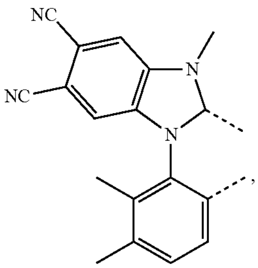
LA156
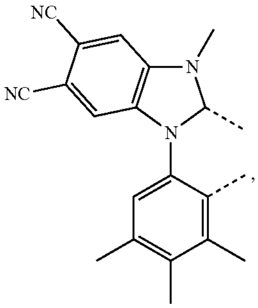
LA157
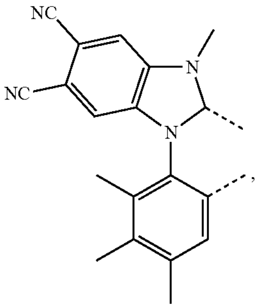
LA158
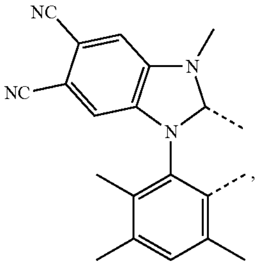
LA159
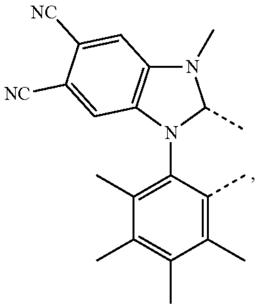
-continued
LA160
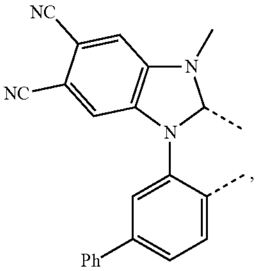
LA161
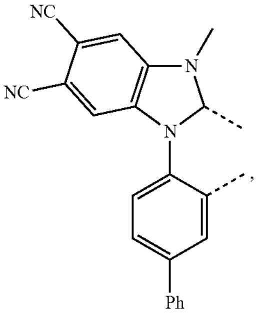
LA162
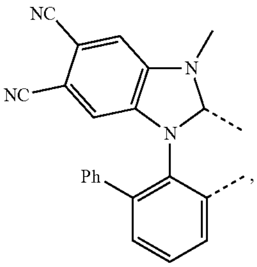
LA163
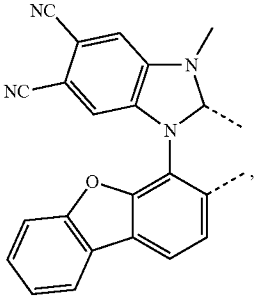
LA164
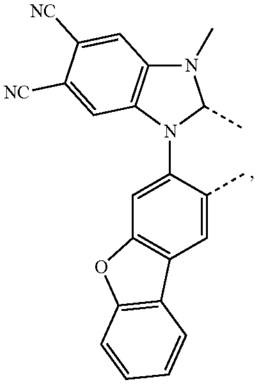

-continued
LA165
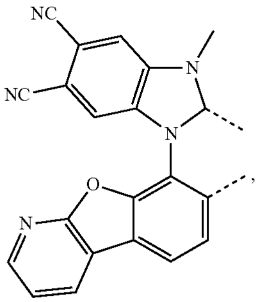
LA166
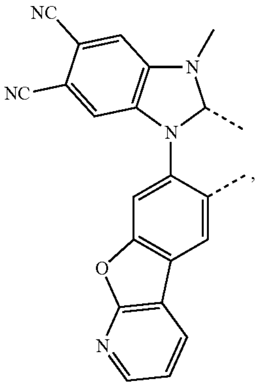
LA167
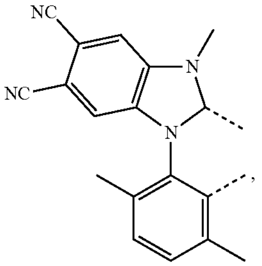
LA168
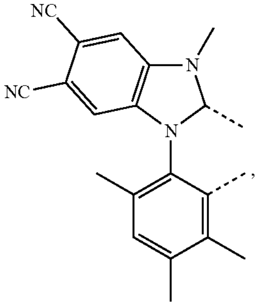
LA169
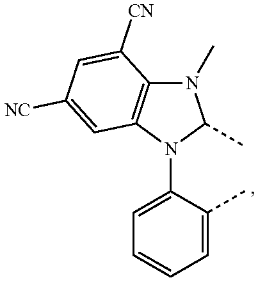
-continued
LA170
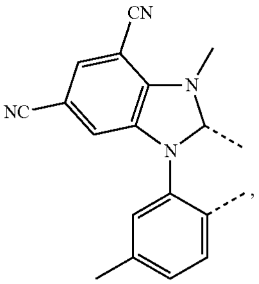
LA171
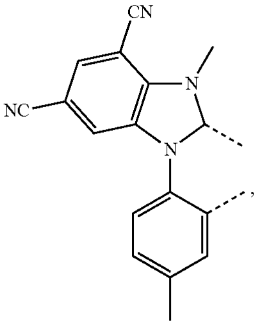
LA172
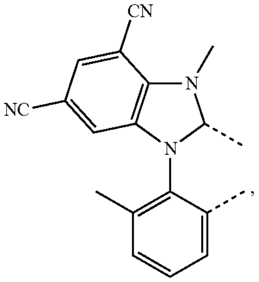
LA173
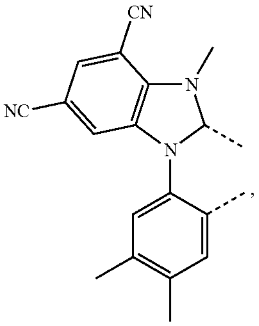
LA174
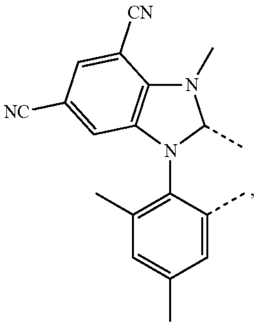

-continued
LA175
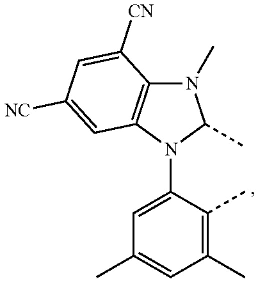
LA176
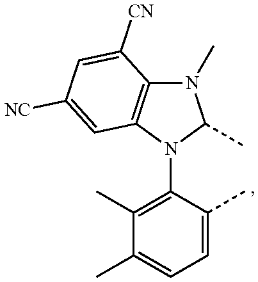
LA177
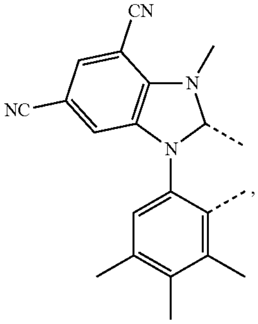
LA178
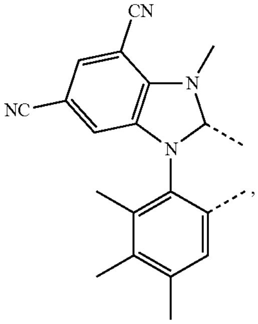
LA179
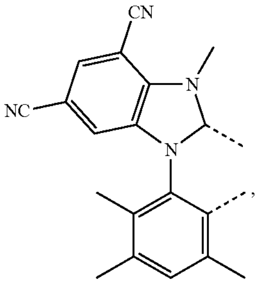
-continued
LA180
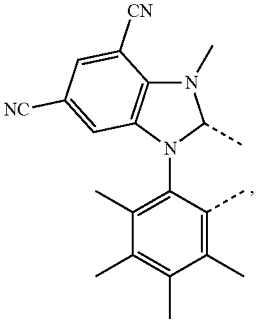
LA181
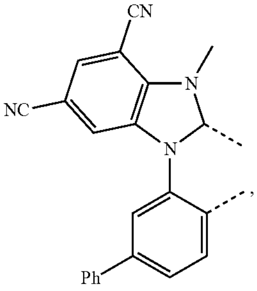
LA182
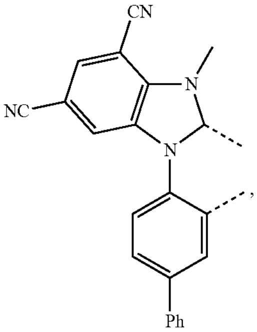
LA183
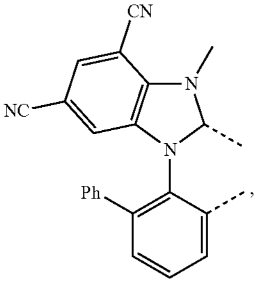
LA184
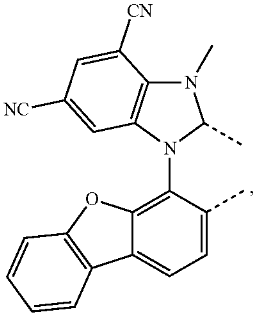

-continued
LA185
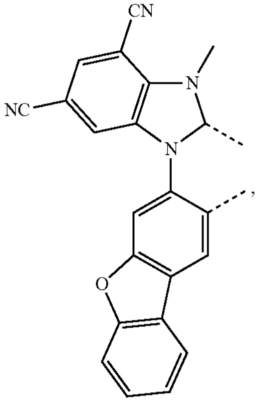
LA186
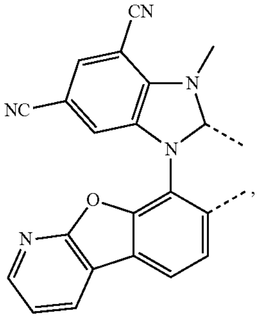
LA187
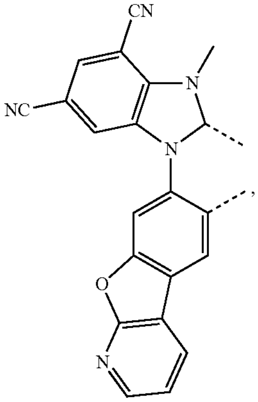
LA188
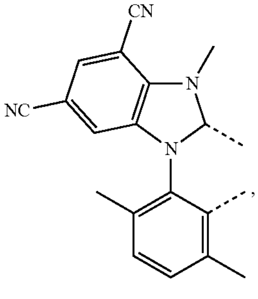
-continued
LA189
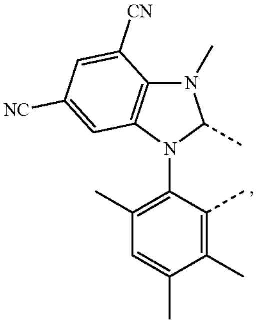
LA190
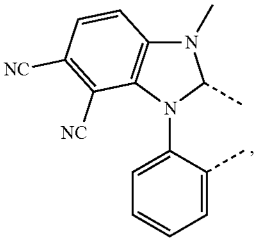
LA191
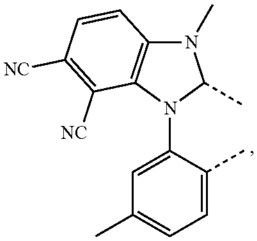
LA192
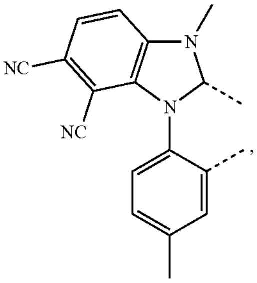
LA193
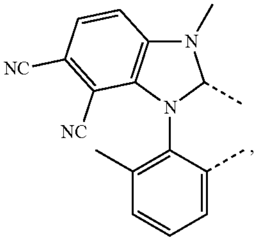

-continued
LA194
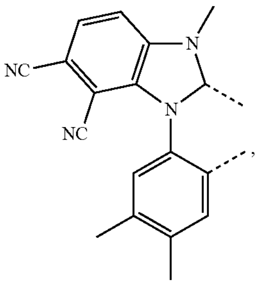
LA195
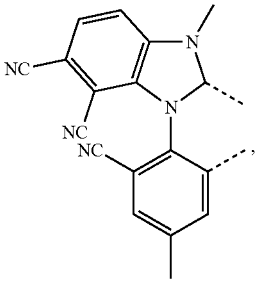
LA196
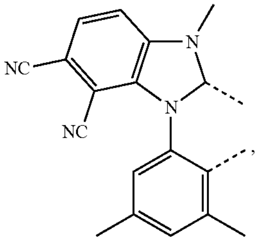
LA197
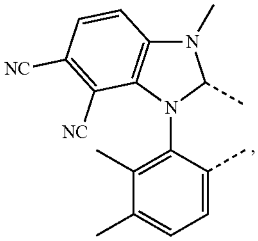
LA198
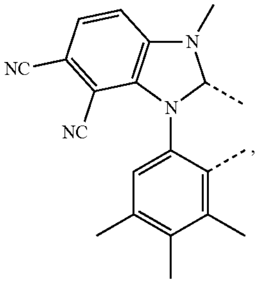
-continued
LA199
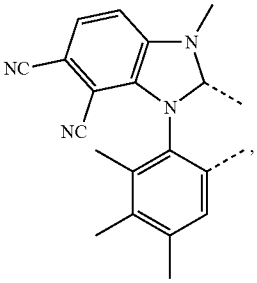
LA200
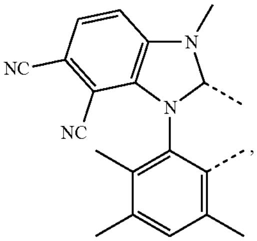
LA201
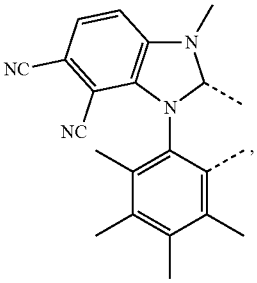
LA202
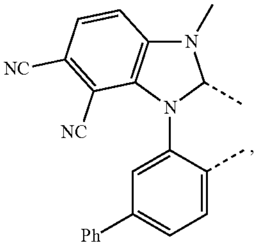
LA203
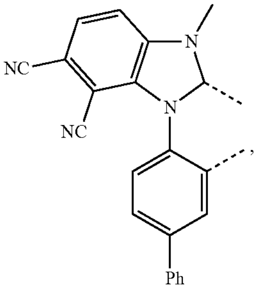
LA204
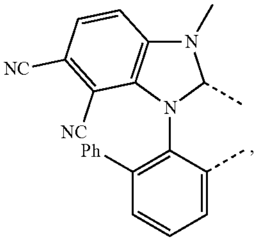

-continued
LA205
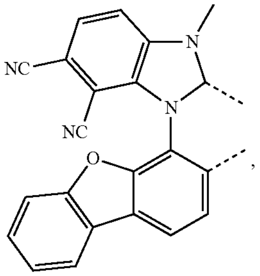
LA206
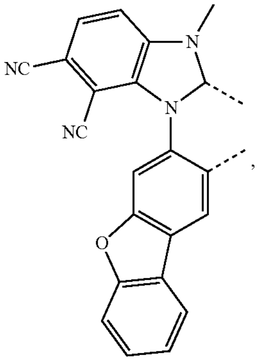
LA207
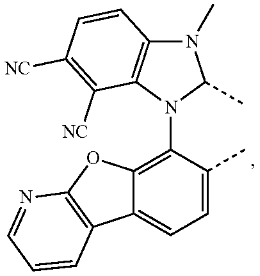
LA208
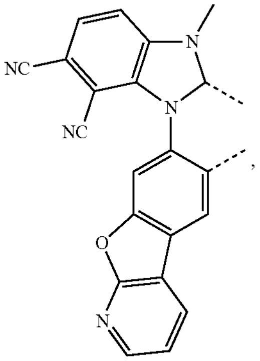
LA209
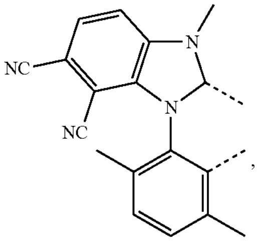
-continued
LA210
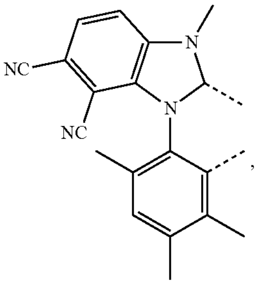
LA211
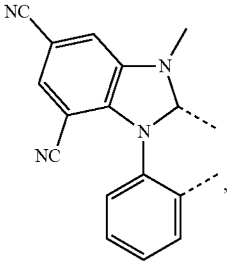
LA212
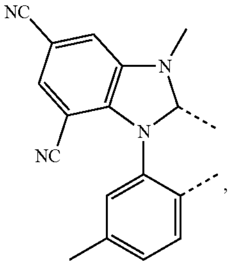
LA213
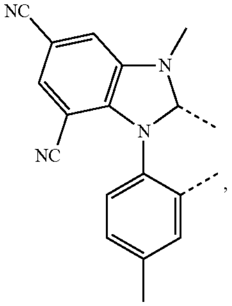
LA214
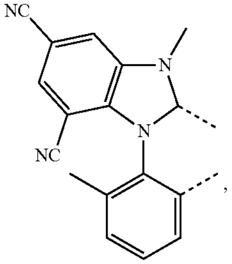

-continued
LA215
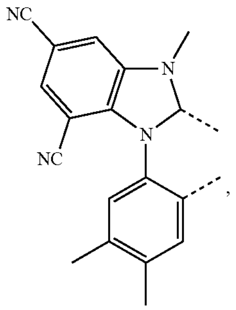
LA216
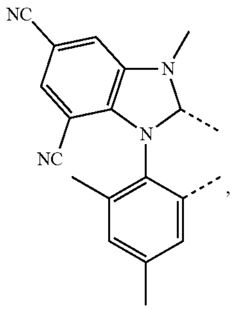
LA217
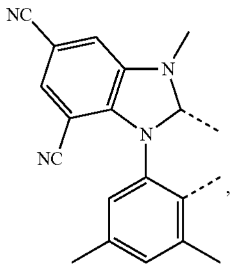
LA218
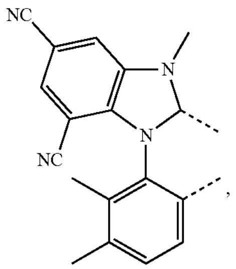
LA219
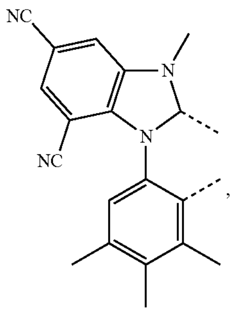
-continued
LA220
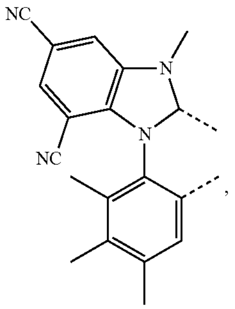
LA221
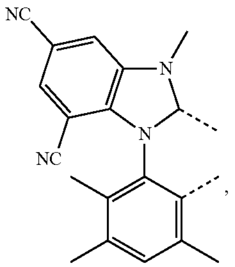
LA222
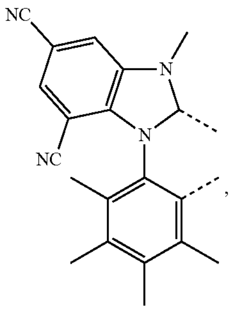
LA223
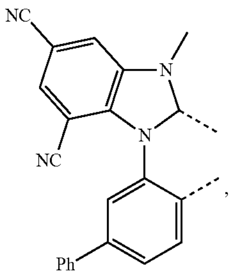
LA224
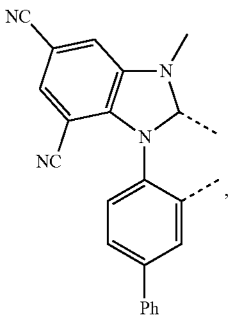

-continued
LA225
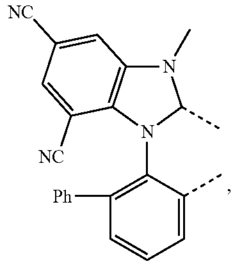
LA226
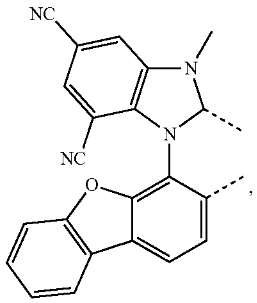
LA227
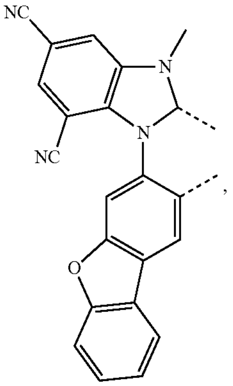
LA228
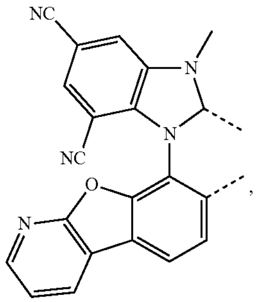
-continued
LA229
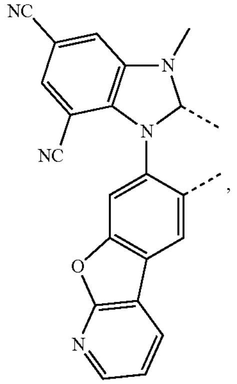
LA230
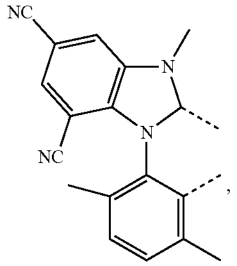
LA231
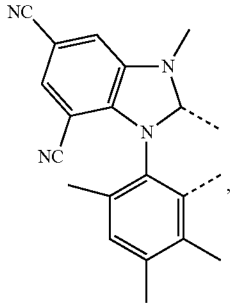
LA232
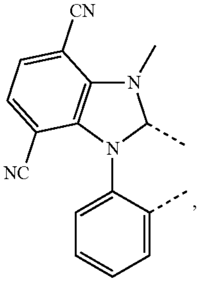
LA233
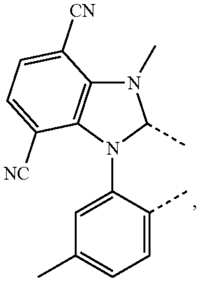

-continued
LA234
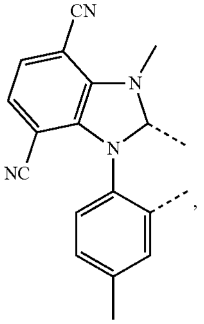
LA235
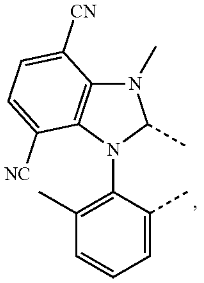
LA236
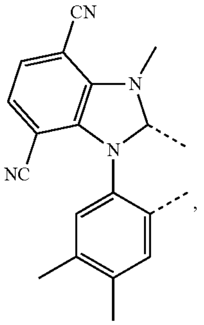
LA237
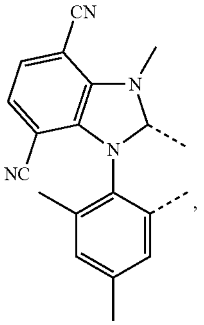
LA238
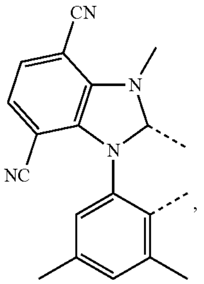
-continued
LA239
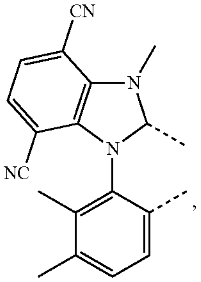
LA240
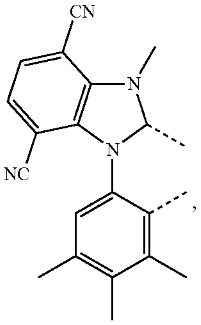
LA241
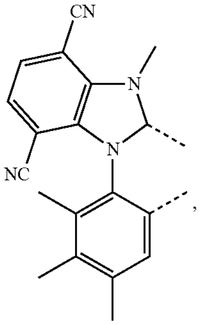
LA242
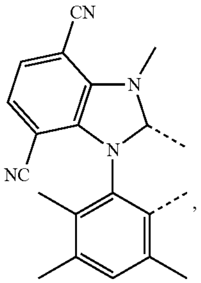
LA243
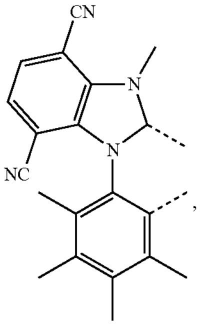

-continued
LA244
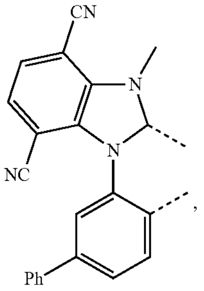
LA245
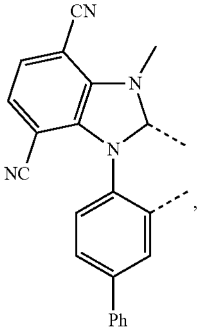
LA246
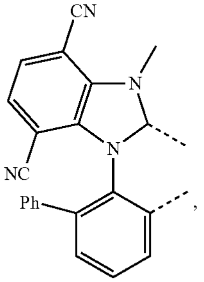
LA247
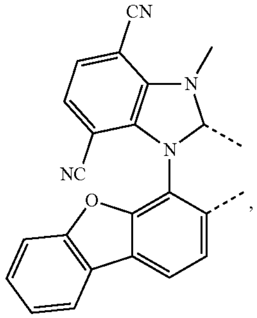
LA248
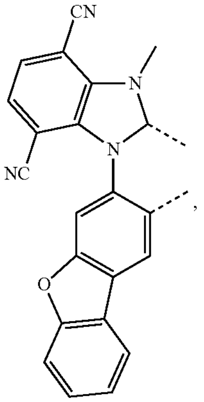
-continued
LA249
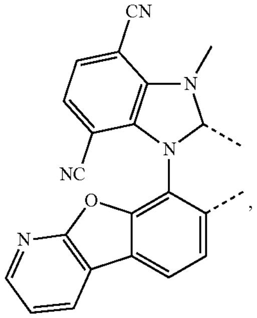
LA250
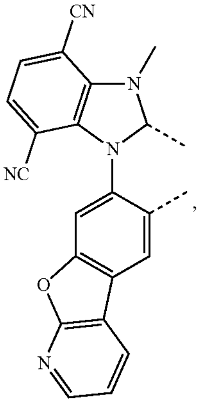
LA251
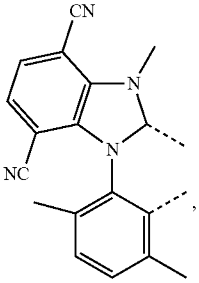
LA252
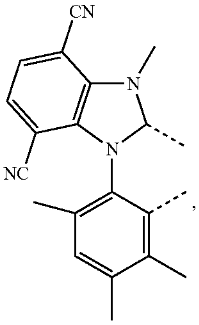
LA253
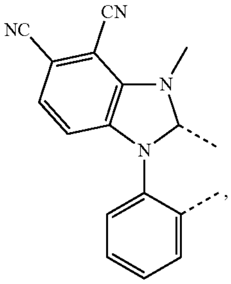

-continued
LA254
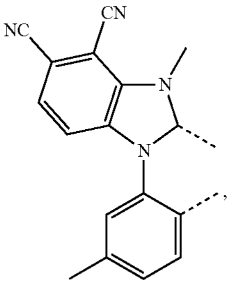
LA255
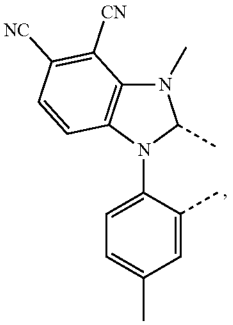
LA256
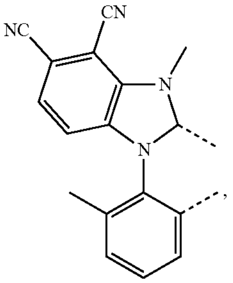
LA257
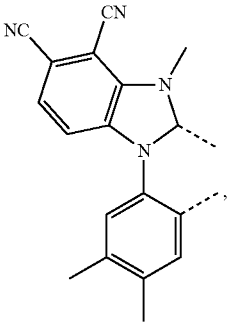
LA258
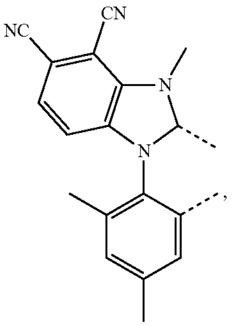
-continued
LA259
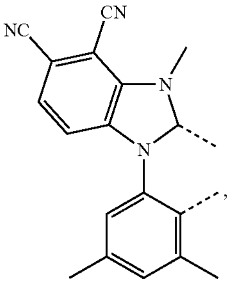
LA260
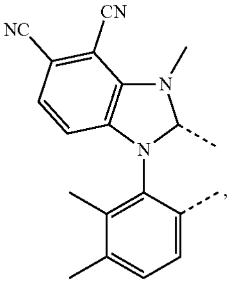
LA261
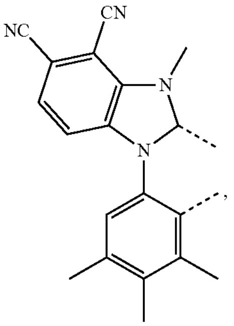
LA262
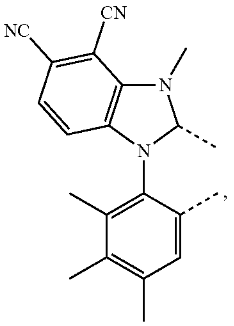
LA263
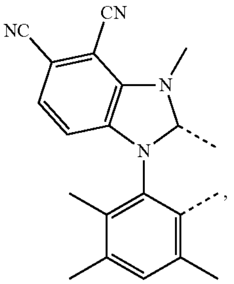

LA264
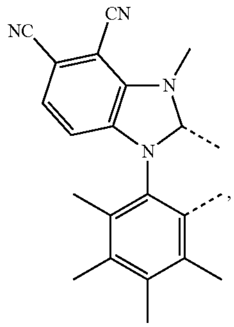
LA265
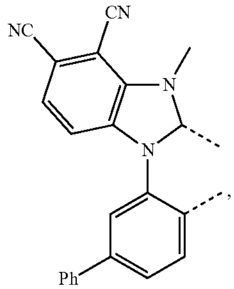
LA266
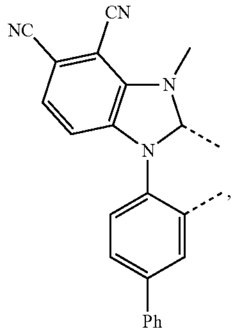
LA267
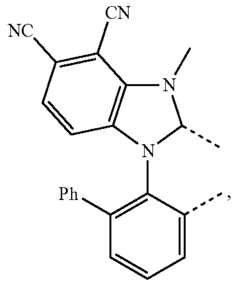
LA268
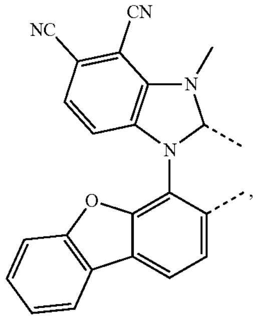
LA269
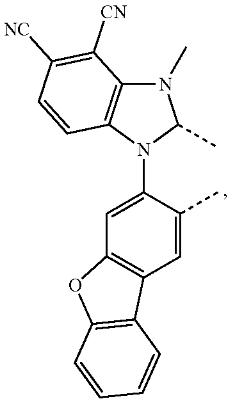
LA270
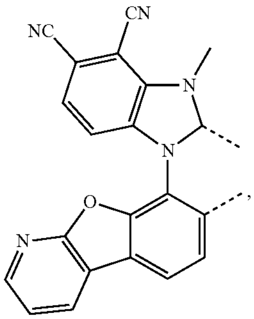
LA271
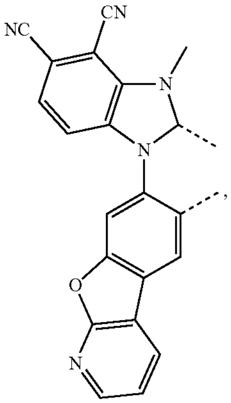
LA272
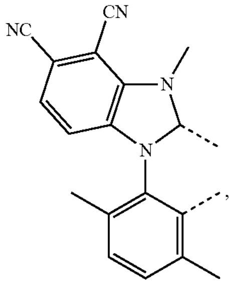
and -continued

LA273

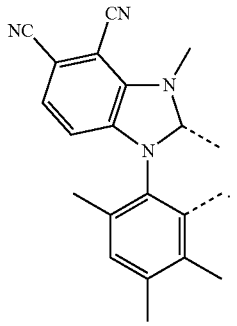

4. The compound of claim 1, wherein the compound has a formula of $M(L_A)_n(L_B)_{m-n}$;

wherein M is Ir or Pt;

wherein $L_B$ is a bidentate ligand; and when M is Ir, m is 3, and n is 1, 2, or 3; and when M is Pt, m is 2, and n is 1 or 2.

5. The compound of claim 4, wherein the compound has a formula selected from the group consisting of $Ir(L_A)_3$, $Ir(L_A)(L_B)_2$, and $Ir(L_A)_2(L_B)$, wherein $L_B$ is different from $L_A$.

6. The compound of claim 4, wherein $L_B$ is selected from the group consisting of:

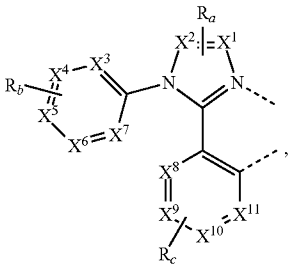

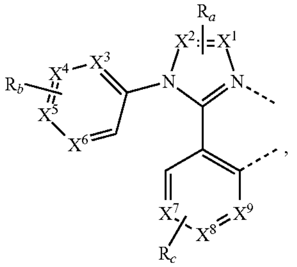

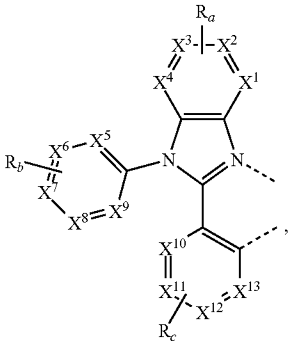

-continued

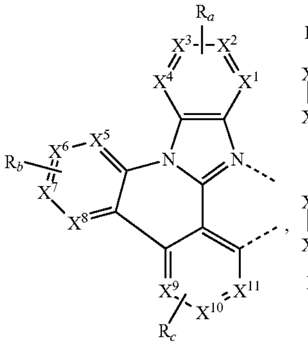

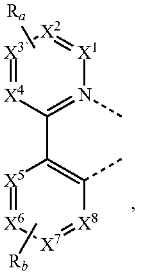

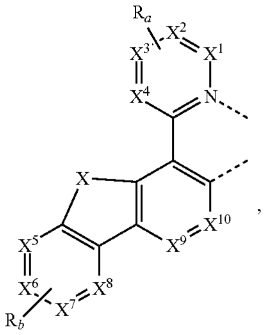

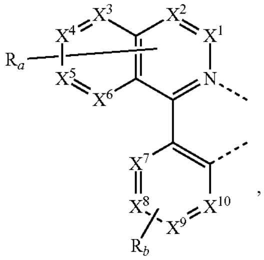

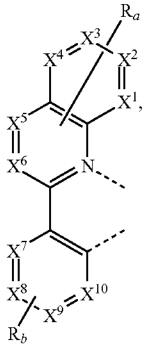

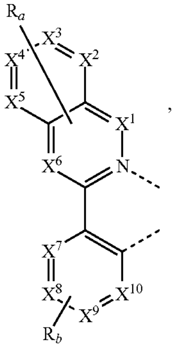

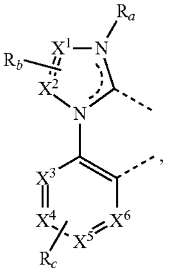

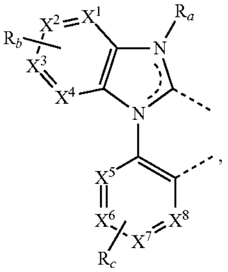

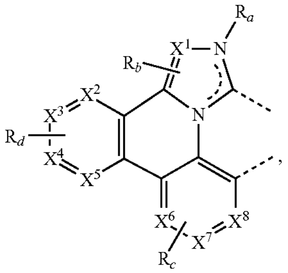

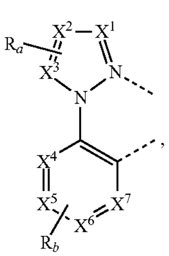

-continued

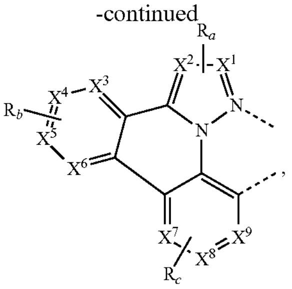

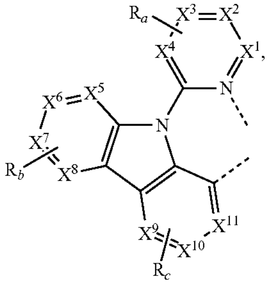

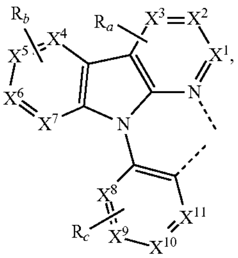

and

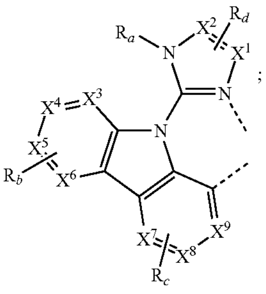

;

wherein each $X^1$ to $X^{13}$ are independently selected from the group consisting of carbon and nitrogen;

wherein X is selected from the group consisting of BR', NR', PR', O, S, Se, C═O, S═O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

7. The compound of claim 6, wherein $L_B$ is selected from the group consisting of:

LB1

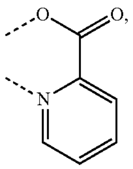

-continued

LB2

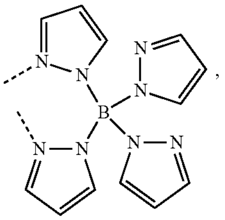

LB3

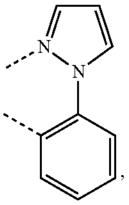

LB4

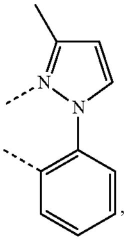

LB5

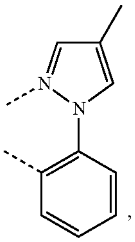

LB6

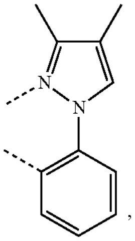

LB7

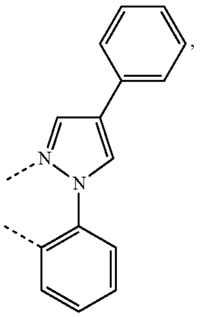

-continued
LB8
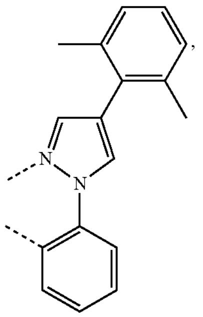
LB9
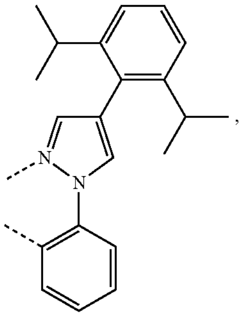
LB10
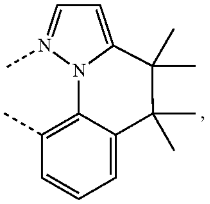
LB11
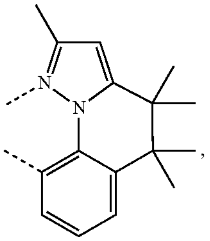
LB12
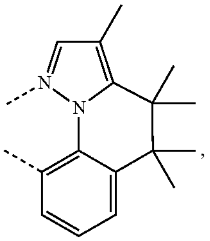
LB13
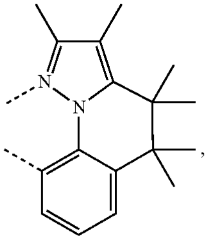
-continued
LB14
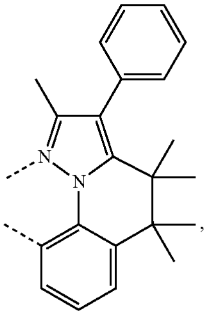
LB15
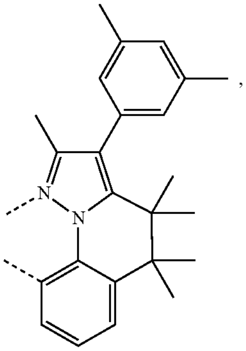
LB16
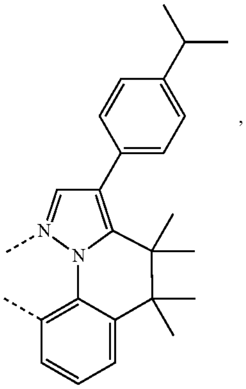
LB17
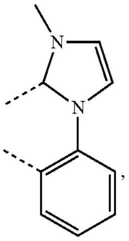
LB18
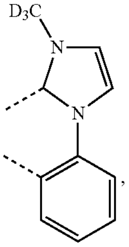

-continued
LB19
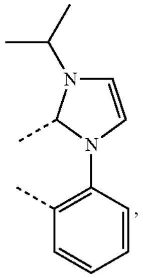
LB20
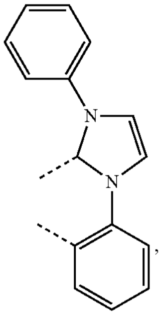
LB21
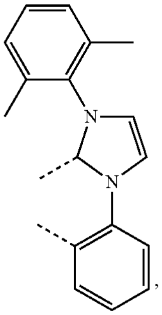
LB22
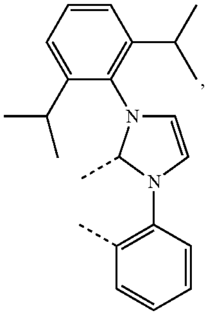
LB23
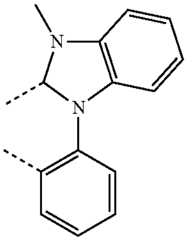
-continued
LB24
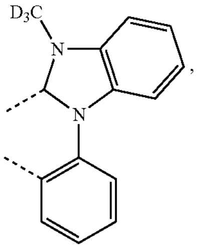
LB25
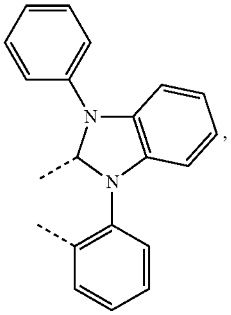
LB26
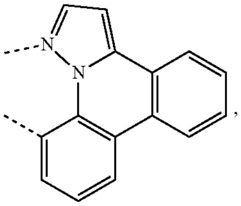
LB27
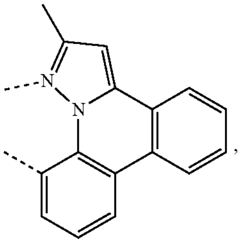
LB28
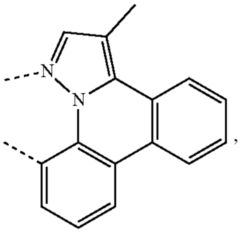
LB29
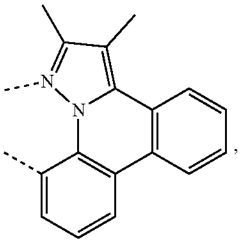

-continued
LB30
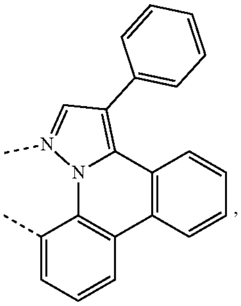
LB31
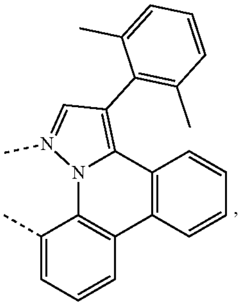
LB32
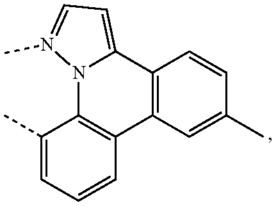
LB33
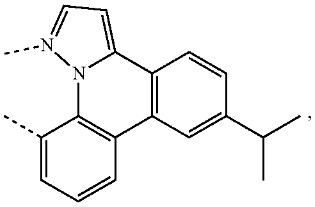
LB34
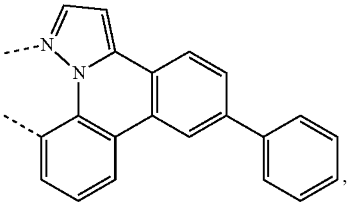
LB35
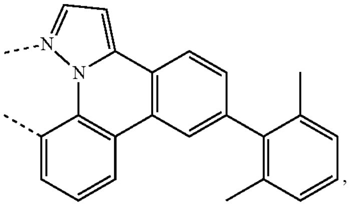
-continued
LB36
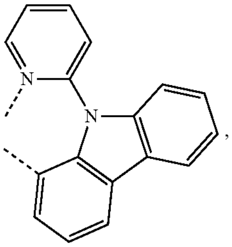
LB37
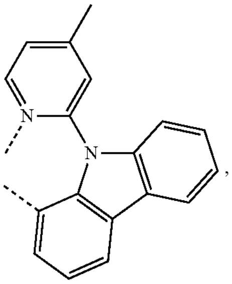
LB38
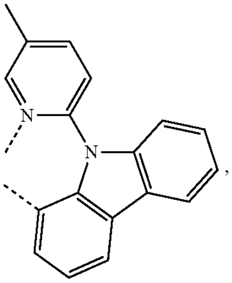
LB39
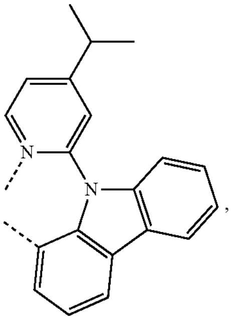
LB40
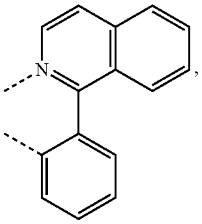

LB41
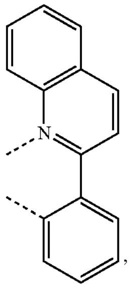
LB42
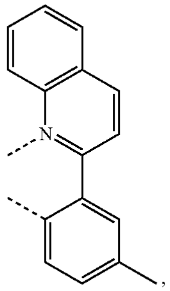
LB43
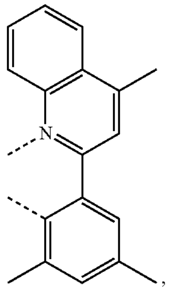
LB44
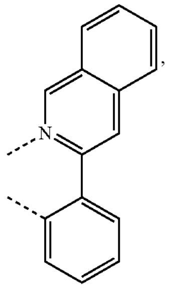
LB45
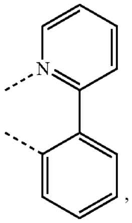
LB46
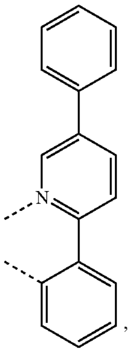
LB47
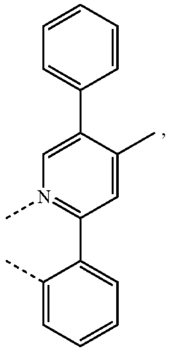
LB48
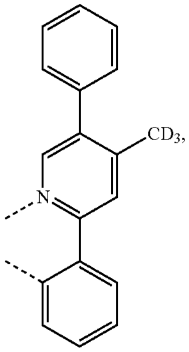
LB49
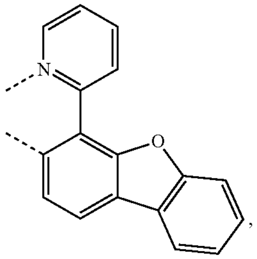
LB50
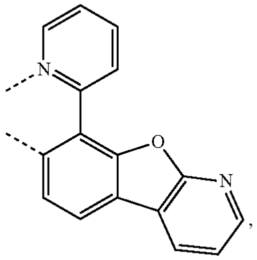

-continued

LB51

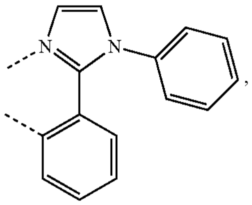

LB52

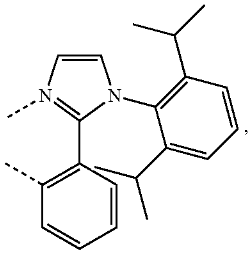

LB53

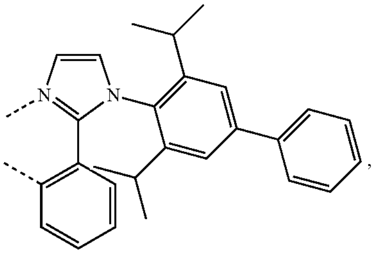

LB54

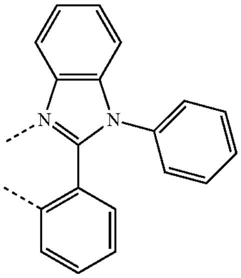

and

LB55

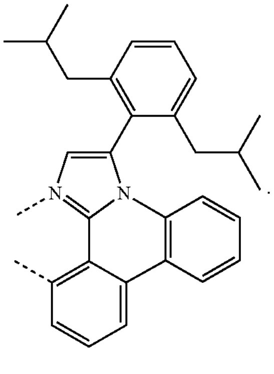

8. The compound of claim 3, wherein the compound is Compound Ax having the formula $Ir(L_{Ai})_3$, Compound By having the formula $Ir(L_{Ai})(L_{Bj})_2$, or Compound Cz having the formula $Ir(L_{Ai})_2(L_{Bj})$;

wherein x=i and i is an integer from 1 to 273;

wherein y=55i+j−55; i is an integer from 1 to 273, and j is an integer from 1 to 55;

wherein z=55i+j−55; i is an integer from 1 to 273, and j is an integer from 1 to 55; and wherein $L_{B1}$ to $L_{B55}$ have the following structure:

LB1

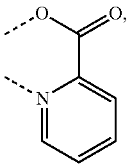

LB2

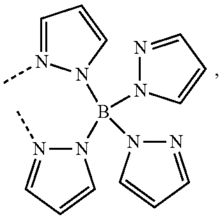

LB3

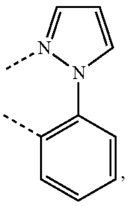

LB4

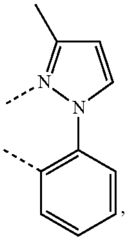

LB5

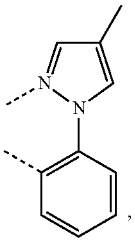

LB6

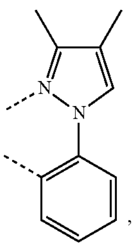

-continued
LB7
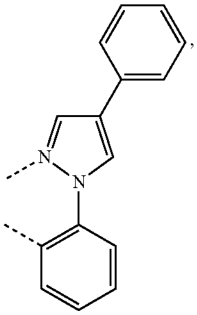,
LB8
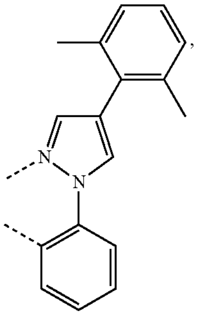,
LB9
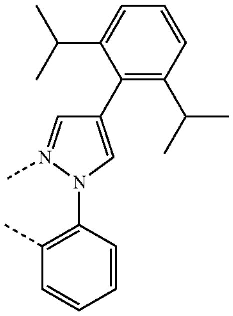,
LB10
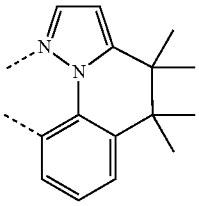,
LB11
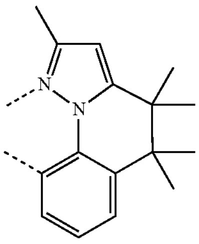,
-continued
LB12
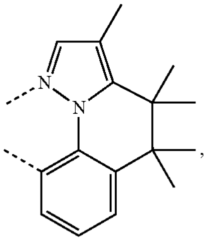,
LB13
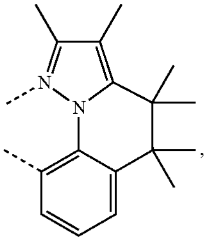,
LB14
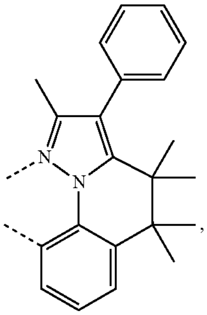,
LB15
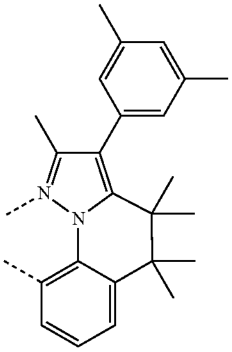,
LB16
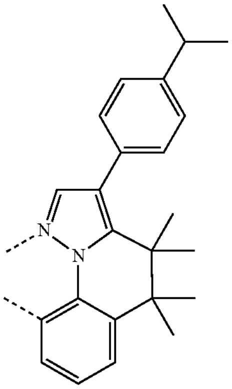, -continued
LB17
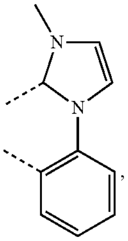
LB18
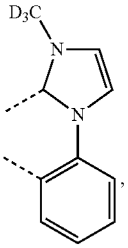
LB19
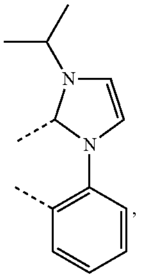
LB20
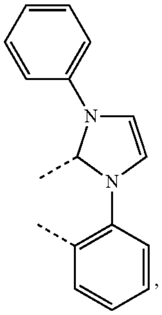
LB21
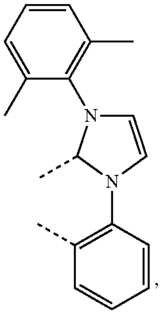
-continued
LB22
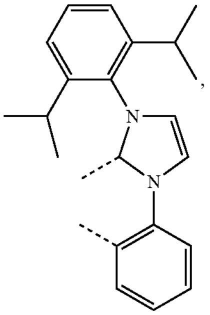
LB23
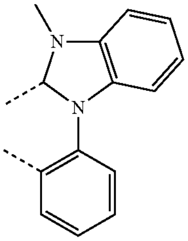
LB24
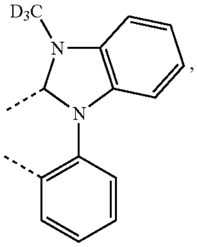
LB25
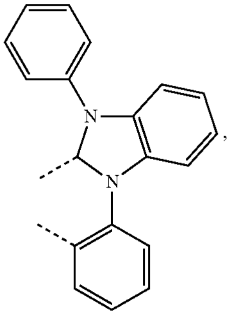
LB26
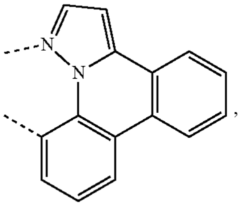
LB27
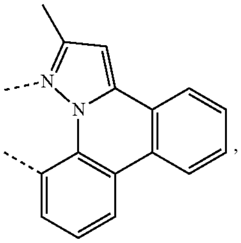

-continued
LB28
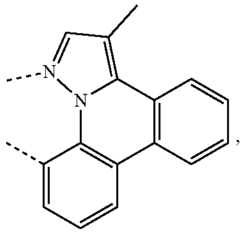
LB29
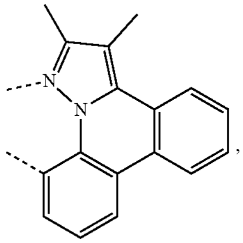
LB30
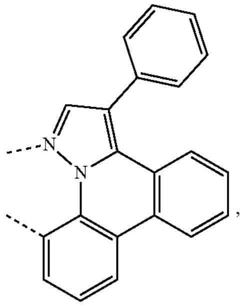
LB31
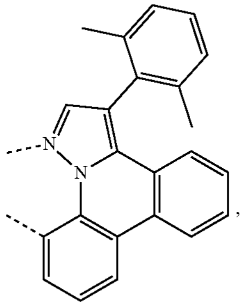
LB32
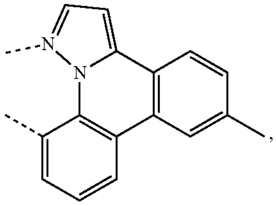
LB33
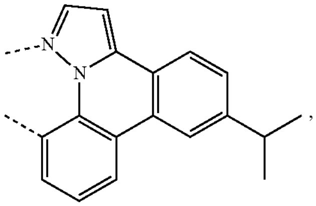
-continued
LB34
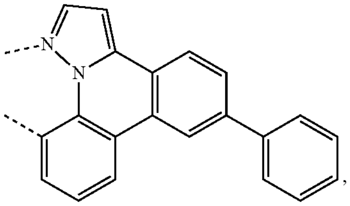
LB35
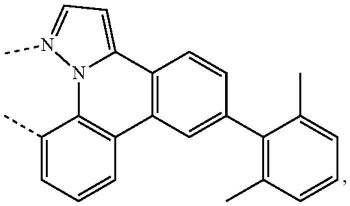
LB36
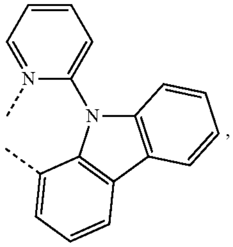
LB37
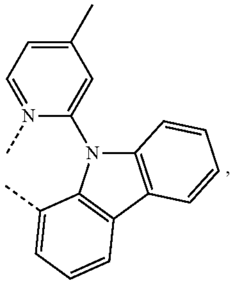
LB38
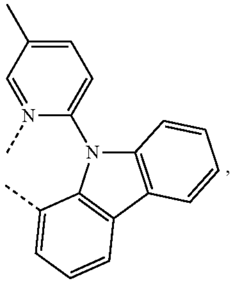
LB39
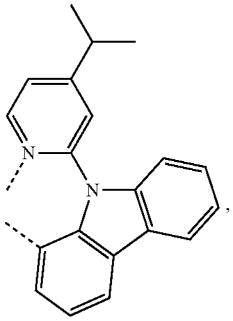

-continued
LB40
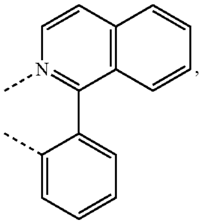
LB41
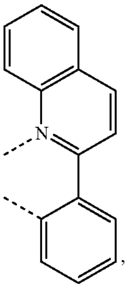
LB42
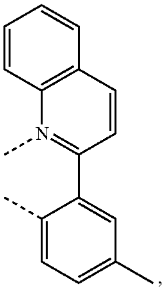
LB43
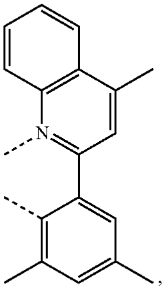
LB44
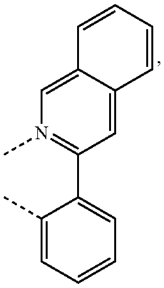
-continued
LB45
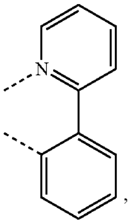
LB46
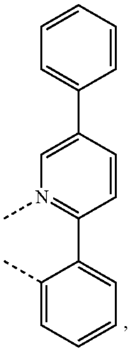
LB47
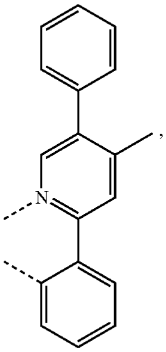
LB48
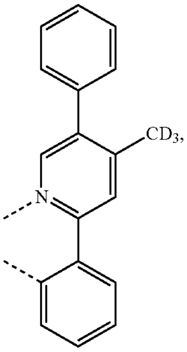
LB49
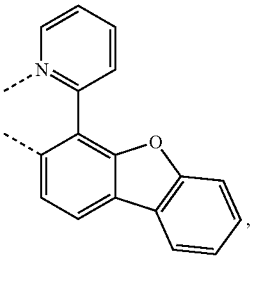

-continued

LB50

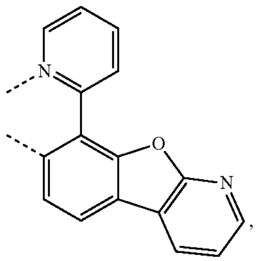

LB51

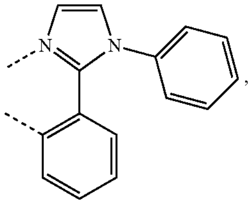

LB52

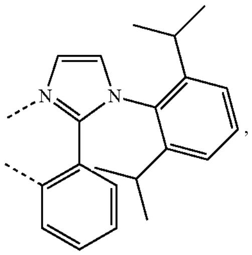

LB53

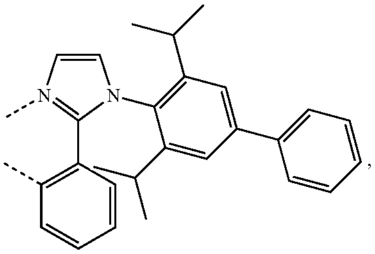

LB54

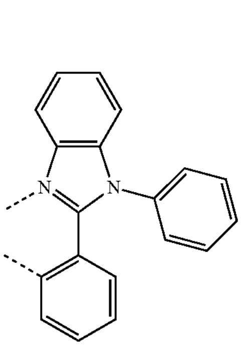

and

-continued

LB55

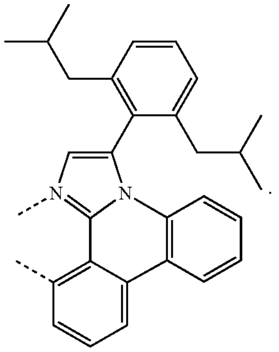

9. An organic light emitting device (OLED) comprising:

an anode;

a cathode; and an organic layer, disposed between the anode and the cathode, comprising a compound comprising a carbene ligand $L_A$ selected from the group consisting of:

Formula I

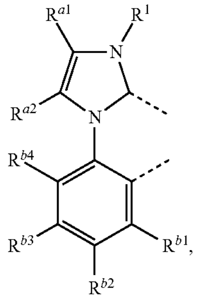

and

Formula II

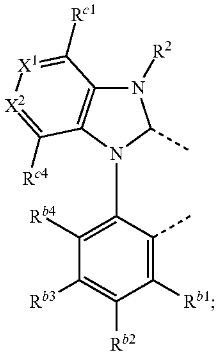

wherein $X^1$ is $CR^{c2}$ or N, $X^2$ is $CR^{c3}$ or N;

wherein $R^{a1}$, $R^{a2}$, $R^{b1}$, $R^{b2}$, $R^{b3}$, $R^{b4}$, $R^{c1}$, $R^{c2}$, $R^{c3}$, $R^{c4}$, $R^1$ and $R^2$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof;

wherein at least one of $R^1$, $R^{a1}$, $R^{a2}$, $R^{c1}$, $R^{c3}$, and $R^{c4}$ comprises an acceptor group selected from the group consisting of CN, F directly attached to an aromatic ring, $Si_mF_{2m+1}$, NCO, NCS, OCN, SCN, $OC_mF_{2m+1}$, and $SC_mF_{2m+1}$, where m≥1, but $R^{a1}$ cannot be CN;

wherein any adjacent substituents of $R^{b1}$, $R^{b2}$, $R^{b3}$, and $R^{b4}$ are optionally joined or fused into a ring;

wherein the ligand $L_A$ is coordinated to a metal M; and wherein the ligand $L_A$ is optionally linked with other ligands to comprise a tridentate, tetradentate, pentadentate or hexadentate ligand;

wherein at least one of the following is true:

(i) $R^1$ and $R^2$ are each independently selected from the group consisting of halide, haloalkyl, cycloalkyl, heteroalkyl, alkoxy, thioalkoxy, aryloxy, thioaryloxy, amino, silyl, halosilyl, cycloalkenyl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$ and combinations thereof;

(ii) at least one of $R^1$, $R^{a1}$, $R^{a2}$, $R^{c1}$, $R^{c3}$, and $R^{c4}$ comprises an acceptor group selected from the group consisting of $Si_mF_{2m+1}$, NCO, NCS, OCN, SCN, $OC_mF_{2m+1}$, and $SC_mF_{2m+1}$, where m≥1;

(iii) the ligand $L_A$ is a ligand of Formula II and at least one of $R^{c1}$, $R^{c3}$, and $R^{c4}$ is CN.

10. The OLED of claim 9, wherein the OLED is incorporated into a device selected from the group consisting of a consumer product, an electronic component module, and a lighting panel.

11. The OLED of claim 9, wherein the organic layer is an emissive layer and the compound is an emissive dopant or a non-emissive dopant.

12. The OLED of claim 9, wherein the organic layer further comprises a host, wherein host comprises at least one chemical group selected from the group consisting of triphenylene, tetraphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

13. The OLED of claim 9, wherein the organic layer further comprises a host, wherein the host is selected from the group consisting of:

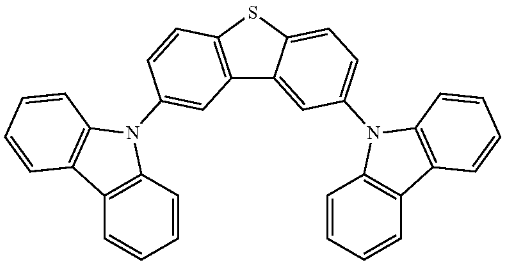

,

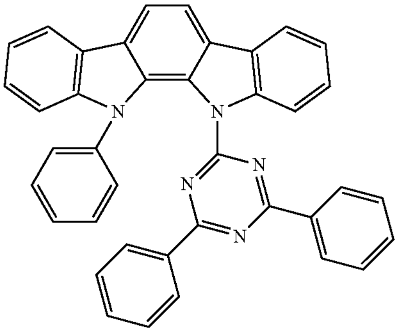

,

-continued

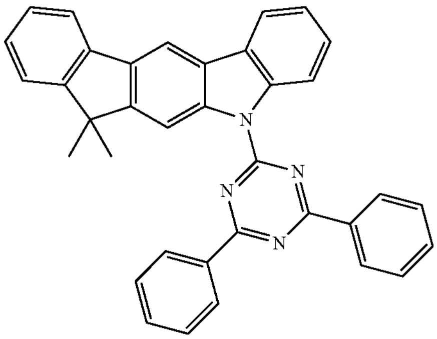

,

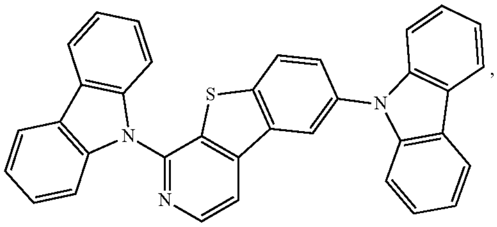

,

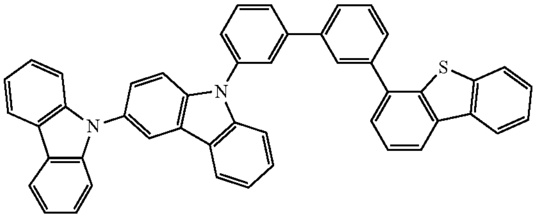

,

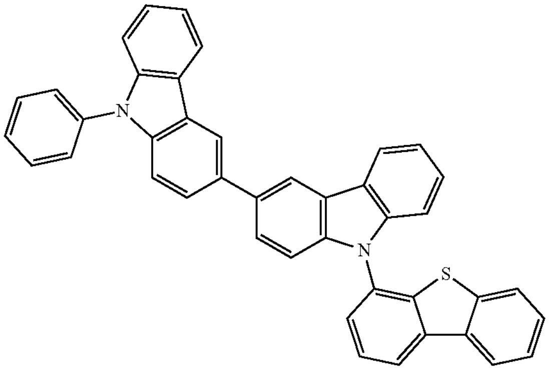

,

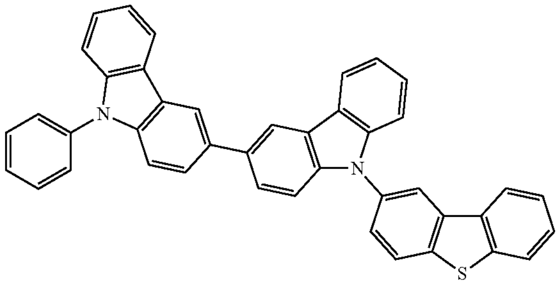

,

-continued
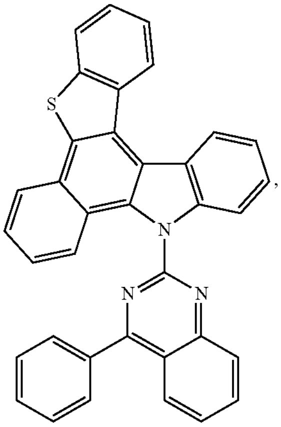,
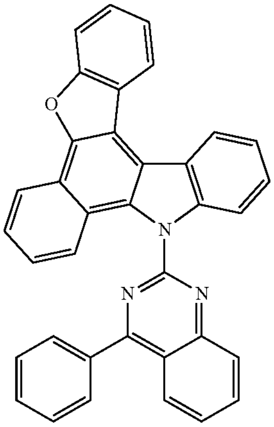,
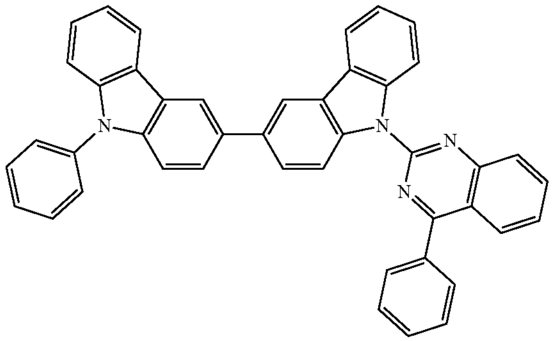,
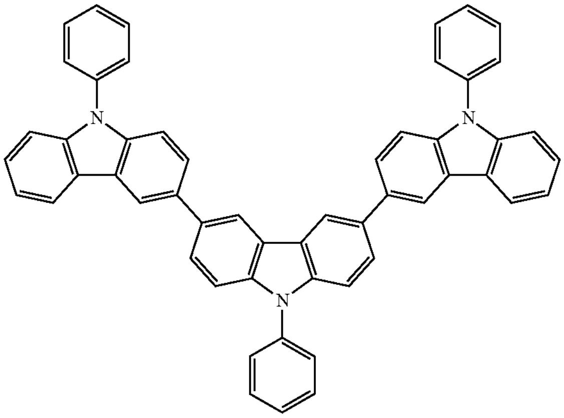,
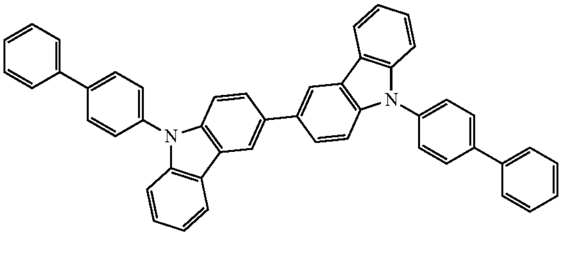,
-continued
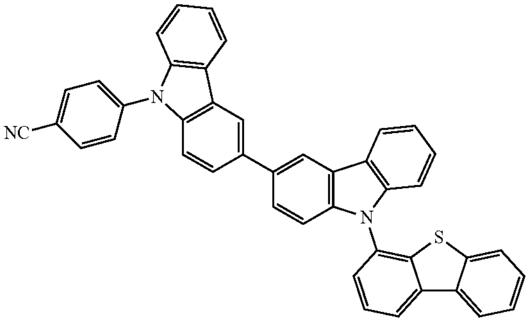,
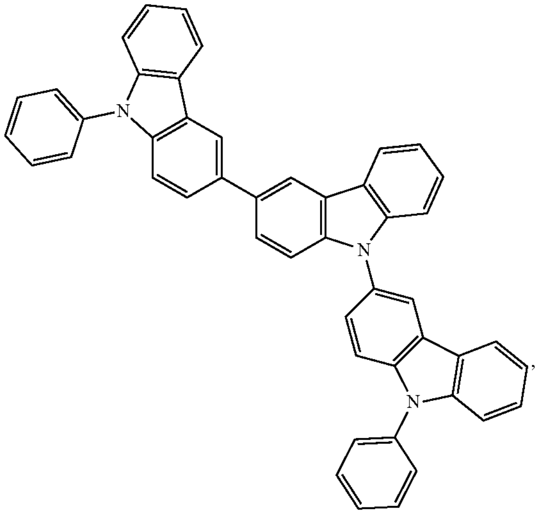,
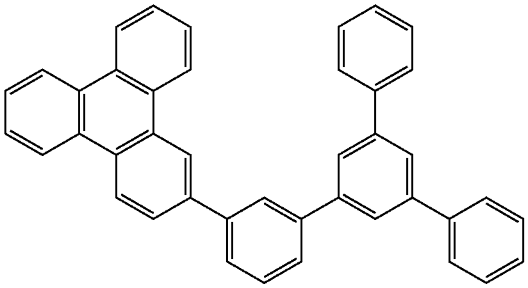,
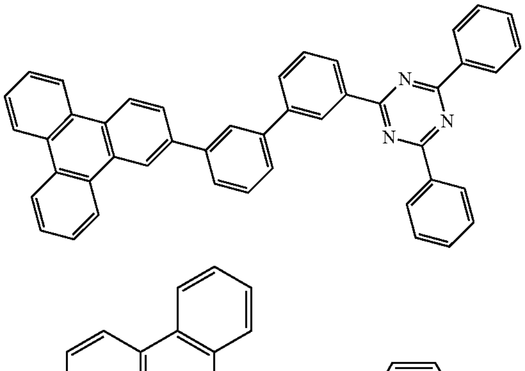,
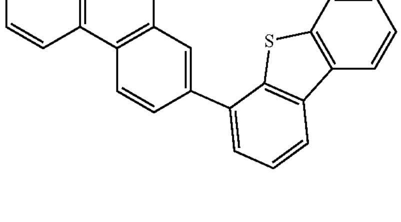, -continued

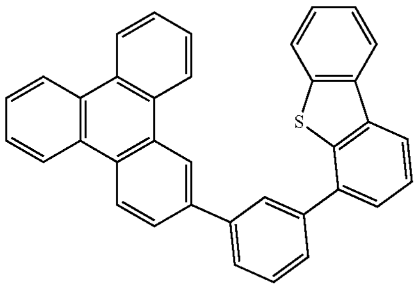

,

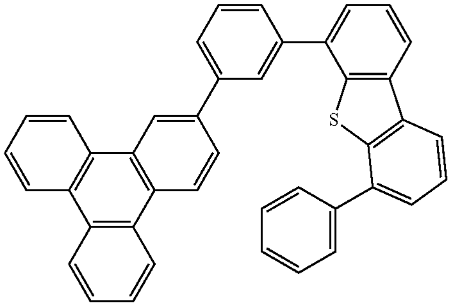

,

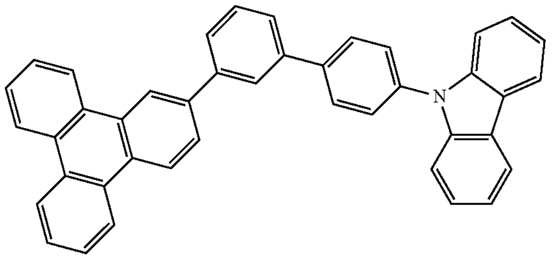

,

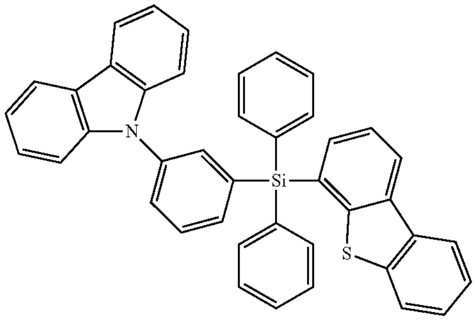

,

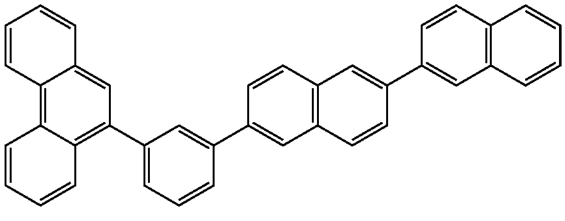

, and combinations thereof.

14. The OLED of claim 9, wherein the organic layer further comprises a host, wherein the host comprises a metal complex.

15. A formulation comprising a compound comprising a carbene ligand $L_A$ selected from the group consisting of:

Formula I

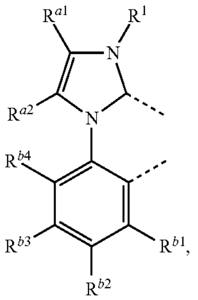

and

Formula II

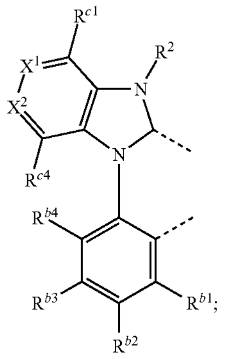

wherein $X^1$ is $CR^{c2}$ or N, $X^2$ is $CR^{c3}$ or N;

wherein $R^{a1}$, $R^{a2}$, $R^{b1}$, $R^{b2}$, $R^{b3}$, $R^{b4}$, $R^{c1}$, $R^{c2}$, $R^{c3}$, $R^{c4}$, $R^1$ and $R^2$ are each independently selected from the group consisting of hydrogen, deuterium, halide, alkyl, haloalkyl, cycloalkyl, heteroalkyl, arylalkyl, alkoxy, thioalkoxy, aryloxy, thioaryloxy, amino, silyl, halosilyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof;

wherein at least one of $R^1$, $R^{a1}$, $R^{a2}$, $R^{c1}$, $R^{c3}$, and $R^{c4}$ comprises an acceptor group selected from the group consisting of CN, F directly attached to an aromatic ring, $Si_mF_{2m+1}$, NCO, NCS, OCN, SCN, $OC_mF_{2m+1}$, and $SC_mF_{2m+1}$, where $m \geq 1$, but $R^{a1}$ cannot be CN;

wherein any adjacent substituents of $R^{b1}$, $R^{b2}$, $R^{b3}$, and $R^{b4}$ are optionally joined or fused into a ring;

wherein the ligand $L_A$ is coordinated to a metal M; and wherein the ligand $L_A$ is optionally linked with other ligands to comprise a tridentate, tetradentate, pentadentate or hexadentate ligand wherein at least one of the following is true:

(i) $R^1$ and $R^2$ are each independently selected from the group consisting of halide, haloalkyl, cycloalkyl, heteroalkyl, alkoxy, thioalkoxy, aryloxy, thioaryloxy, amino, silyl, halosilyl, cycloalkenyl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$ and combinations thereof;

(ii) at least one of $R^1$, $R^{a1}$, $R^{a2}$, $R^{c1}$, $R^{c3}$, and $R^{c4}$ comprises an acceptor group selected from the group consisting of $Si_mF_{2m+1}$, NCO, NCS, OCN, SCN, $OC_mF_{2m+1}$, and $SC_mF_{2m+1}$, where $m \geq 1$;

(iii) the ligand $L_A$ is a ligand of Formula II and at least one of $R^{c1}$, $R^{c3}$, and $R^{c4}$ is CN.

16. The compound of claim 1, wherein (i) $R^1$ and $R^2$ are each independently selected from the group consisting of halide, haloalkyl, cycloalkyl, heteroalkyl, alkoxy, thioalkoxy, aryloxy, thioaryloxy, amino, silyl, halosilyl, cycloalkenyl, acyl, carbonyl, carboxylic acids, ester, nitrile, isonitrile, sulfanyl, sulfinyl, sulfonyl, phosphino, NCO, NCS, OCN, SCN, $OC_mF_{2m+1}$ or $SC_mF_{2m+1}$, and combinations thereof; or (ii) wherein at least one of $R^1$, $R^{a1}$, $R^{a2}$, $R^{c1}$, $R^{c3}$, and $R^{c4}$ comprises an acceptor group selected from the group consisting of $Si_mF_{2m+1}$, NCO, NCS, OCN, SCN, $OC_mF_{2m+1}$, and $SC_mF_{2m+1}$, where $m \geq 1$; or (iii) both conditions (i) and (ii).

17. The compound of claim 1, wherein the ligand is a ligand of Formula II and at least one of $R^{c1}$, $R^{c3}$, and $R^{c4}$ is CN.

18. The compound of claim 17, wherein the ligand is a ligand of Formula II, wherein $X^1$ is $CR^{c2}$ and $X^2$ is $CR^{c3}$.

19. The compound of claim 18, wherein $R^{b1}$, $R^{b2}$, $R^{b3}$, and $R^{b4}$ are each independently selected from the group consisting of hydrogen, deuterium, halide, alkyl, aryloxy, and combinations thereof.

20. The compound of claim 19, wherein $R^{b1}$, $R^{b2}$, $R^{b3}$, and $R^{b4}$ are each independently selected from the group consisting of hydrogen and alkyl.

* * * * *